(12) United States Patent
Cha et al.

(10) Patent No.: US 11,001,752 B2
(45) Date of Patent: May 11, 2021

(54) DOUBLE SPIRO ORGANIC COMPOUND AND ORGANIC ELECTRONIC ELEMENT COMPRISING SAME

(71) Applicant: LG CHEM, LTD., Seoul (KR)

(72) Inventors: Yongbum Cha, Daejeon (KR); Sung Kil Hong, Daejeon (KR); Seongmi Cho, Daejeon (KR)

(73) Assignee: LG CHEM, LTD., Seoul (KR)

( * ) Notice: Subject to any disclaimer, the term of this patent is extended or adjusted under 35 U.S.C. 154(b) by 433 days.

(21) Appl. No.: 15/575,696

(22) PCT Filed: Jun. 7, 2016

(86) PCT No.: PCT/KR2016/006010
§ 371 (c)(1),
(2) Date: Nov. 20, 2017

(87) PCT Pub. No.: WO2016/195458
PCT Pub. Date: Dec. 8, 2016

(65) Prior Publication Data
US 2018/0148640 A1 May 31, 2018

(30) Foreign Application Priority Data
Jun. 5, 2015 (KR) .................. 10-2015-0080194

(51) Int. Cl.
| | | |
|---|---|---|
| *H01L 51/54* | (2006.01) | |
| *C09K 11/06* | (2006.01) | |
| *C07D 401/04* | (2006.01) | |
| *C07D 403/04* | (2006.01) | |
| *C07D 405/04* | (2006.01) | |
| *C07D 209/82* | (2006.01) | |
| *C07C 13/567* | (2006.01) | |
| *C07C 13/58* | (2006.01) | |
| *C07C 13/72* | (2006.01) | |
| *H01L 51/50* | (2006.01) | |
| *H01L 51/00* | (2006.01) | |

(52) U.S. Cl.
CPC ............ *C09K 11/06* (2013.01); *C07C 13/567* (2013.01); *C07C 13/58* (2013.01); *C07C 13/72* (2013.01); *C07D 209/82* (2013.01); *C07D 401/04* (2013.01); *C07D 403/04* (2013.01); *C07D 405/04* (2013.01); *H01L 51/0072* (2013.01); *H01L 51/50* (2013.01); *H01L 51/0085* (2013.01); *H01L 51/5016* (2013.01); *H01L 51/5056* (2013.01)

(58) Field of Classification Search
CPC ........ C09K 11/06; C07C 13/567; C07C 13/58; C07C 13/72; C07D 209/82; C07D 401/00; C07D 401/02; C07D 401/04; C07D 405/00; C07D 405/02; C07D 405/04; C07D 403/00; C07D 403/02; C07D 403/04; H01L 51/0032; H01L 51/005; H01L 51/0067; H01L 51/0072; H01L 51/0073; H01L 51/0074; H01L 51/0085; H01L 51/50; H01L 51/5012; H01L 51/5016; H01L 51/5056
USPC ........ 428/690, 691, 917, 411.4, 336; 427/58, 427/66; 313/500–512; 257/40, 98–104, 257/E51.001–E51.052; 252/301.16–301.35
See application file for complete search history.

(56) References Cited

U.S. PATENT DOCUMENTS

| | | | |
|---|---|---|---|
| 2004/0251816 A1 | 12/2004 | Leo et al. | |
| 2006/0043858 A1* | 3/2006 | Ikeda | .................. C07C 43/257 313/250 |
| 2014/0103322 A1 | 4/2014 | Watanabe et al. | |
| 2014/0225040 A1* | 8/2014 | Parham | ............... C07F 9/65685 252/500 |
| 2017/0025616 A1 | 1/2017 | Suzuki et al. | |

FOREIGN PATENT DOCUMENTS

| | | | |
|---|---|---|---|
| CN | 1338499 A | 3/2002 | |
| JP | 2012-240951 A | 12/2012 | |
| JP | 2014527522 A | 10/2014 | |
| KR | 10-2002-0008315 A | 1/2002 | |
| KR | 10-2012-0052034 A | 5/2012 | |
| KR | 10-2014-0118849 A | 10/2014 | |
| WO | 2002-088274 A1 | 11/2002 | |
| WO | 2003-012890 A2 | 2/2003 | |
| WO | 2011136484 A1 | 11/2011 | |
| WO | 2012-141229 A1 | 10/2012 | |
| WO | WO-2013017189 A1 * | 2/2013 | ........... C07D 307/94 |

OTHER PUBLICATIONS

Wee et al. J. Org. Chem. 2009, 74, 8472-8475. (Year: 2009).*

\* cited by examiner

*Primary Examiner* — Andrew K Bohaty
(74) *Attorney, Agent, or Firm* — Dentons US LLP

(57) ABSTRACT

The present specification provides a novel compound capable of greatly enhancing lifespan, efficiency, electrochemical stability and thermal stability of an organic electronic device, and an organic electronic device containing the compound in an organic compound layer.

29 Claims, 2 Drawing Sheets

【FIG. 1】
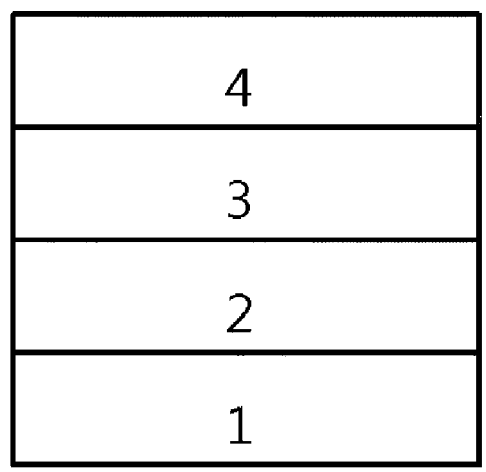

[FIG. 2]
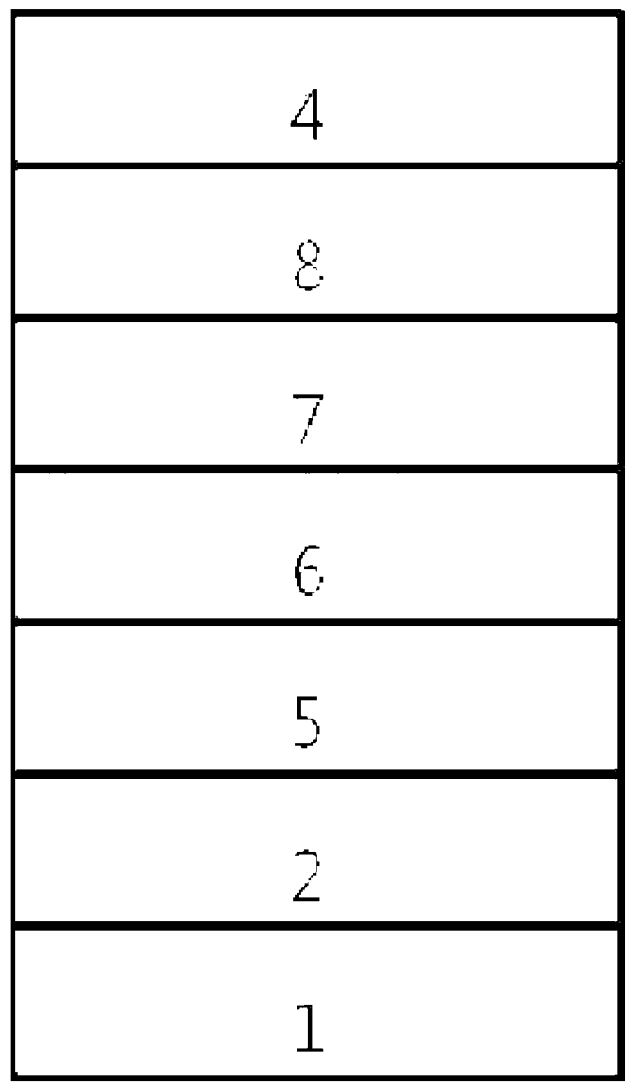

DOUBLE SPIRO ORGANIC COMPOUND AND ORGANIC ELECTRONIC ELEMENT COMPRISING SAME

This application is a National Stage Entry of International Application No. PCT/KR2016/006010, filed Jun. 7, 2016, and claims the benefit of and priority to Korean Application No. 10-2015-0080194, filed on Jun. 5, 2015, all of which are hereby incorporated by reference in their entirety for all purposes as if fully set forth herein.

TECHNICAL FIELD

The present specification claims priority to and the benefits of Korean Patent Application No. 10-2015-0080194, filed with the Korean Intellectual Property Office on Jun. 5, 2015, the entire contents of which are incorporated herein by reference.

The present specification relates to an organic compound having a double spiro structure and an organic electronic device comprising the same.

BACKGROUND ART

In the present specification, an organic electronic device is an electronic device using an organic semiconductor material, and requires hole and/or electron exchanges between an electrode and the organic semiconductor material. An organic electronic device may be categorized into two main groups depending on an operation principle. First is an electronic device in which excitons form in an organic material layer by the photons brought into the device from an external light source, these excitons are separated into electrons and holes, and these electrons and holes are used as a current source (voltage source) by each of these being transferred to other electrodes. Second is an electronic device in which holes and/or electrons are injected to an organic semiconductor material layer that forms an interface with an electrode by applying a voltage or a current to two or more electrodes, and the device is operated by the injected electrons and holes.

Examples of an organic electronic device include an organic light emitting device, an organic solar cell, an organic photo conductor (OPC) drum, an organic transistor and the like, and these all need an electron/hole injection material, an electron/hole extraction material, an electron/hole transfer material or a light emitting material for the driving of the device. Hereinafter, an organic light emitting device will be described in detail mostly, however, in the organic electronic devices described above, the electron/hole injection material, the electron/hole extraction material, the electron/hole transfer material or the light emitting material is all used under similar principles.

An organic light emission phenomenon generally refers to a phenomenon converting electrical energy to light energy using an organic material. An organic light emitting device using an organic light emission phenomenon normally has a structure including an anode, a cathode, and an organic material layer therebetween. Herein, the organic material layer is often formed in a multilayer structure formed with different materials in order to increase efficiency and stability of the organic light emitting device, and for example, may include a hole injection layer, a hole transfer layer, a light emitting layer, an electron transfer layer, an electron injection layer and the like. When a voltage is applied between the two electrodes in such an organic light emitting device structure, holes and electrons are injected to the organic material layer from the anode and the cathode, respectively, and when the injected holes and electrons meet, excitons are formed, and light emits when these excitons fall back to the ground state. Such an organic light emitting device is known to have properties such as spontaneous emission, high luminance, high efficiency, low driving voltage, wide viewing angle, high contrast and high rate response.

In an organic light emitting device, materials as an organic material layer may be divided into a light emitting material and a charge transfer material such as a hole injection material, a hole transfer material, an electron transfer material and an electron injection material depending on the function. The light emitting material includes, depending on the light emitting color, blue, green and red light emitting materials, and yellow and orange light emitting materials required for obtaining better natural color.

In addition, a host/dopant series may be used as a light emitting material in order to increase color purity and increase light emission efficiency through energy transfer. The principle is that, when a dopant having a smaller energy band gap than a host mostly forming a light emitting layer and having excellent light emission efficiency is mixed in a small quantity in the light emitting layer, excitons generated in the host are transferred to the dopant emitting light with high efficiency. Herein, light with a target wavelength may be obtained depending on the dopant type used since a wavelength of the host moves to a wavelength range of the dopant.

In order to sufficiently exhibit the excellent properties described above that an organic light emitting device has, materials forming an organic material layer in the device, for example, a hole injection material, a hole transfer material, a light emitting material, an electron transfer material, an electron injection material and the like need to be supported by stable and efficient materials first, however, stable and efficient organic material layer materials for an organic light emitting device have not yet been sufficiently developed, and accordingly, development of new materials has been continuously required.

DISCLOSURE

Technical Problem

The present specification describes an organic compound having a double spiro structure and an organic electronic device comprising the same.

Technical Solution

One embodiment of the present specification provides a compound represented by the following Chemical Formula 1:

[Chemical Formula 1]

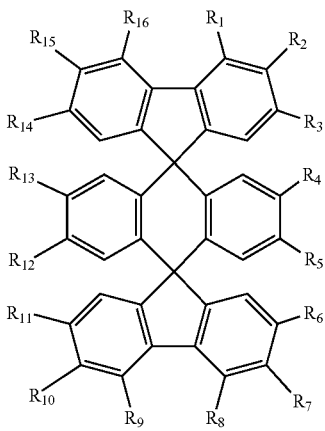

In Chemical Formula 1, at least one of $R_1$ to $R_{16}$ bonds to adjacent groups to form a ring structure of Chemical Formula 1-1, groups that do not form the ring among $R_1$ to $R_{16}$ are each independently selected from the group consisting of hydrogen; deuterium; a halogen group; a nitrile group; a nitro group; a hydroxyl group; a carbonyl group; an ester group; an imide group; an amino group; a substituted or unsubstituted silyl group; a substituted or unsubstituted boron group; a substituted or unsubstituted alkyl group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylphosphine group; a substituted or unsubstituted phosphine oxide group; a substituted or unsubstituted aryl group; and a substituted or unsubstituted heterocyclic group,

[Chemical Formula 1-1]

in Chemical Formula 1-1, m is an integer of 0 to 5, when m is 2 or greater, Ls are the same as or different from each other, L is a direct bond; a substituted or unsubstituted arylene group; or a substituted or unsubstituted heteroarylene group, $Ar_1$ is hydrogen; deuterium; a halogen group; a nitrile group; a nitro group; a hydroxyl group; a carbonyl group; an ester group; an imide group; an amino group; a substituted or unsubstituted silyl group; a substituted or unsubstituted boron group; a substituted or unsubstituted alkyl group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylphosphine group; a substituted or unsubstituted phosphine oxide group; a substituted or unsubstituted aryl group; or a substituted or unsubstituted heterocyclic group, when $(L)_m$-$Ar_1$ is an unsubstituted phenyl group, groups that do not form the ring of Chemical Formula 1-1 among $R_1$ to $R_{16}$ are hydrogen, and $R_{1a}$ to $R_{4a}$ are the same as or different from each other, and each independently hydrogen; deuterium; a halogen group; a nitrile group; a nitro group; a hydroxyl group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphine oxide group; a substituted or unsubstituted aryl group; or a substituted or unsubstituted heterocyclic group, or bond to adjacent groups to form a substituted or unsubstituted ring.

Another embodiment of the present specification provides an organic electronic device comprising a first electrode, a second electrode, and one or more organic material layers disposed between the first electrode and the second electrode, wherein one or more layers of the organic material layers comprise the organic compound having a double spiro structure of Chemical Formula 1.

Advantageous Effects

A novel compound according to the present specification is capable of being used as a material of an organic material layer of an organic electronic device comprising an organic light emitting device, and by using the novel compound, efficiency enhancement, low driving voltage and/or lifespan property enhancement can be obtained in an organic electronic device including an organic light emitting device.

DESCRIPTION OF DRAWINGS

FIG. 1 illustrates an organic light emitting device formed with a substrate (1), an anode (2), a light emitting layer (3) and a cathode (4).

FIG. 2 illustrates an organic light emitting device formed with a substrate (1), an anode (2), a hole injection layer (5), a hole transfer layer (6), a light emitting layer (7), an electron transfer layer (8) and a cathode (4).

1: Substrate
2: Anode
3: Light Emitting Layer
4: Cathode
5: Hole Injection Layer
6: Hole Transfer Layer
7: Light Emitting Layer
8: Electron Transfer Layer

BEST MODE FOR DISCLOSURE

Hereinafter, the present specification will be described in more detail.

One embodiment of the present specification provides a compound represented by Chemical Formula 1.

Examples of the substituents are described below, however, the substituents are not limited thereto.

The term "substituted or unsubstituted" in the present specification means being substituted with one or more substituents selected from the group consisting of deuterium; a halogen group; a nitrile group; a nitro group; a hydroxyl group; a germanium group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; or a heterocyclic group, or being unsubstituted, or being substituted with a substituent linking two or more substituents among the substituents illustrated above, or being unsubstituted. For example, "a substituent linking two or more substituents" may include a biphenyl group. In other words, a biphenyl group may be an aryl group, or interpreted as a substituent linking two phenyl groups.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

In the present specification,

means a site bonding to other substituents or bonding sites.

In the present specification, examples of the halogen group may include fluorine, chlorine, bromine or iodine.

In the present specification, the number of carbon atoms of the carbonyl group is not particularly limited, but is preferably from 1 to 40. Specifically, compounds having structures as below may be included, but the carbonyl group is not limited thereto.

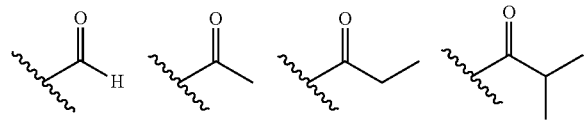

-continued

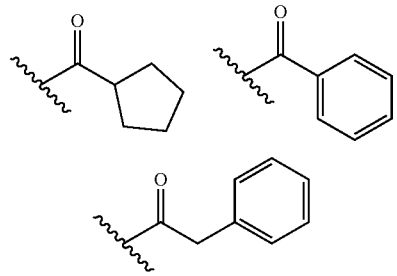

In the present specification, in the ester group, the oxygen of the ester group may be substituted with a linear, branched or cyclic alkyl group having 1 to 25 carbon atoms or an aryl group having 6 to 25 carbon atoms. Specifically, compounds having the following structural formulae may be included, but the ester group is not limited thereto.

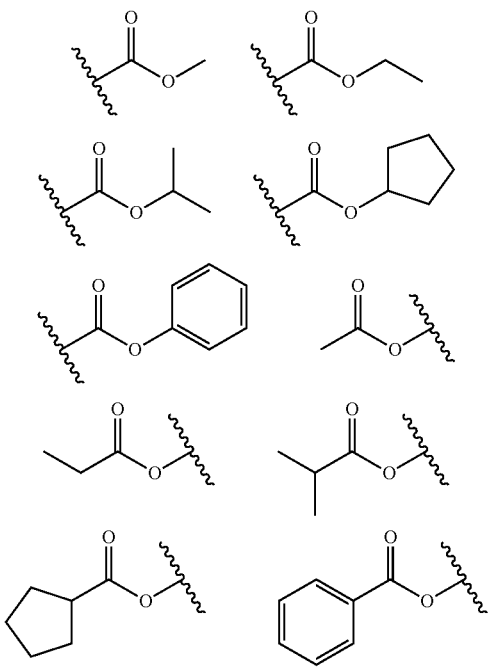

In the present specification, the number of carbon atoms of the imide group is not particularly limited, but is preferably from 1 to 25. Specifically, compounds having structures as below may be included, but the imide group is not limited thereto.

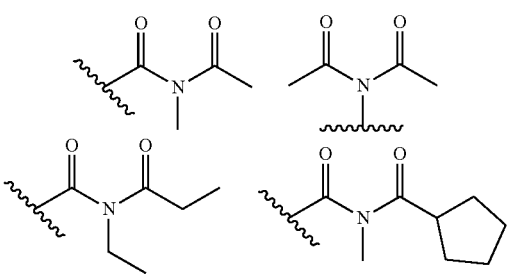

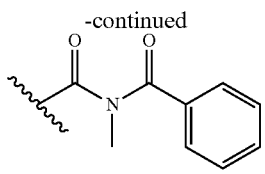

In the present specification, the silyl group may be represented by the chemical formula of —SiRR'R", and R, R' and R" may each be hydrogen; a substituted or unsubstituted alkyl group; or a substituted or unsubstituted aryl group. Specific examples of the silyl group may include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the boron group may be represented by the chemical formula of —BRR'R", and R, R' and R" may each be hydrogen; a substituted or unsubstituted alkyl group; or a substituted or unsubstituted aryl group. Specific examples of the boron group may include a trimethylboron group, a triethylboron group, a t-butyldimethylboron group, a triphenylboron group, a phenylboron group and the like, but are not limited thereto.

In the present specification, the alkyl group may be linear or branched, and although not particularly limited thereto, the number of carbon atoms is preferably from 1 to 40. According to one embodiment, the number of carbon atoms of the alkyl group is from 1 to 20. According to another embodiment, the number of carbon atoms of the alkyl group is from 1 to 10. According to another embodiment, the number of carbon atoms of the alkyl group is from 1 to 6. Specific examples of the alkyl group may include methyl, ethyl, propyl, n-propyl, isopropyl, butyl, n-butyl, isobutyl, tert-butyl, sec-butyl, 1-methylbutyl, 1-ethylbutyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethylpropyl, 1,1-dimethylpropyl, isohexyl, 4-methylhexyl, 5-methylhexyl and the like, but are not limited thereto.

In the present specification, the cycloalkyl group is not particularly limited, but preferably has 3 to 60 carbon atoms, and according to one embodiment, the number of carbon atoms of the cycloalkyl group is from 3 to 40. According to another embodiment, the number of the carbon atoms of the cycloalkyl group is from 3 to 20. According to another embodiment, the number of carbon atoms of the cycloalkyl group is from 3 to 6. Specific examples thereof may include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present specification, the alkoxy group may be linear, branched or cyclic. The number of carbon atoms of the alkoxy group is not particularly limited, but is preferably from 1 to 20. Specific examples thereof may include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

The alkyl group, the alkoxy group and other substituents including an alkyl group part described in the present specification include both a linear or a branched form.

In the present specification, the alkenyl group may be linear or branched, and although not particularly limited thereto, the number of carbon atoms is preferably from 2 to 40. According to one embodiment, the number of carbon atoms of the alkenyl group is from 2 to 20. According to another embodiment, the number of carbon atoms of the alkenyl group is from 2 to 10. According to another embodiment, the number of carbon atoms of the alkenyl group is from 2 to 6. Specific examples thereof may include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group and the like, but are not limited thereto.

In the present specification, descriptions on the alkenyl group provided above may be applied to the alkenyl group in the aralkenyl group.

In the present specification, examples of the heteroarylamine group include a substituted or unsubstituted monoheteroarylamine group, a substituted or unsubstituted diheteroarylamine group, or a substituted or unsubstituted triheteroarylamine group. The heteroaryl group in the heteroarylamine group may be a monocyclic heterocyclic group or a multicyclic heterocyclic group. The heteroarylamine group including two or more heterocyclic groups may include monocyclic heterocyclic groups, multicyclic heterocyclic groups, or both monocyclic heterocyclic groups and multicyclic heterocyclic groups.

In the present specification, examples of the arylamine group include a substituted or unsubstituted monoarylamine group, a substituted or unsubstituted diarylamine group, or a substituted or unsubstituted triarylamine group. The aryl group in the arylamine group may be a monocyclic aryl group or a multicyclic aryl group. The arylamine group including two or more aryl groups may include monocyclic aryl groups, multicyclic aryl groups, or both monocyclic aryl groups and multicyclic aryl groups.

Specific examples of the arylamine group may include phenylamine, naphthylamine, biphenylamine, anthracenylamine, 3-methylphenylamine, 4-methylnaphthylamine, 2-methylbiphenylamine, 9-methylanthracenylamine, a diphenylamine group, a phenylnaphthylamine group, a ditolylamine group, a phenyltolylamine group, carbazole, a triphenylamine group and the like, but are not limited thereto.

In the present specification, the arylheteroarylamine group means an amine group substituted with an aryl group and a heterocyclic group.

In the present specification, the number of carbon atoms of the amine group is not particularly limited, but is preferably from 1 to 30. In the amine group, the N atom may be substituted with an aryl group, an alkyl group, an arylalkyl group, a heterocyclic group and the like. Specific examples of the amine group may include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, a phenylnaphthylamine group, a ditolylamine group, a phenyltolylamine group, a triphenylamine group and the like, but are not limited thereto.

In the present specification, examples of the arylphosphine group include a substituted or unsubstituted monoarylphosphine group, a substituted or unsubstituted diarylphosphine group, or a substituted or unsubstituted triarylphosphine group. The aryl group in the arylphosphine group may be a monocyclic aryl group or a multicyclic aryl group. The arylphosphine group including two or more aryl groups may include monocyclic aryl groups, multicyclic aryl groups, or both monocyclic aryl groups and multicyclic aryl group.

In the present specification, the aryl group is not particularly limited, but preferably has 6 to 60 carbon atoms, and may be a monocyclic aryl group or a multicyclic aryl group. According to one embodiment, the number of carbon atoms of the aryl group is from 6 to 40. According to one embodiment, the number of carbon atoms of the aryl group is from 6 to 20. When the aryl group is a monocyclic aryl group, examples thereof may include a phenyl group, a biphenyl group, a terphenyl group and the like, but are not limited thereto. Examples of the multicyclic aryl group may include a naphthyl group, an anthracenyl group, a phenanthryl group, a pyrenyl group, a perylenyl group, a chrysenyl group, a fluorenyl group and the like, but are not limited thereto.

In the present specification, the fluorenyl group may be substituted, and two substituents bond to each other to form a spiro structure.

When the fluorenyl group is substituted,

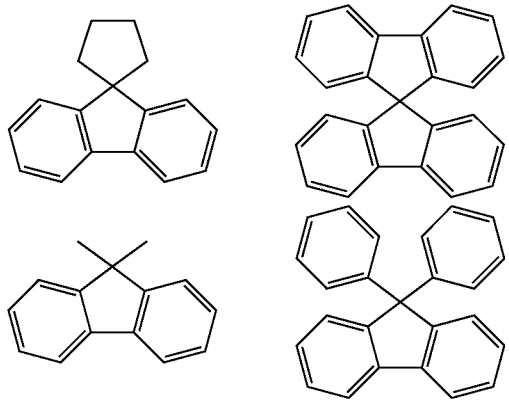

and the like may be included. However, the structure is not limited thereto.

In the present specification, the heterocyclic group is a heterocyclic group including one or more of N, O, P, S, Si and Se as a heteroatom, and although not particularly limited thereto, the number of carbon atoms is preferably from 1 to 60. According to one embodiment, the number of carbon atoms of the heterocyclic group is from 1 to 40. According to one embodiment, the number of carbon atoms of the heterocyclic group is from 1 to 20. According to one embodiment, the number of atoms forming a ring of the heterocyclic group is from 5 to 60. According to one embodiment, the number of atoms forming a ring of the heterocyclic group is from 5 to 30. According to one embodiment, the number of atoms forming a ring of the heterocyclic group is from 5 to 14. According to one embodiment, the number of atoms forming a ring of the heterocyclic group is from 15 to 60. Examples of the heterocyclic group may include a pyridyl group, a pyrrole group, a pyrimidyl group, a pyridazinyl group, a furanyl group, a thiophenyl group, an imidazole group, a pyrazole group, an oxazole group, an isoxazole group, a triazole group, an isothiazole group, a triazole group, an oxadiazole group, a thiadiazole group, dithiazole group, a tetrazole group, a pyranyl group, a thiopyranyl group, a pyrazinyl group, an oxazinyl group, a triazinyl group, a dioxynyl group, a triazinyl group, a tetrazinyl group, a quinolinyl group, an isoquinolinyl group, a quinolyl group, a quinazolinyl group, a quinoxalinyl group, a naphthyridinyl group, an acridyl group, a xanthenyl group, a phenanthridinyl group, a diazanaphthalenyl group, a triazaindenyl group, an indole group, an indolinyl group, an indolizinyl group, a phthalazinyl group, a pyridopyrimidinyl group, a pyridopyrazinyl group, a pyrazinopyrazinyl group, a benzothiazole group, a benzoxazole group, a benzimidazole group, a benzothiophene group, a benzofuranyl group, a dibenzothiophenyl group, a dibenzofuranyl group, a carbazole group, a benzocarbazole group, a dibenzocarbazole group, an indolocarbazole group, an indenocarbazole group, a phenazinyl group, an imidazopyridine group, a phenoxazinyl group, a phenanthridine group, a phenanthroline group, a phenothiazine group or the like, but are not limited thereto. In addition, examples of the heterocyclic group may include an imidazopyridine group, a benzofluorenyl group, a benzophenanthrenyl group, an imidazophenanthrenyl group, a benzophenanthridinyl group, an imidazophenanthridinyl group, a benzocarbazole group, a dibenzocarbazole group, an indolocarbazole group, a benzoacridinyl group, an indoloacridinyl group, a benzimidazoquinazoline group, a benzimidazophenanthridine group or the like, but are not limited thereto.

In the present specification, the germanium group may be represented by the chemical formula of —GeR$_a$R$_b$R$_c$, and R$_a$, R$_b$ and R$_c$ may each be hydrogen; a substituted or unsubstituted alkyl group; or a substituted or unsubstituted aryl group. Specific examples of the germanium group may include a trimethylgermanium group, a triethylgermanium group, a t-butyldimethylgermanium group or the like, but are not limited thereto.

In the present specification, descriptions on the aryl group provided above may be applied to the aryl group in the aryloxy group, the arylthio group, the arylthioxy group, the arylsulfoxy group, the arylphosphine group, the aralkyl group, the aralkylamine group, the aralkenyl group, the alkylaryl group, the arylamine group and the arylheteroarylamine group.

In the present specification, descriptions on the alkoxy group provided above may be applied to the alkoxy group in the alkoxycarbonyl group, and descriptions on the carbonyl group provided above may be applied to the carbonyl group in the alkoxycarbonyl group.

In the present specification, descriptions on the alkyl group provided above may be applied to the alkyl group in the alkylthioxy group, the alkylsulfoxy group, the aralkyl group, the aralkylamine group, the alkylaryl group and the alkylamine group.

In the present specification, descriptions on the heterocyclic group provided above may be applied to the heteroaryl group in the heteroaryl group, the heteroarylamine group and the arylheteroarylamine group.

In the present specification, descriptions on the heterocyclic group provided above may be applied to the heteroaryl group except for being an aromatic group.

In the present specification, descriptions on the aryl group provided above may be applied to the arylene except for being a divalent.

In the present specification, descriptions on the heterocyclic group provided above may be applied to the heteroarylene except for being a divalent.

In the present specification, the meaning of bonding to adjacent groups to form a ring means bonding to adjacent groups to form a substituted or unsubstituted aliphatic hydrocarbon ring; a substituted or unsubstituted aromatic hydrocarbon ring; a substituted or unsubstituted aliphatic heteroring; a substituted or unsubstituted aromatic heteroring; or a fused ring thereof.

In the present specification, the aliphatic hydrocarbon ring means a ring formed only with carbon and hydrogen atoms as a ring that is not aromatic. Specifically, examples of the aliphatic hydrocarbon ring may include cyclopropane, cyclobutane, cyclobutene, cyclopentane, cyclopentene, cyclohexane, cyclohexene, 1,4-cyclohexadiene, cycloheptane, cycloheptene, cyclooctane, cyclooctene and the like, but are not limited thereto.

In the present specification, the aromatic hydrocarbon ring means an aromatic ring formed only with carbon and hydrogen atoms. Specifically, examples of the aromatic hydrocarbon ring may include benzene, naphthalene, anthracene, phenanthrene, perylene, fluoranthene, triphenylene, phenalene, pyrene, tetracene, chrysene, pentacene, fluorene, indene, acenaphthylene, benzofluorene, spirofluorene and the like, but are not limited thereto.

In the present specification, the aliphatic heteroring means an aliphatic ring including one or more of heteroatoms. Specifically, examples of the aliphatic heteroring may include oxirane, tetrahydrofuran, 1,4-dioxane, pyrrolidine, piperidine, morpholine, oxepane, azocane, thiocane and the like, but are not limited thereto.

In the present specification, the aromatic heteroring means an aromatic ring including one or more of heteroatoms. Specifically, examples of the aromatic heteroring may include pyridine, pyrrole, pyrimidine, pyridazine, furan, thiophene, imidazole, pyrazole, oxazole, isoxazole, triazole, isothiazole, triazole, oxadiazole, thiadiazole, dithiazole, tetrazole, pyran, thiopyran, diazine, oxazine, triazine, dioxin, triazine, tetrazine, isoquinoline, quinoline, quinol, quinazoline, quinoxaline, naphthyridine, acridine, phenanthridine, diazanaphthalene, triazaindene, indole, indolizine, benzothiazole, benzoxazole, benzimidazole, benzothiophene, benzofuran, dibenzothiophene, dibenzofuran, carbazole, benzocarbazole, dibenzocarbazole, phenazine, imidazopyridine, phenoxazine, phenanthridine, indolocarbazole, indenocarbazole and the like, but are not limited thereto.

In the present specification, the aliphatic hydrocarbon ring, the aromatic hydrocarbon ring, the aliphatic heteroring and the aromatic heteroring may be monocyclic or multicyclic.

According to one embodiment of the present disclosure, the organic compound having a double spiro structure of Chemical Formula 1 is an organic compound having a double spiro structure represented by any one of the following Chemical Formula 2 to Chemical Formula 7.

[Chemical Formula 2]

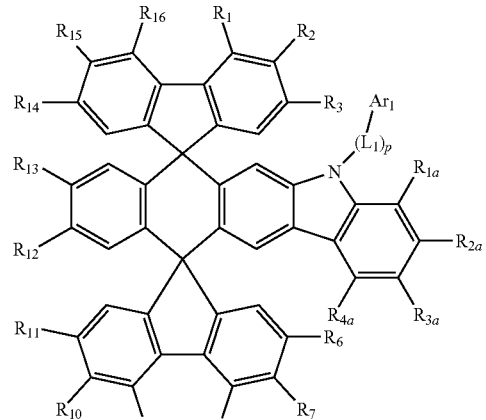

[Chemical Formula 3]

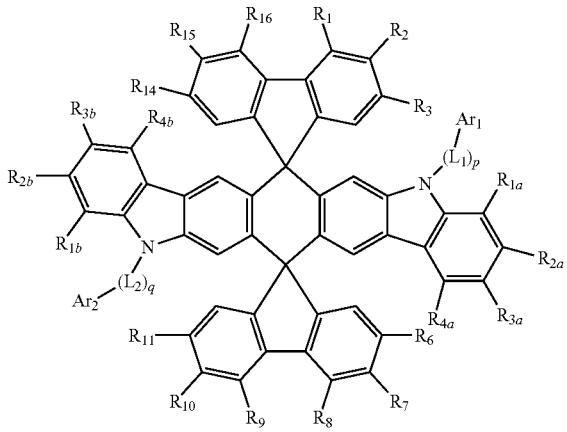

[Chemical Formula 4]

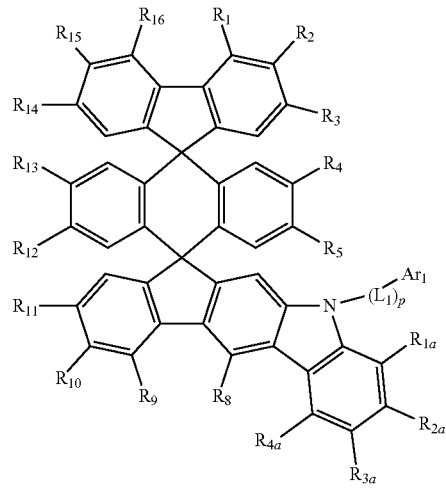

[Chemical Formula 5]

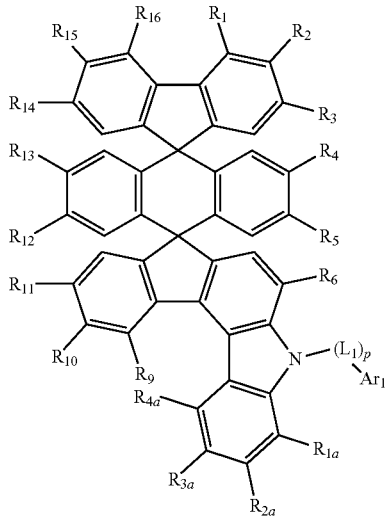

[Chemical Formula 6]

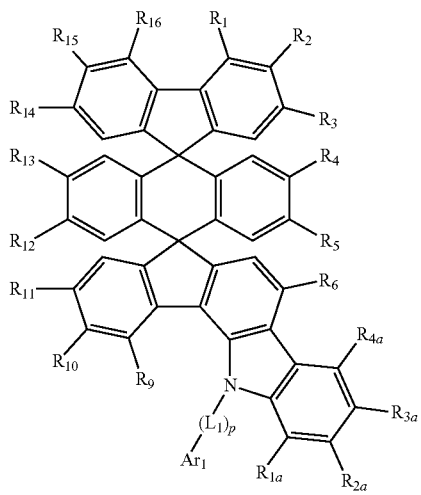

[Chemical Formula 7]

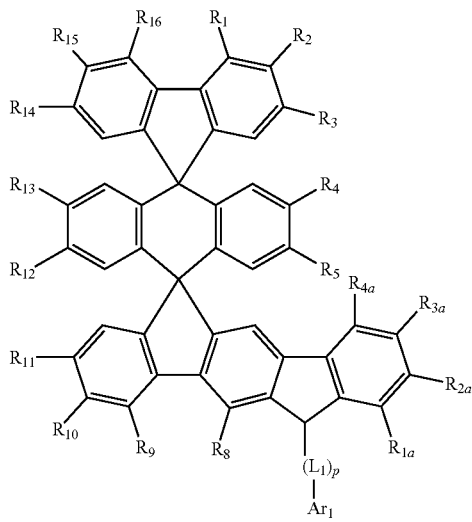

In Chemical Formula 2 to Chemical Formula 7, $R_1$ to $R_{16}$ each independently have the same definition as in Chemical Formula 1, p and q are each independently an integer of 0 to 5, when p is 2 or greater, $L_1$s are the same as or different from each other, when q is 2 or greater, $L_2$s are the same as or different from each other, $L_1$ and $L_2$ are the same as or different from each other, and each independently have the same definition as L in Chemical Formula 1-1, $Ar_1$ and $Ar_2$ are the same as or different from each other, and each independently have the same definition as $Ar_1$ in Chemical Formula 1-1, and $R_{1a}$ to $R_{4a}$ and $R_{1b}$ to $R_{4b}$ each independently have the same definition as $R_{1a}$ to $R_{4a}$ in Chemical Formula 1-1.

According to one embodiment of the present disclosure, the organic compound having a double spiro structure is represented by any one of the following Chemical Formula 8 to Chemical Formula 17.

[Chemical Formula 8]

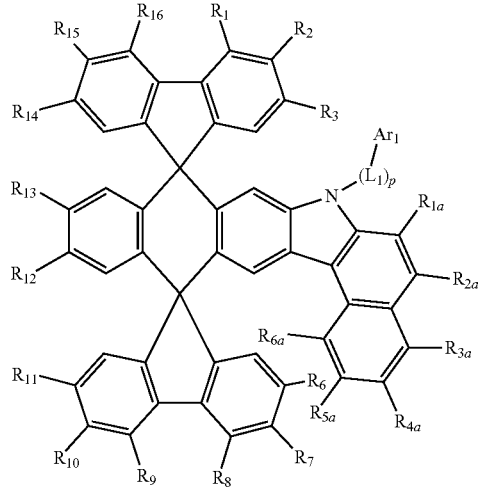

[Chemical Formula 9]

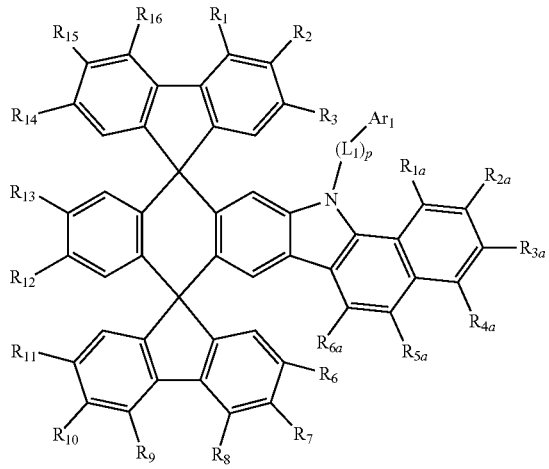

[Chemical Formula 10]
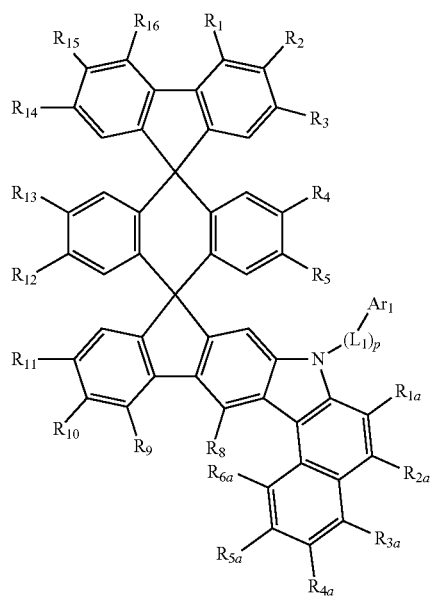
[Chemical Formula 12]
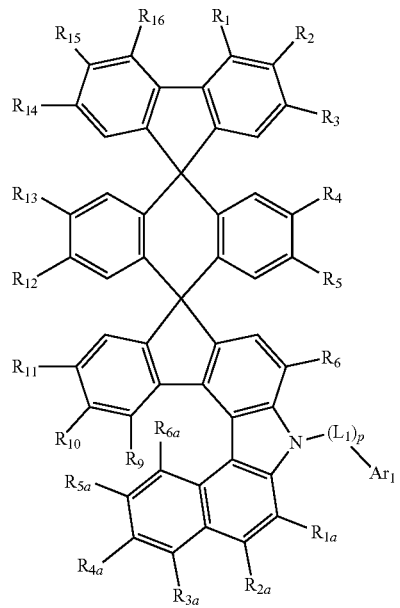
[Chemical Formula 11]
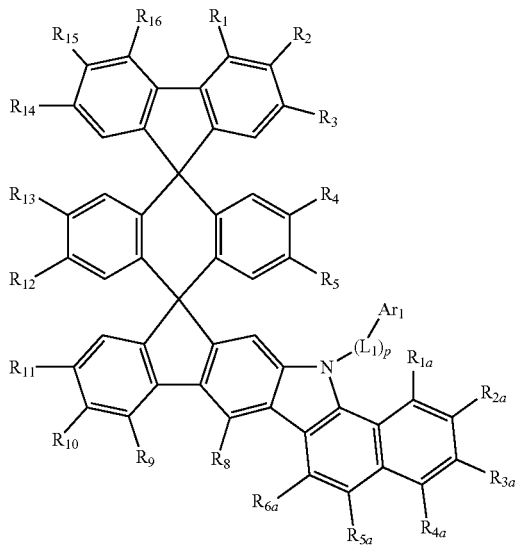
[Chemical Formula 13]
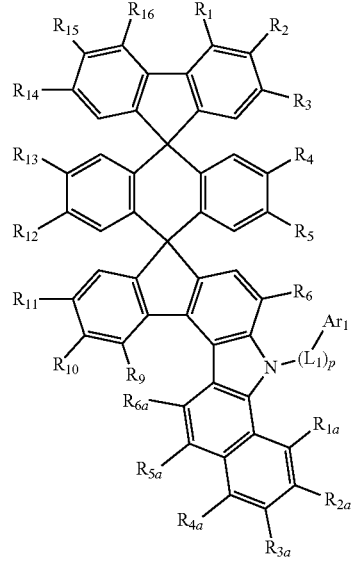

[Chemical Formula 14]

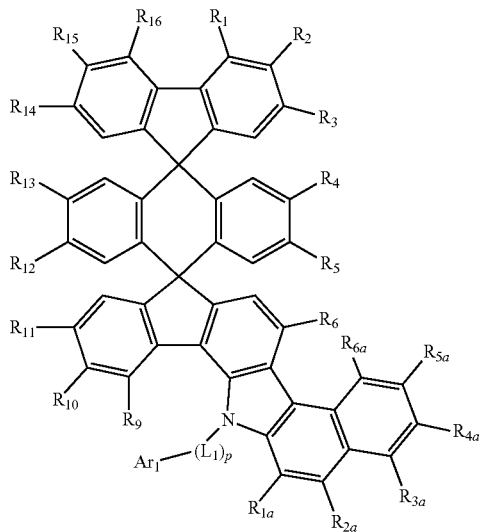

[Chemical Formula 15]

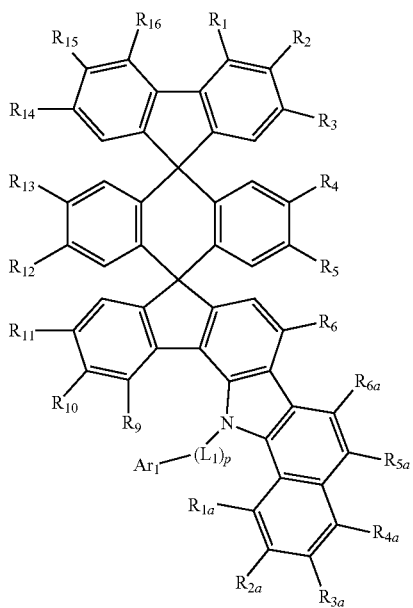

[Chemical Formula 16]

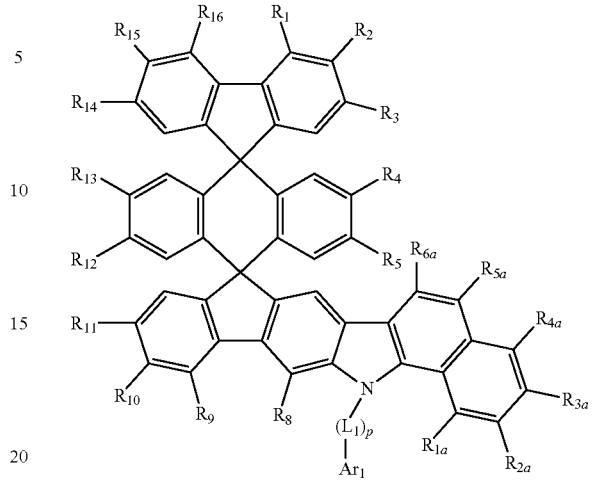

[Chemical Formula 17]

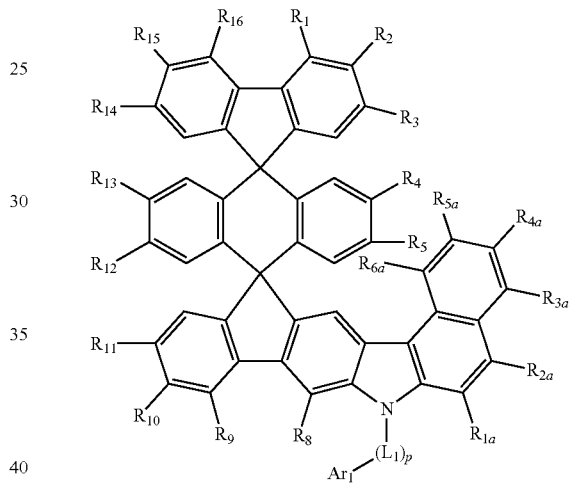

In Chemical Formula 8 to Chemical Formula 17, $R_1$ to $R_{16}$ each independently have the same definition as in Chemical Formula 1, p is an integer of 0 to 5, when p is 2 or greater, $L_1$s are the same as or different from each other, $L_1$ has the same definition as L in Chemical Formula 1-1, $Ar_1$ has the same definition as in Chemical Formula 1-1, and $R_{1a}$ to $R_{6a}$ are the same as or different from each other, and each independently have the same definition as $R_{1a}$ to $R_{4a}$ in Chemical Formula 1-1.

In one embodiment of the present disclosure, L, $L_1$ and $L_2$ are the same as or different from each other, and each independently a direct bond; a substituted or unsubstituted arylene group; or a substituted or unsubstituted heteroarylene group.

In one embodiment of the present disclosure, L, $L_1$ and $L_2$ are the same as or different from each other, and each independently a direct bond; a substituted or unsubstituted arylene group having 6 to 30 carbon atoms; or a substituted or unsubstituted heteroarylene group having 1 to 30 carbon atoms.

In addition, in one embodiment of the present disclosure, L, $L_1$ and $L_2$ are the same as or different from each other, and each independently unsubstituted or substituted with one or more substituents selected from the group consisting of a direct bond; a substituted or unsubstituted phenylene group; a substituted or unsubstituted biphenylene group; a substituted or unsubstituted terphenylene group; a substituted or unsubstituted naphthylene group; a substituted or unsubstituted pyrenylene group; a substituted or unsubstituted phenanthrenylene group; a substituted or unsubstituted perylenylene group; a substituted or unsubstituted tetracenylene group; a substituted or unsubstituted triphenylene group; a substituted or unsubstituted fluoranthenylene group; a substituted or unsubstituted fluorenylene group; a substituted or unsubstituted pyrrolylene group; a substituted or unsubstituted furanylene group; a substituted or unsubstituted thiophenylene group; a substituted or unsubstituted pyridinylene group; a substituted or unsubstituted pyrazolylene group; a substituted or unsubstituted imidazolylene group; a substituted or unsubstituted oxazolylene group; a substituted or unsubstituted isoxazolylene group; a substituted or unsubstituted thiazolylene group; a substituted or unsubstituted isothiazolylene group; a substituted or unsubstituted pyridazinylene group; a substituted or unsubstituted pyrimidinylene group; a substituted or unsubstituted indolylene group; a substituted or unsubstituted isoindolylene group; a substituted or unsubstituted indolizinylene group; a substituted or unsubstituted quinolinylene group; a substituted or unsubstituted isoquinolinylene group; a substituted or unsubstituted furanylene group; a substituted or unsubstituted dibenzofuranylene group; a substituted or unsubstituted dibenzothiophenylene group; a substituted or unsubstituted xanthenylene group; and a substituted or unsubstituted carbazolylene group, or unsubstituted or substituted with a substituent linking two or more of the substituents illustrated above.

In one embodiment of the present disclosure, L, $L_1$ and $L_2$ are the same as or different from each other, and each independently a direct bond; a substituted or unsubstituted phenylene group; a substituted or unsubstituted biphenylene group; a substituted or unsubstituted naphthylene group; a substituted or unsubstituted fluorenylene group; a substituted or unsubstituted pyridinylene group; a substituted or unsubstituted pyrimidinylene group; a substituted or unsubstituted triazinylene group; a substituted or unsubstituted quinolylene group; a substituted or unsubstituted quinazolylene group; a substituted or unsubstituted dibenzothiophenylene group; a substituted or unsubstituted dibenzofuranylene group; or a substituted or unsubstituted carbazolylene group.

In addition, in one embodiment of the present disclosure, L, $L_1$ and $L_2$ are the same as or different from each other, and preferably each independently a direct bond or any one substituent selected from the following group, but are not limited thereto.

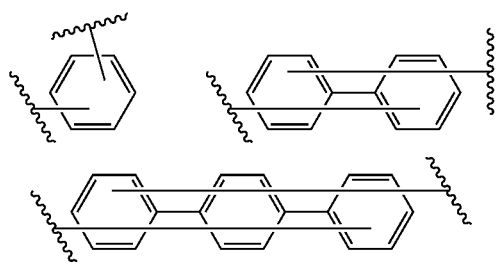

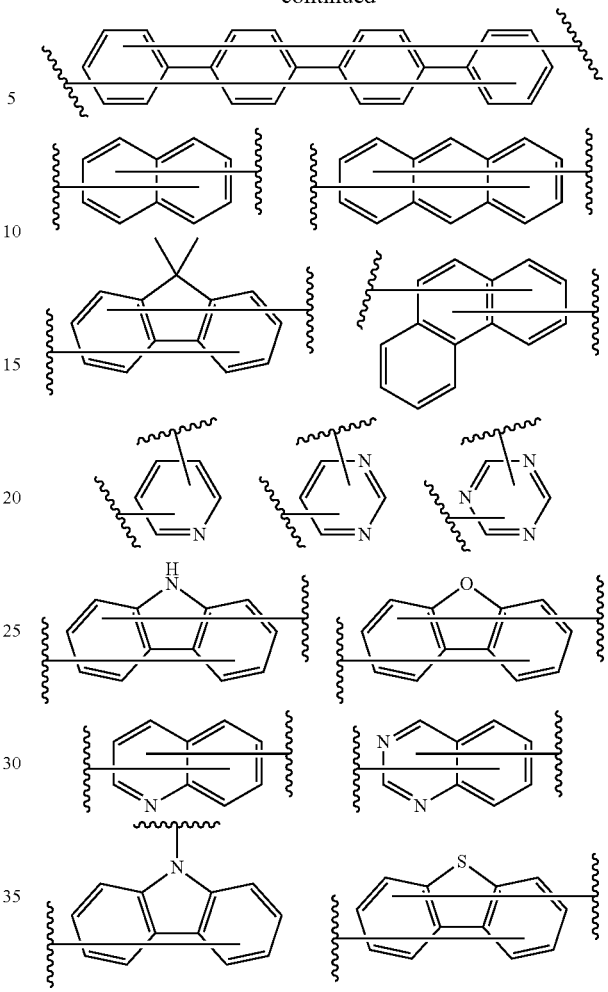

The structures may be unsubstituted or substituted with one or more substituents selected from the group consisting of deuterium; a halogen group; a nitrile group; a nitro group; a hydroxyl group; a carbonyl group; an ester group; an imide group; an amine group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylheteroarylamine group; an arylphosphine group; or a heterocyclic group.

In one embodiment of the present disclosure, L, $L_1$ and $L_2$ are the same as or different from each other, and each independently a direct bond; phenylene; biphenylene; naphthylene; dimethylfluorenylene; pyridinylene unsubstituted or substituted with a phenyl group; pyrimidinylene unsubstituted or substituted with a phenyl group; triazinylene unsubstituted or substituted with a phenyl group; quinolylene unsubstituted or substituted with a phenyl group; quinazolylene unsubstituted or substituted with a phenyl group; dibenzothiophenylene; dibenzofuranylene; or carbazolylene unsubstituted or substituted with a phenyl group.

In one embodiment of the present disclosure, $Ar_1$ and $Ar_2$ are the same as or different from each other, and each independently hydrogen; deuterium; a halogen group; a nitrile group; a nitro group; a hydroxyl group; a carbonyl group; an ester group; an imide group; an amino group; a substituted or unsubstituted silyl group; a substituted or unsubstituted boron group; a substituted or unsubstituted alkyl group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylphosphine group; a substituted or unsubstituted phosphine oxide group; a substituted or unsubstituted aryl group; or a substituted or unsubstituted heterocyclic group.

In one embodiment of the present disclosure, $Ar_1$ and $Ar_2$ are the same as or different from each other, and each independently selected from the group consisting of hydrogen; deuterium; a monocyclic or multicyclic substituted or unsubstituted aryl group having 6 to 60 carbon atoms; a monocyclic or multicyclic substituted or unsubstituted arylamine group having 6 to 60 carbon atoms; and a monocyclic or multicyclic substituted or unsubstituted heteroring having 1 to 60 carbon atoms.

In one embodiment of the present disclosure, $Ar_1$ and $Ar_2$ are the same as or different from each other, and each independently hydrogen; deuterium; a monocyclic or multicyclic substituted or unsubstituted aryl group having 6 to 30 carbon atoms; a primary, secondary or tertiary substituted or unsubstituted arylamine group having 6 to 30 carbon atoms; or a substituted or unsubstituted heterocyclic group having 1 to 30 carbon atoms.

In one embodiment of the present disclosure, $Ar_1$ and $Ar_2$ are the same as or different from each other, and may be each independently hydrogen; deuterium; aryl such as phenyl, biphenyl, terphenyl, quaterphenyl, naphthyl, anthracenyl, phenanthrenyl or fluorenyl; arylamine such as diphenylamine, phenylbiphenylamine, dibiphenylamine, phenylnaphthylamine, phenylphenanthreneamine, triphenylamine, dinaphthylamine, biphenylnaphthylamine, N-phenylfluoreneamine; or a heteroring such as pyridyl, pyrrole, pyridyl, pyridazinyl, furanyl, thiophene, imidazole, pyrazole, oxazole, isoxazole, triazole, isothiazole, triazole, pyrazinyl, triazine, a quinolinyl group, isoquinolinyl, quinazolinyl, quinoxalinyl, naphthyridinyl, an acridly group, a xanthenyl group, phenanthridinyl, diazanaphthalenyl, triazaindenyl, indole, indolinyl, indolizinyl, phthalazinyl, pyridopyrimidinyl, pyridopyrazinyl, pyrazinopyrazinyl, carbazole, benzothiophene, benzofuranyl, benzimidazole, benzothiazole, benzoxazole, benzocarbazole, dibenzothiophene, dibenzofuranyl, dibenzocarbazole, indolocarbazole, indenocarbazole, phenanthroline, phenazinyl, phenoxazinyl, phenothiazinyl, imidazopyridinyl, imidazophenanthridine, benzimidazoquinazolinyl or benzimidazophenanthridinyl, and these may be unsubstituted or substituted with one or more substituents selected from the group consisting of deuterium; a halogen group; a nitrile group; a nitro group; a hydroxyl group; a carbonyl group; an ester group; an imide group; an amine group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylheteroarylamine group; an arylphosphine group; and a heterocyclic group.

According to one embodiment of the present specification, $Ar_1$ and $Ar_2$ are the same as or different from each other, and each independently hydrogen, deuterium or any one selected from among the following structures.

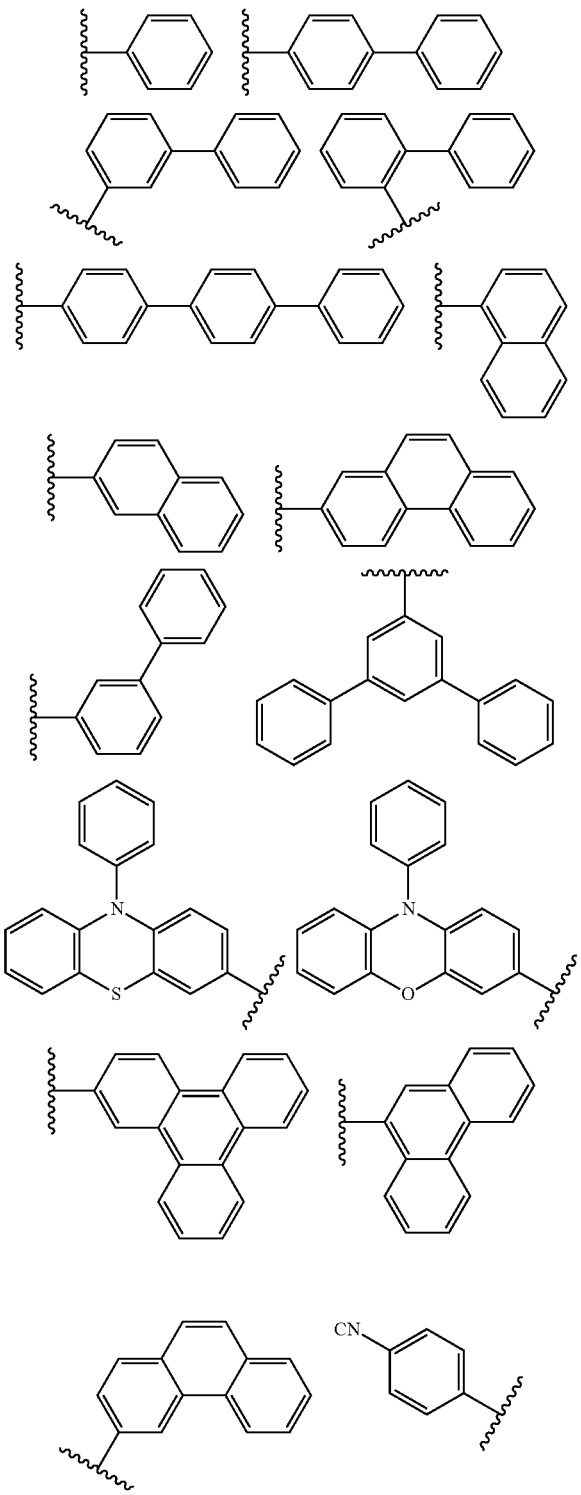

-continued
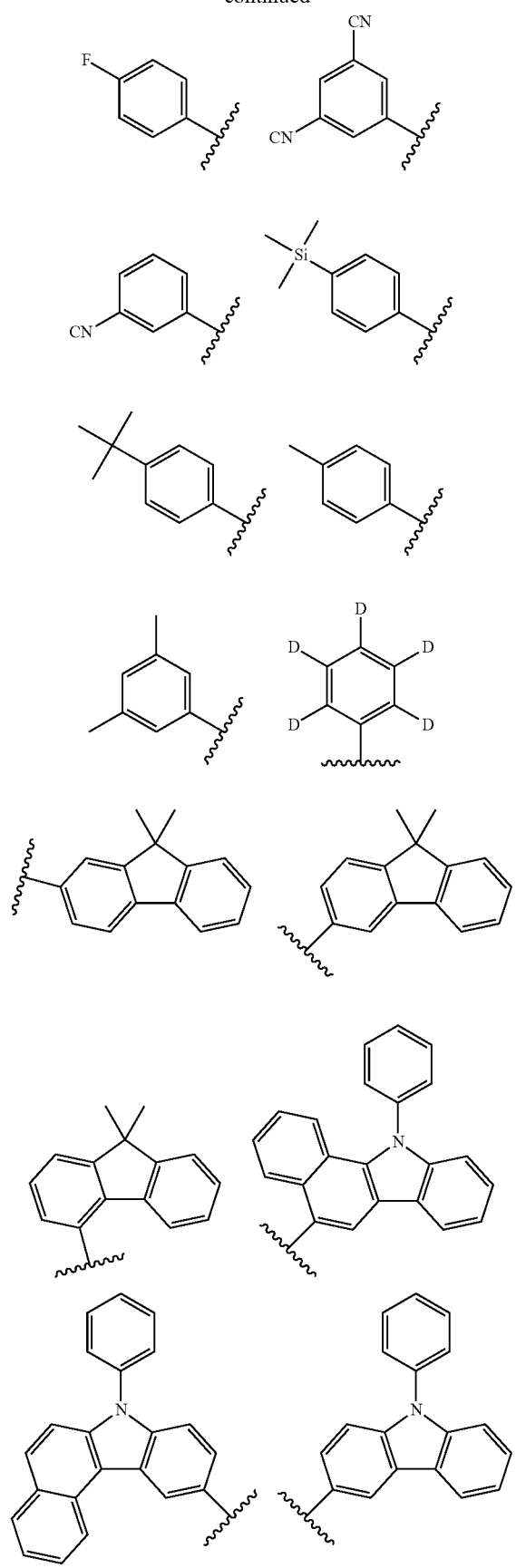
-continued
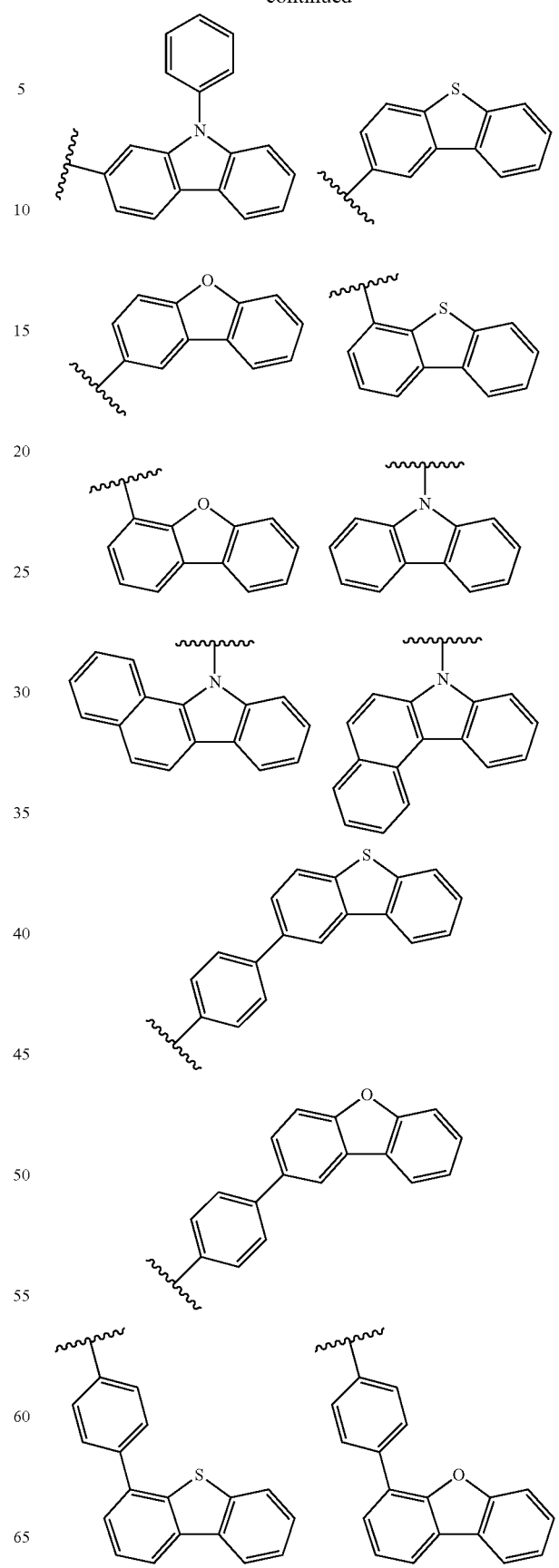

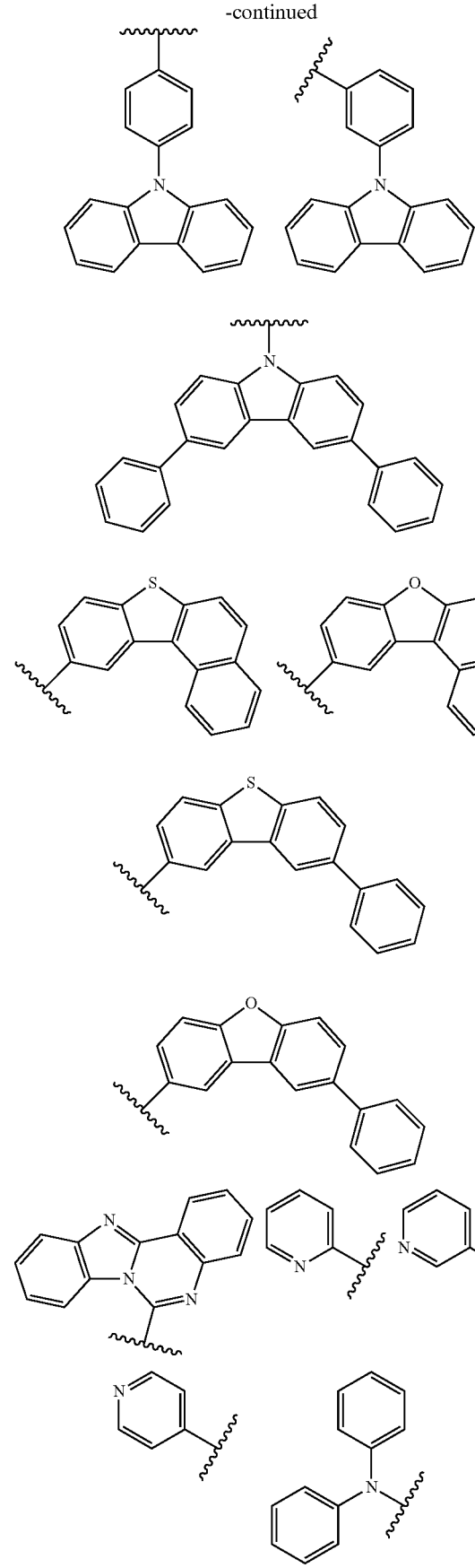
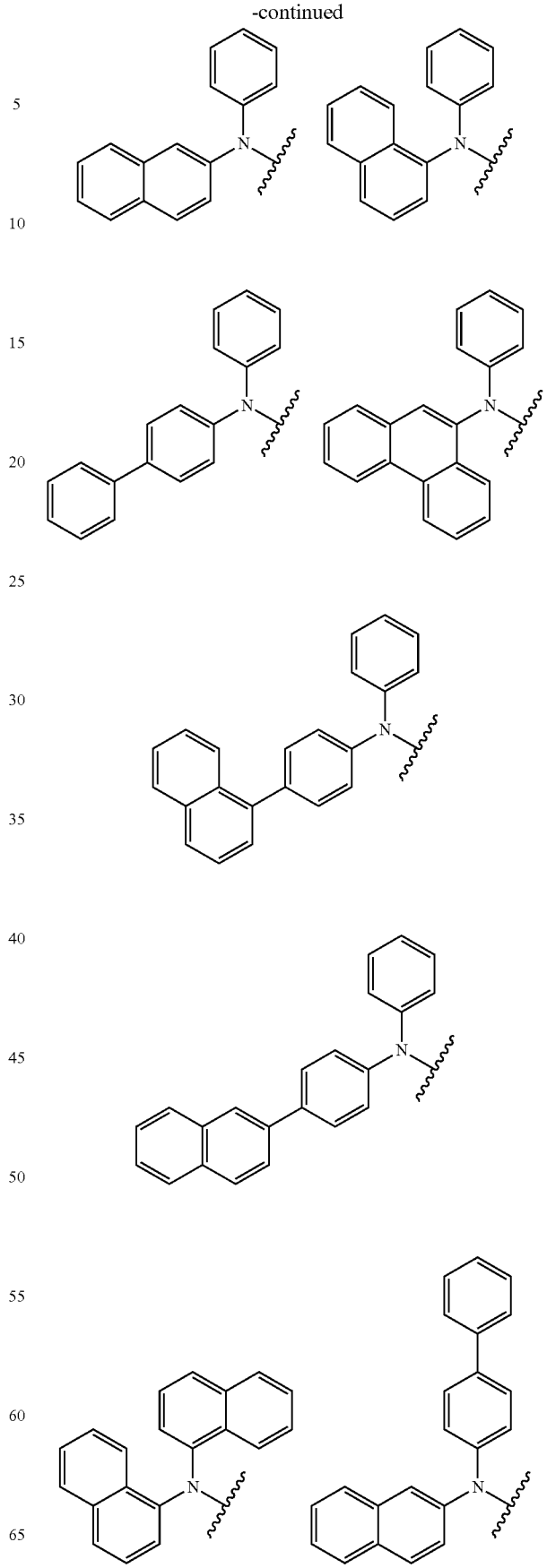

27
-continued
28
-continued
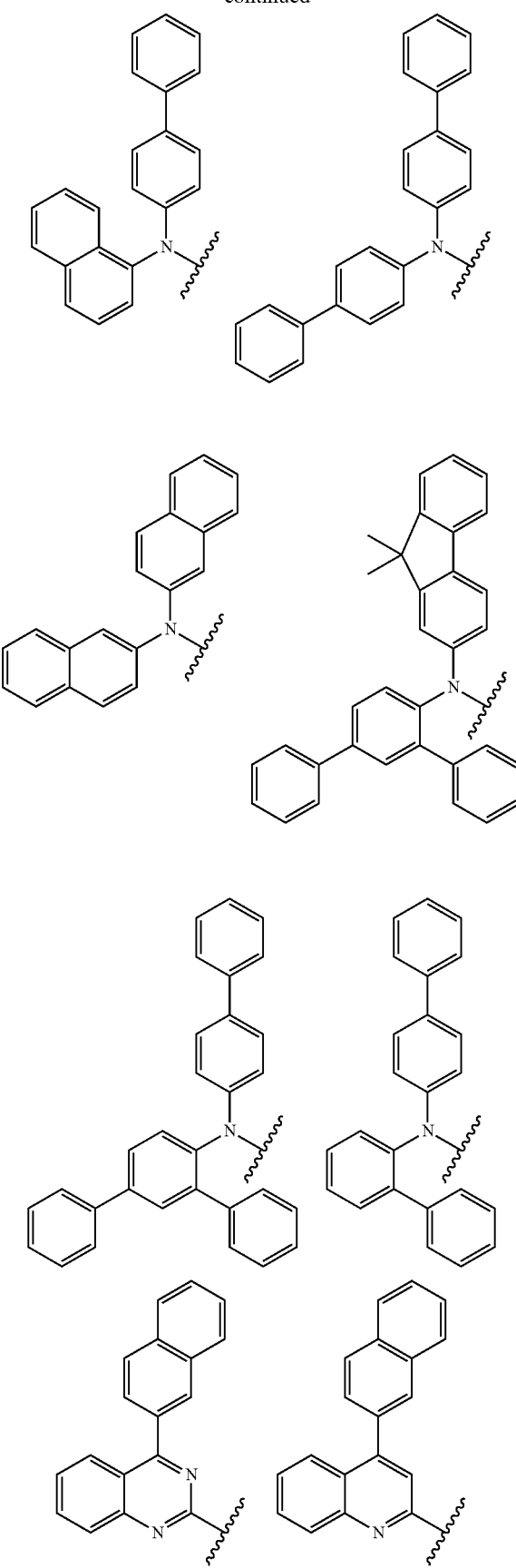

-continued
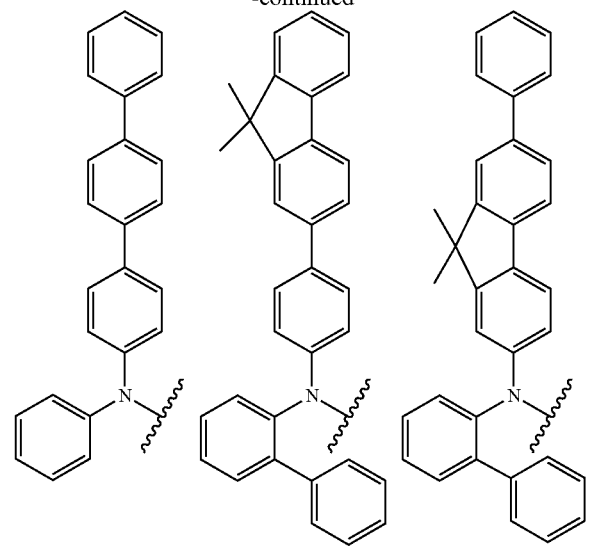
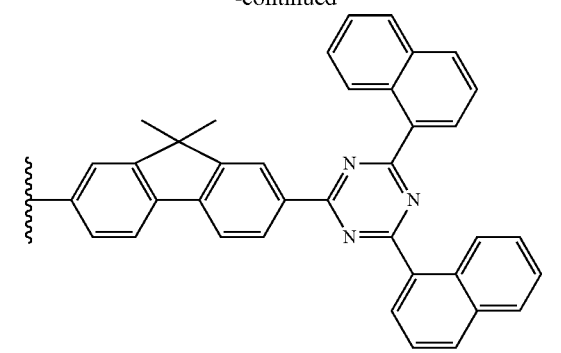
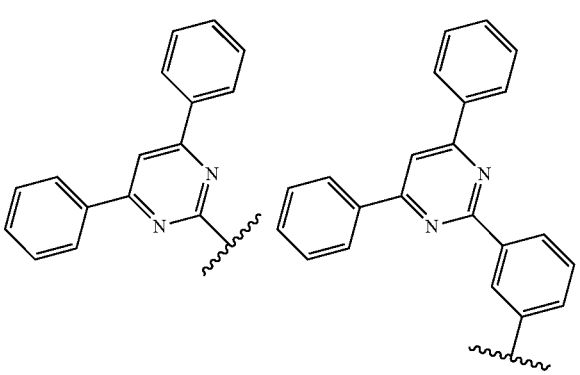
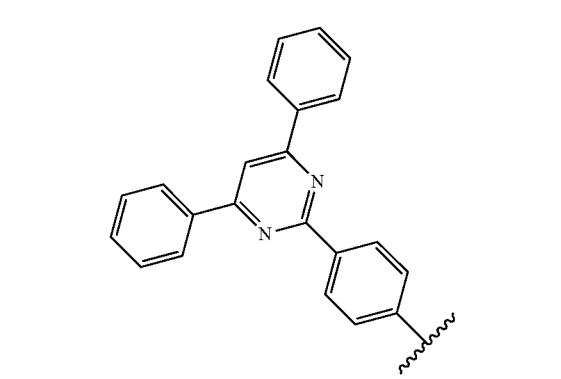
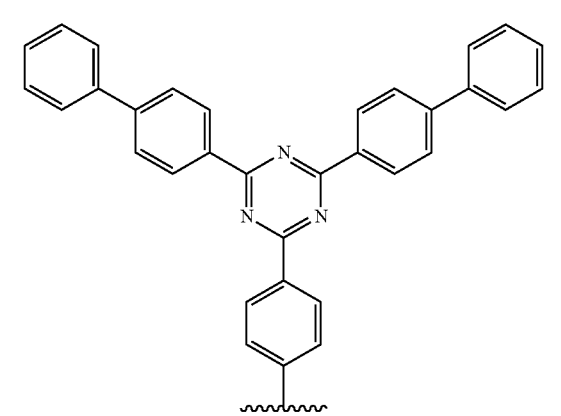

31
-continued
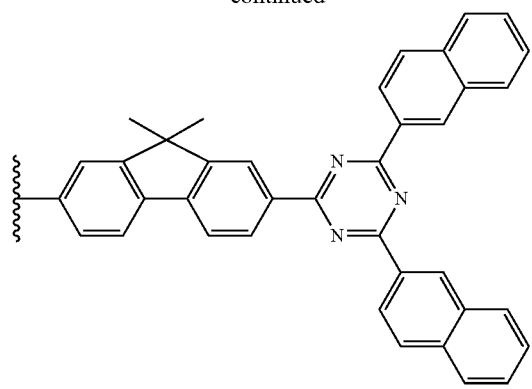
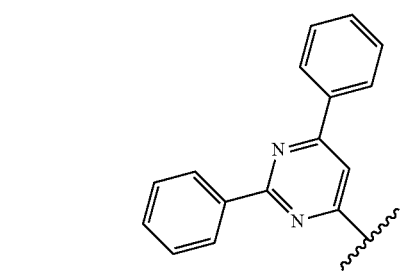
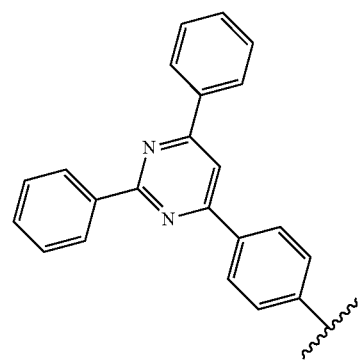
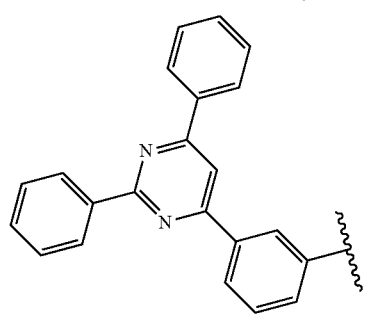
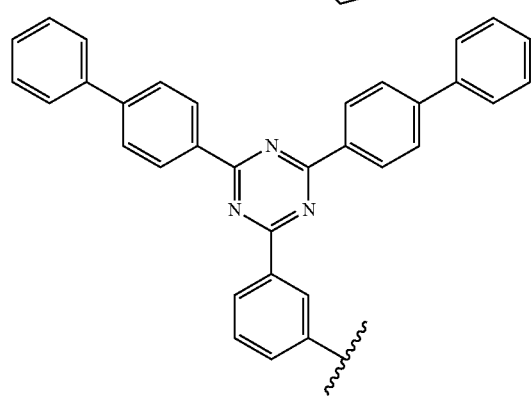
32
-continued
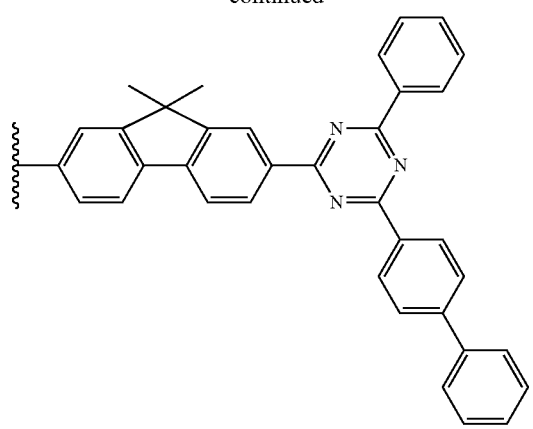
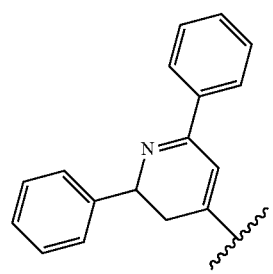
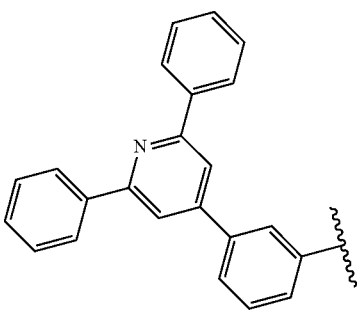
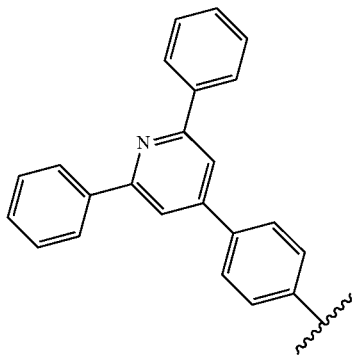

33
-continued
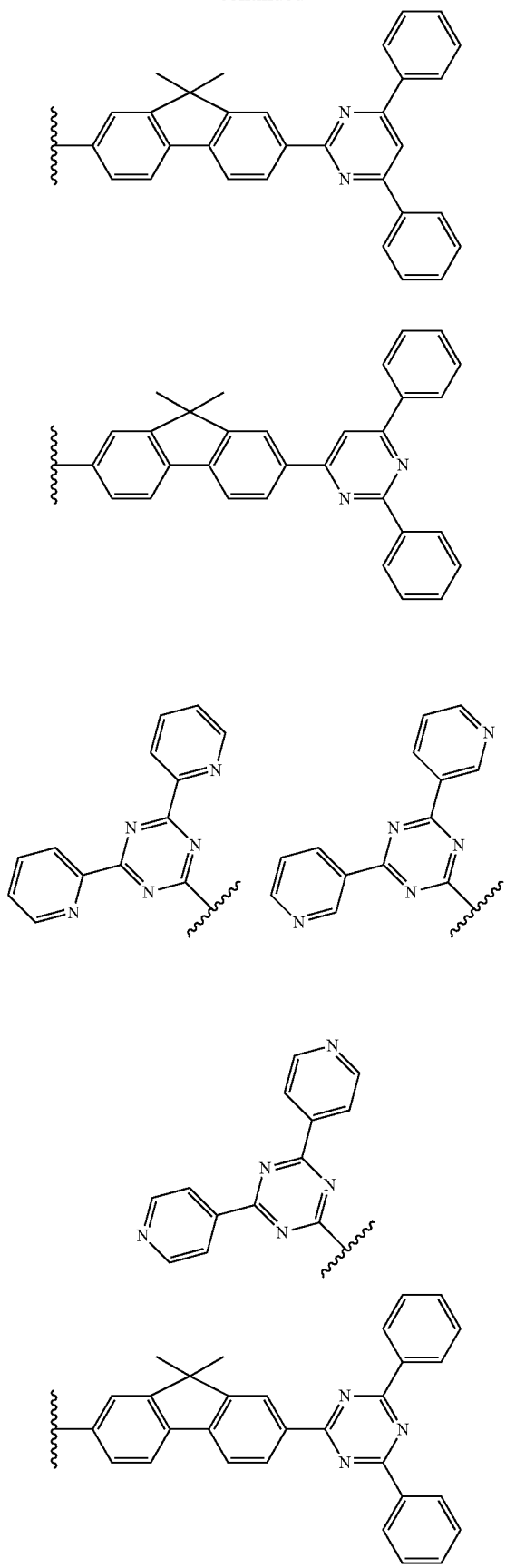
34
-continued
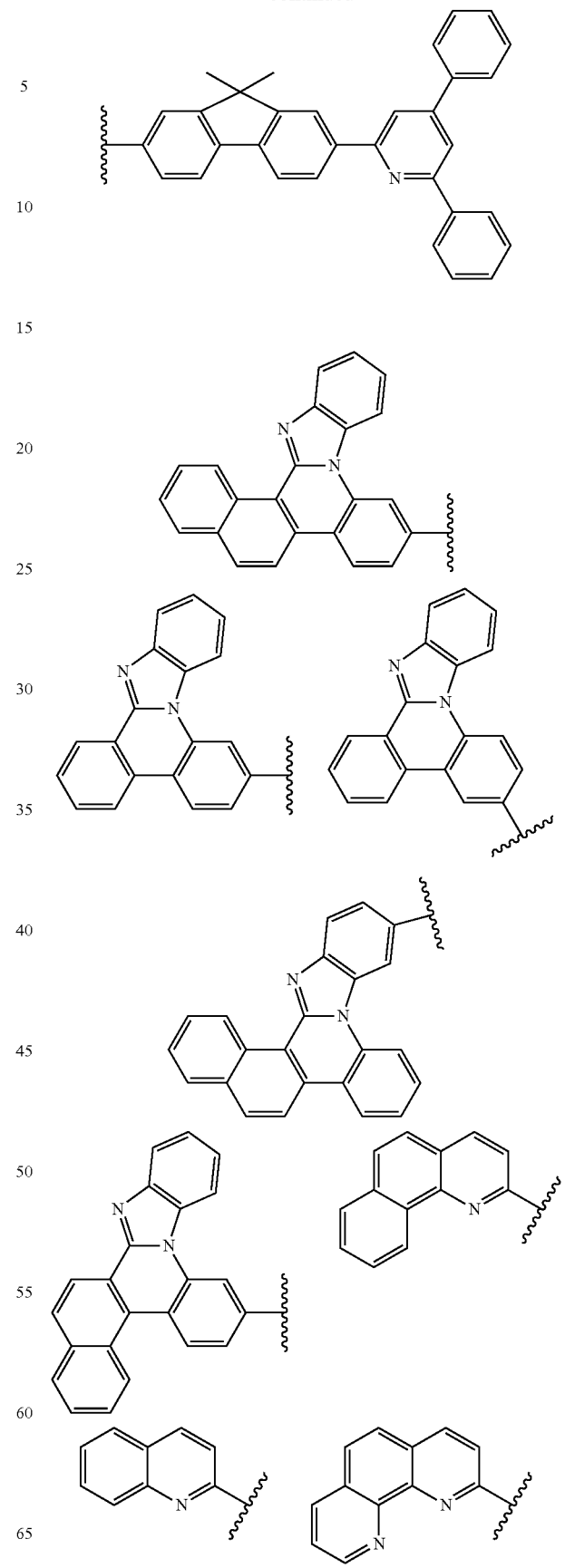

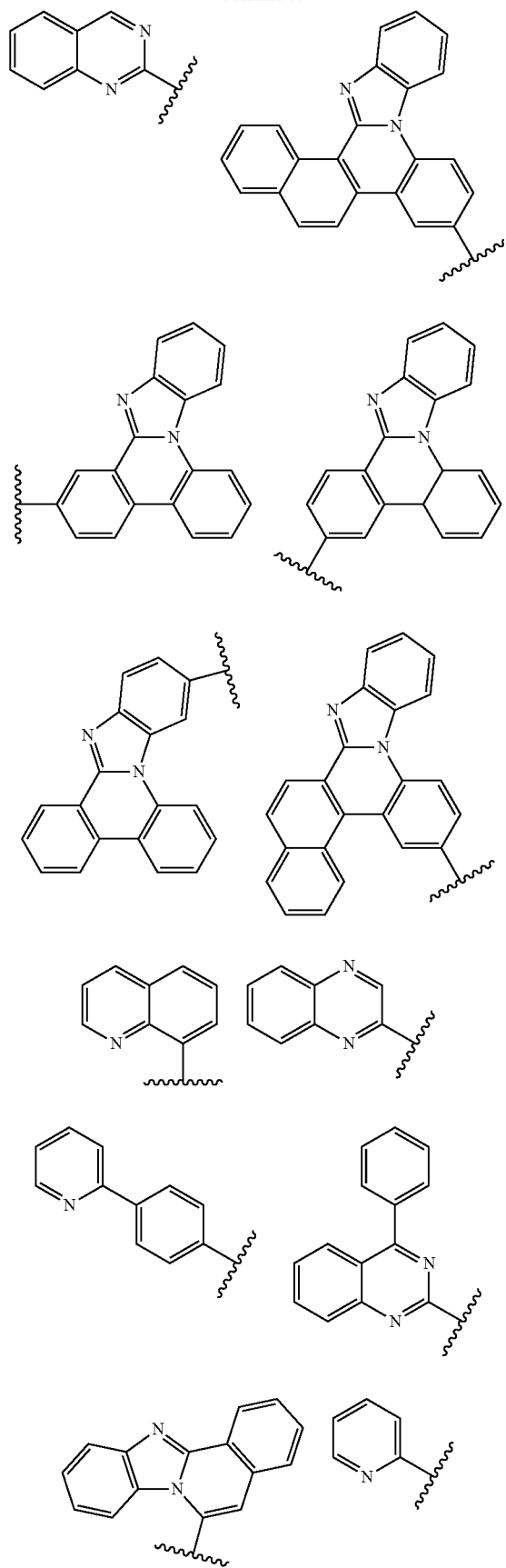
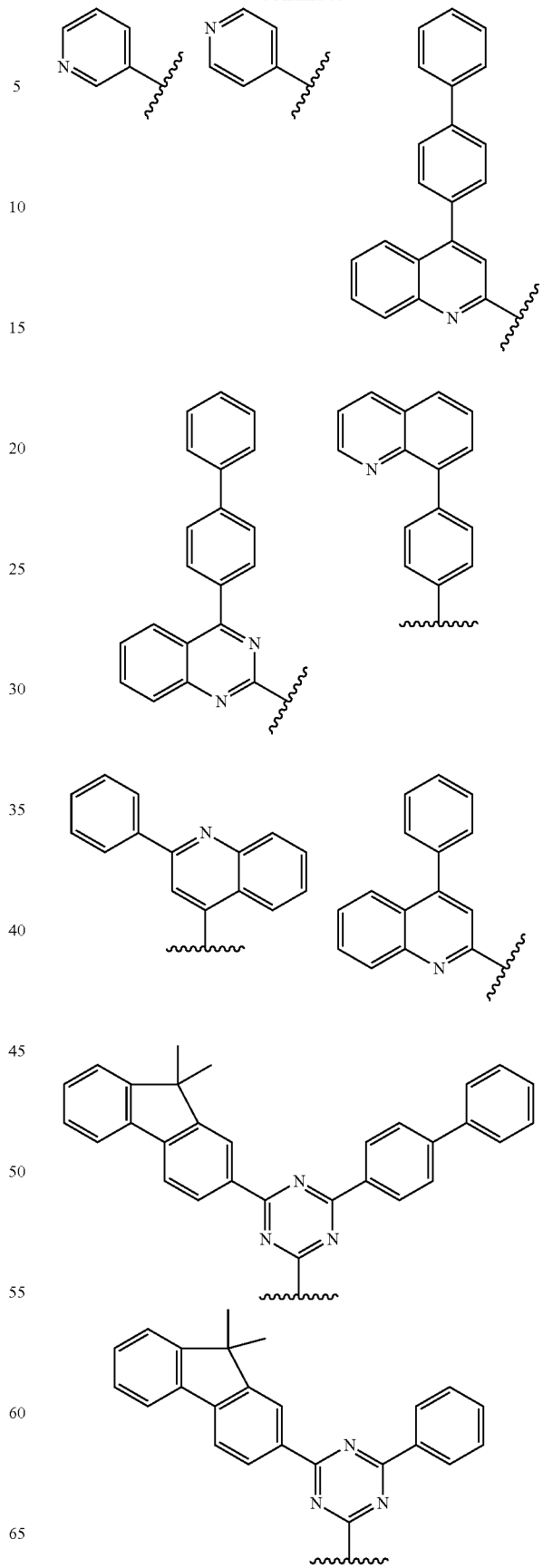

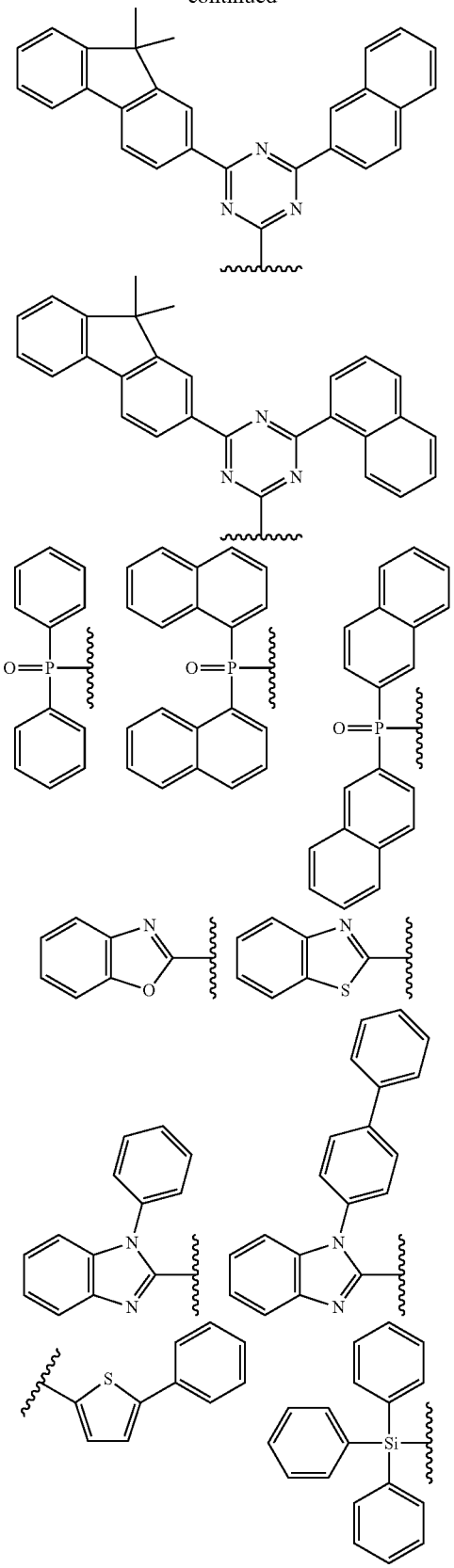

These structures may be unsubstituted or substituted with one or more substituents selected from the group consisting of deuterium; a halogen group; a nitrile group; a nitro group; a hydroxyl group; a carbonyl group; an ester group; an imide group; an amine group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylheteroarylamine group; an arylphosphine group; or a heterocyclic group.

More specifically, $Ar_1$ and $Ar_2$ are the same as or different from each other, and each independently hydrogen; deuterium; a substituted or unsubstituted phenyl group; a substituted or unsubstituted biphenyl group; a substituted or unsubstituted terphenyl group; a substituted or unsubstituted naphthyl group; a substituted or unsubstituted phenanthrenyl group; a substituted or unsubstituted fluorenyl group; a substituted or unsubstituted diphenylamine group; a substituted or unsubstituted triphenylamine group; a substituted or unsubstituted carbazole group; a substituted or unsubstituted benzocarbazole group; a substituted or unsubstituted dibenzothiophene group; a substituted or unsubstituted dibenzofuran group; a substituted or unsubstituted dibenzocarbazole group; a substituted or unsubstituted indolocarbazole group; a substituted or unsubstituted indenocarbazole group; a substituted or unsubstituted imidazopyridinyl group, a substituted or unsubstituted imidazophenanthridine group; a substituted or unsubstituted benzimidazoquinazolinyl group; or substituted or unsubstituted benzimidazophenanthridinyl.

In another embodiment, $Ar_1$ and $Ar_2$ are the same as or different from each other, and each independently hydrogen; deuterium; a substituted or unsubstituted phenyl group; a substituted or unsubstituted biphenyl group; a substituted or unsubstituted naphthyl group; a substituted or unsubstituted fluorenyl group; a substituted or unsubstituted diphenylamine group; a substituted or unsubstituted triphenylamine group; a substituted or unsubstituted pyridyl group; a substituted or unsubstituted pyrimidinyl group; a substituted or unsubstituted triazinyl group; a substituted or unsubstituted quinazoline group; a substituted or unsubstituted dibenzothiophene group; a substituted or unsubstituted dibenzofuranyl group; or a substituted or unsubstituted carbazole group.

In one embodiment of the present disclosure, $Ar_1$ and $Ar_2$ are the same as or different from each other, and each independently hydrogen; deuterium; a phenyl group unsubstituted or substituted with one or more types of substituents selected from the group consisting of a halogen group, a nitro group, a methyl group and phenyl group; a biphenyl group; a naphthyl group; a dimethylfluorenyl group; a diphenylamine group; a triphenylamine group; a pyridinyl group unsubstituted or substituted with a phenyl group; a pyrimidinyl group unsubstituted or substituted with a phenyl group; a triazinyl group unsubstituted or substituted with a phenyl group; a quinazoline group unsubstituted or substituted with a phenyl group; a dibenzothiophene group; a dibenzofuranyl group; or a carbazole group unsubstituted or substituted with a phenyl group.

According to one embodiment of the present disclosure, $R_{1a}$ to $R_{6a}$ and $R_{1b}$ to $R_{4b}$ are the same as or different from each other, and each independently selected from the group consisting of hydrogen, deuterium, halogen, linear or branched substituted or unsubstituted alkyl having 1 to 60 carbon atoms, linear or branched substituted or unsubstituted alkenyl having 2 to 60 carbon atoms, linear or branched substituted or unsubstituted alkynyl having 2 to 60 carbon atoms, monocyclic or multicyclic substituted or unsubstituted cycloalkyl having 3 to 60 carbon atoms, monocyclic or multicyclic substituted or unsubstituted heterocycloalkyl having 1 to 60 carbon atoms, monocyclic or multicyclic substituted or unsubstituted aryl having 6 to 60 carbon atoms, and a monocyclic or multicyclic substituted or unsubstituted heteroring having 1 to 60 carbon atoms.

According to one embodiment of the present disclosure, $R_{1a}$ to $R_{6a}$ and $R_{1b}$ to $R_{4b}$ are the same as or different from each other, and each independently selected from the group consisting of hydrogen, deuterium, monocyclic or multicyclic substituted or unsubstituted aryl having 6 to 30 carbon atoms and a monocyclic or multicyclic substituted or unsubstituted heteroring having 1 to 30 carbon atoms.

According to one embodiment of the present disclosure, $R_{1a}$ to $R_{6a}$ and $R_{1b}$ to $R_{4b}$ are the same as or different from each other, and may be each independently hydrogen; deuterium; an aryl group such as a phenyl group, a biphenyl group, a terphenyl group, a naphthyl group, an anthracenyl group, a phenanthryl group, a pyrenyl group, a perylenyl group, a chrysenyl group or a fluorenyl group; or a heterocyclic group such as a pyridyl group, a pyrrole group, a pyrimidyl group, a pyridazinyl group, a furanyl group, a thiophenyl group, an imidazole group, a pyrazole group, an oxazole group, an isoxazole group, a triazole group, an isothiazole group, a triazole group, an oxadiazole group, a thiadiazole group, a dithiazole group, a tetrazole group, a pyranyl group, a thiopyranyl group, a pyrazinyl group, an oxazinyl group, a triazinyl group, a dioxynyl group, a triazinyl group, a tetrazinyl group, a quinolinyl group, an isoquinolinyl group, a quinolyl group, a quinazolinyl group, a quinoxalinyl group, a naphthyridinyl group, an acridyl group, a xanthenyl group, a phenanthridinyl group, a diazanaphthalenyl group, a triazaindenyl group, an indole group, an indolinyl group, an indolizinyl group, a phthalazinyl group, a pyridopyrimidinyl group, a pyridopyrazinyl group, a pyrazinopyrazinyl group, a benzothiazole group, a benzoxazole group, a benzimidazole group, a benzothiophene group, a benzofuranyl group, a dibenzothiophenyl group, a dibenzofuranyl group, a carbazole group, a benzocarbazole group, a dibenzocarbazole group, an indolocarbazole group, an indenocarbazole group, a phenazinyl group, an imidazopyridine group, a phenoxazinyl group, a phenanthridine group, a phenanthroline group, a phenothiazine group, an imidazopyridine group, an imidazophenanthridine group, a benzimidazoquinazoline group or a benzimidazophenanthridine group, and these may be further substituted.

According to one embodiment of the present disclosure, $R_{1a}$ to $R_{6a}$ and $R_{1b}$ to $R_{4b}$ are hydrogen.

According to one embodiment of the present disclosure, $R_{1a}$ to $R_{6a}$ and $R_{1b}$ to $R_{4b}$ may bond to adjacent groups to form a substituted or unsubstituted ring.

According to one embodiment of the present disclosure, $R_{1a}$ to $R_{6a}$ and $R_{1b}$ to $R_{4b}$ may bond to adjacent groups to form a substituted or unsubstituted aliphatic or aromatic hydrocarbon ring; or a substituted or unsubstituted aliphatic or aromatic heteroring.

According to one embodiment of the present disclosure, the ring formed by $R_{1a}$ to $R_{6a}$ and $R_{1b}$ to $R_{4b}$ bonding to adjacent groups may be an aromatic hydrocarbon ring such as benzene, naphthalene, anthracene, phenanthrene, perylene, fluoranthene, triphenylene, phenalene, pyrene, tetracene, chrysene, pentacene, fluorene, indene, acenaphthylene, benzofluorene or spirofluorene; or a heteroring such as pyridine, pyrrole, pyrimidine, pyridazine, furan, thiophene, imidazole, pyrazole, oxazole, isoxazole, triazole, isothiazole, triazole, oxadiazole, thiadiazole, dithiazole, tetrazole, pyran, thiopyran, diazine, oxazine, triazine, dioxin, triazine, tetrazine, isoquinoline, quinoline, quinol, quinazoline, quinoxaline, naphthyridine, acridine, phenanthridine, diazanaphthalene, triazaindene, indole, indolizine, benzothiazole, benzoxazole, benzimidazole, benzothiophene, benzofuran, dibenzothiophene, dibenzofuran, carbazole, benzocarbazole, dibenzocarbazole, phenazine, imidazopyridine, phenoxazine, phenanthridine, indolocarbazole or indenocarbazole, and these may be further substituted.

More specifically, the ring formed by $R_{1a}$ to $R_{6a}$ and $R_{1b}$ to $R_{4b}$ bonding to adjacent groups may be substituted or unsubstituted benzene, substituted or unsubstituted naphthalene, substituted or unsubstituted anthracene, substituted or unsubstituted phenanthrene, substituted or unsubstituted fluorene, substituted or unsubstituted pyridine, substituted or unsubstituted pyrimidine; substituted or unsubstituted triazine; substituted or unsubstituted quinoline;

substituted or unsubstituted quinoxaline; substituted or unsubstituted quinazoline; substituted or unsubstituted phenanthridine; substituted or unsubstituted dibenzothiophene; substituted or unsubstituted dibenzofuran; or substituted or unsubstituted carbazole.

According to one embodiment of the present disclosure, $R_{1a}$ to $R_{6a}$ and $R_{1b}$ to $R_{4b}$ may bond to adjacent groups to form a benzene ring, and the benzene ring may be unsubstituted or substituted with one or more substituents selected from the group consisting of deuterium; a halogen group; a nitrile group; a nitro group; a hydroxyl group; a carbonyl group; an ester group; an imide group; an amine group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylheteroarylamine group; an arylphosphine group; and a heterocyclic group.

According to one embodiment of the present disclosure, $R_{1a}$ to $R_{6a}$ and $R_{1b}$ to $R_{4b}$ bond to adjacent groups to form a benzene ring.

According to one embodiment of the present disclosure, at least one of $R_1$ to $R_{16}$ bonds to adjacent groups to form the ring structure of Chemical Formula 1-1.

According to one embodiment of the present disclosure, $R_1$ and $R_2$ bond to adjacent groups to form the ring structure of Chemical Formula 1-1.

According to one embodiment of the present disclosure, $R_2$ and $R_3$ bond to adjacent groups to form the ring structure of Chemical Formula 1-1.

According to one embodiment of the present disclosure, $R_4$ and $R_5$ bond to adjacent groups to form the ring structure of Chemical Formula 1-1.

According to one embodiment of the present disclosure, $R_6$ and $R_7$ bond to adjacent groups to form the ring structure of Chemical Formula 1-1.

According to one embodiment of the present disclosure, $R_7$ and $R_8$ bond to adjacent groups to form the ring structure of Chemical Formula 1-1.

According to one embodiment of the present disclosure, $R_9$ and $R_{10}$ bond to adjacent groups to form the ring structure of Chemical Formula 1-1.

According to one embodiment of the present disclosure, $R_{10}$ and $R_{11}$ bond to adjacent groups to form the ring structure of Chemical Formula 1-1.

According to one embodiment of the present disclosure, $R_{12}$ and $R_{13}$ bond to adjacent groups to form the ring structure of Chemical Formula 1-1.

According to one embodiment of the present disclosure, $R_{14}$ and $R_{15}$ bond to adjacent groups to form the ring structure of Chemical Formula 1-1.

According to one embodiment of the present disclosure, $R_{15}$ and $R_{16}$ bond to adjacent groups to form the ring structure of Chemical Formula 1-1.

According to one embodiment of the present disclosure, groups that do not form the ring of Chemical Formula 1-1 among $R_1$ to $R_{16}$ may be each independently selected from the group consisting of hydrogen; deuterium; a halogen group; a nitrile group; a nitro group; a hydroxyl group; a carbonyl group; an ester group; an imide group; an amino group; a substituted or unsubstituted silyl group; a substituted or unsubstituted boron group; a substituted or unsubstituted alkyl group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group;

a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylphosphine group; a substituted or unsubstituted phosphine oxide group; a substituted or unsubstituted aryl group; or a substituted or unsubstituted heterocyclic group.

According to one embodiment of the present disclosure, groups that do not form the ring of Chemical Formula 1-1 among $R_1$ to $R_{16}$ may be each independently selected from the group consisting of hydrogen; deuterium; a halogen group; a nitrile group; a nitro group; a hydroxyl group; a substituted or unsubstituted silyl group; a substituted or unsubstituted boron group; a substituted or unsubstituted alkyl group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylphosphine group; a substituted or unsubstituted aryl group; or a substituted or unsubstituted heterocyclic group having 15 to 60 ring members.

According to one embodiment of the present disclosure, groups that do not form the ring of Chemical Formula 1-1 among $R_1$ to $R_{16}$ are the same as or different from each other, and may be each independently selected from the group consisting of hydrogen, deuterium, halogen, linear or branched substituted or unsubstituted alkyl having 1 to 60 carbon atoms, linear or branched substituted or unsubstituted alkenyl having 2 to 60 carbon atoms, linear or branched substituted or unsubstituted alkynyl having 2 to 60 carbon atoms, monocyclic or multicyclic substituted or unsubstituted cycloalkyl having 3 to 60 carbon atoms, monocyclic or multicyclic substituted or unsubstituted heterocycloalkyl having 1 to 60 carbon atoms, monocyclic or multicyclic substituted or unsubstituted aryl having 6 to 60 carbon atoms, and a monocyclic or multicyclic substituted or unsubstituted heteroring having 1 to 60 carbon atoms.

According to one embodiment of the present disclosure, groups that do not form the ring of Chemical Formula 1-1 among $R_1$ to $R_{16}$ are the same as or different from each other, and may be each independently selected from the group consisting of hydrogen, deuterium, monocyclic or multicyclic substituted or unsubstituted aryl having 6 to 60 carbon atoms and a monocyclic or multicyclic substituted or unsubstituted heteroring having 1 to 60 carbon atoms.

According to one embodiment of the present disclosure, groups that do not form the ring of Chemical Formula 1-1 among $R_1$ to $R_{16}$ are the same as or different from each other, and may be each independently hydrogen; deuterium; an aryl group such as phenyl, biphenyl, terphenyl, quaterphenyl, naphthyl, anthracenyl, phenanthrenyl, fluorenyl, pyridinyl, phenanthridinyl, dibenzothiophene, carbazolyl or phenanthrolinyl; or a heterocyclic group such as pyridyl, pyrrole, pyridyl, pyridazinyl, furanyl, thiophene, imidazole, pyrazole, oxazole, isoxazole, triazole, isothiazole, triazole, pyrazinyl, triazine, a quinolinyl group, isoquinolinyl, quinazolinyl, quinoxalinyl, naphthyridinyl, an acridly group, a xanthenyl group, phenanthridinyl, diazanaphthalenyl, triazaindenyl, indole, indolinyl, indolizinyl, phthalazinyl, pyridopyrimidinyl, pyridopyrazinyl, pyrazinopyrazinyl, carbazole, benzothiophene, benzofuranyl, benzimidazole, benzothiazole, benzoxazole, benzocarbazole, dibenzothiophene, dibenzofuranyl, dibenzocarbazole, indolocarbazole, indenocarbazole, phenanthroline, phenazinyl, phenoxazinyl, phenothiazinyl, imidazopyridinyl, imidazophenanthridine, benzimidazoquinazolinyl or benzimidazophenanthridinyl, and these may be further substituted.

According to one embodiment of the present disclosure, groups that do not form the ring of Chemical Formula 1-1 among $R_1$ to $R_{16}$ are the same as or different from each other, and may be each independently hydrogen, deuterium, a heterocyclic group having 15 to 60 ring members such as benzofluorenyl, benzophenanthrenyl, imidazophenanthrenyl, benzophenanthridinyl, imidazophenanthridinyl, benzocarbazole, dibenzocarbazole, indolocarbazole, benzoacridinyl, indoloacridinyl, benzimidazoquinazolinyl or benzimidazophenanthridinyl, and these may be further substituted.

According to one embodiment of the present disclosure, when L is a substituted or unsubstituted monocyclic arylene group or $Ar_1$ is a substituted or unsubstituted monocyclic aryl group in Chemical Formula 1, groups that do not form the ring of Chemical Formula 1-1 among $R_1$ to $R_{16}$ are hydrogen.

According to one embodiment of the present disclosure, when L is a substituted or unsubstituted phenylene group or $Ar_1$ is a substituted or unsubstituted phenyl group in Chemical Formula 1, groups that do not form the ring of Chemical Formula 1-1 among $R_1$ to $R_{16}$ are hydrogen.

According to one embodiment of the present disclosure, when L is a phenylene group or $Ar_1$ is a phenyl group in Chemical Formula 1, groups that do not form the ring of Chemical Formula 1-1 among $R_1$ to $R_{16}$ are hydrogen.

According to one embodiment of the present disclosure, when L is a phenylene group in Chemical Formula 1, groups that do not form the ring of Chemical Formula 1-1 among $R_1$ to $R_{16}$ are hydrogen.

According to one embodiment of the present disclosure, when $L_1$ is a substituted or unsubstituted monocyclic arylene group or $Ar_1$ is a substituted or unsubstituted monocyclic aryl group in Chemical Formula 2, 8 or 9, groups that do not form the ring of Chemical Formula 1-1 among $R_1$ to $R_{16}$ are hydrogen.

According to one embodiment of the present disclosure, when $L_1$ is a substituted or unsubstituted phenylene group or $Ar_1$ is a substituted or unsubstituted phenyl group in Chemical Formula 2, 8 or 9, groups that do not form the ring of Chemical Formula 1-1 among $R_1$ to $R_{16}$ are hydrogen.

According to one embodiment of the present disclosure, when $L_1$ is a phenylene group or $Ar_1$ is a phenyl group in Chemical Formula 2, 8 or 9, groups that do not form the ring of Chemical Formula 1-1 among $R_1$ to $R_{16}$ are hydrogen.

According to one embodiment of the present disclosure, when $L_1$ is a substituted or unsubstituted monocyclic arylene group or $Ar_1$ is a substituted or unsubstituted monocyclic aryl group in Chemical Formula 4, 10 or 11, groups that do not form the ring of Chemical Formula 1-1 among $R_1$ to $R_{16}$ are hydrogen.

According to one embodiment of the present disclosure, when $L_1$ is a substituted or unsubstituted phenylene group or $Ar_1$ is a substituted or unsubstituted phenyl group in Chemical Formula 4, 10 or 11, groups that do not form the ring of Chemical Formula 1-1 among $R_1$ to $R_{16}$ are hydrogen.

According to one embodiment of the present disclosure, when $L_1$ is a phenylene group or $Ar_1$ is a phenyl group in Chemical Formula 4, 10 or 11, groups that do not form the ring of Chemical Formula 1-1 among $R_1$ to $R_{16}$ are hydrogen. According to one embodiment of the present disclosure, when $L_1$ is a substituted or unsubstituted monocyclic arylene group or $Ar_1$ is a substituted or unsubstituted monocyclic aryl group in Chemical Formula 5, 12 or 13, groups that do not form the ring of Chemical Formula 1-1 among $R_1$ to $R_{16}$ are hydrogen. According to one embodiment of the present disclosure, when $L_1$ is a substituted or unsubstituted phenylene group or $Ar_1$ is a substituted or unsubstituted phenyl group in Chemical Formula 5, 12 or 13, groups that do not form the ring of Chemical Formula 1-1 among $R_1$ to $R_{16}$ are hydrogen.

According to one embodiment of the present disclosure, when $L_1$ is a phenylene group or $Ar_1$ is a phenyl group in Chemical Formula 5, 12 or 13, groups that do not form the ring of Chemical Formula 1-1 among $R_1$ to $R_{16}$ are hydrogen.

According to one embodiment of the present disclosure, when $L_1$ is a substituted or unsubstituted monocyclic arylene group or $Ar_1$ is a substituted or unsubstituted monocyclic aryl group in Chemical Formula 6, 14 or 15, groups that do not form the ring of Chemical Formula 1-1 among $R_1$ to $R_{16}$ are hydrogen.

According to one embodiment of the present disclosure, when $L_1$ is a substituted or unsubstituted phenylene group or $Ar_1$ is a substituted or unsubstituted phenyl group in Chemical Formula 6, 14 or 15, groups that do not form the ring of Chemical Formula 1-1 among $R_1$ to $R_{16}$ are hydrogen.

According to one embodiment of the present disclosure, when $L_1$ is a phenylene group or $Ar_1$ is a phenyl group in Chemical Formula 6, 14 or 15, groups that do not form the ring of Chemical Formula 1-1 among $R_1$ to $R_{16}$ are hydrogen.

According to one embodiment of the present disclosure, when $L_1$ is a substituted or unsubstituted monocyclic arylene group or $Ar_1$ is a substituted or unsubstituted monocyclic aryl group in Chemical Formula 7, 16 or 17, groups that do not form the ring of Chemical Formula 1-1 among $R_1$ to $R_{16}$ are hydrogen.

According to one embodiment of the present disclosure, when $L_1$ is a substituted or unsubstituted phenylene group or $Ar_1$ is a substituted or unsubstituted phenyl group in Chemical Formula 7, 16 or 17, groups that do not form the ring of Chemical Formula 1-1 among $R_1$ to $R_{16}$ are hydrogen.

According to one embodiment of the present disclosure, when $L_1$ is a phenylene group or $Ar_1$ is a phenyl group in Chemical Formula 7, 16 or 17, groups that do not form the ring of Chemical Formula 1-1 among $R_1$ to $R_{16}$ are hydrogen.

According to one embodiment of the present disclosure, when $L_1$ and $L_2$ are different from each other and at least one of $L_1$ or $L_2$ is a substituted or unsubstituted monocyclic arylene group in Chemical Formula 3, groups that do not form the ring of Chemical Formula 1-1 among $R_1$ to $R_{16}$ are hydrogen.

According to one embodiment of the present disclosure, when $L_1$ and $L_2$ are different from each other and at least one of $L_1$ or $L_2$ is a substituted or unsubstituted phenylene group in Chemical Formula 3, groups that do not form the ring of Chemical Formula 1-1 among $R_1$ to $R_{16}$ are hydrogen.

According to one embodiment of the present disclosure, when $L_1$ and $L_2$ are different from each other and at least one of $L_1$ or $L_2$ is a phenylene group in Chemical Formula 3, groups that do not form the ring of Chemical Formula 1-1 among $R_1$ to $R_{16}$ are hydrogen.

According to one embodiment of the present disclosure, when $L_1$ and $L_2$ are the same as each other and $L_1$ and $L_2$ are a substituted or unsubstituted monocyclic arylene group in Chemical Formula 3, groups that do not form the ring of Chemical Formula 1-1 among $R_1$ to $R_{16}$ are hydrogen.

According to one embodiment of the present disclosure, when $L_1$ and $L_2$ are the same as each other and $L_1$ and $L_2$ are a substituted or unsubstituted phenylene group in Chemical Formula 3, groups that do not form the ring of Chemical Formula 1-1 among $R_1$ to $R_{16}$ are hydrogen.

According to one embodiment of the present disclosure, when $L_1$ and $L_2$ are the same as each other and $L_1$ and $L_2$ are a phenylene group in Chemical Formula 3, groups that do not form the ring of Chemical Formula 1-1 among $R_1$ to $R_{16}$ are hydrogen.

According to one embodiment of the present disclosure, when $Ar_1$ and $Ar_2$ are different from each other and at least one of $Ar_1$ or $Ar_2$ is a substituted or unsubstituted monocyclic aryl group in Chemical Formula 3, groups that do not form the ring of Chemical Formula 1-1 among $R_1$ to $R_{16}$ are hydrogen.

According to one embodiment of the present disclosure, when $Ar_1$ and $Ar_2$ are different from each other and at least one of $Ar_1$ or $Ar_2$ is a substituted or unsubstituted phenyl group in Chemical Formula 3, groups that do not form the ring of Chemical Formula 1-1 among $R_1$ to $R_{16}$ are hydrogen.

According to one embodiment of the present disclosure, when $Ar_1$ and $Ar_2$ are different from each other and at least one of $Ar_1$ or $Ar_2$ is a phenyl group in Chemical Formula 3, groups that do not form the ring of Chemical Formula 1-1 among $R_1$ to $R_{16}$ are hydrogen.

According to one embodiment of the present disclosure, when $Ar_1$ and $Ar_2$ are the same as each other and $Ar_1$ and $Ar_2$ are a substituted or unsubstituted monocyclic aryl group in Chemical Formula 3, groups that do not form the ring of Chemical Formula 1-1 among $R_1$ to $R_{16}$ are hydrogen.

According to one embodiment of the present disclosure, when $Ar_1$ and $Ar_2$ are the same as each other and $Ar_1$ and $Ar_2$ are a substituted or unsubstituted phenyl group in Chemical Formula 3, groups that do not form the ring of Chemical Formula 1-1 among $R_1$ to $R_{16}$ are hydrogen.

According to one embodiment of the present disclosure, when $Ar_1$ and $Ar_2$ are the same as each other and $Ar_1$ and $Ar_2$ are a phenyl group in Chemical Formula 3, groups that do not form the ring of Chemical Formula 1-1 among $R_1$ to $R_{16}$ are hydrogen.

According to one embodiment of the present disclosure, groups that do not form the ring of Chemical Formula 1-1 among $R_1$ to $R_{16}$ are hydrogen.
According to one embodiment of the present disclosure, $R_{1a}$ to $R_{6a}$, $R_{1b}$ to $R_{4b}$, and groups that do not form the ring of Chemical Formula 1-1 among $R_1$ to $R_{16}$ are hydrogen.
2-1
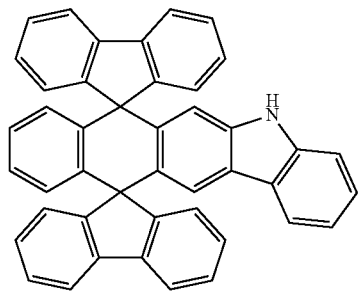
2-2
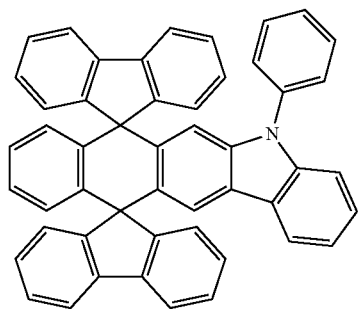
2-3
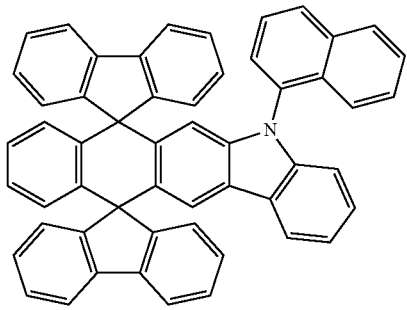
2-4
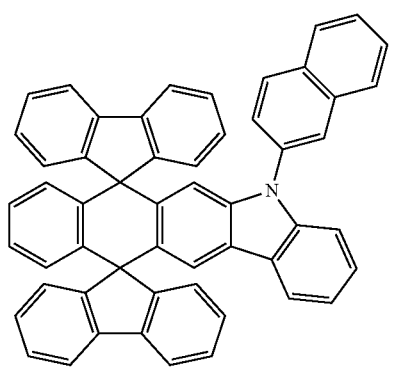
-continued
2-5
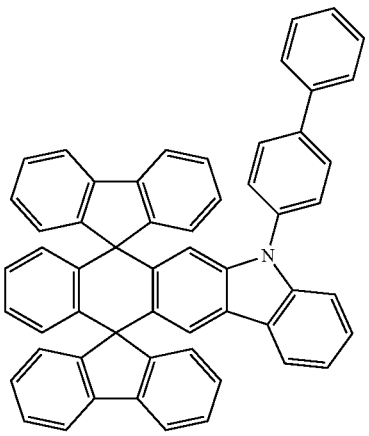
2-6
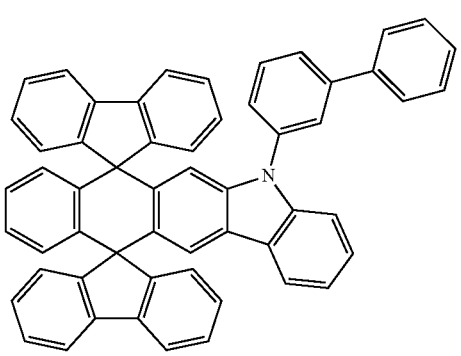
2-7
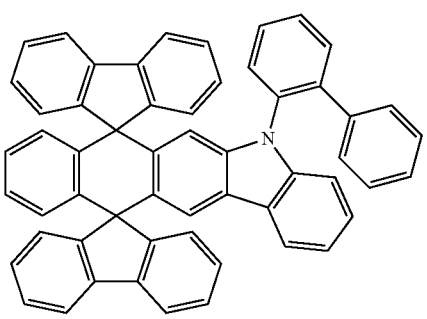
2-8
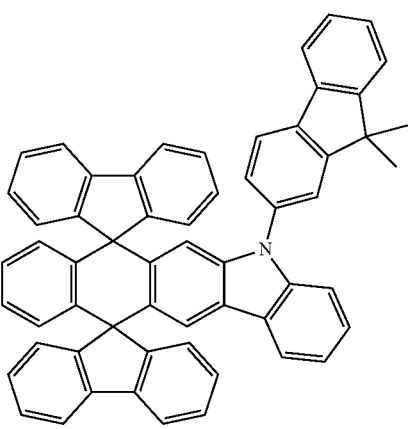

2-9
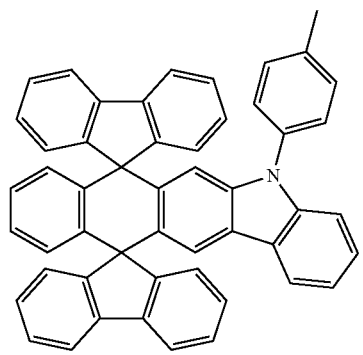
2-10
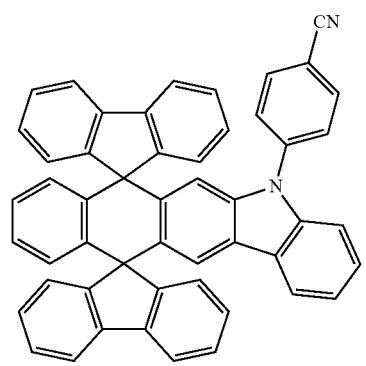
2-11
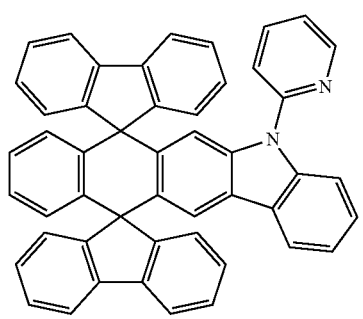
2-12
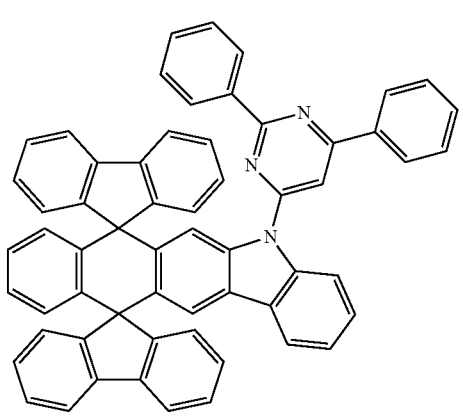
2-13
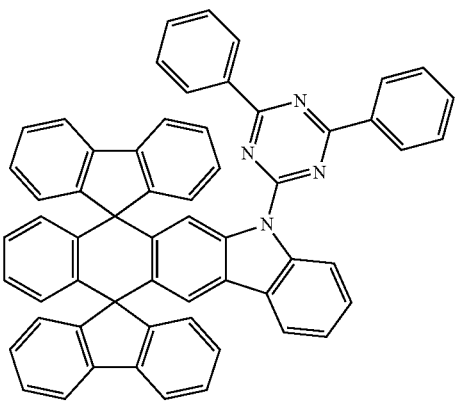
2-14
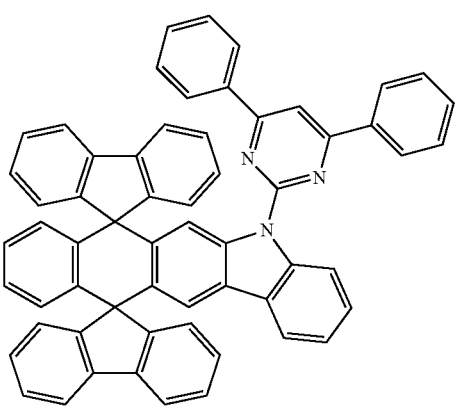
2-15
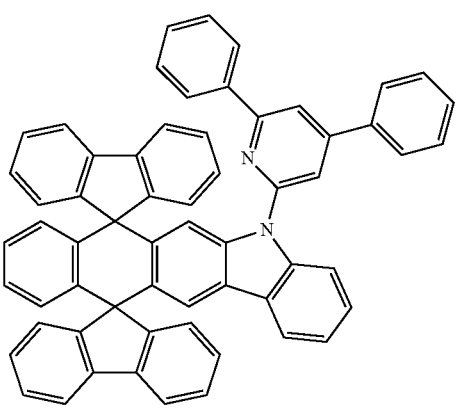

2-16
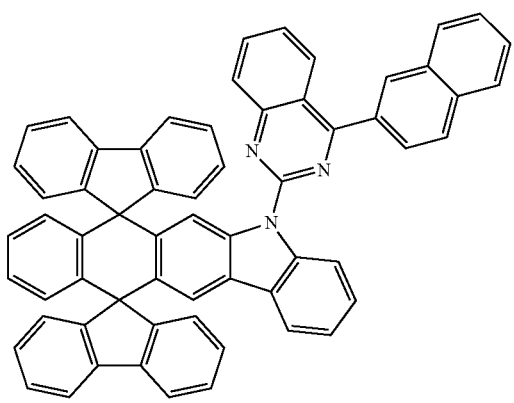
2-17
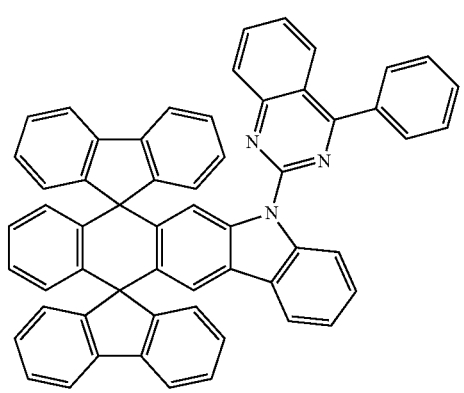
2-18
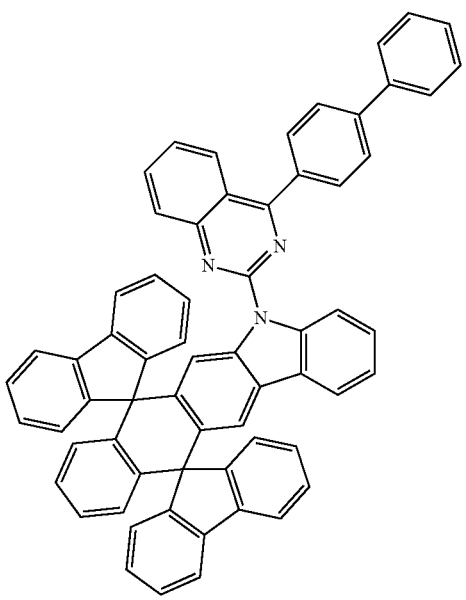
2-19
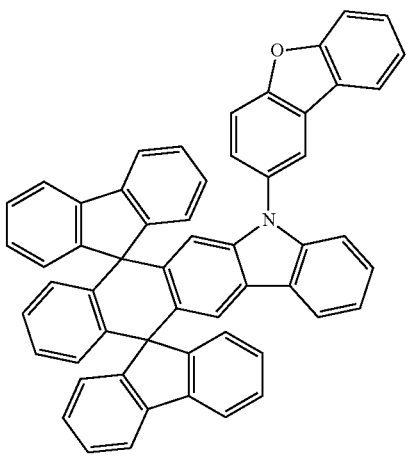
2-20
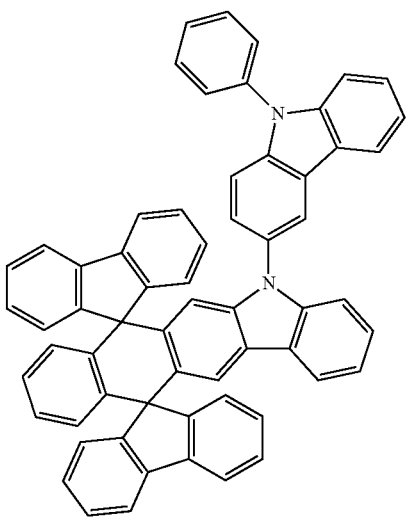
2-21
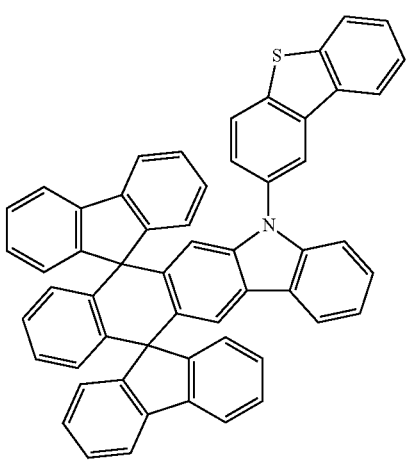

2-22
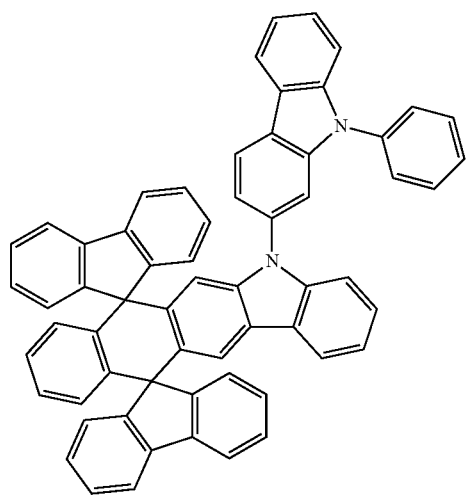
2-23
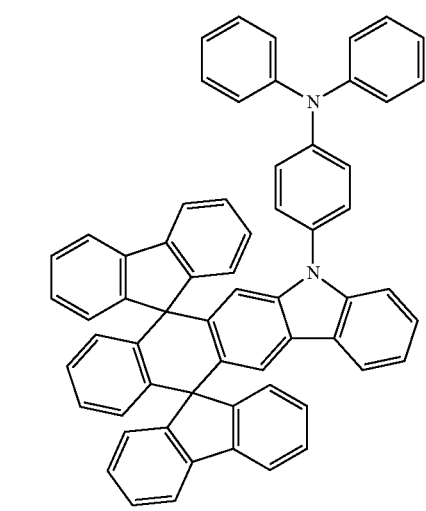
2-24
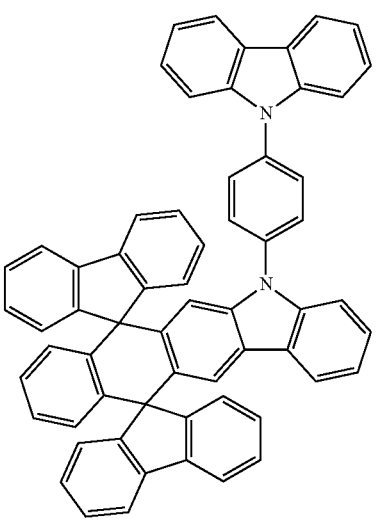
2-25
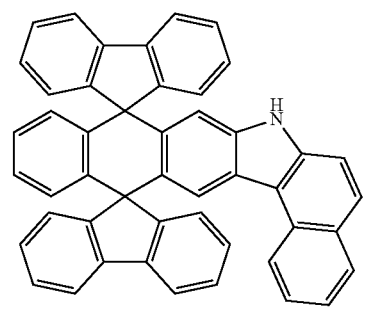
2-26
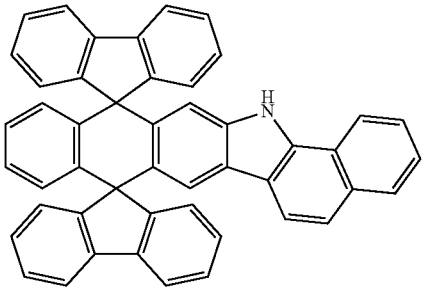
According to one embodiment of the present disclosure, the compound of Chemical Formula 1 may be any one selected from among the following compounds.
3-1
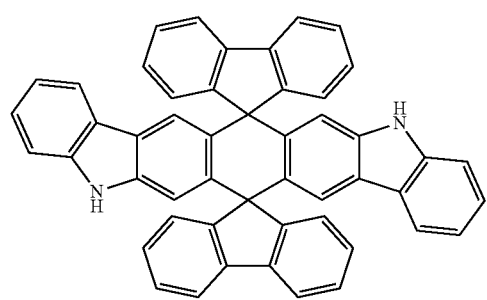
3-2
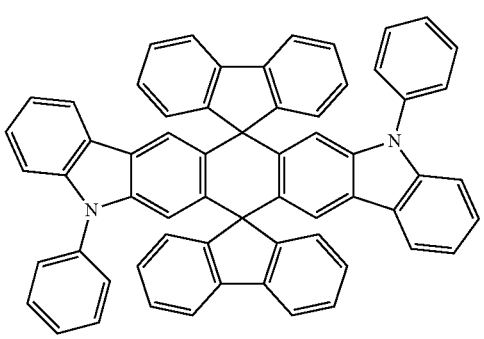

-continued
3-3
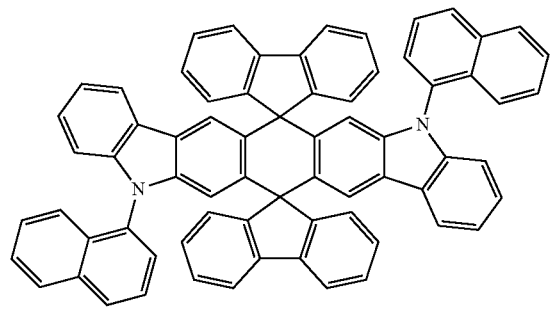
3-4
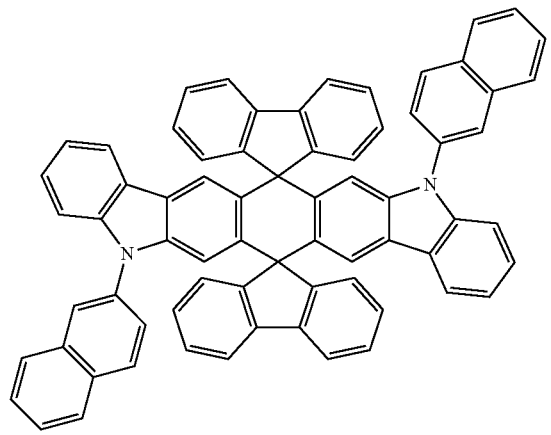
3-5
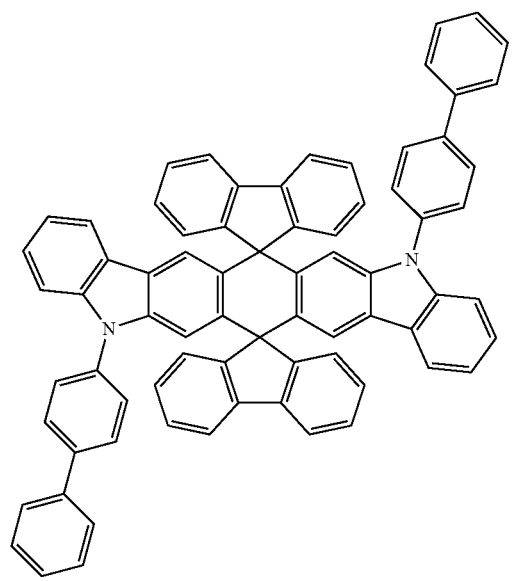
3-6
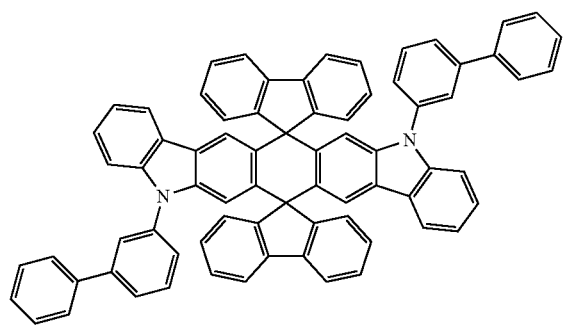
3-7
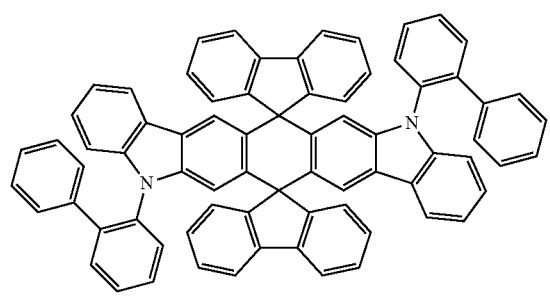
3-8
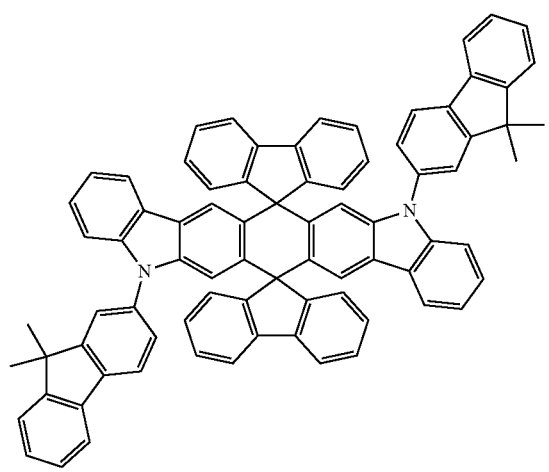

3-9
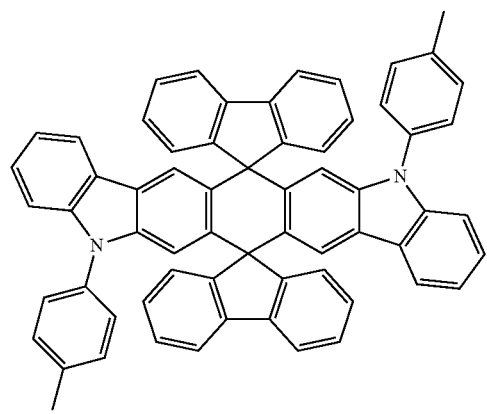
3-10
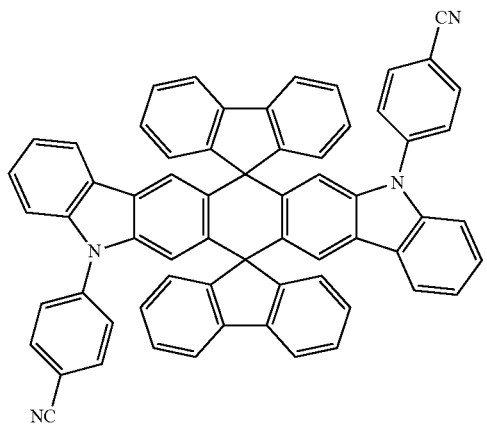
3-11
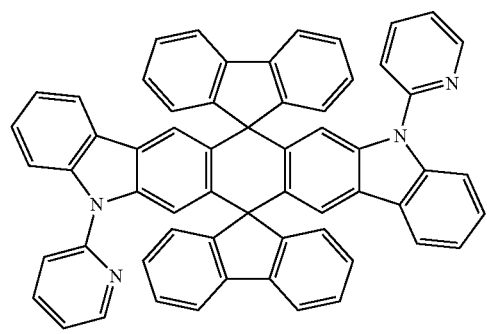
3-12
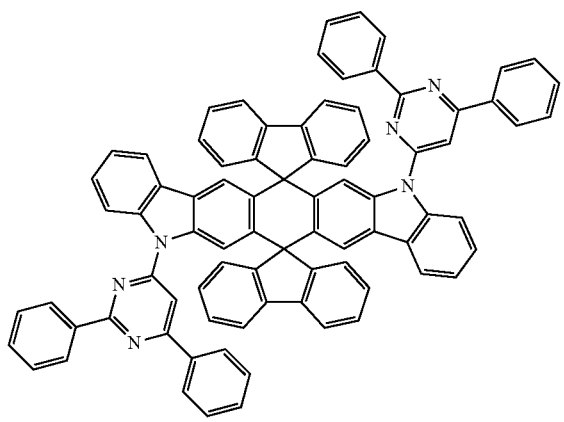
3-13
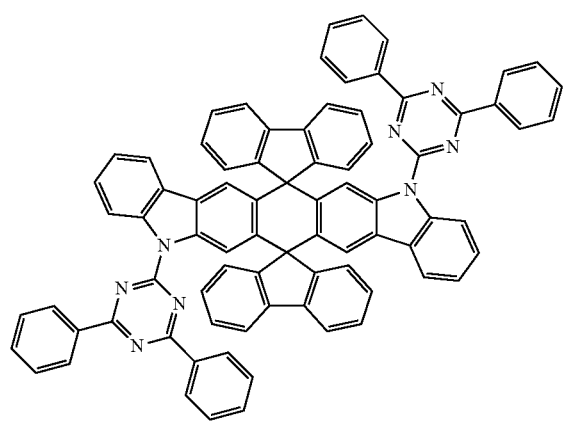
3-14
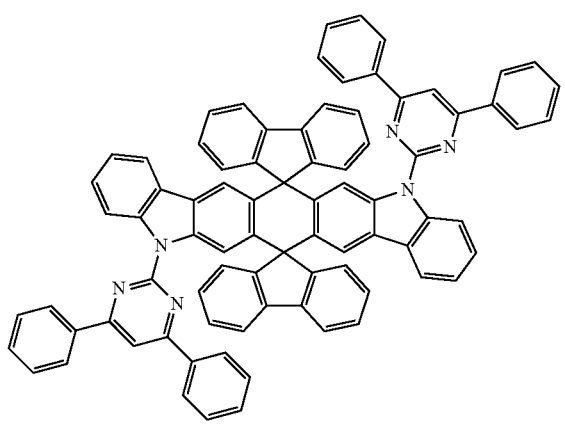

-continued
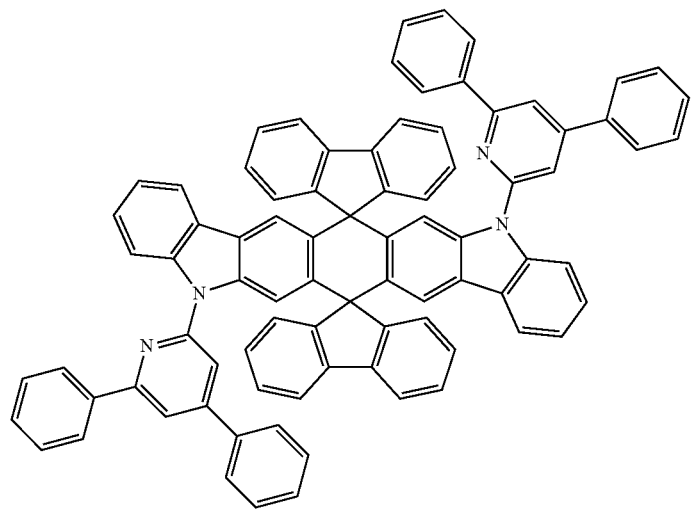
3-15
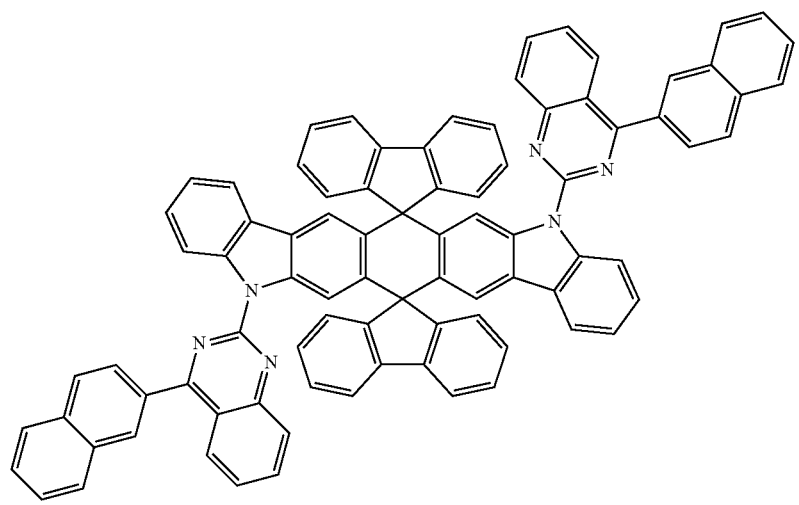
3-16
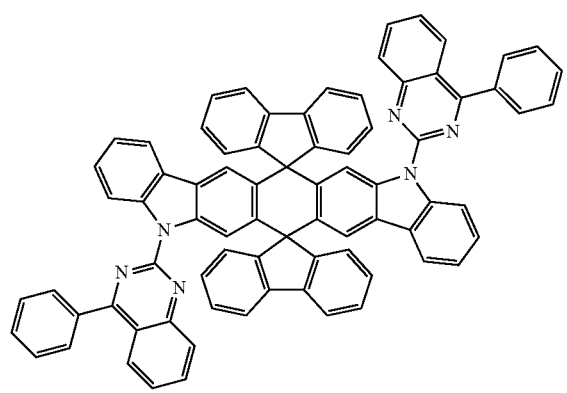
3-17
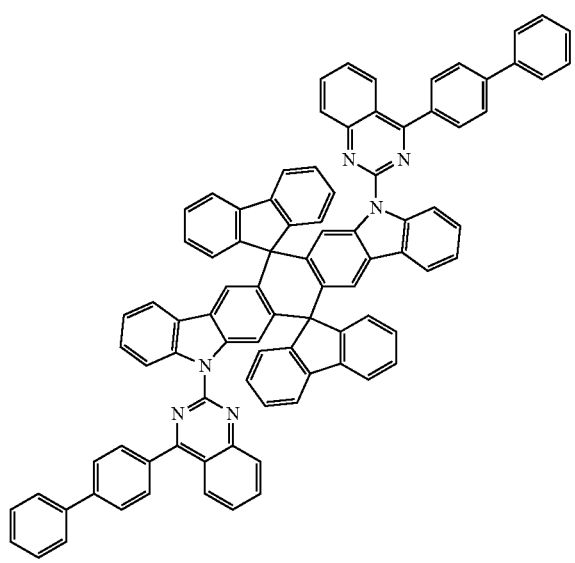
3-18

-continued
3-19
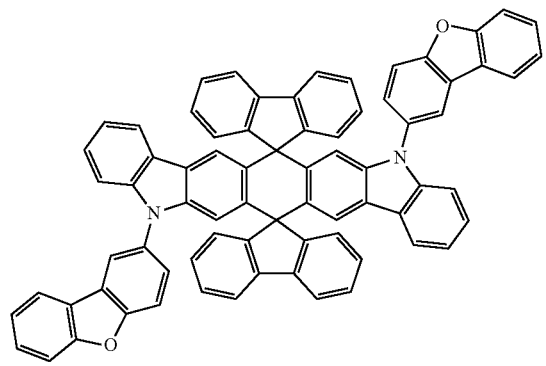
3-20
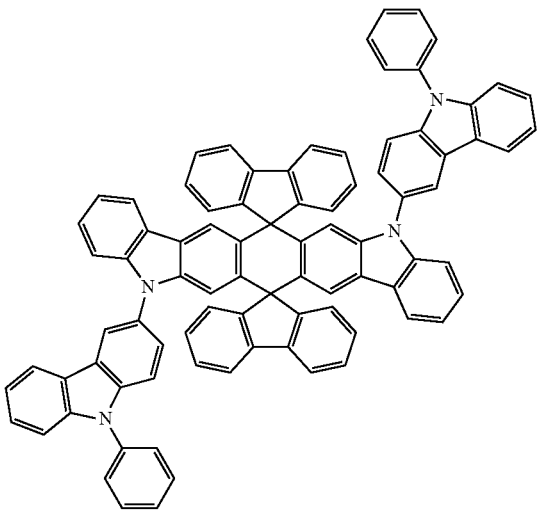
3-21
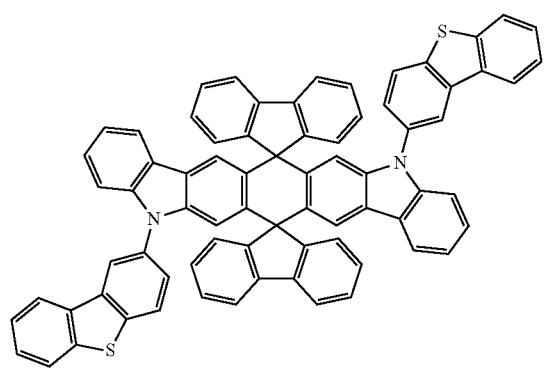
3-22
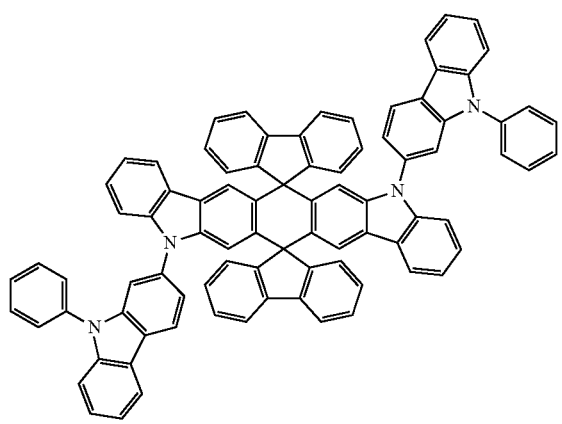
3-23
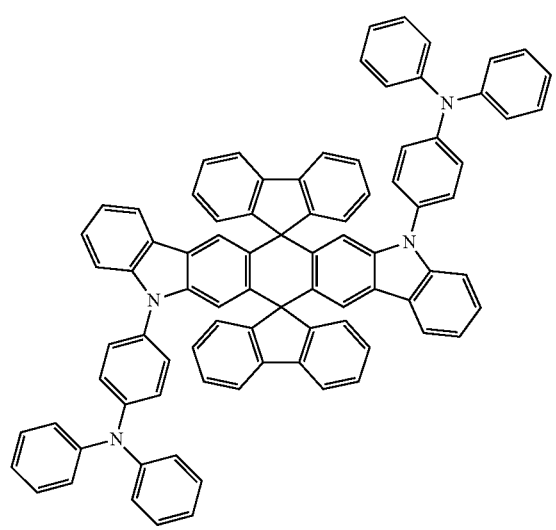
3-24
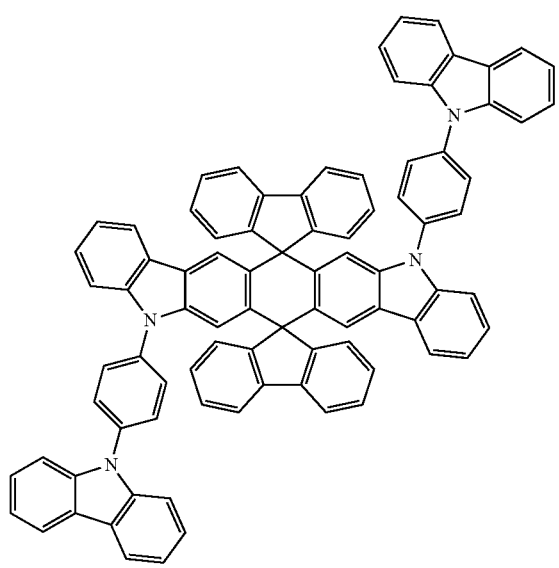

According to one embodiment of the present disclosure, the compound of Chemical Formula 1 may be any one selected from among the following compounds.
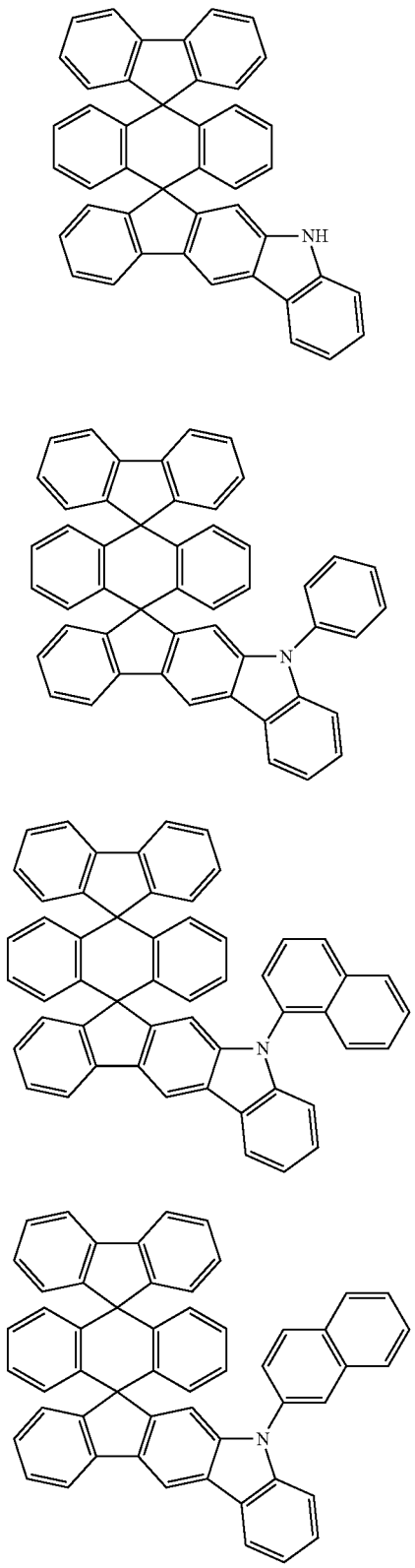
4-1
4-2
4-3
4-4
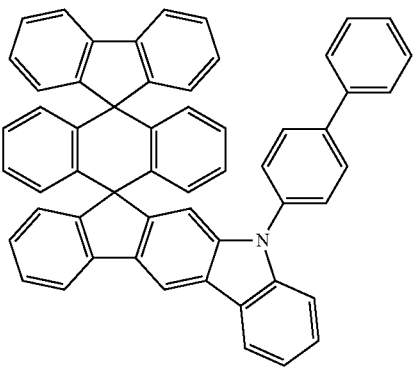
4-5
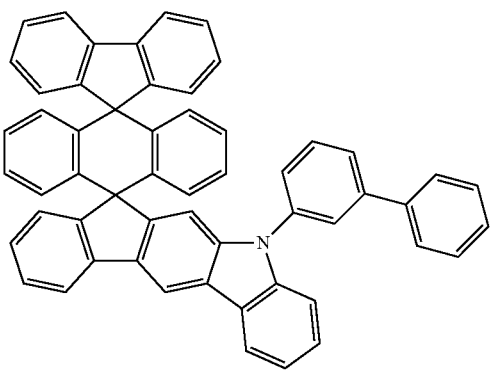
4-6
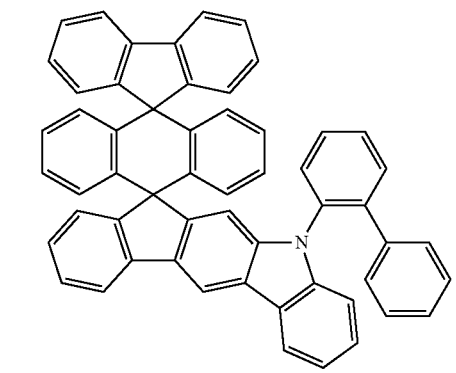
4-7
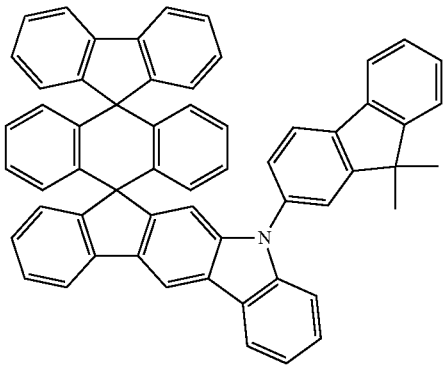
4-8

4-9
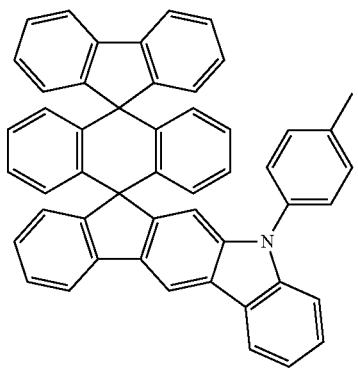
4-10
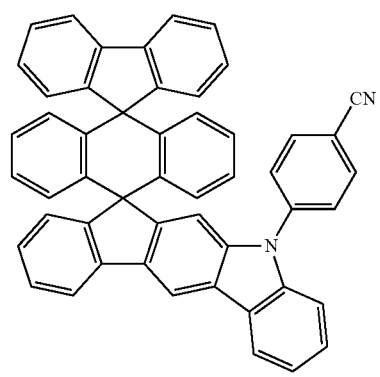
4-11
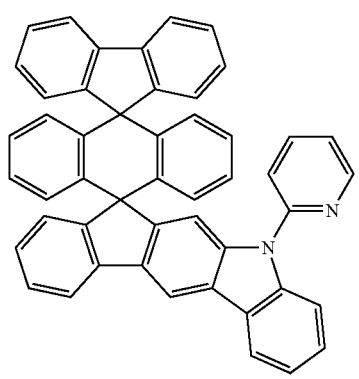
4-12
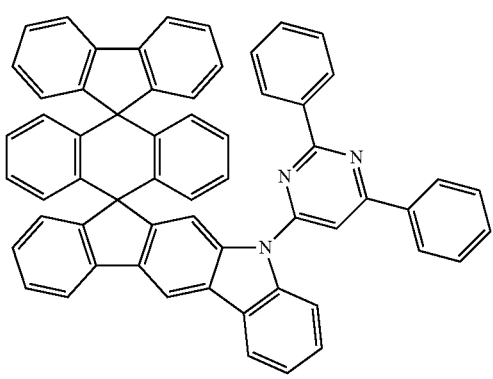
4-13
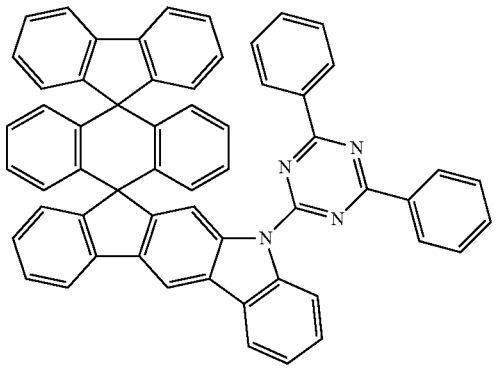
4-14
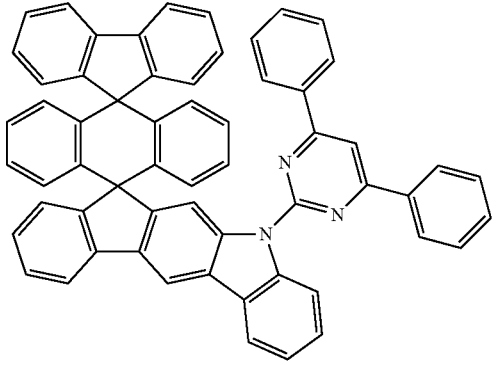
4-15
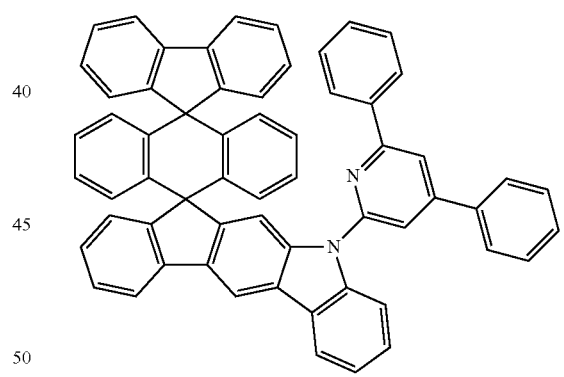
4-16
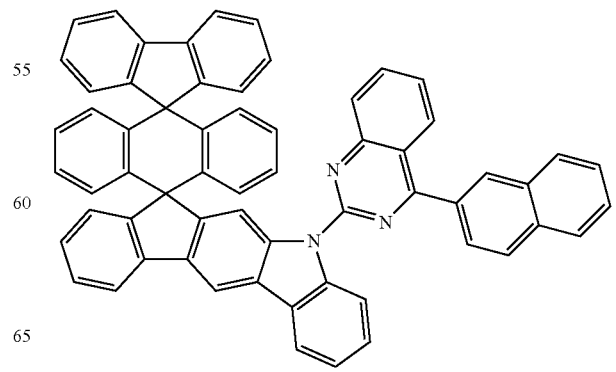

-continued
4-17
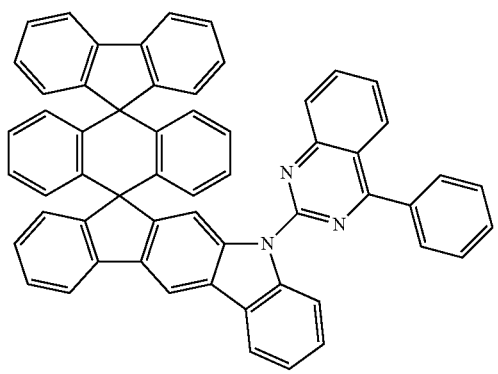
4-18
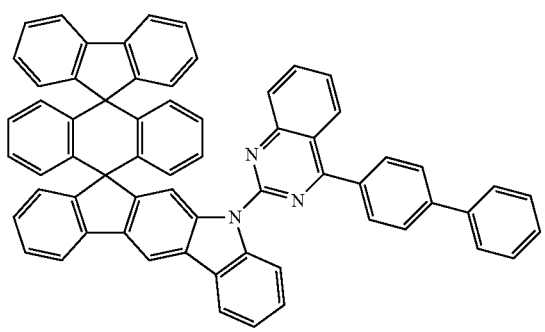
4-19
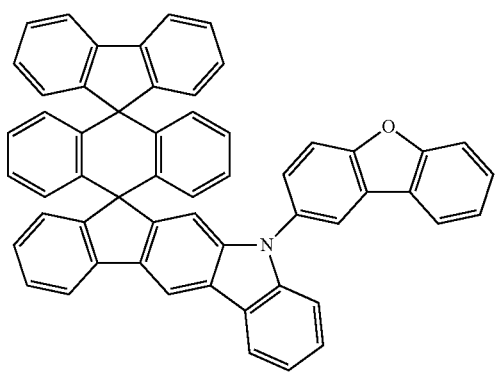
4-20
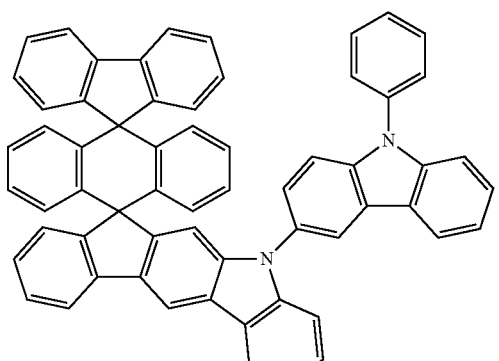
-continued
4-21
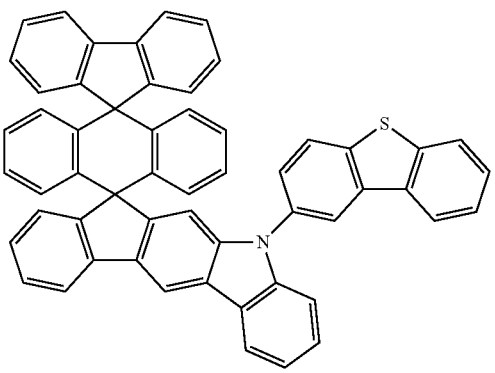
4-22
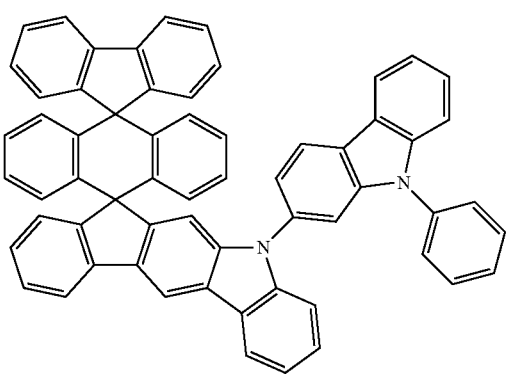
4-23
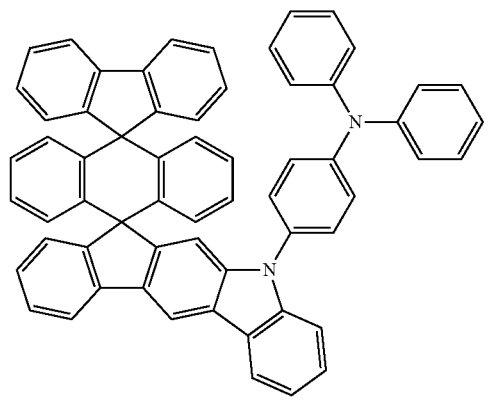
4-24
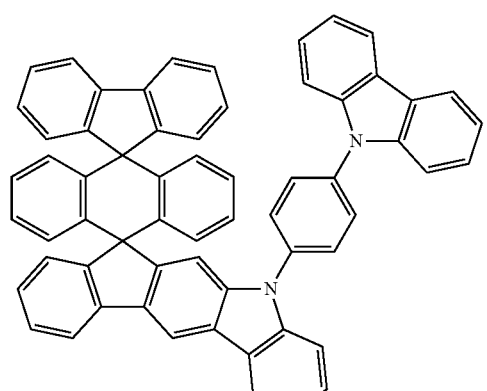

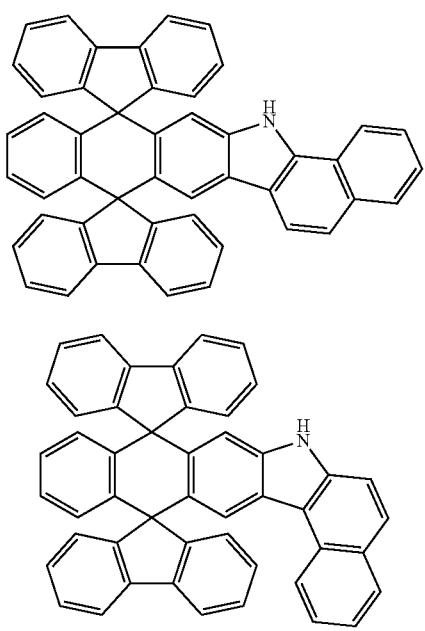
4-25
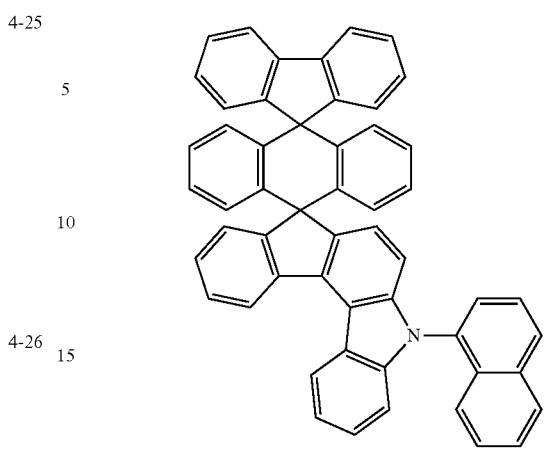
5-3
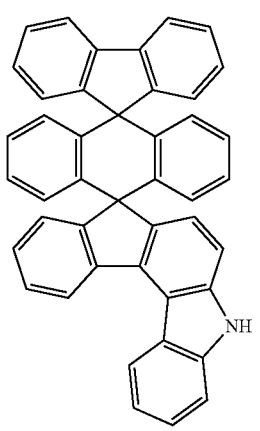
4-26
According to one embodiment of the present disclosure, the compound of Chemical Formula 1 may be any one selected from among the following compounds.
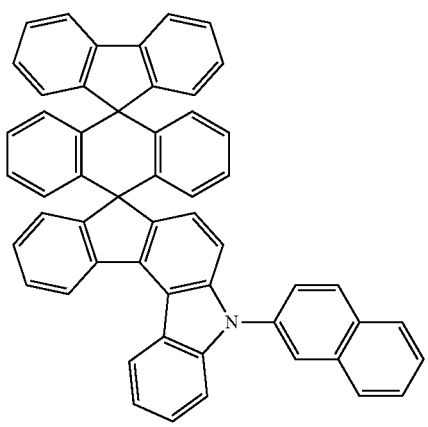
5-4
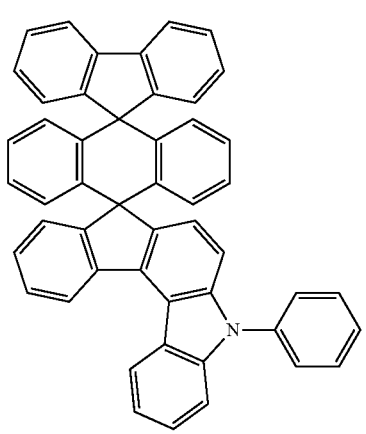
5-1
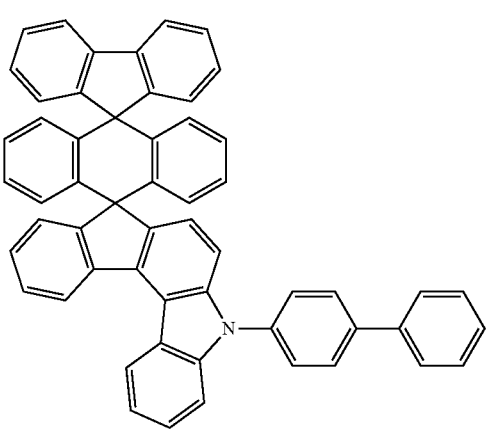
5-2
5-5

-continued
5-6
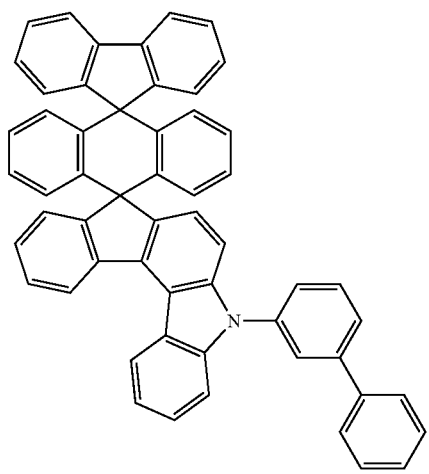
5-7
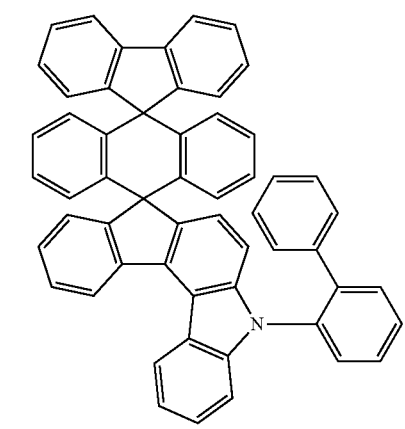
5-8
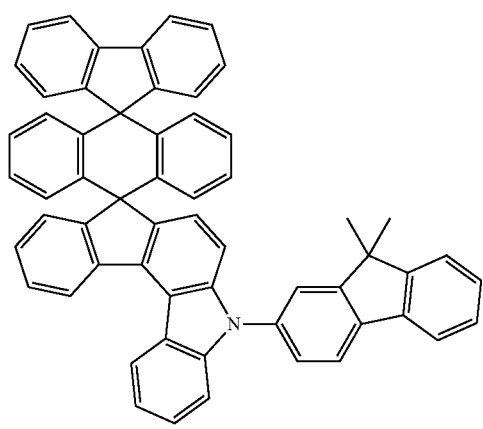
-continued
5-9
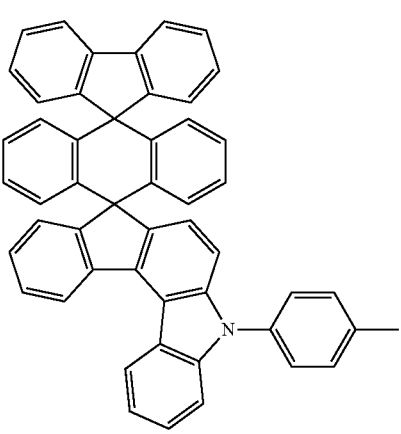
5-10
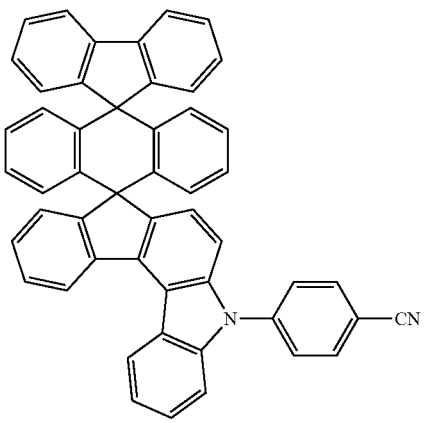
5-11
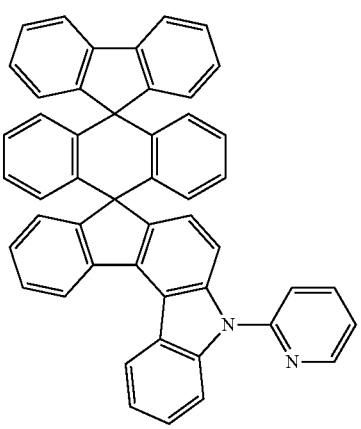

5-12
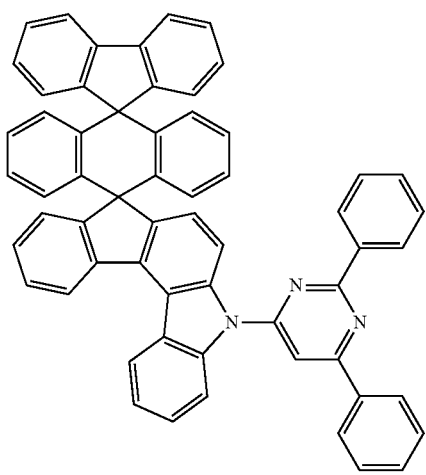
5-13
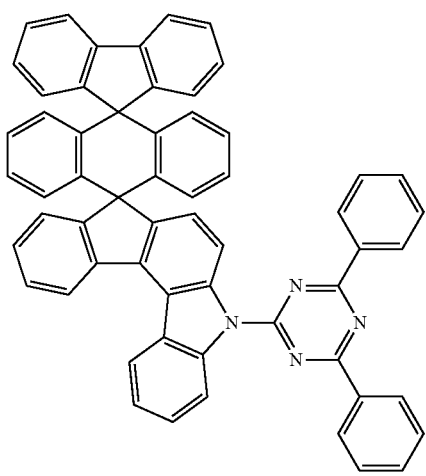
5-14
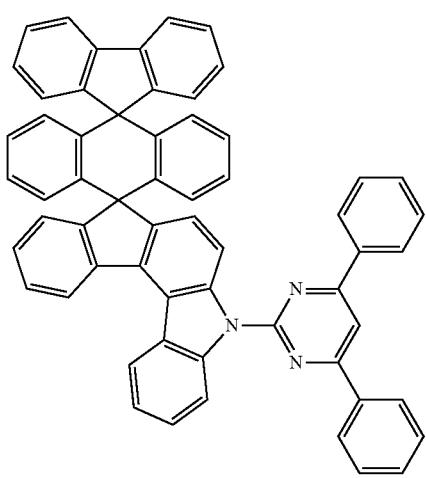
5-15
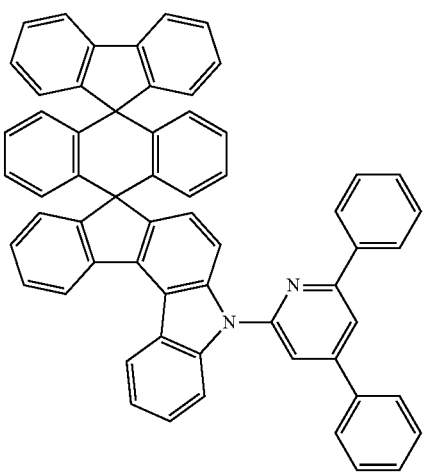
5-16
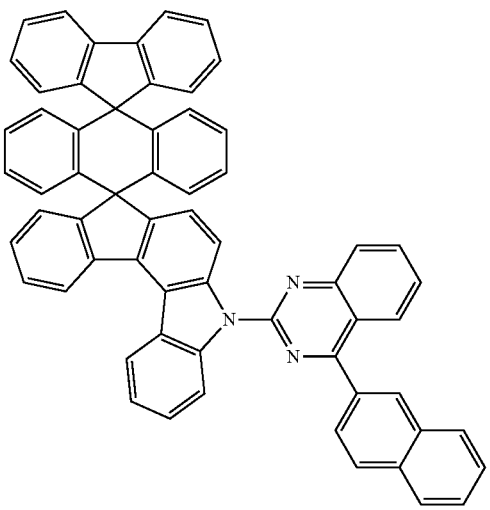
5-17
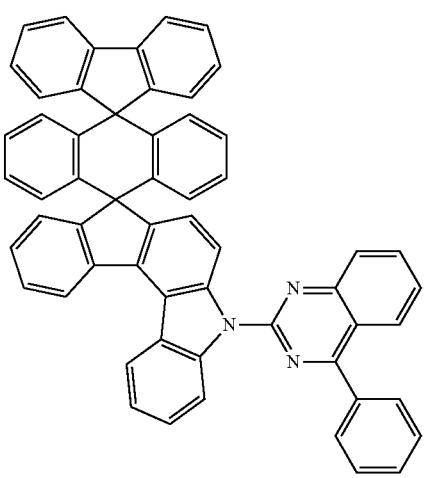

-continued
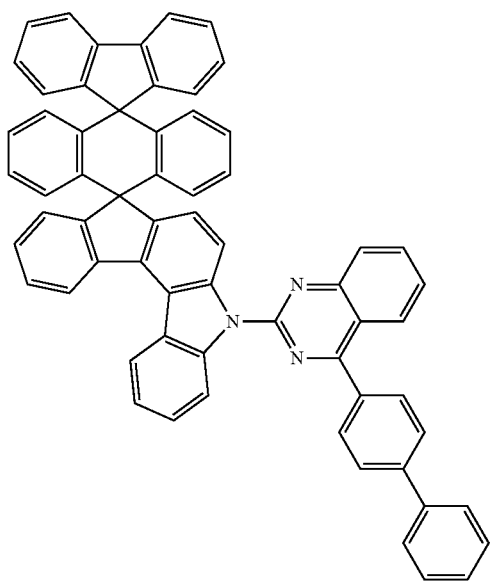
5-18
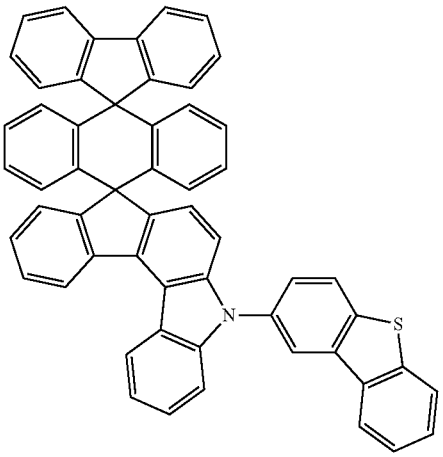
5-21
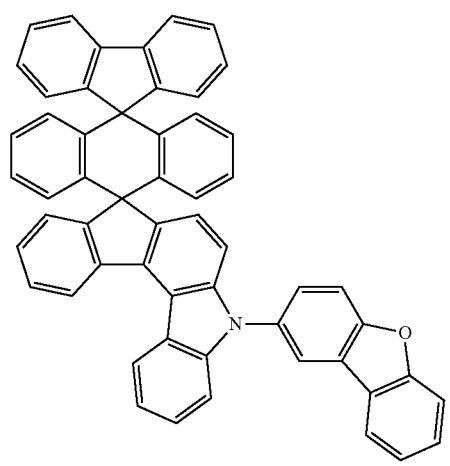
5-19
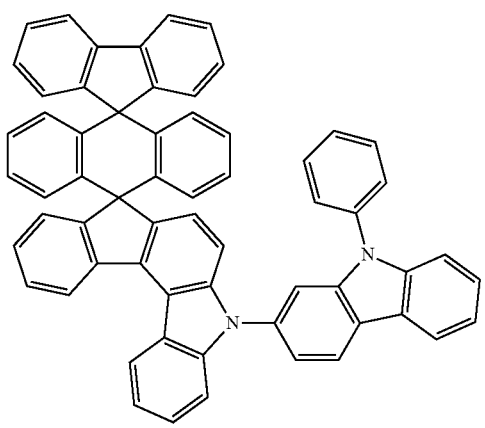
5-22
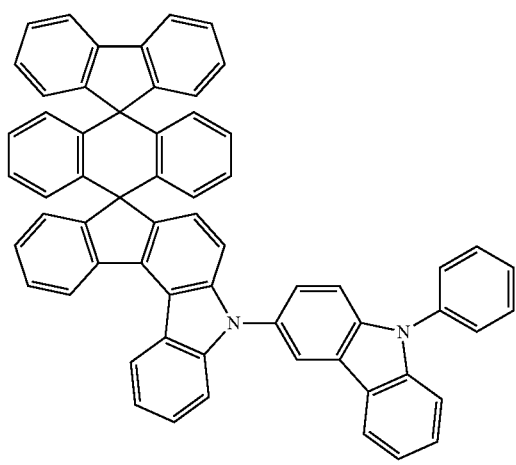
5-20
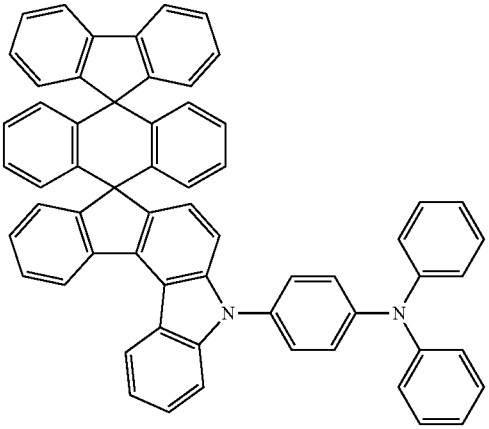
5-23

-continued
5-24
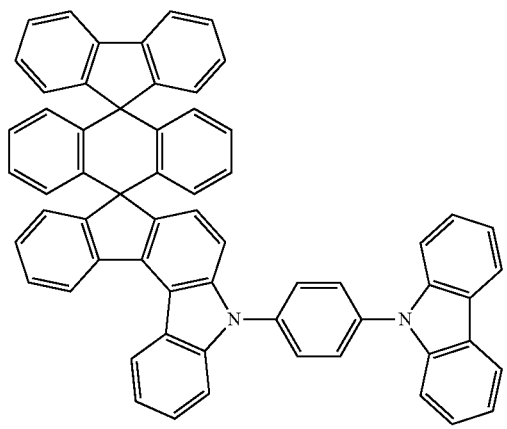
5-25
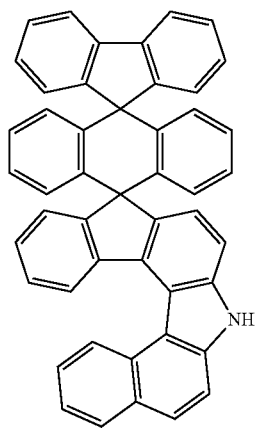
5-26
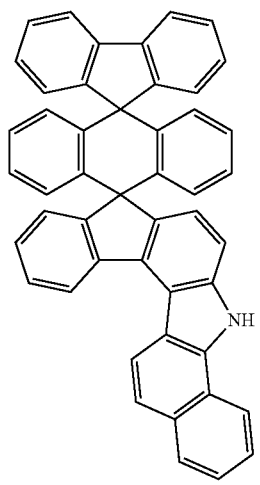
6-1
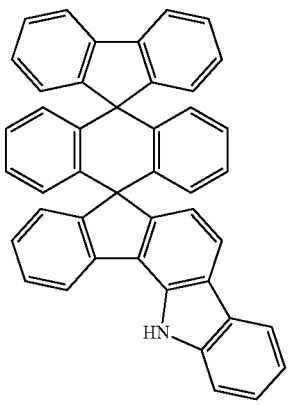
6-2
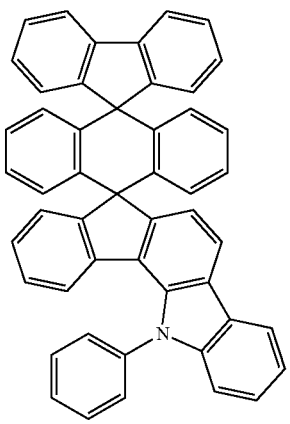
6-3
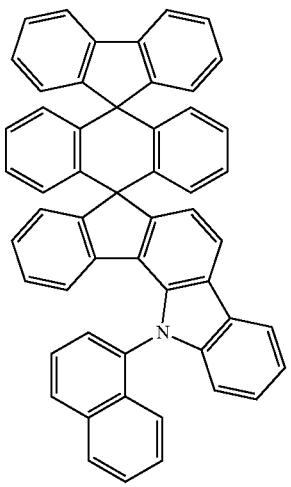
According to one embodiment of the present disclosure, the compound of Chemical Formula 1 may be any one selected from among the following compounds.

6-4
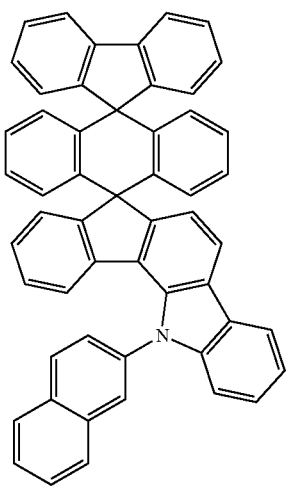
6-5
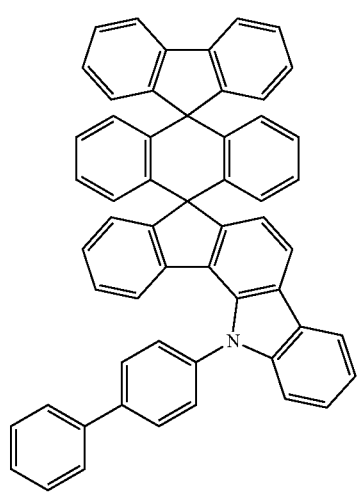
6-6
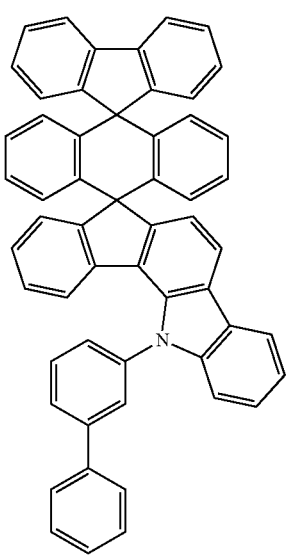
6-7
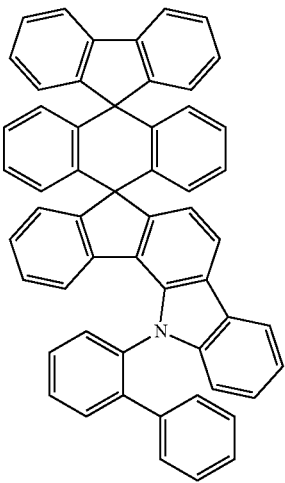
6-8
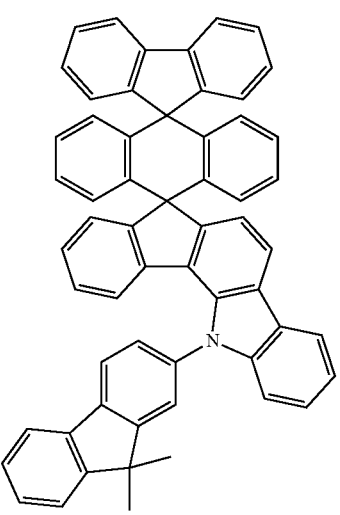
6-9

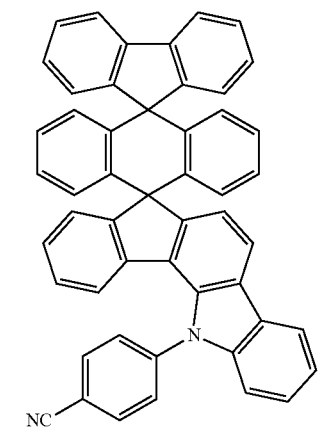
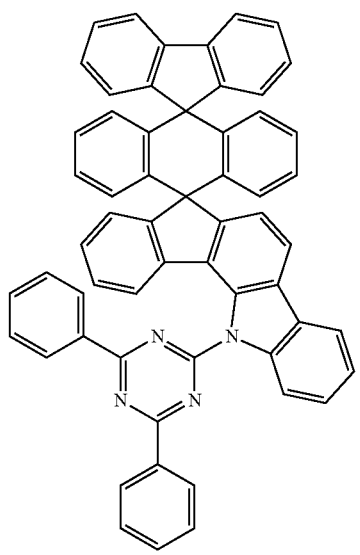

6-16
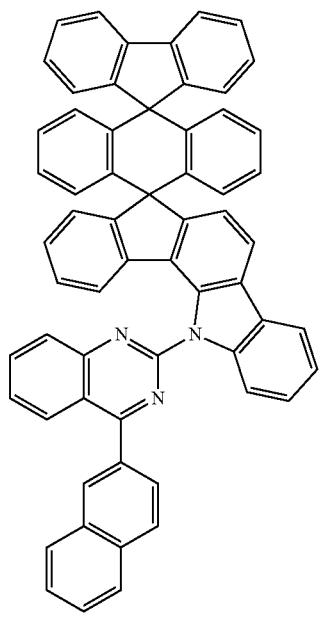
6-18
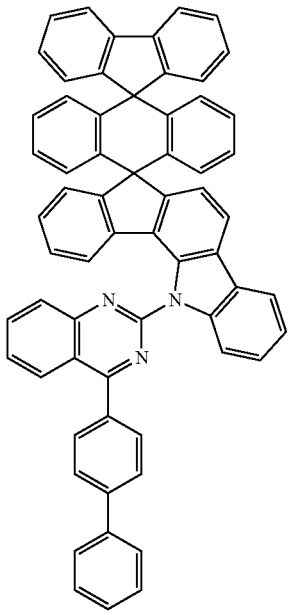
6-17
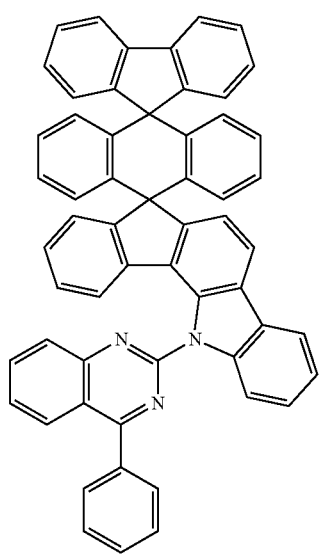
6-19
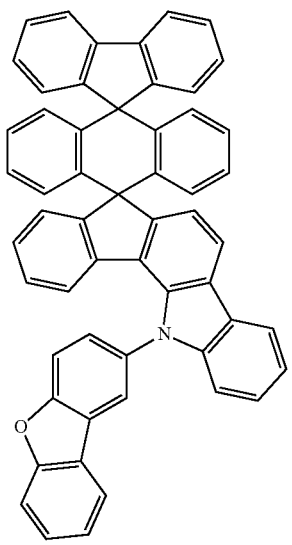

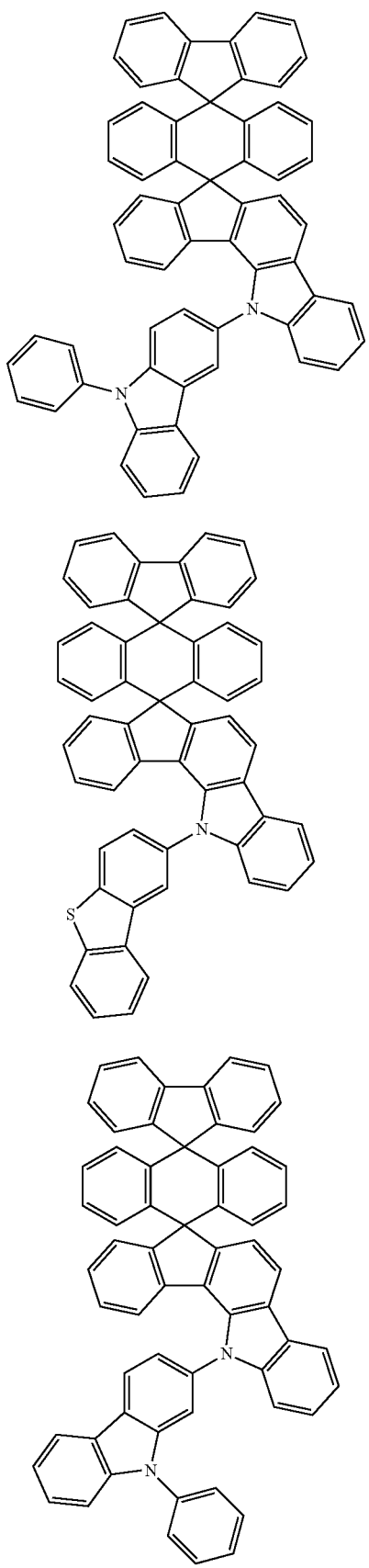
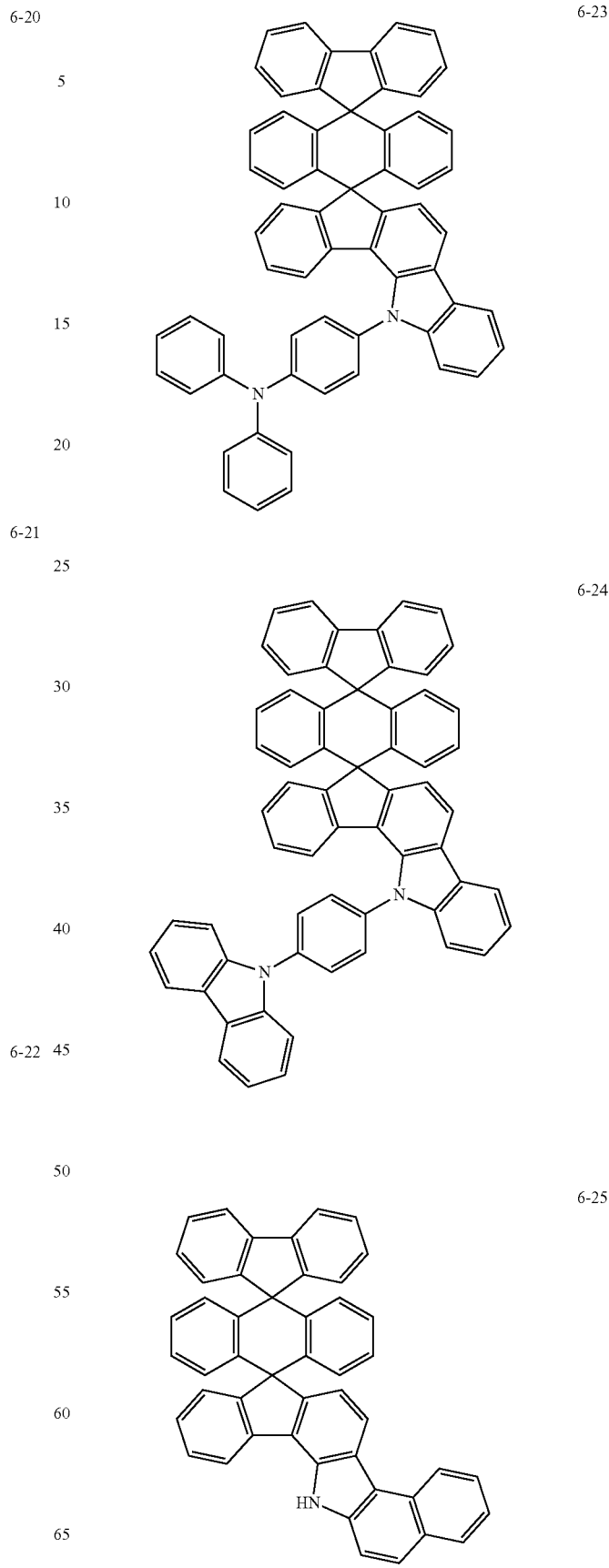

-continued
6-26
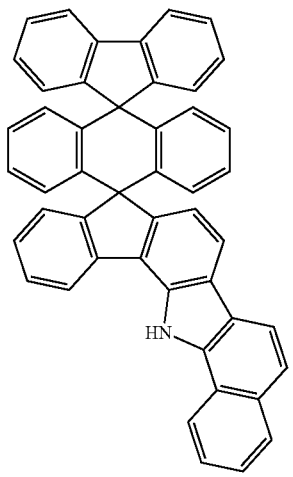
According to one embodiment of the present disclosure, the compound of Chemical Formula 1 may be any one selected from among the following compounds.
7-1
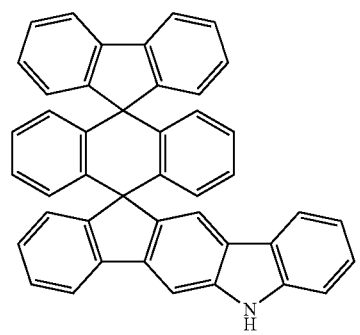
7-2
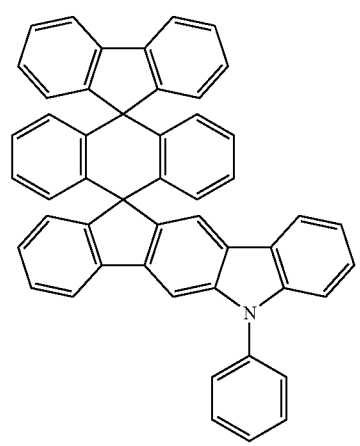
-continued
7-3
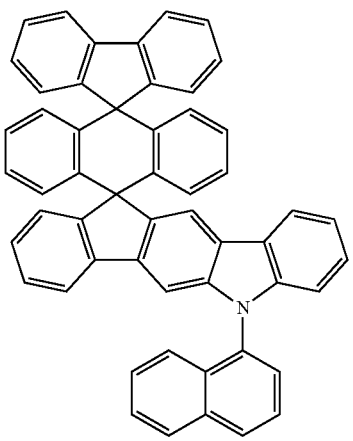
7-4
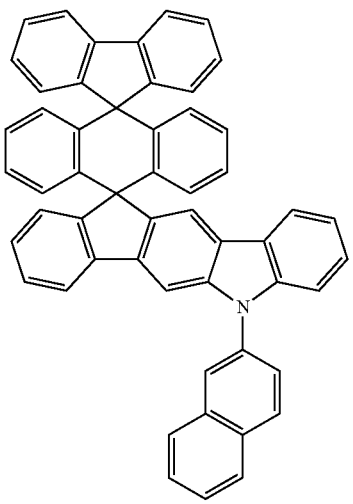
7-5
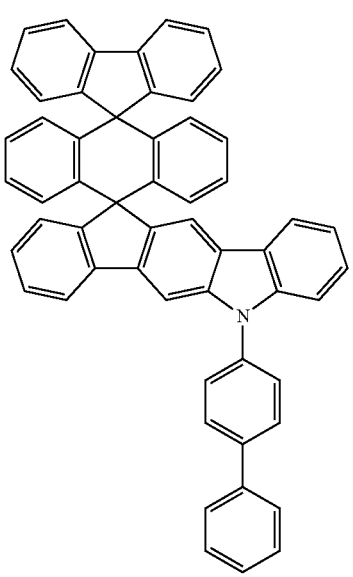

7-6
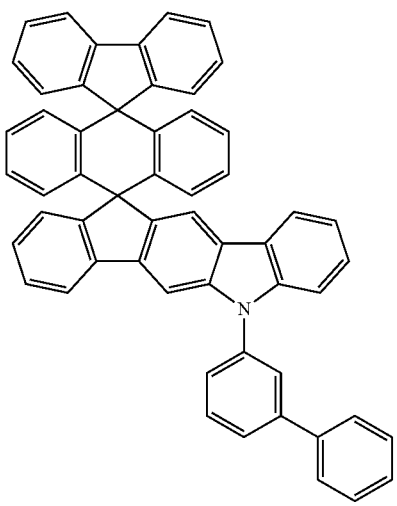
7-9
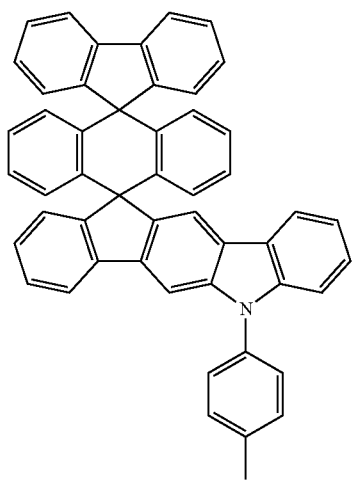
7-7
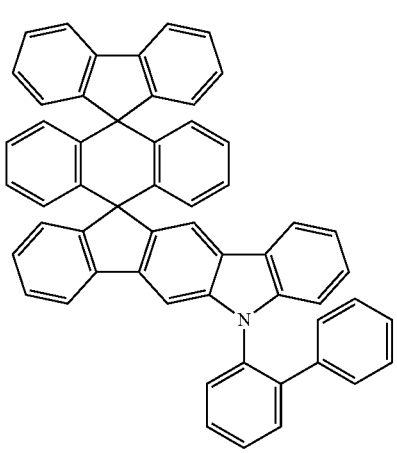
7-10
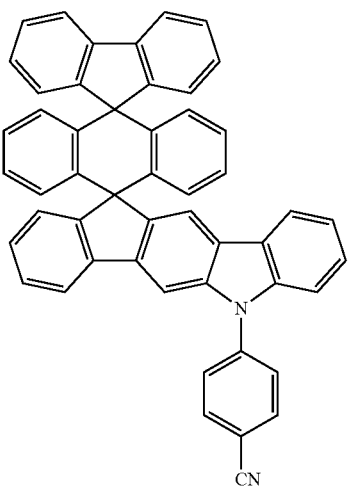
7-8
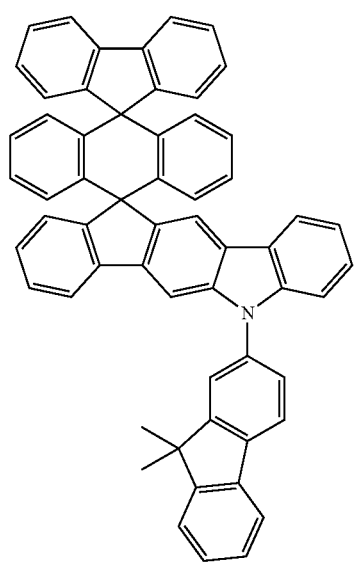
7-11
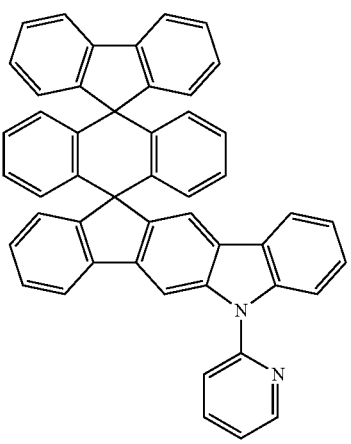

7-12
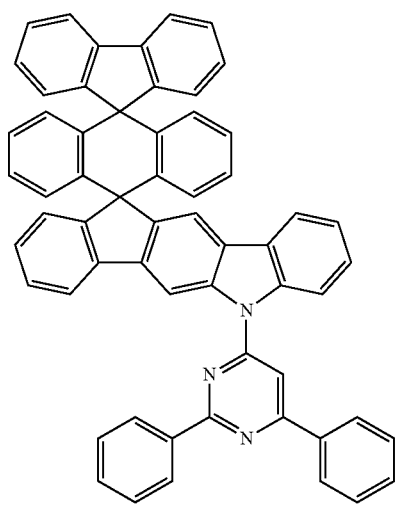
7-13
7-14
7-15
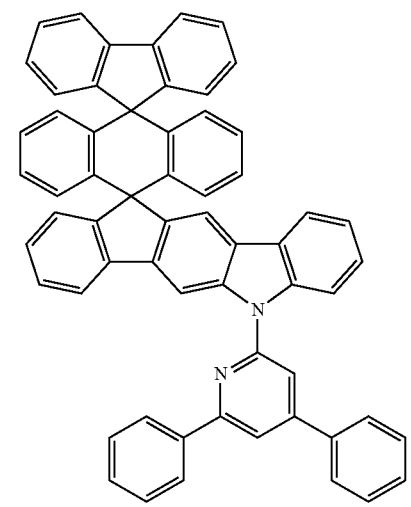
7-16
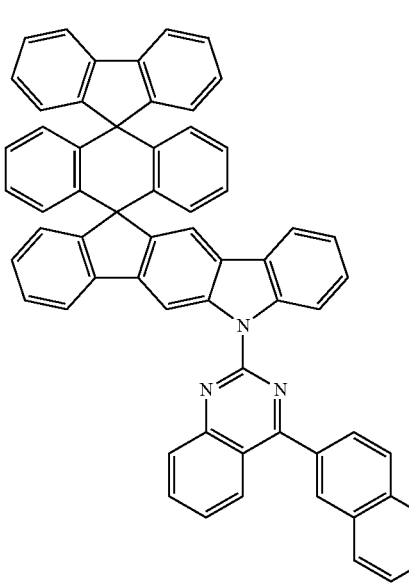
7-17
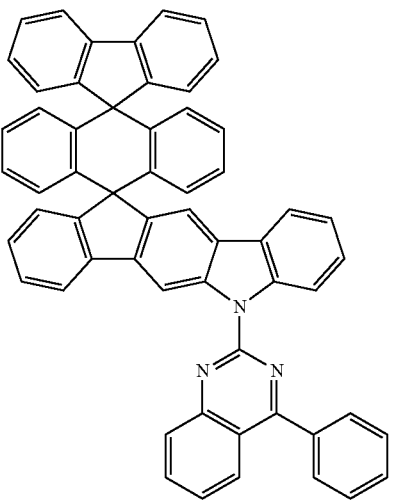

-continued
7-18
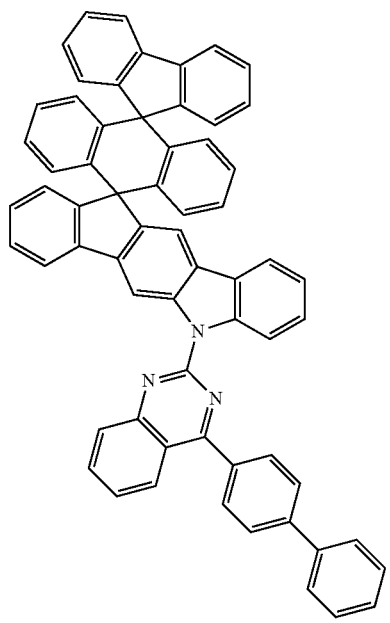
7-19
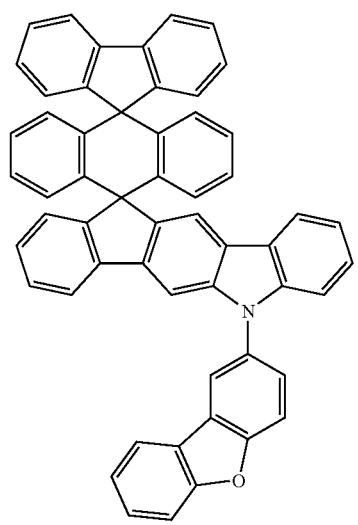
7-20
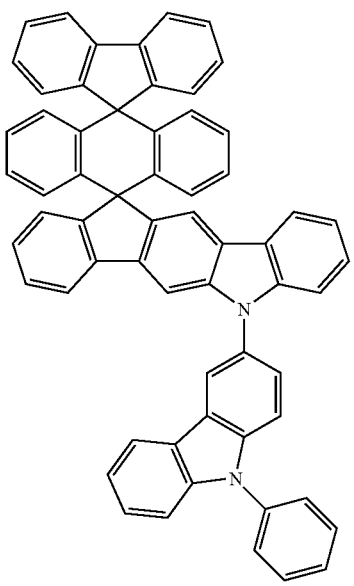
7-21
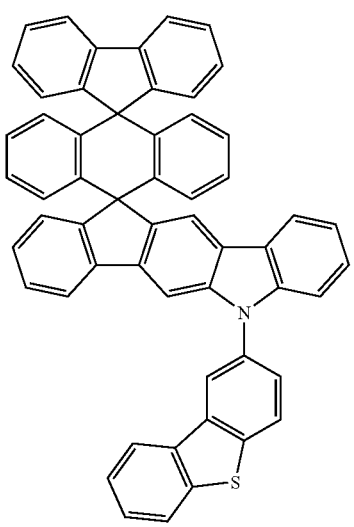
7-22
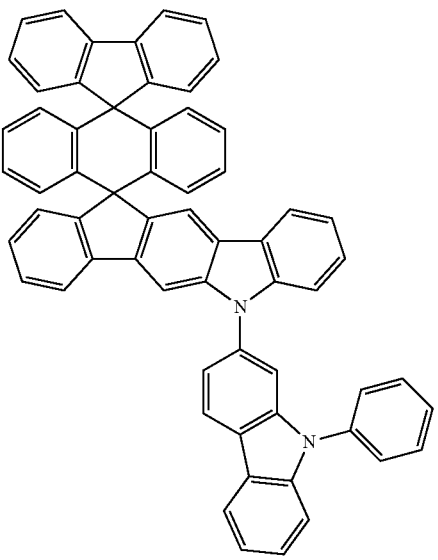

7-23
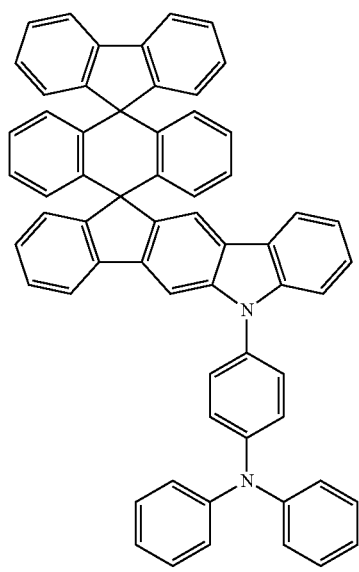
7-24
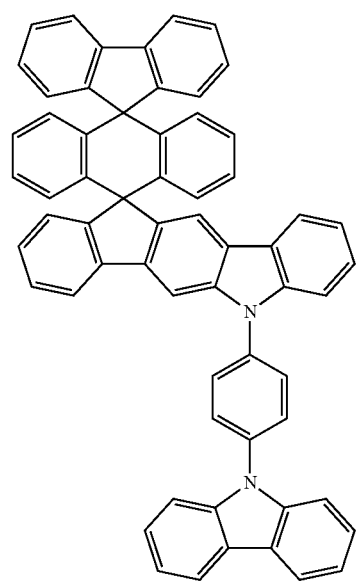
7-25
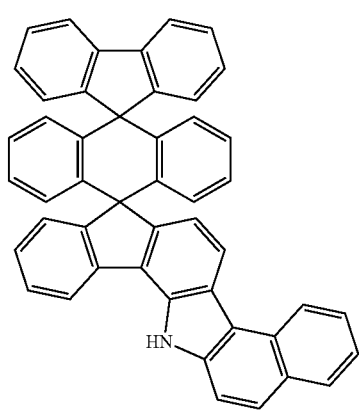
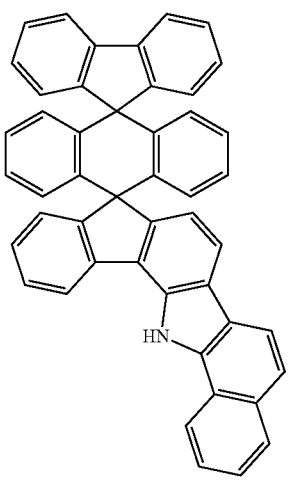 [SMILES: c1ccc2c(c1)-c1ccccc1C21c2ccccc2C2(c3ccccc3-c3c2ccc2c3[nH]c3c4ccccc4ccc23)c2ccccc21]
According to one embodiment of the present disclosure, the compound of Chemical Formula 1 may be any one selected from among the following compounds.
8-1
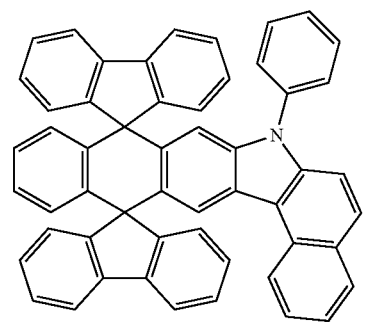
8-2
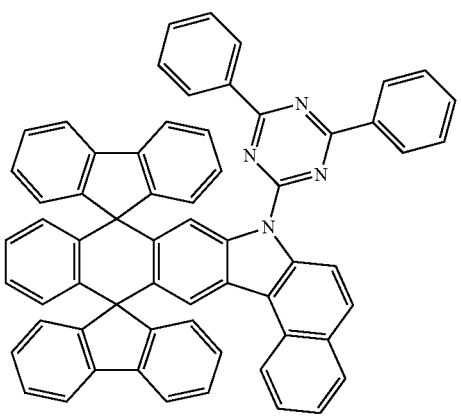

-continued
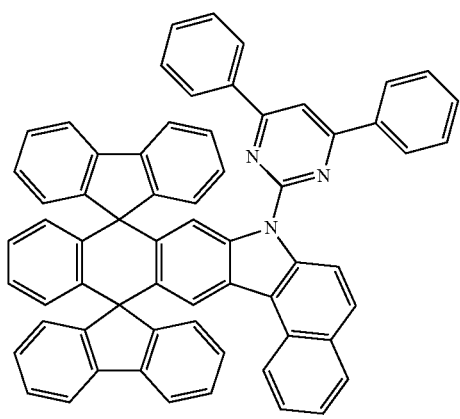
8-3
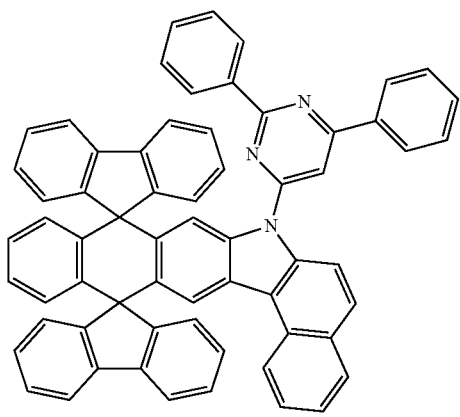
8-4
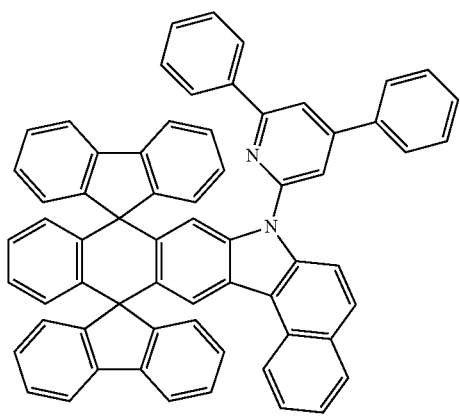
8-5
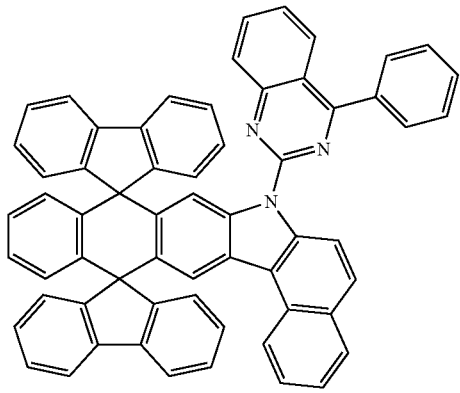
8-6
-continued
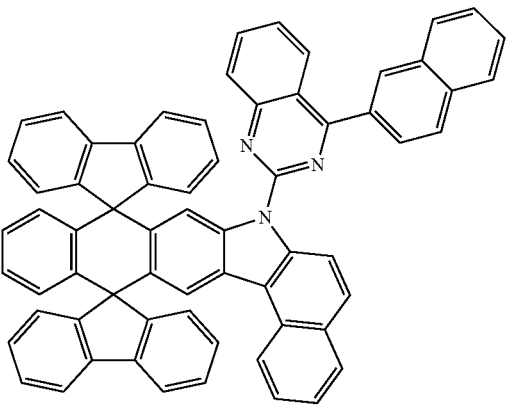
8-7
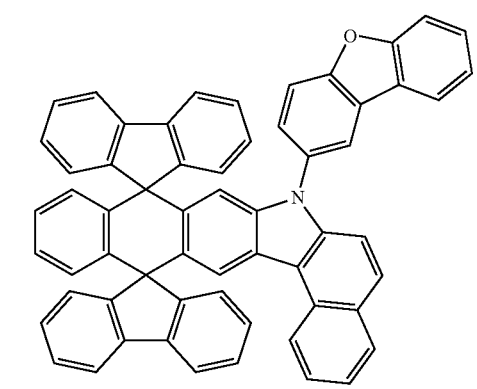
8-8
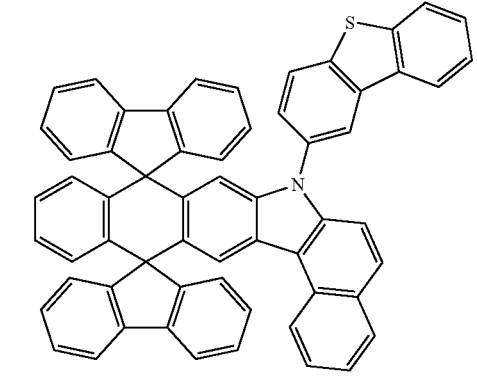
8-9
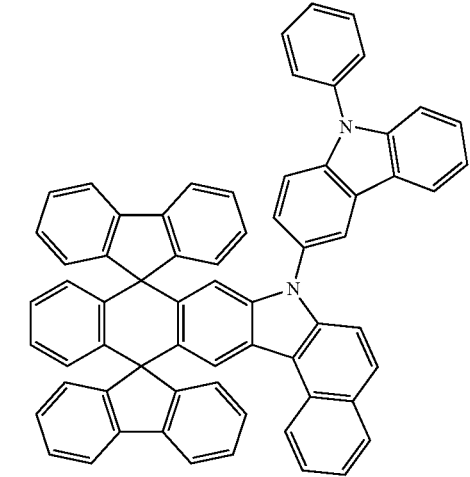
8-10

8-11
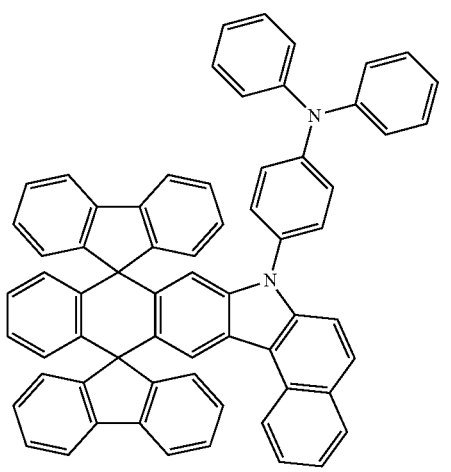
9-1
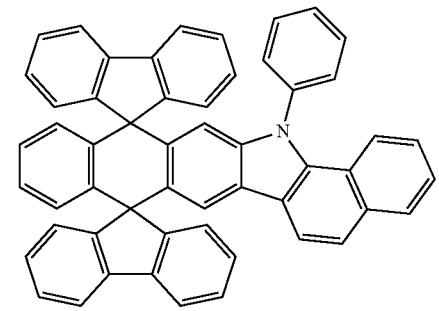
9-2
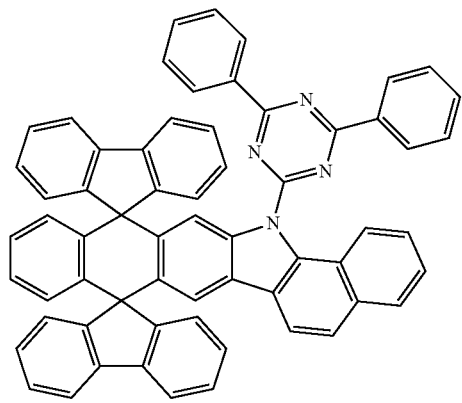
9-3
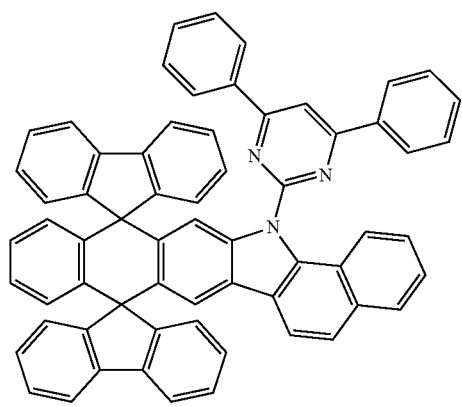
9-4
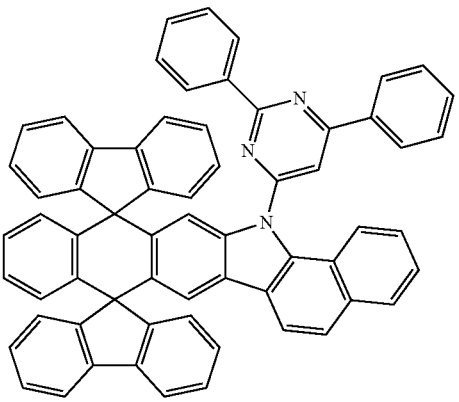
9-5
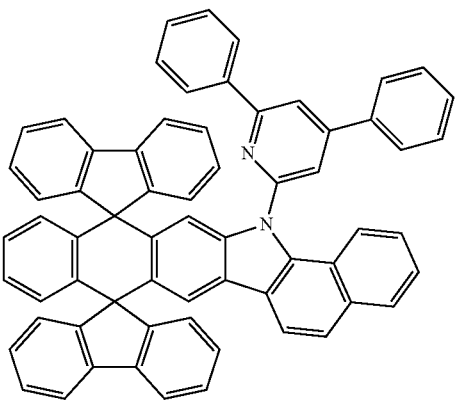
9-6
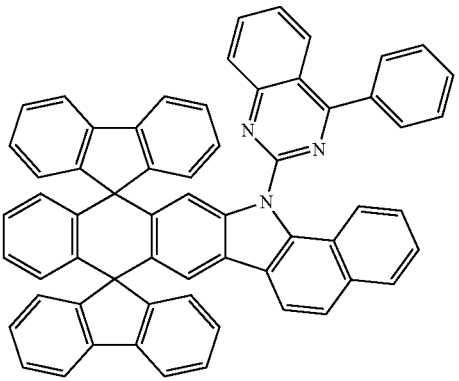
9-7
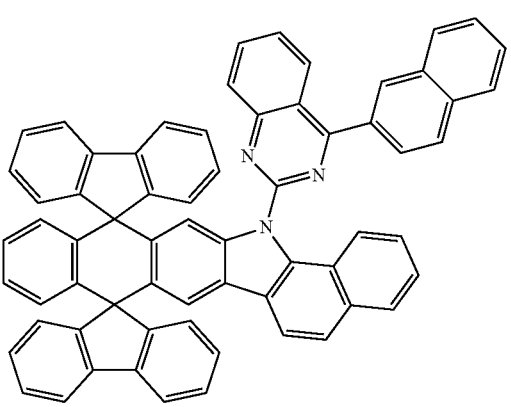

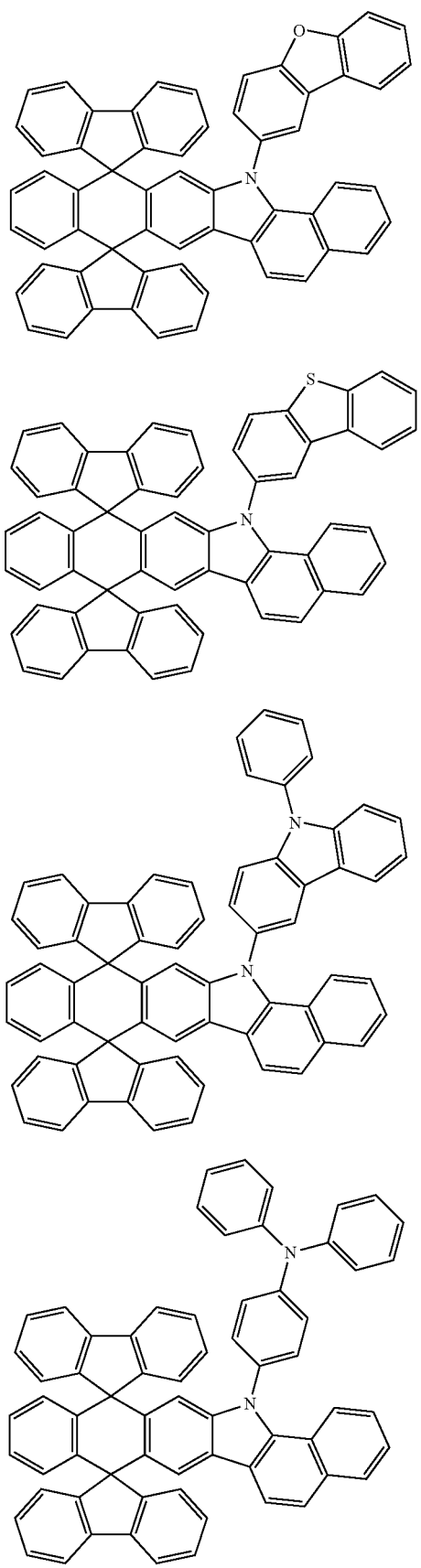
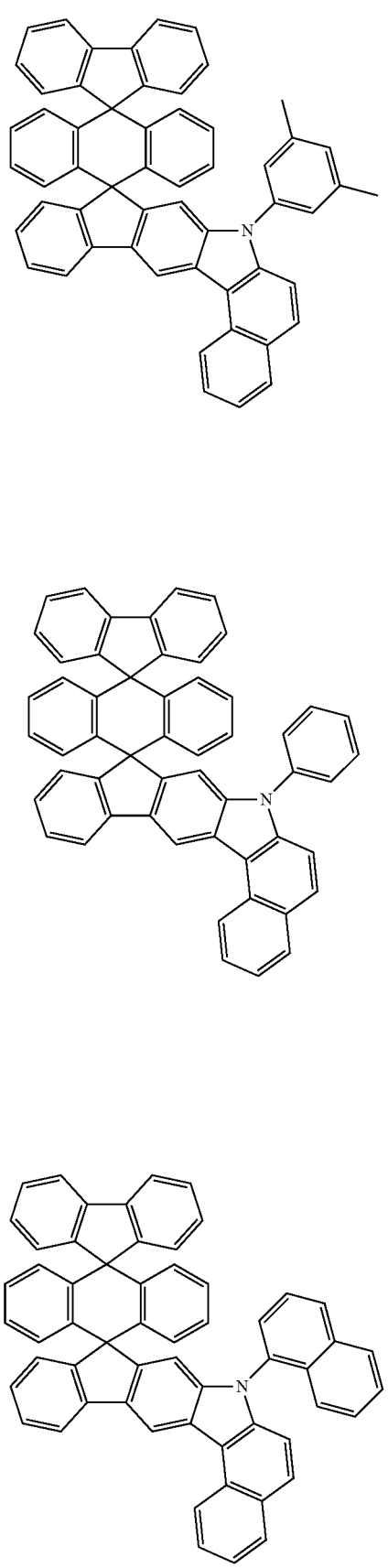

-continued
10-4
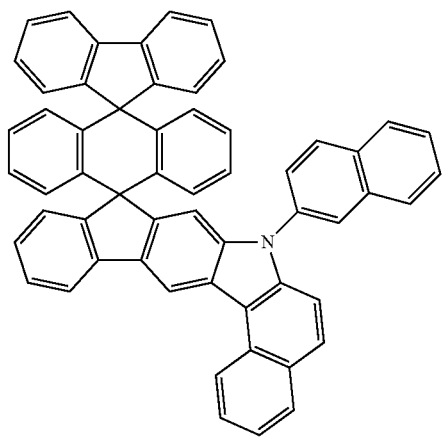
10-5
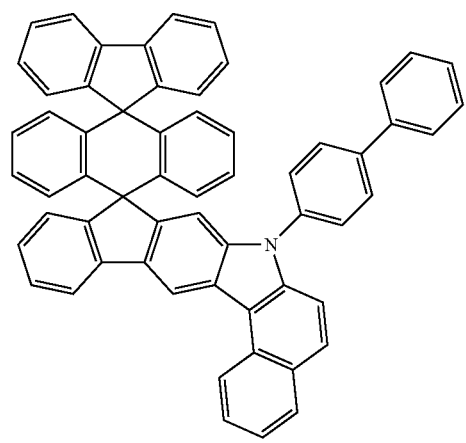
10-6
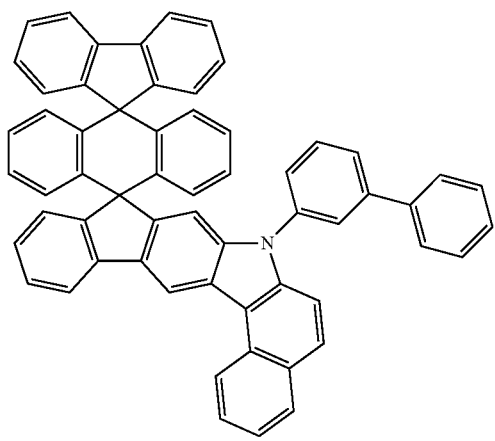
-continued
10-7
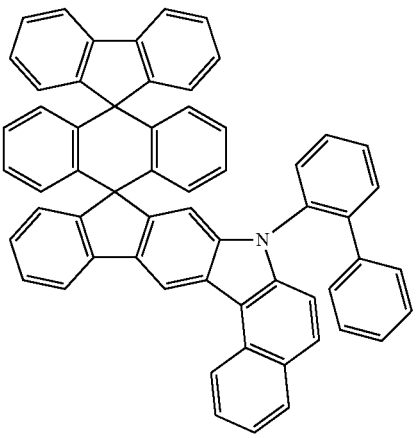
10-8
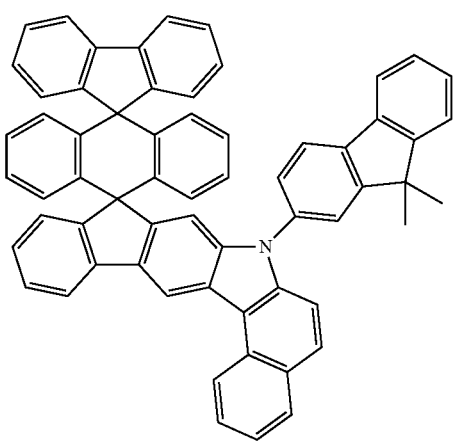
10-9
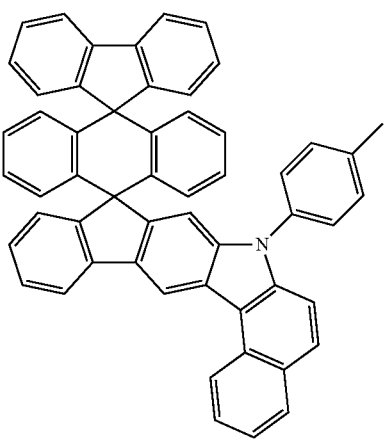

-continued
10-10
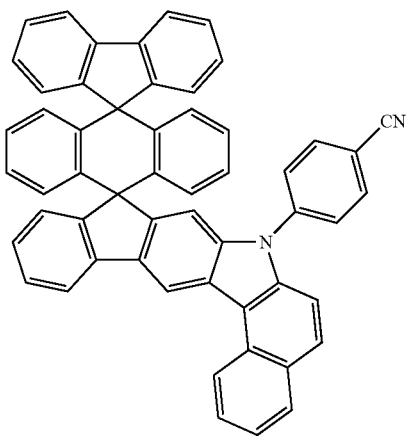
10-11
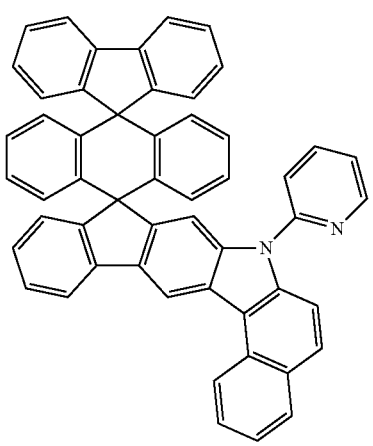
10-12
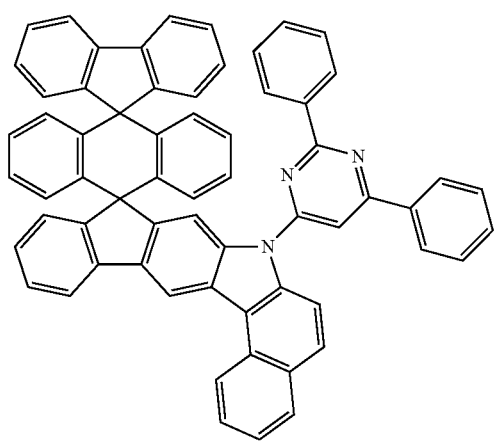
-continued
10-13
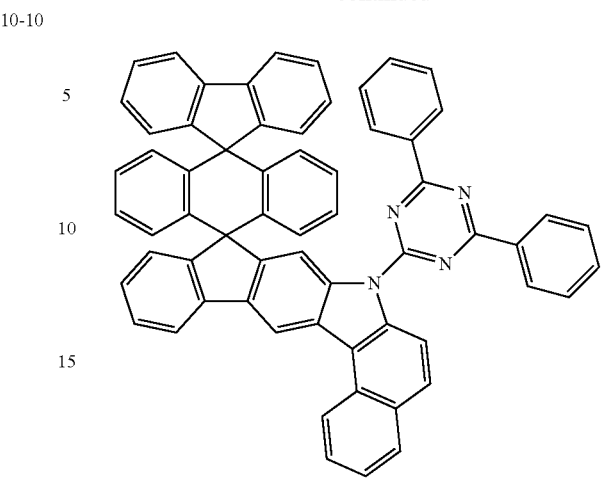
10-14
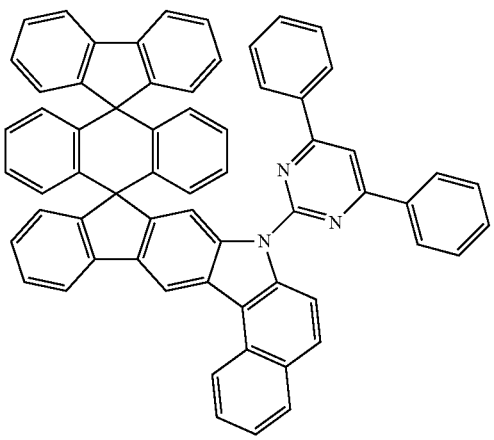
10-15
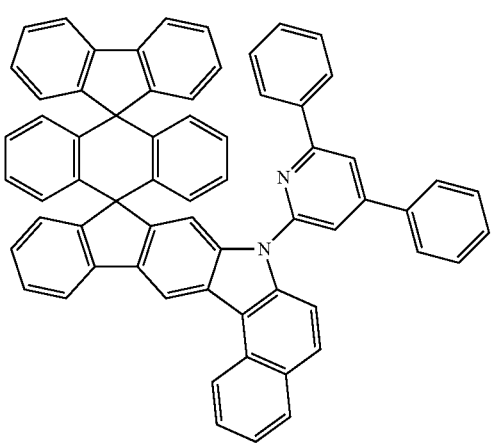

10-16
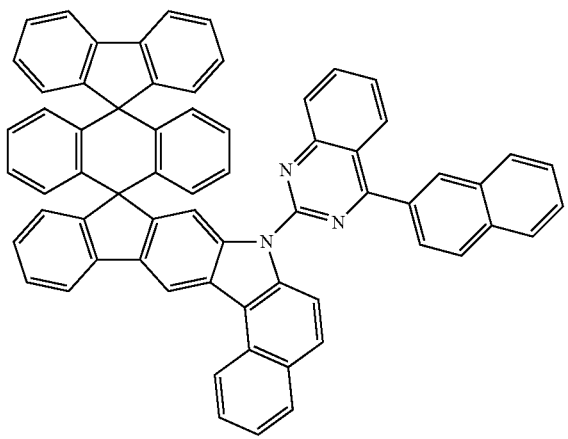
10-17
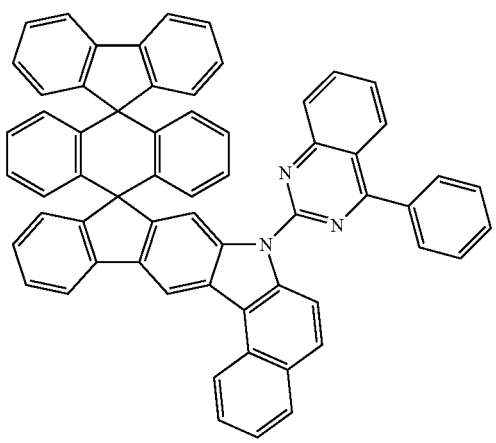
10-18
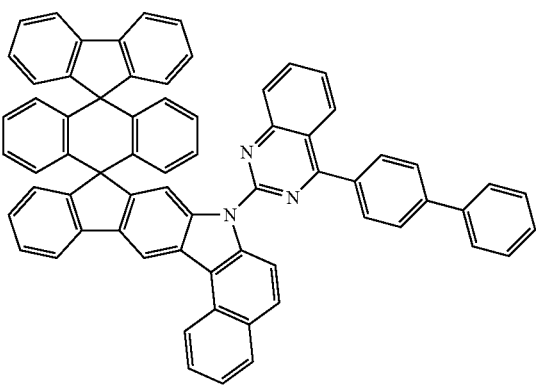
10-19
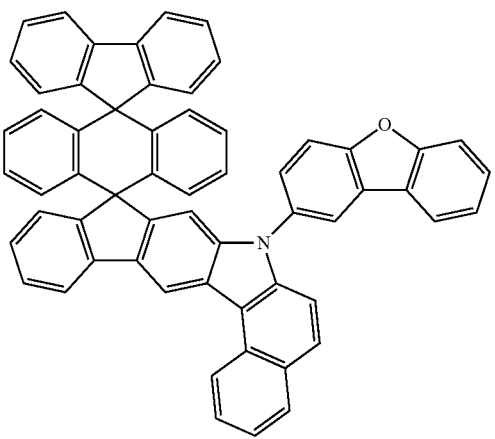
10-20
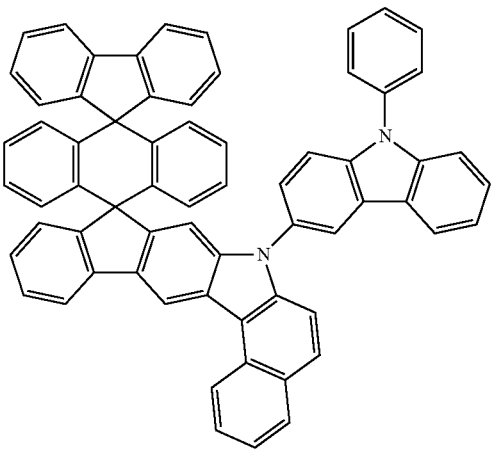
10-21
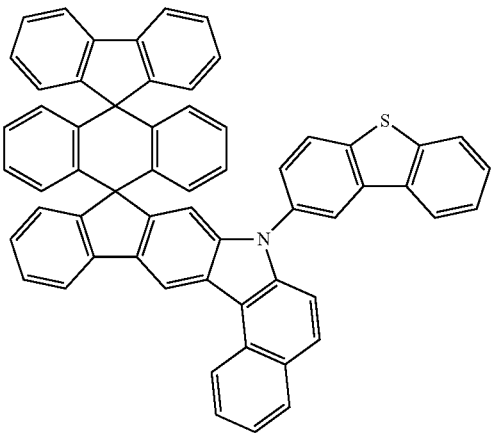

10-22
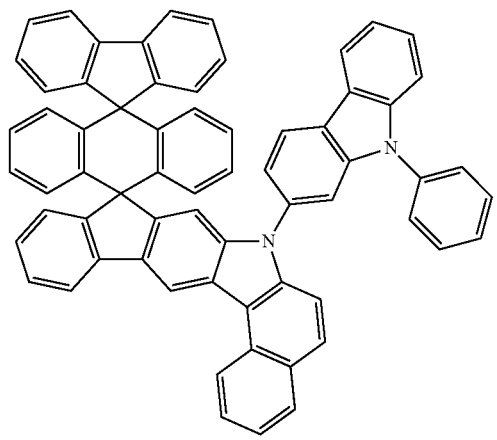
10-23
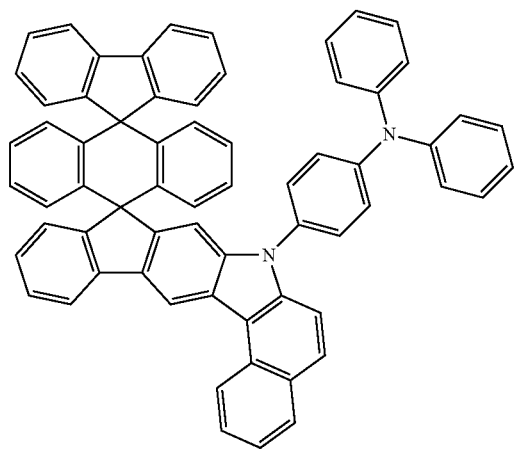
10-24
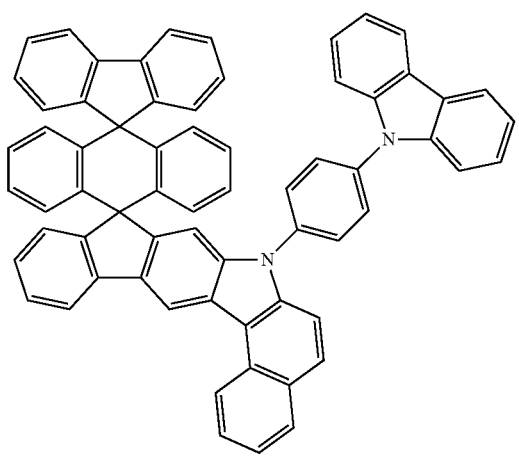
11-1
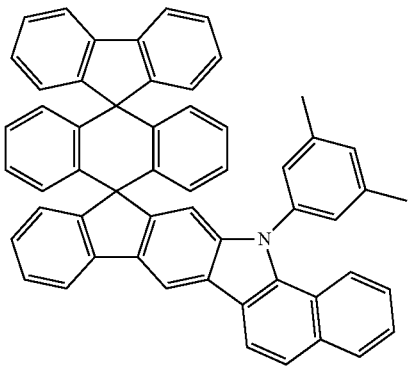
11-2
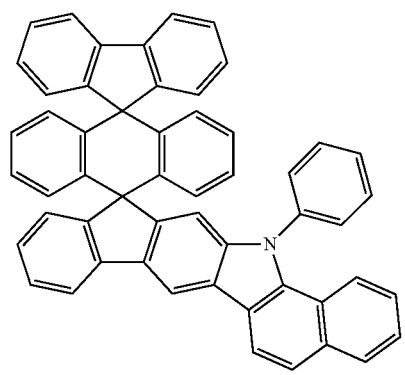
11-3
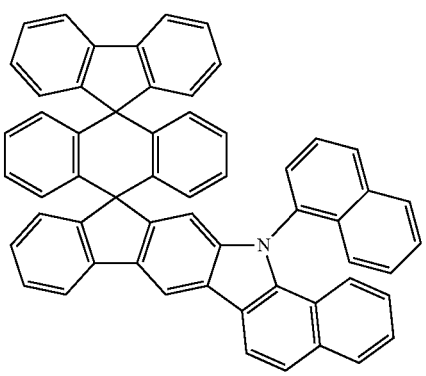
11-4
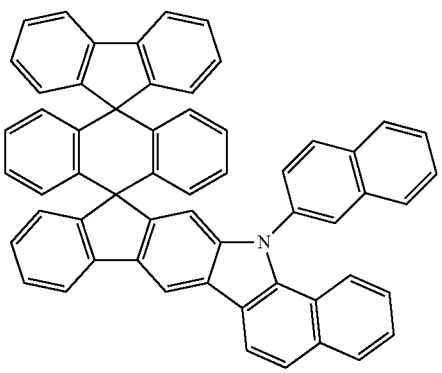

11-5
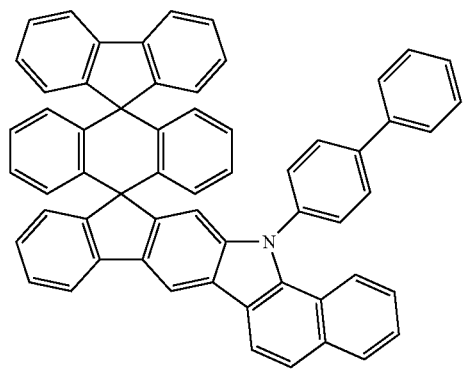
11-9
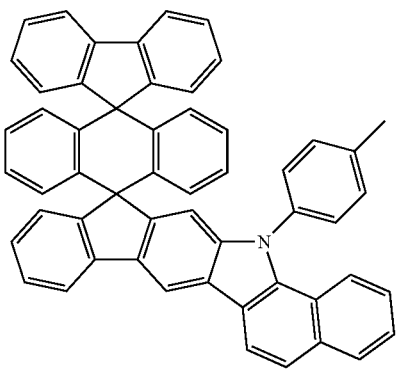
11-6
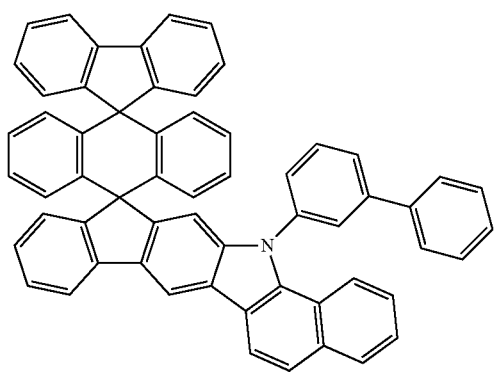
11-10
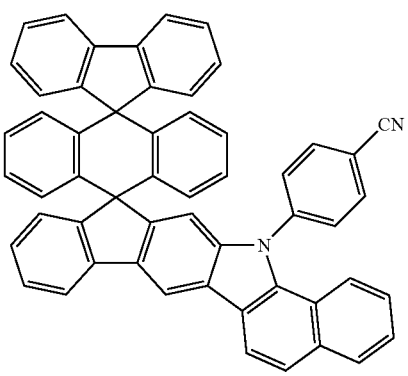
11-7
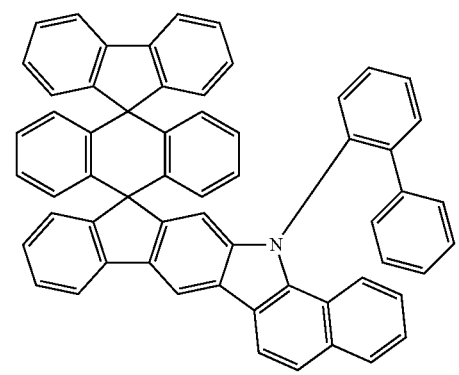
11-11
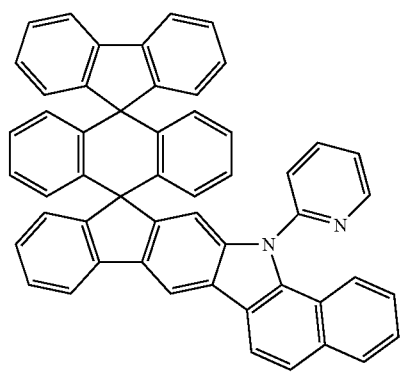
11-8
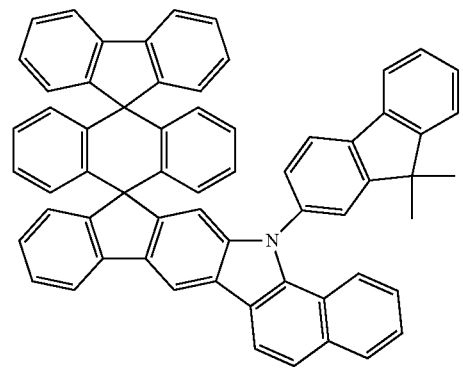
11-12
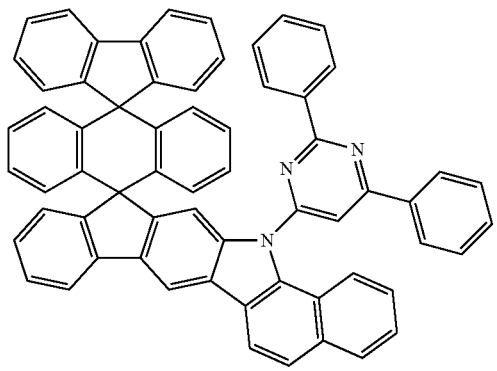

111
-continued
11-13
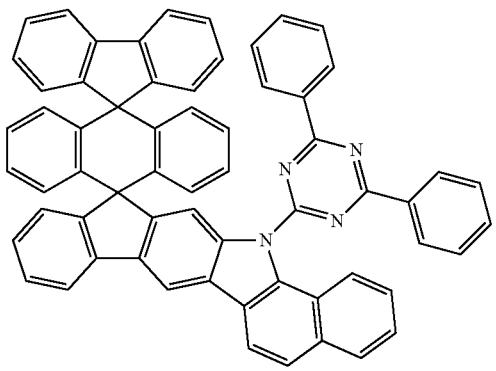
11-14
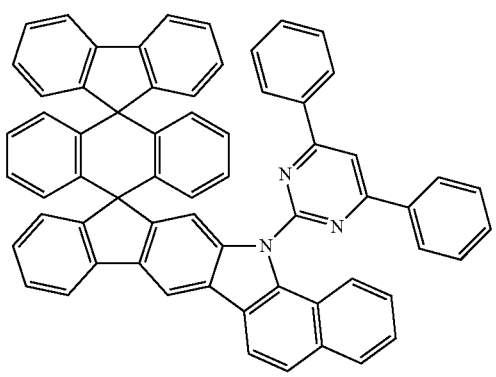
11-15
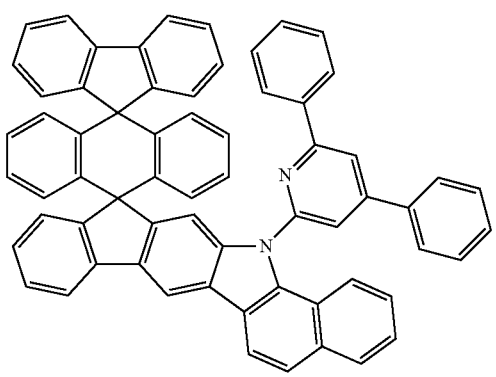
11-16
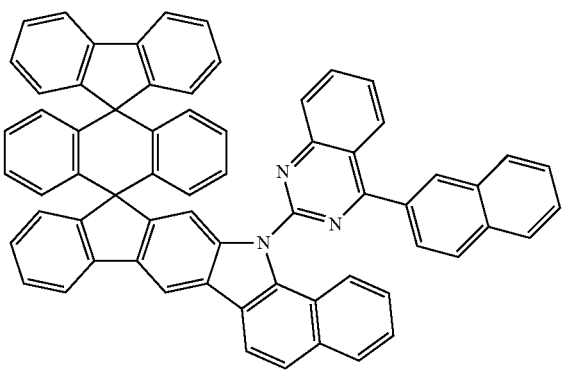
112
-continued
11-17
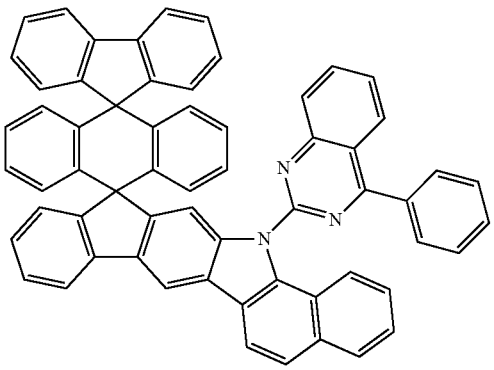
11-18
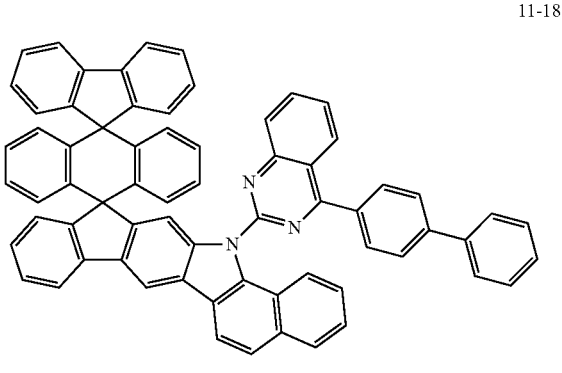
11-19
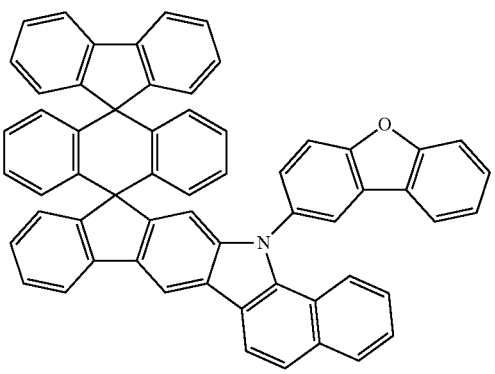
11-20
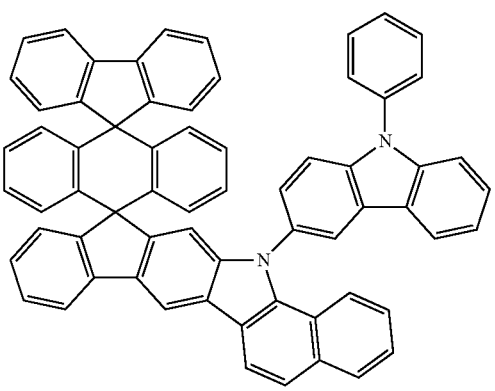

11-21
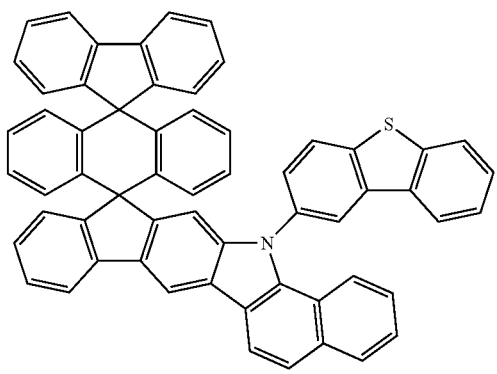
11-22
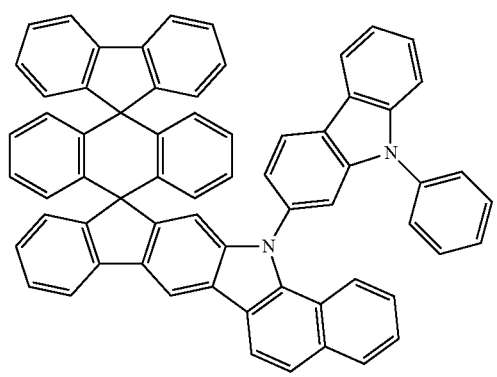
11-23
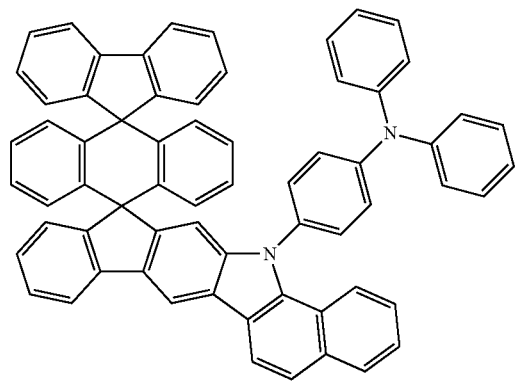
11-24
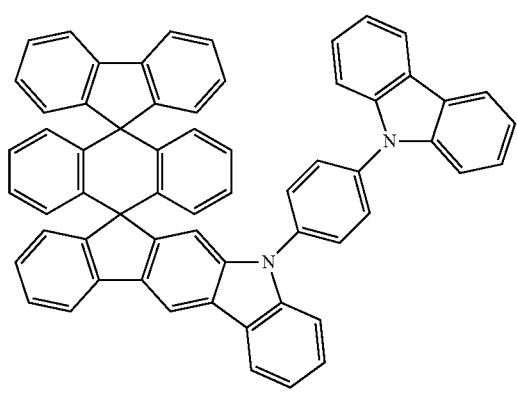
12-1
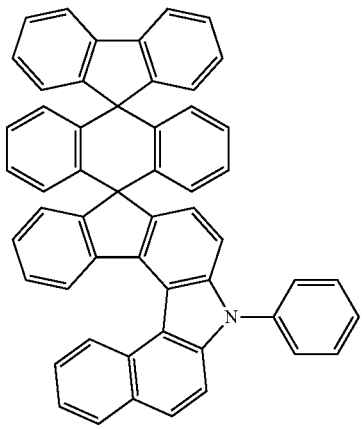
12-2
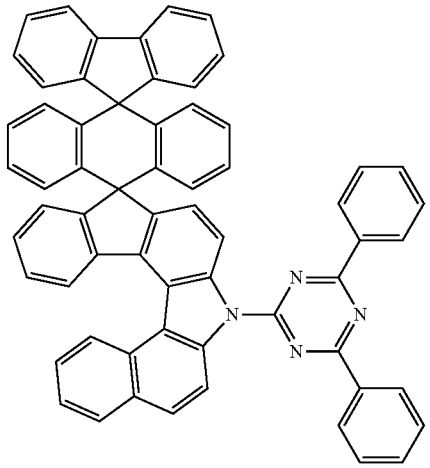
12-3
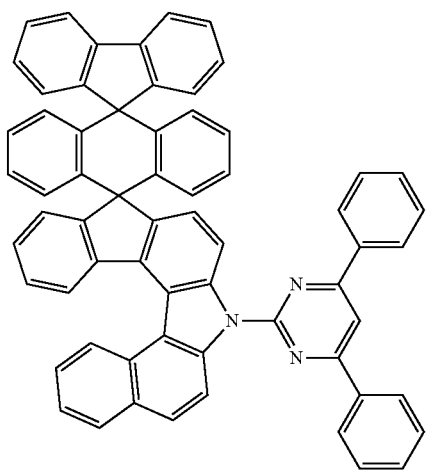

12-4
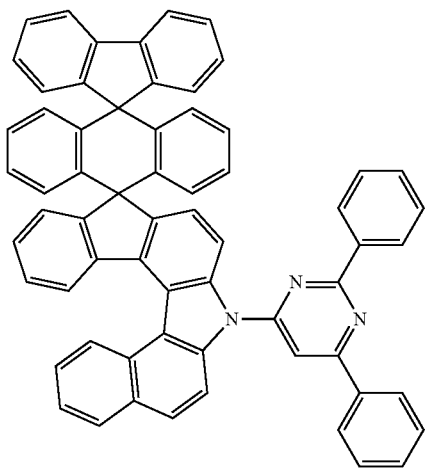
12-7
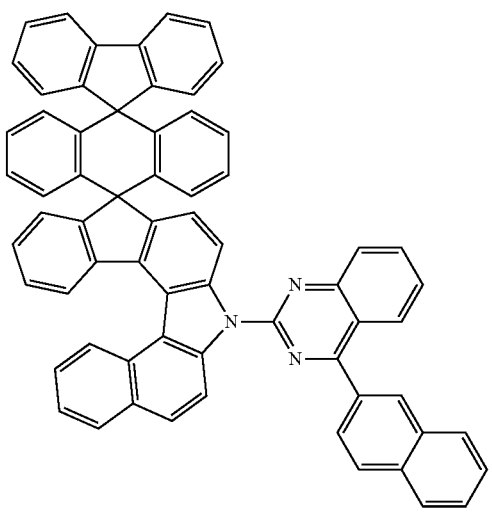
12-5
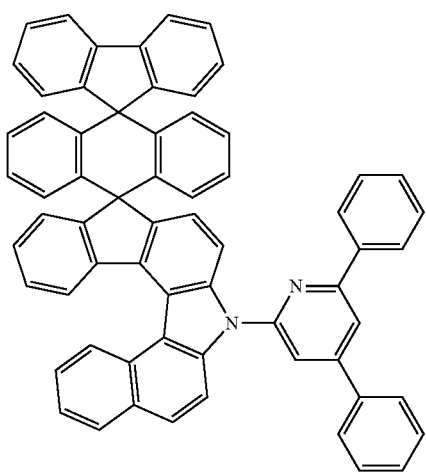
12-8
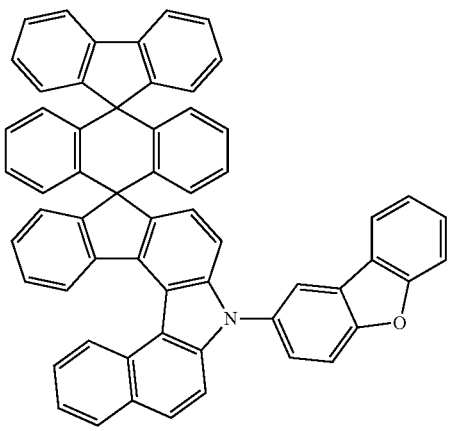
12-6
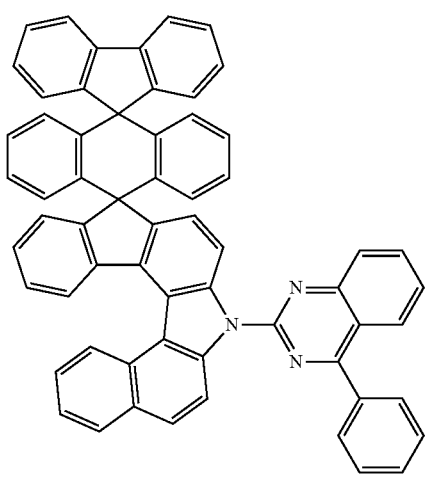
12-9
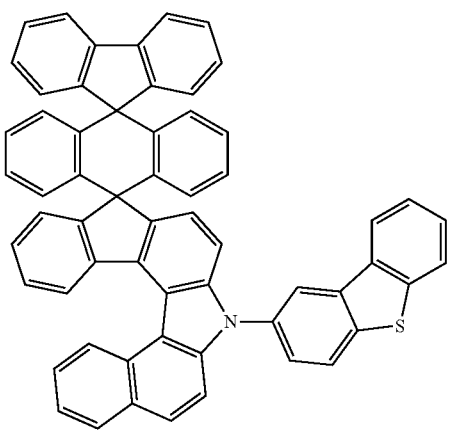

12-10
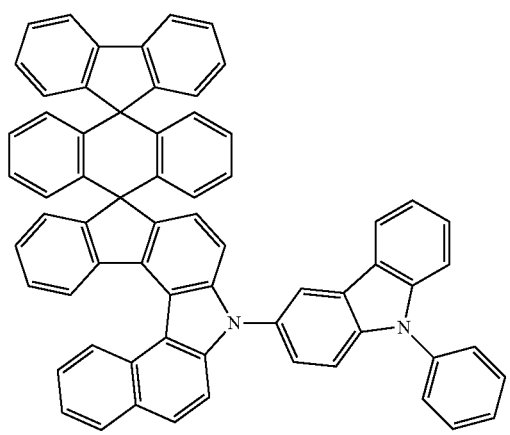
13-2
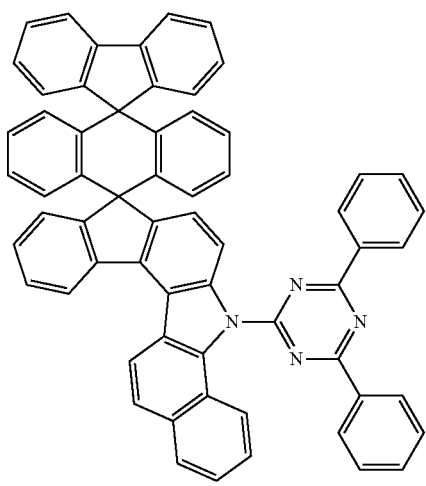
12-11
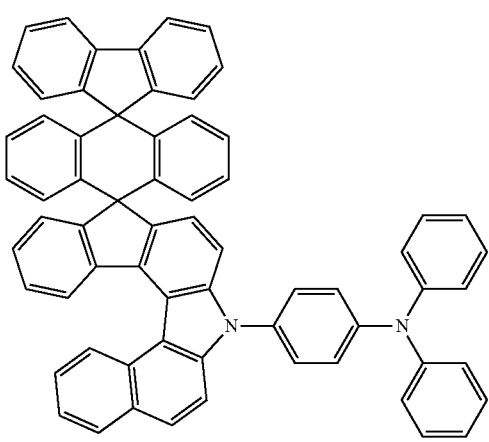
13-3
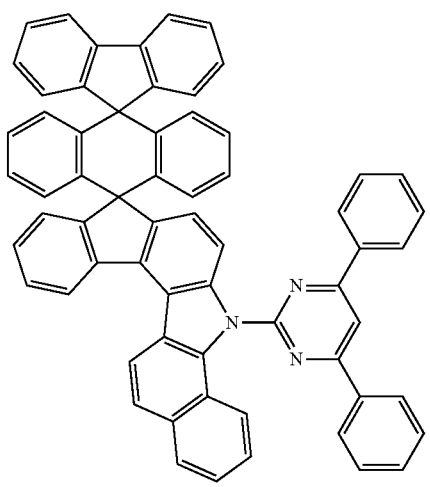
13-1
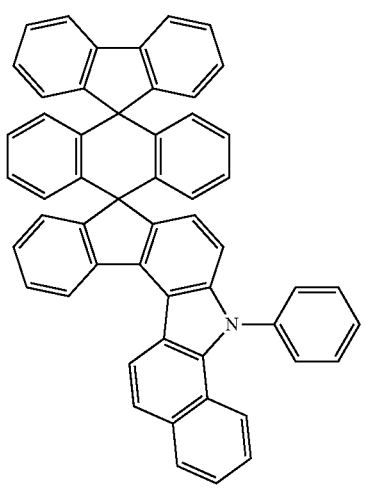
13-4
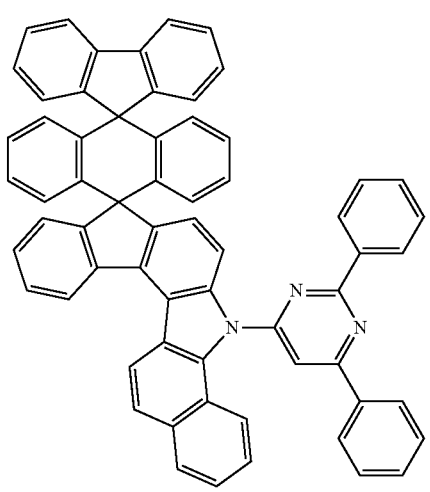

-continued
13-5
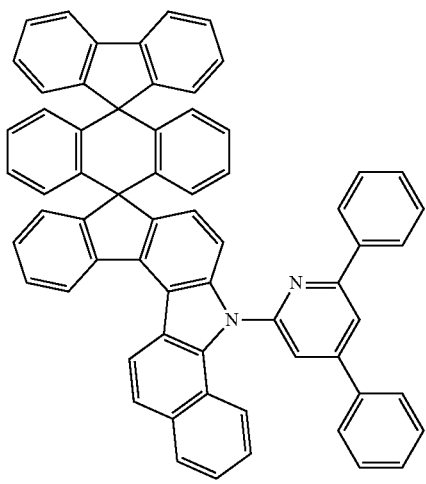
13-6
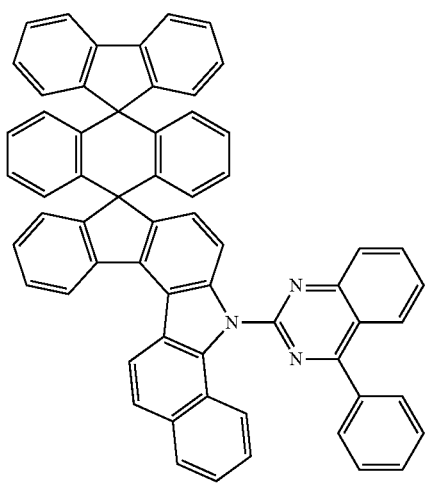
13-7
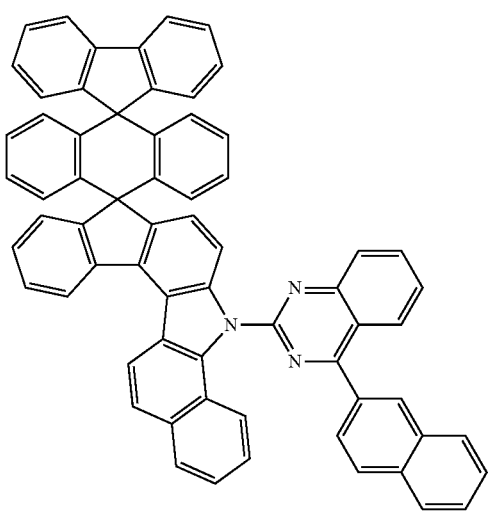
-continued
13-8
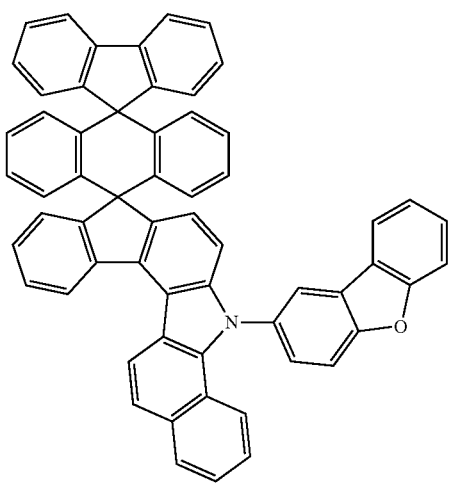
13-9
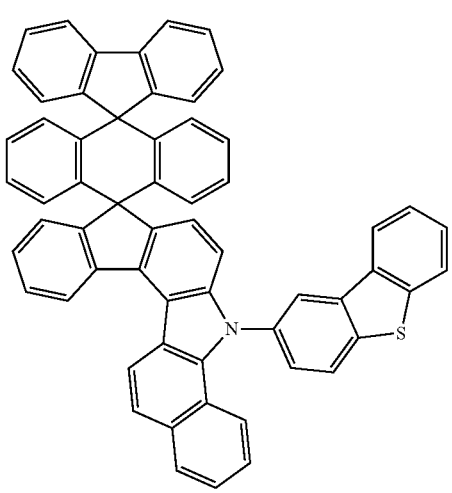
13-10
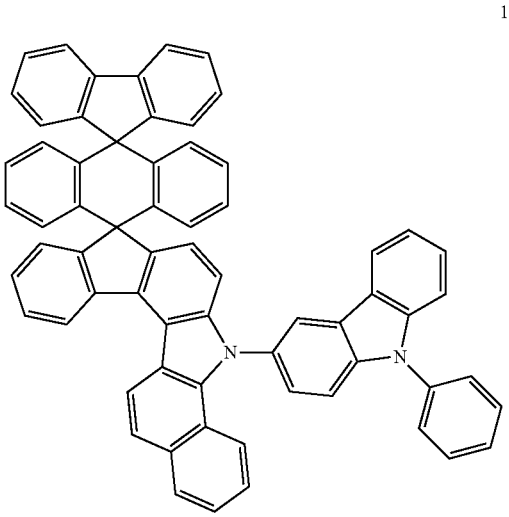

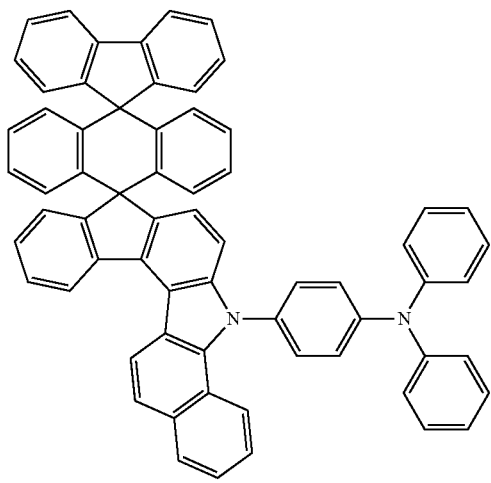
13-11
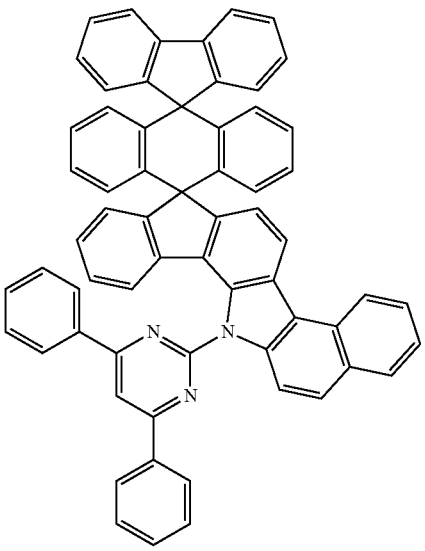
14-3
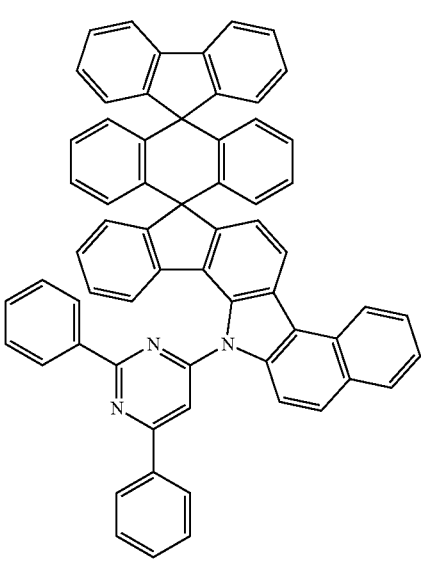
14-4
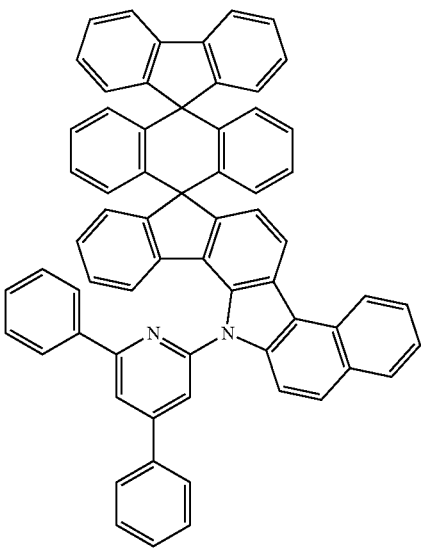
14-5

-continued
14-6
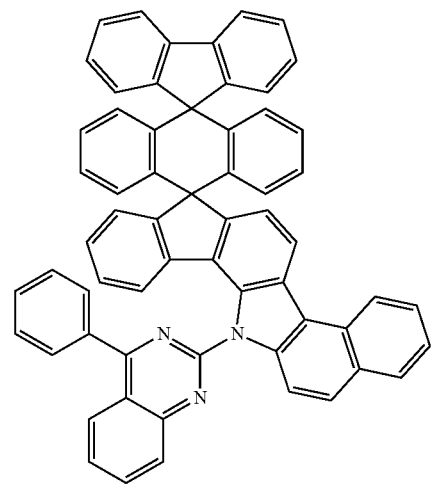
14-7
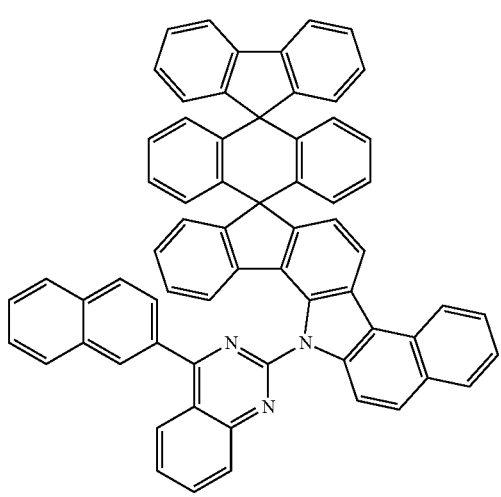
14-8
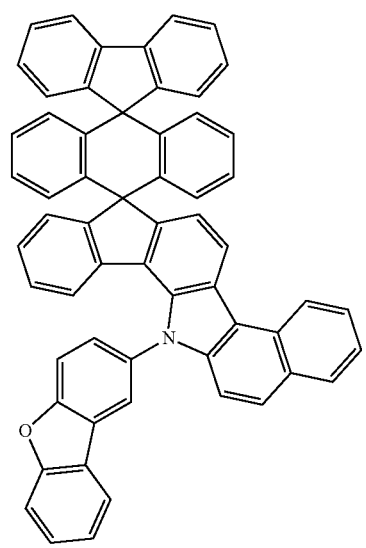
-continued
14-9
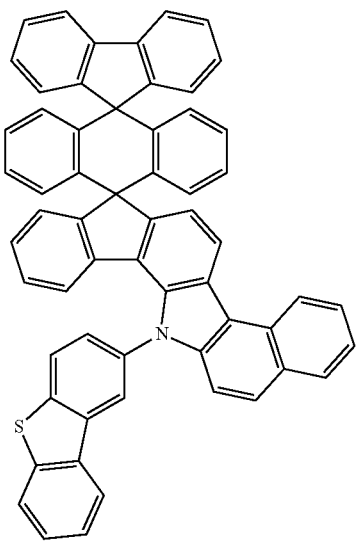
14-10
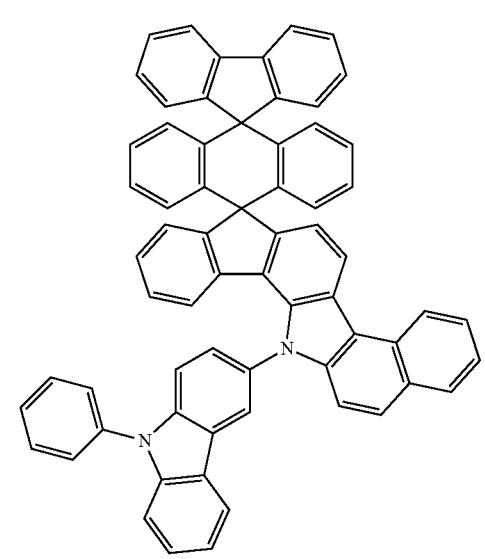
14-11
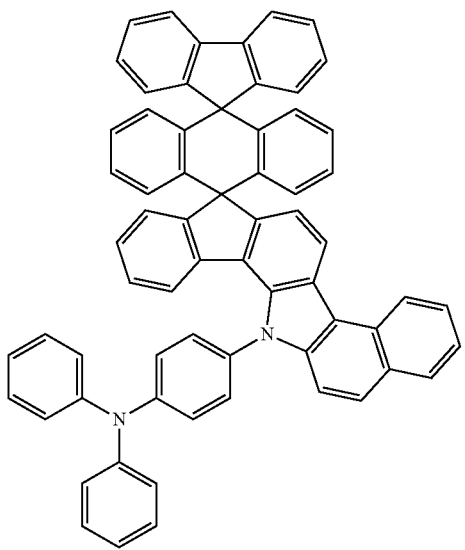

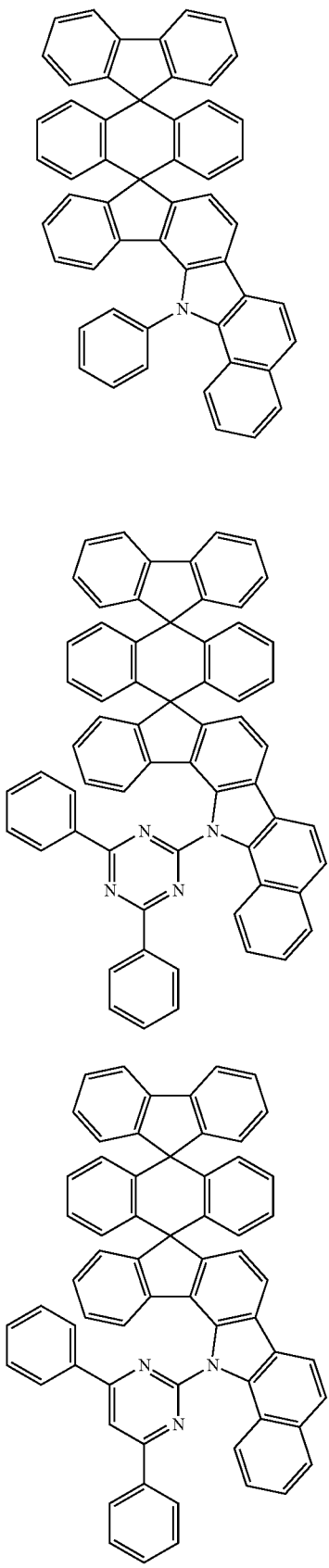
15-1
15-2
15-3
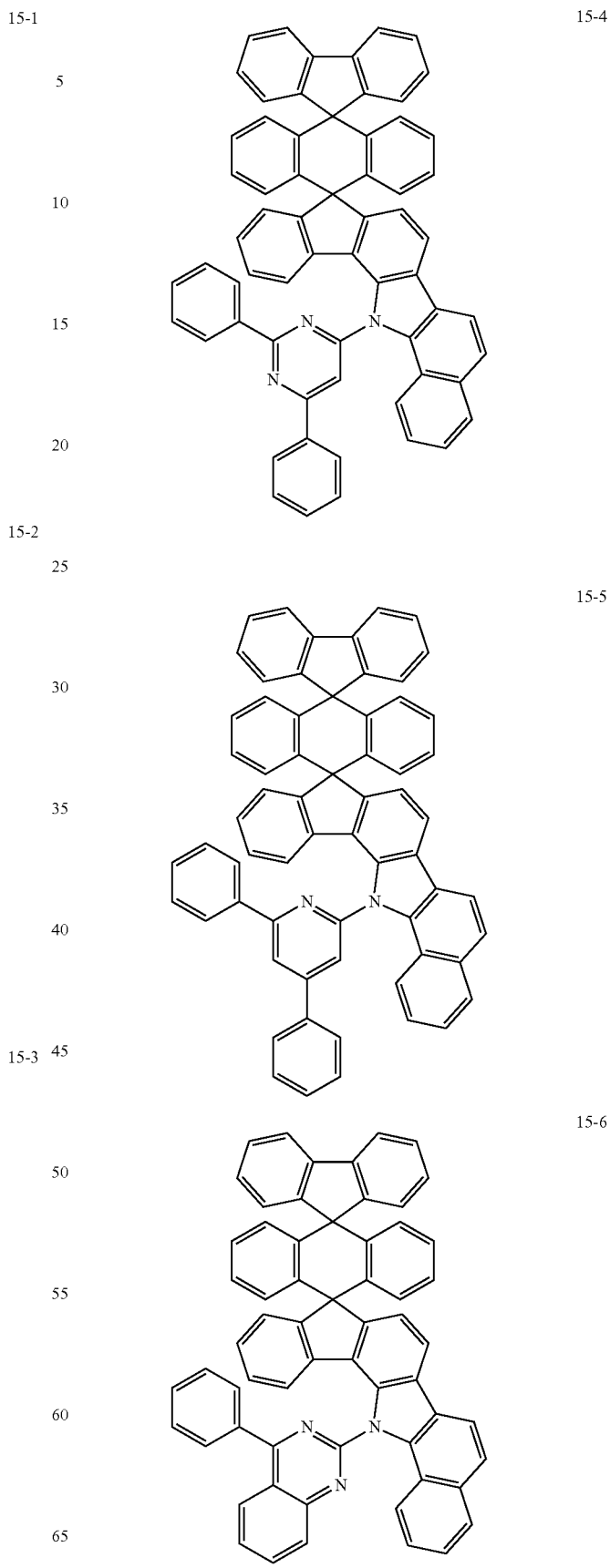
15-4
15-5
15-6

15-7
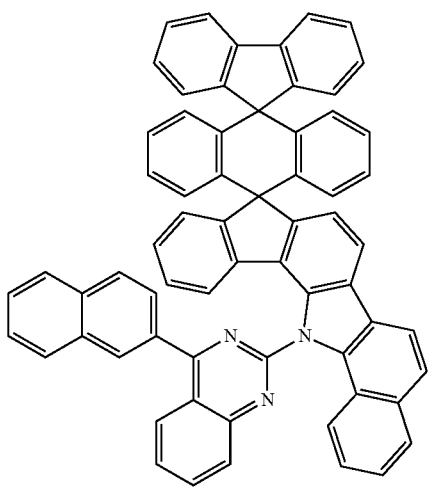
15-8
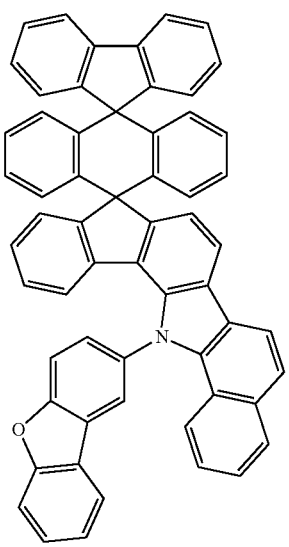
15-9
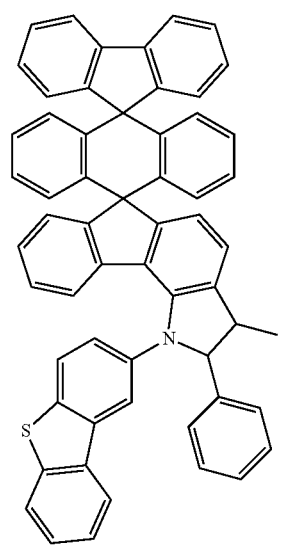
15-10
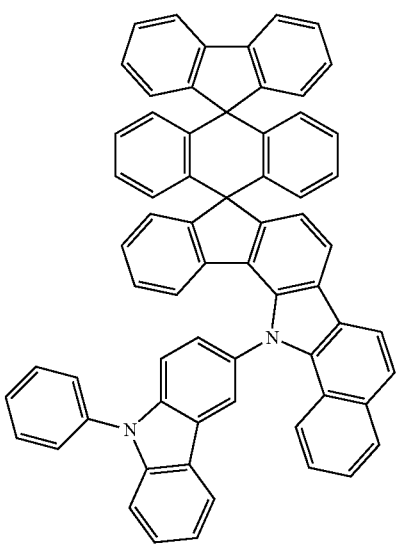
15-11
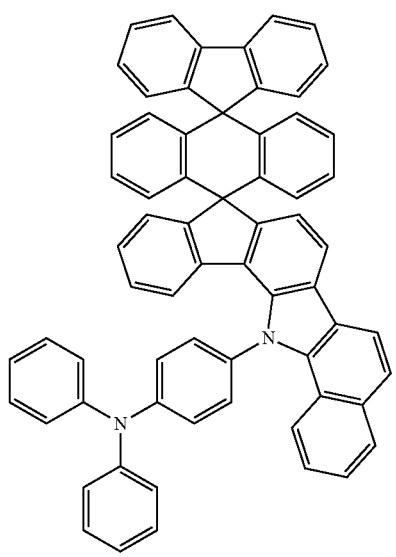
16-1
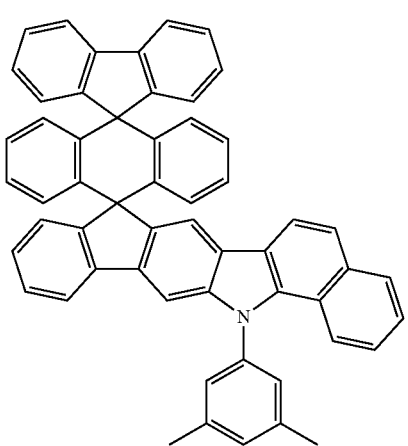

16-2
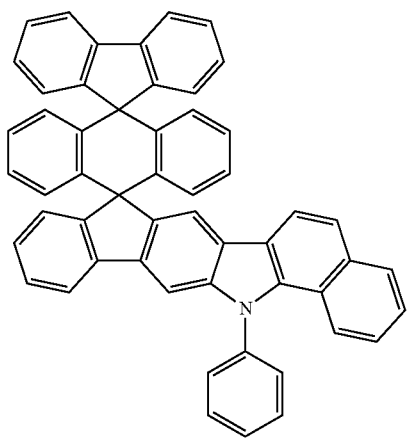
16-3
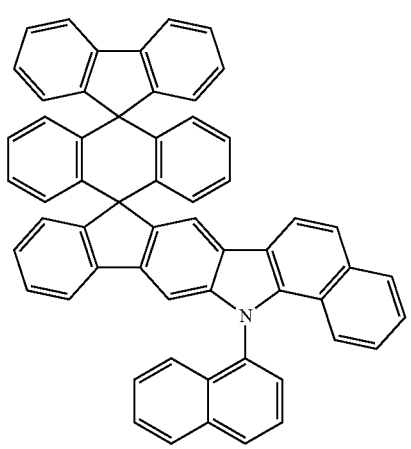
16-4
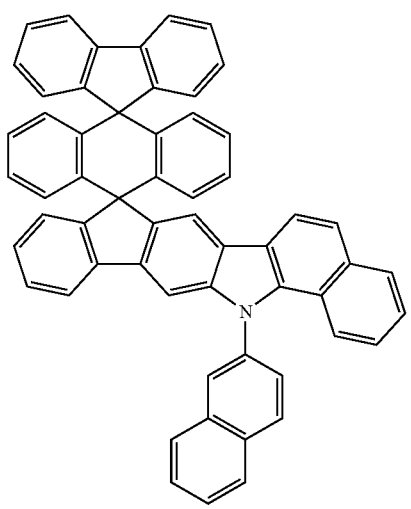
16-5
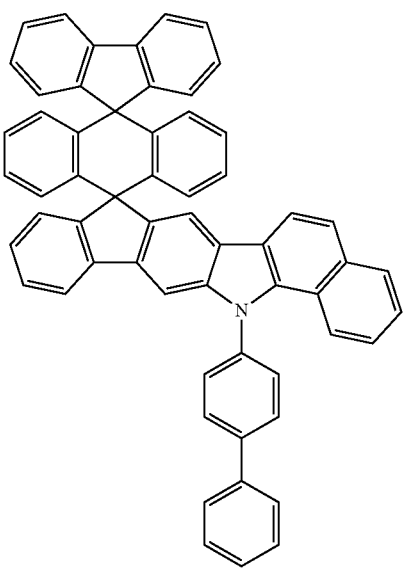
16-6
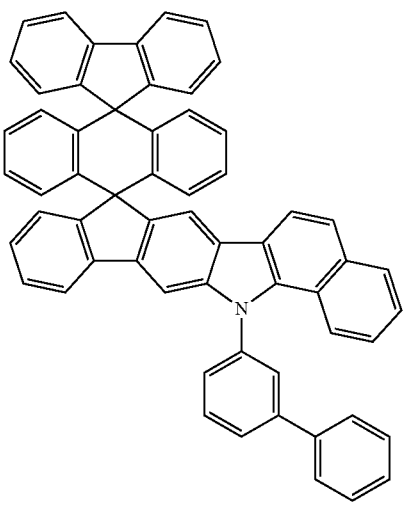
16-7
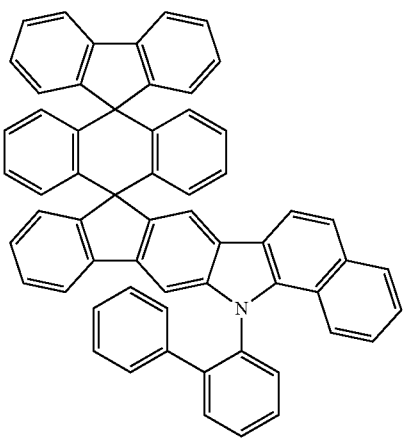

16-8
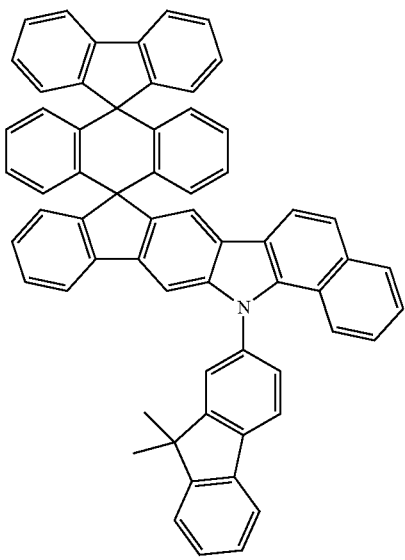
16-9
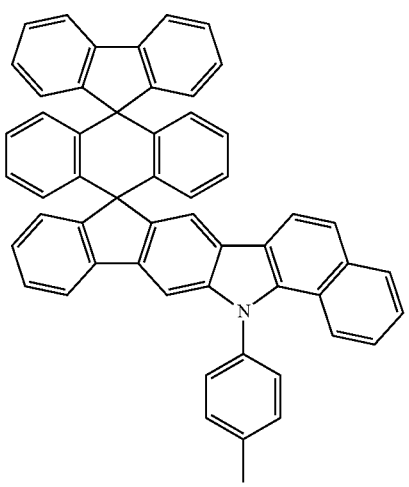
16-10
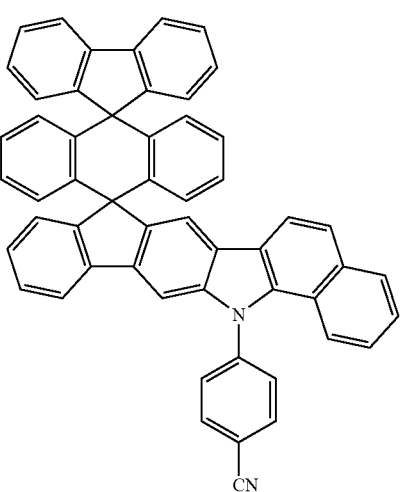
16-11
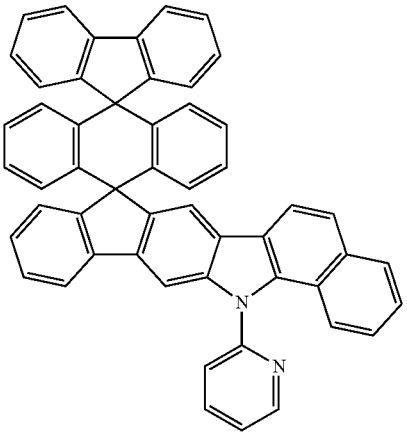
16-12
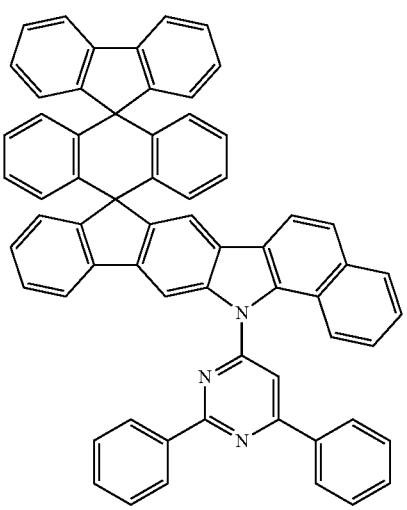
16-13
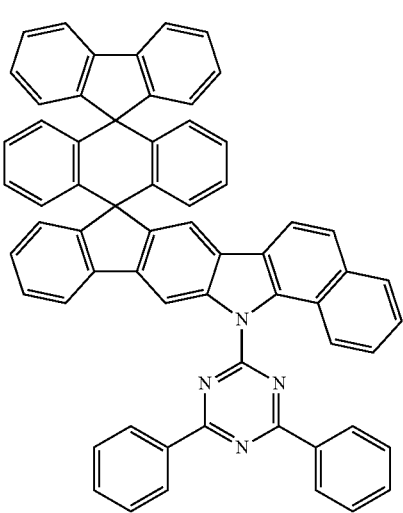

16-14
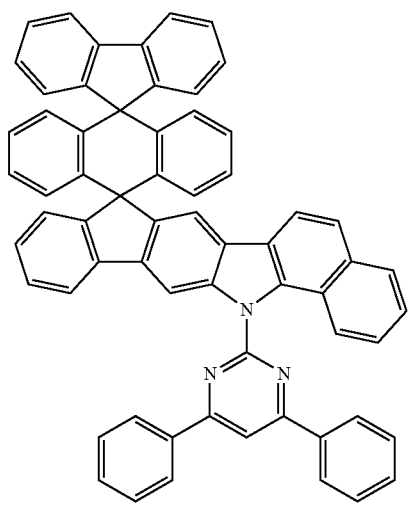
16-15
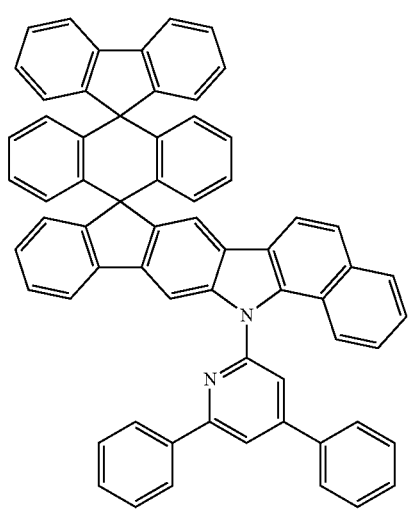
16-16
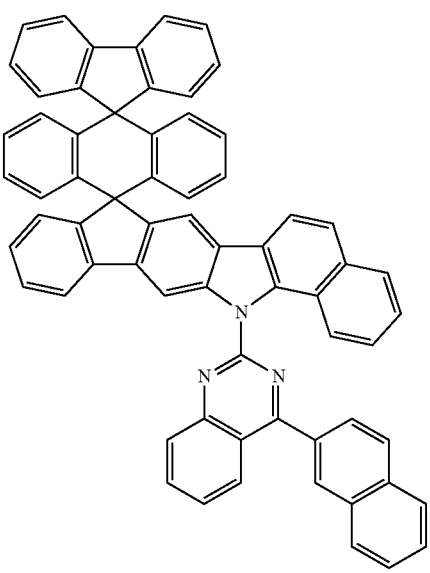
16-17
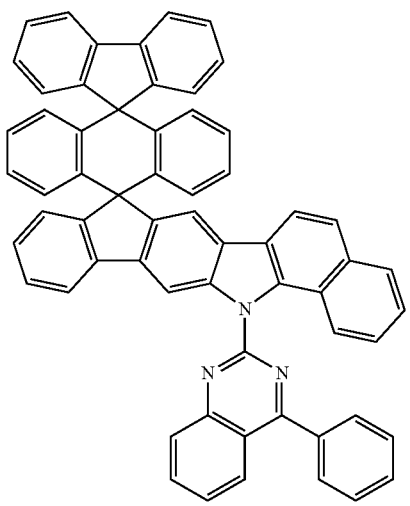
16-18
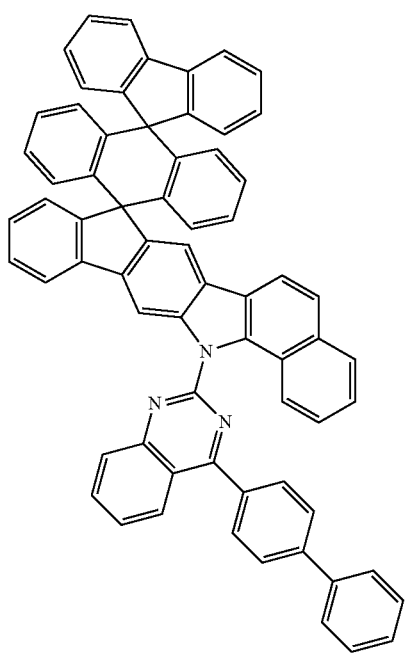
16-19
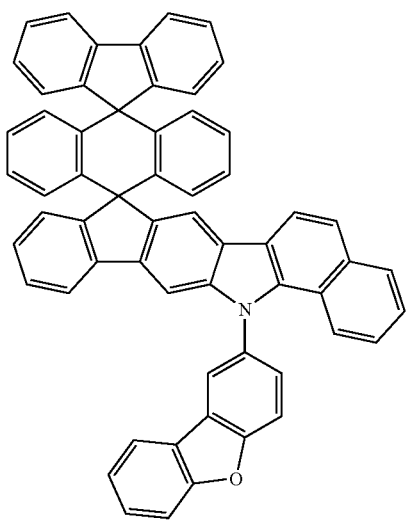

16-20
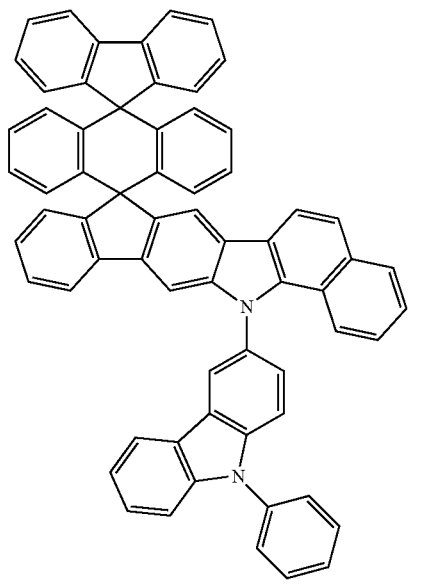
16-21
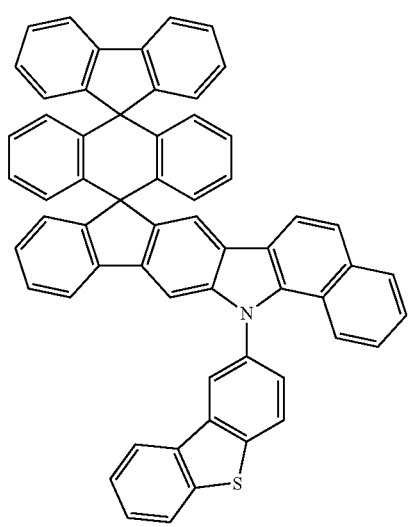
16-22
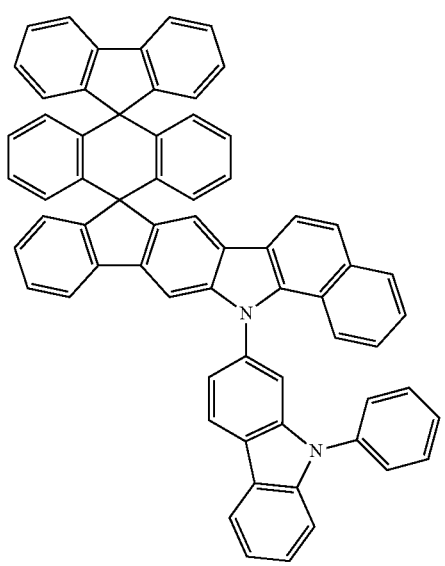
16-23
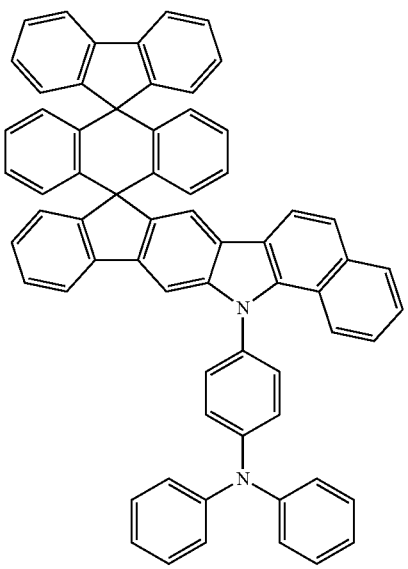
16-24
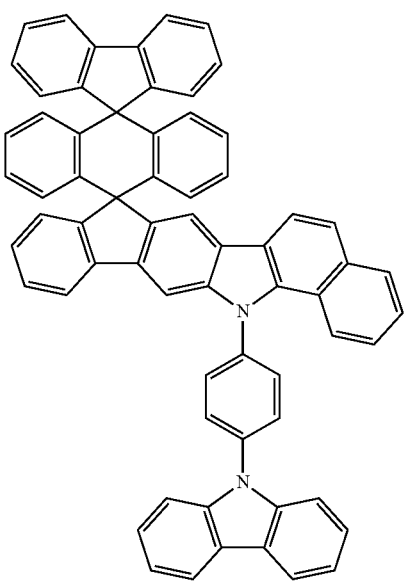
17-1
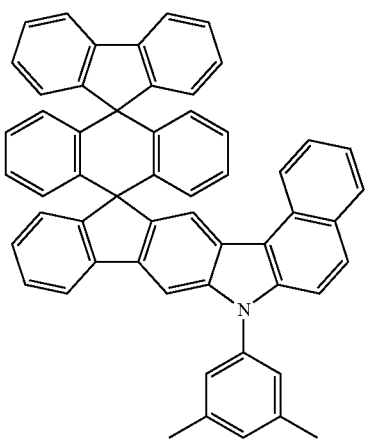

-continued
17-2
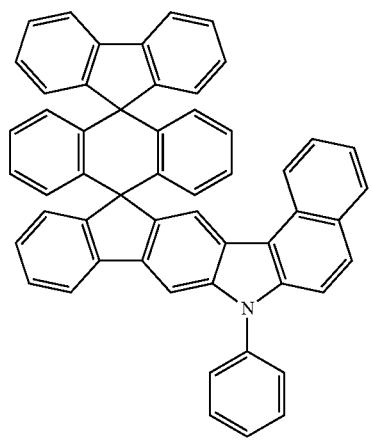
17-3
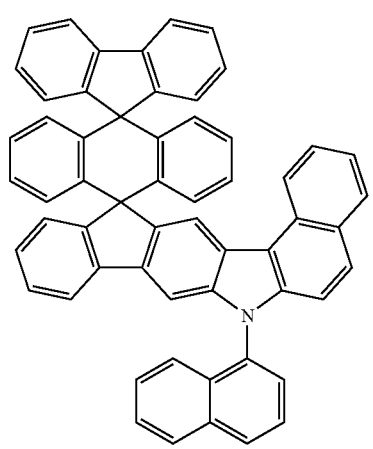
17-4
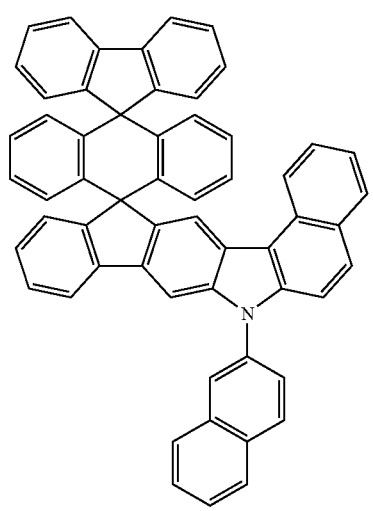
17-5
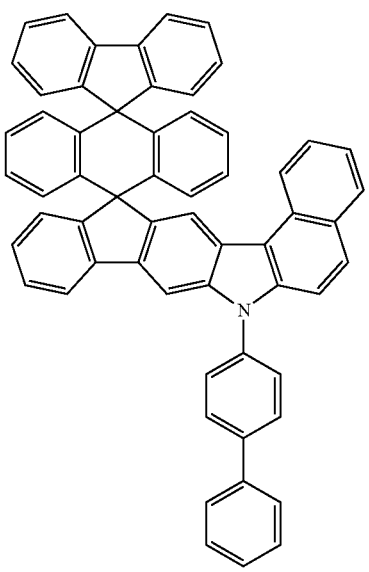
17-6
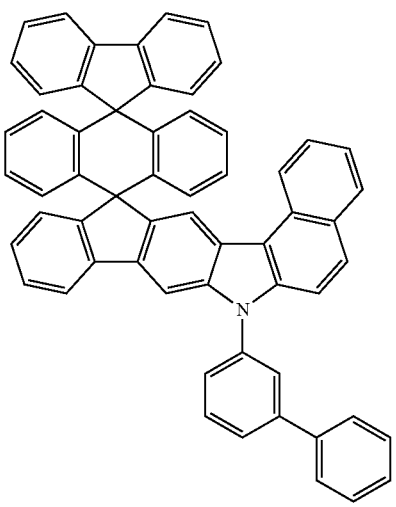
17-7
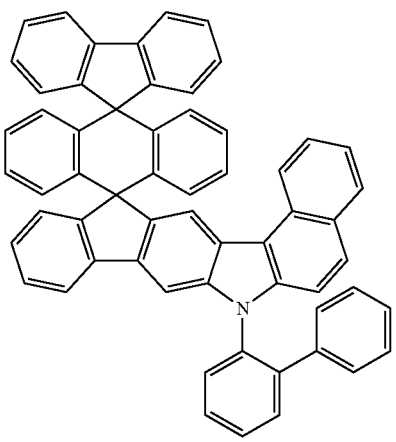

17-8
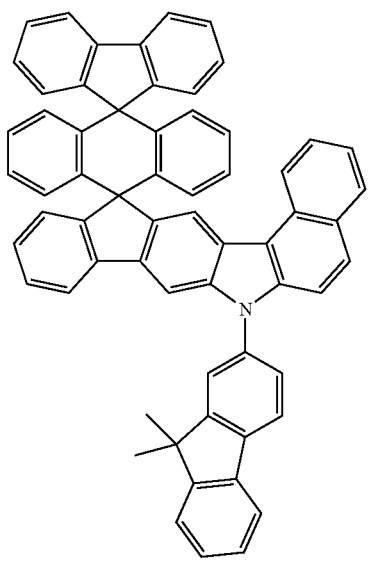
17-9
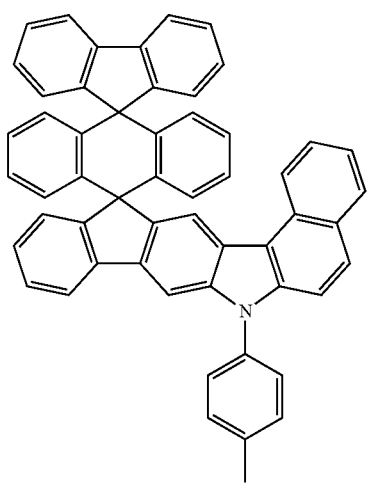
17-10
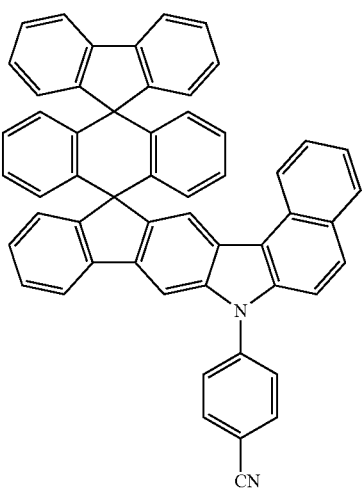
17-11
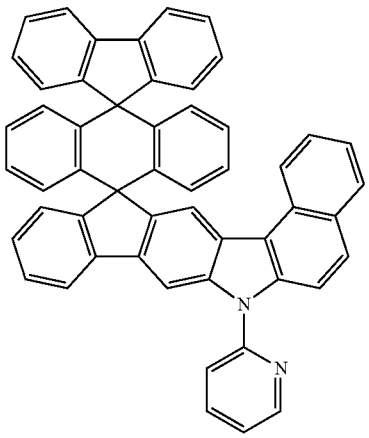
17-12
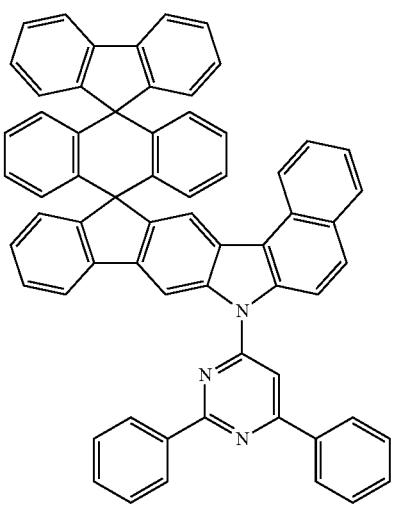
17-13
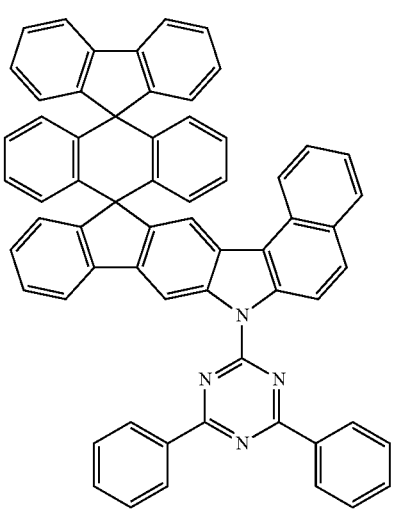

17-14
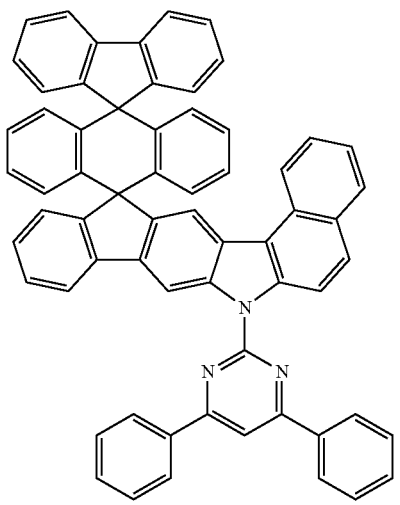
17-15
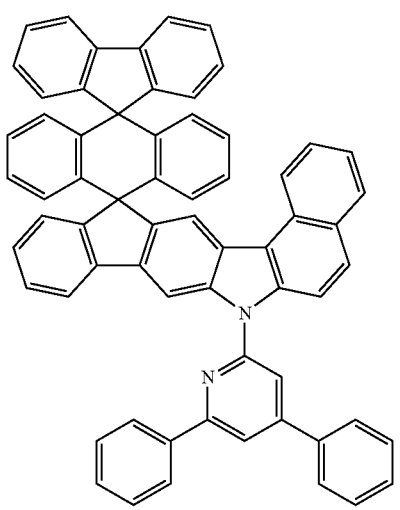
17-16
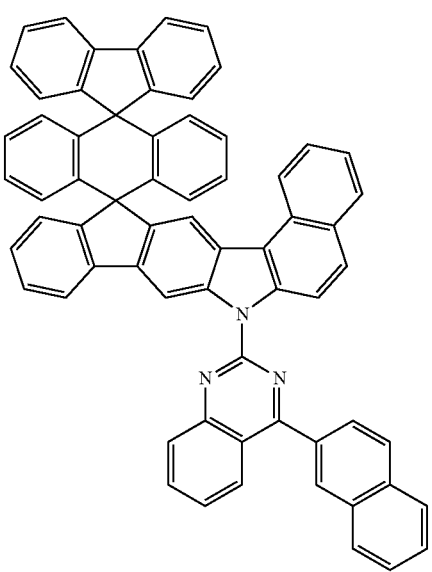
17-17
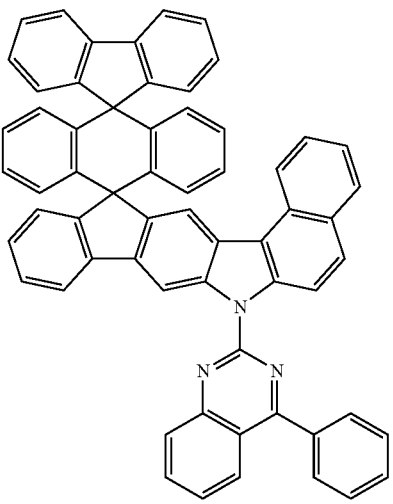
17-18
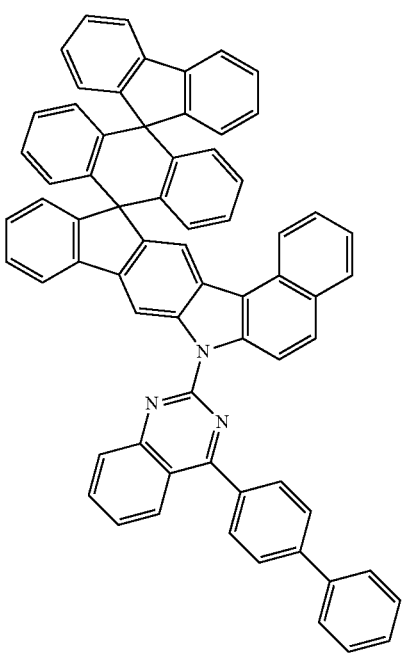
17-19
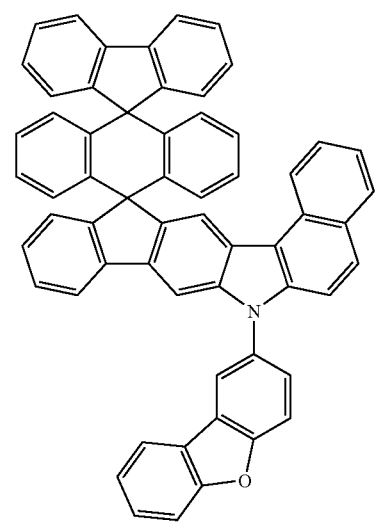

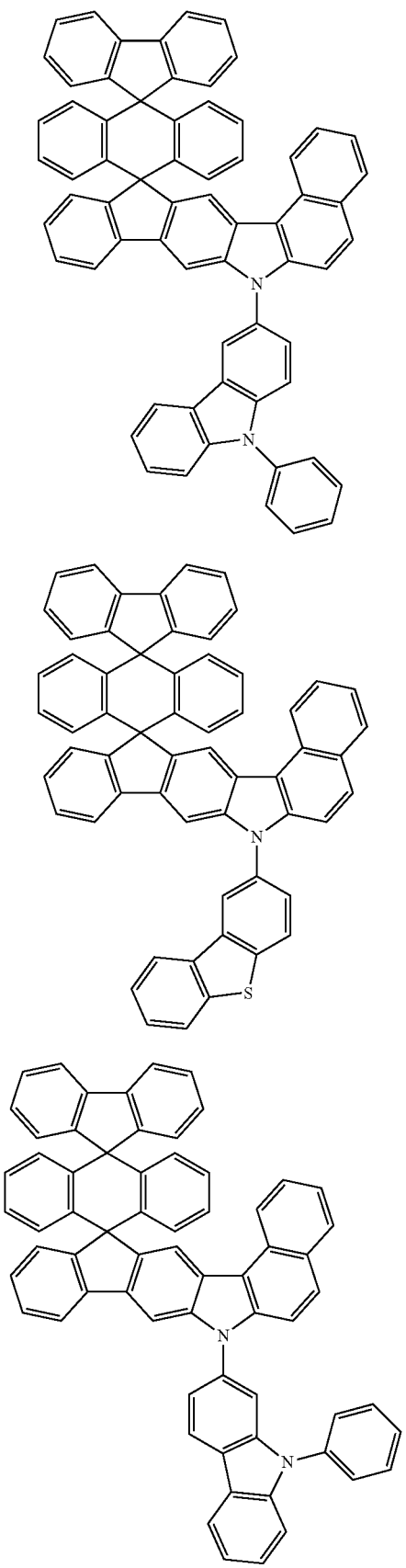
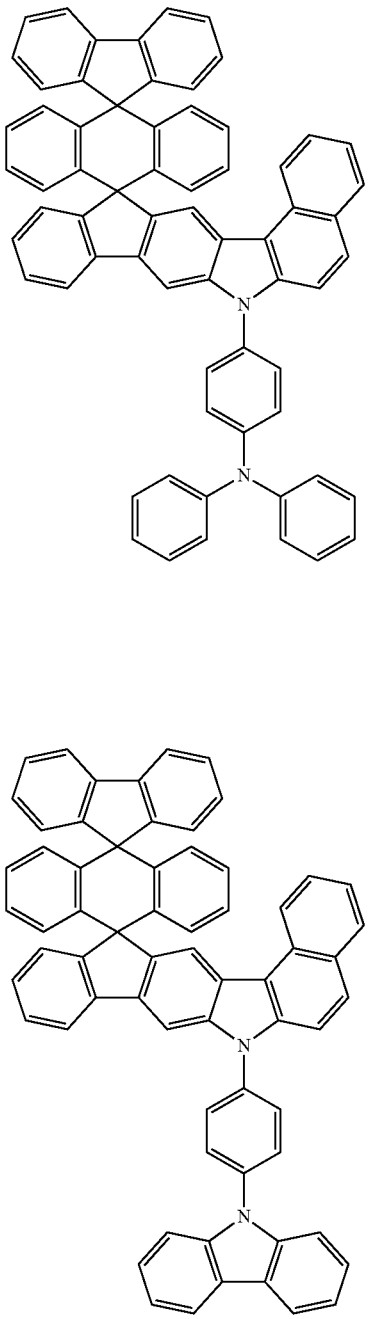

In addition, one embodiment of the present specification provides an organic electronic device comprising the organic compound represented by Chemical Formula 1.

In one embodiment of the present specification, the organic electronic device may be formed to have a structure including a first electrode, a second electrode and one or more organic material layers disposed therebetween.

One embodiment of the present specification relates to an organic electronic device comprising the organic compound having a double spiro structure represented by Chemical Formula 1 in one or more layers of the organic material layers, and including a compound of the following Chemical Formula 18 in a light emitting layer.

[Chemical Formula 18]

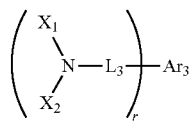

In Chemical Formula 18,

Ar$_3$ is a benzofluorene skeleton, a fluoranthene skeleton, a pyrene skeleton or a chrysene skeleton, L$_3$ is a single bond, a C$_6$ to C$_{30}$ arylene group or a C$_5$ to C$_{30}$ divalent heterocyclic group, X$_1$ and X$_2$ are the same as or different from each other, and each independently selected from the group consisting of a substituted or unsubstituted C$_6$ to C$_{30}$ aryl group, a substituted or unsubstituted C$_5$ to C$_{30}$ heterocyclic group, a substituted or unsubstituted C$_1$ to C$_{30}$ alkyl group and a substituted or unsubstituted C$_7$ to C$_{30}$ aralkyl group, and X$_1$ and X$_2$ may bond to each other to form a saturated or unsaturated ring, r is an integer of 1 or greater, and when r is 2 or greater, X$_1$s are the same as or different from each other, and X$_2$s are the same as or different from each other.

In one embodiment of the present specification, L$_3$ is a single bond or a C$_6$ to C$_{30}$ arylene group.

In another embodiment, L$_3$ is a single bond.

In one embodiment of the present specification, Ar$_3$ is a benzofluorene skeleton, a fluoranthene skeleton or a pyrene skeleton.

In another embodiment, Ar$_3$ is a pyrene skeleton.

In one embodiment of the present specification, X$_1$ and X$_2$ are the same as or different from each other, and each independently a substituted or unsubstituted C$_6$ to C$_{30}$ aryl group, a substituted or unsubstituted C$_5$ to C$_{30}$ heterocyclic group or a substituted or unsubstituted C$_1$ to C$_{30}$ alkyl group.

In another embodiment, X$_1$ and X$_2$ are the same as or different from each other, and each independently a substituted or unsubstituted C$_6$ to C$_{30}$ aryl group.

In another embodiment, X$_1$ and X$_2$ are the same as or different from each other, and each independently a phenyl group unsubstituted or substituted with a germanium group.

In another embodiment, X$_1$ and X$_2$ are the same as or different from each other, and each independently a phenyl group unsubstituted or substituted with a trimethylgermanium group.

In one embodiment of the present specification, Ar$_3$ is a pyrene skeleton, L$_3$ is a single bond, X$_1$ and X$_2$ are the same as or different from each other and each independently an aryl group unsubstituted or substituted with a germanium group, and r is 2 in the organic electronic device.

In another embodiment, Ar$_3$ is a pyrene skeleton, L$_3$ is a single bond, X$_1$ is a phenyl group, X$_2$ is a phenyl group substituted with a trimethylgermanium group, and r is 2 in the organic electronic device.

In one embodiment of the present specification, the compound of Chemical Formula 18 may be included as a dopant of the light emitting layer.

One embodiment of the present specification relates to an organic electronic device comprising the compound represented by Chemical Formula 1 in one or more layers of the organic material layers, and comprising a compound of the following Chemical Formula 19 in a light emitting layer among the organic material layers.

[Chemical Formula 19]

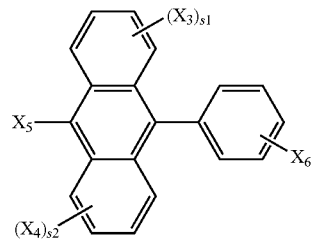

In Chemical Formula 19,

X$_5$ is a substituted or unsubstituted 1-naphthyl group, a substituted or unsubstituted 2-naphthyl group, a substituted or unsubstituted 1-anthryl group, a substituted or unsubstituted 2-anthryl group, a substituted or unsubstituted 1-phenanthryl group, a substituted or unsubstituted 2-phenanthryl group, a substituted or unsubstituted 3-phenanthryl group, a substituted or unsubstituted 4-phenanthryl group, a substituted or unsubstituted 9-phenanthryl group, a substituted or unsubstituted 1-naphthacenyl group, a substituted or unsubstituted 2-naphthacenyl group, a substituted or unsubstituted 9-naphthacenyl group, a substituted or unsubstituted 1-pyrenyl group, a substituted or unsubstituted 2-pyrenyl group, a substituted or unsubstituted 4-pyrenyl group, a substituted or unsubstituted 3-methyl-2-naphthyl group, a substituted or unsubstituted 4-methyl-1-naphthyl group or the following structural formula

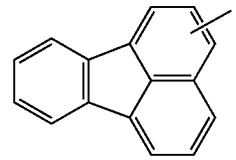

X$_6$ is a group selected from the group consisting of a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, a 4''-t-butyl-p-terphenyl-4-yl group and a 3-fluoranthenyl group, X$_3$ and X$_4$ are the same as or different from each other, and each independently a substituted or unsubstituted aryl group having 6 to 50 carbon atoms, a substituted or unsubstituted heteroaryl group having 5 to 50 nuclear atoms, a substituted or unsubstituted alkyl group having 1 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 nuclear atoms, a substituted or unsubstituted arylthio group having 5 to 50 nuclear atoms, a substituted or unsubstituted alkoxycarbonyl group having 1 to 50 carbon atoms, a carboxyl group, a halogen atom, a cyano group, a nitro group or a hydroxyl group, and s1 and s2 are each an integer of 0 to 4.

In one embodiment of the present specification, $X_5$ is a substituted or unsubstituted 1-naphthyl group or a substituted or unsubstituted 2-naphthyl group.

In another embodiment, $X_5$ is a substituted or unsubstituted 1-naphthyl group.

In another embodiment, $X_5$ is a 1-naphthyl group.

In one embodiment of the present specification, $X_6$ is a phenyl group, a 1-naphthyl group or a 2-naphthyl group.

In another embodiment, $X_6$ is a 2-naphthyl group.

In one embodiment of the present specification, $X_3$ and $X_4$ are the same as or different from each other, and each independently a substituted or unsubstituted $C_6$ to $C_{50}$ aryl group or a substituted or unsubstituted $C_5$ to $C_{50}$ heteroaryl group.

In one embodiment of the present specification, s1 and s2 are each an integer of 0 to 2.

In another embodiment, s1 and s2 are 0.

In one embodiment of the present specification, $X_5$ and $X_6$ are the same as or different from each other, and each independently a 1-naphthyl group or a 2-naphthyl group, and s1 and s2 are 0 in the organic electronic device.

In one embodiment of the present specification, the compound of Chemical Formula 19 may be comprised as a host of the light emitting layer.

In one embodiment of the present specification, one or more layers of the organic material layers comprise the organic compound having a double spiro structure represented by Chemical Formula 1, and the compound of Chemical Formula 18 and the compound of Chemical Formula 19 are comprised in the light emitting layer among the organic material layers in the organic electronic device.

In another embodiment, the organic electronic device comprises the organic compound having a double spiro structure represented by Chemical Formula 1 in one or more layers of the organic material layers, comprises the compound of Chemical Formula 18 in which $Ar_3$ is a pyrene skeleton, $L_3$ is a single bond, $X_1$ and $X_2$ are an aryl group unsubstituted or substituted with a germanium group, and r is 2, and includes the compound of Chemical Formula 19 in which $X_5$ and $X_6$ are the same as or different from each other and each independently a 1-naphthyl group or a 2-naphthyl group, and s1 and s2 are 0.

The organic electronic device may be selected from the group consisting of an organic light emitting device, an organic solar cell and an organic transistor.

In one embodiment of the present specification, the organic electronic device may be an organic light emitting device.

One embodiment of the present specification provides an organic light emitting device including a first electrode, a second electrode, and one or more organic material layers disposed between the first electrode and the second electrode, wherein one or more layers of the organic material layers comprise the organic compound having a double spiro structure represented by Chemical Formula 1.

The organic material layer of the organic light emitting device of the present specification may be formed in a single layer structure, but may be formed in a multilayer structure in which two or more organic material layers are laminated. For example, the organic light emitting device of the present disclosure may have a structure including an electron blocking layer, a hole injection layer, a hole transfer layer, a light emitting layer, an electron transfer layer, an electron injection layer and the like as the organic material layer. However, the structure of the organic light emitting device is not limited thereto, and may comprise less numbers of organic material layers.

Accordingly, in another embodiment of the present specification, the organic material layer of the organic light emitting device may comprise one or more layers of a hole injection layer, a hole transfer layer, and a layer carrying out hole injection and hole transfer at the same time, and one or more layers of the layers may include the compound represented by Chemical Formula 1.

Specifically, the organic material layer of the organic light emitting device may comprise a hole injection layer, and the hole injection layer may comprise the compound represented by Chemical Formula 1.

In another embodiment, the organic material layer of the organic light emitting device may comprise a hole transfer layer, and the hole transfer layer may comprise the compound represented by Chemical Formula 1.

In another embodiment, the organic material layer of the organic light emitting device may comprise a hole transfer layer and a hole injection layer, and the hole transfer layer and the hole injection layer may comprise the compound represented by Chemical Formula 1.

In one embodiment of the present disclosure, the organic material layer comprises an electron blocking layer, and the electron blocking layer comprises the compound represented by Chemical Formula 1.

In addition, the organic material layer may comprise a light emitting layer, and the light emitting layer may comprise the compound represented by Chemical Formula 1. As one embodiment, the compound represented by Chemical Formula 1 may be comprised as a host of the light emitting layer.

As another embodiment, the organic material layer comprising the compound represented by Chemical Formula 1 comprises the compound represented by Chemical Formula 1 as a host, and may comprise other organic compounds, metals or metal compounds as a dopant.

In addition, the organic material layer may comprise one or more layers of an electron transfer layer, an electron injection layer, and a layer carrying out electron transfer and electron injection at the same time, and one or more layers of the layers may comprise the compound represented by Chemical Formula 1.

In another embodiment, the organic material layer comprises a hole transfer layer and an electron blocking layer, and at least one of the hole transfer layer and the electron blocking layer comprises the compound represented by Chemical Formula 1.

Specifically, the organic material layer of the organic light emitting device may comprise an electron injection layer, and the electron injection layer may comprise the compound represented by Chemical Formula 1. In another embodiment, the organic material layer of the organic light emitting device may comprise an electron transfer layer, and the electron transfer layer may include the compound represented by Chemical Formula 1. In another embodiment, the organic material layer of the organic light emitting device may comprise an electron transfer layer and an electron injection layer, and the electron transfer layer and the electron injection layer may comprise the compound represented by Chemical Formula 1.

In such an organic material layer having a multilayer structure, the compound represented by Chemical Formula 1 may be comprised in a light emitting layer, a layer carrying out hole injection/hole transfer and light emission at the same time, a layer carrying out hole transfer and light emission at the same time, or a layer carrying out electron transfer and light emission at the same time, and the like.

In another embodiment, the organic material layer of the organic light emitting device may comprise a hole injection layer or a hole transfer layer comprising a compound comprising an arylamino group, a carbazole group, or a benzocarbazole group in addition to the organic material layer comprising the organic compound having a double spiro structure represented by Chemical Formula 1.

In one embodiment of the present disclosure, the organic light emitting device is a green organic light emitting device, wherein the light emitting layer comprises the compound represented by Chemical Formula 1 as a host.

In one embodiment of the present disclosure, the organic light emitting device is a red organic light emitting device, wherein the light emitting layer comprises the compound represented by Chemical Formula 1 as a host.

In one embodiment of the present specification, the organic electronic device may be an organic solar cell.

One embodiment of the present specification provides an organic solar cell including a first electrode, a second electrode, and one or more organic material layers comprising a photoactive layer disposed between the first electrode and the second electrode, wherein one or more layers of the organic material layers comprise the organic compound having a double spiro structure represented by Chemical Formula 1.

In one embodiment of the present specification, the organic solar cell may comprise an electron transfer layer, and the electron transfer layer may include the compound represented by Chemical Formula 1.

In another embodiment, the photoactive layer may comprise the compound represented by Chemical Formula 1.

In another embodiment, the organic solar cell comprises a photoactive layer, an electron donor and an electron acceptor, and the photoactive layer and the electron donor or the electron acceptor may comprise the compound represented by Chemical Formula 1.

In one embodiment of the present specification, when the organic solar cell receives photons from external light sources, electrons and holes are generated between an electron donor and an electron acceptor. The generated holes are transferred to an anode through the electron donor layer.

In one embodiment of the present specification, the organic solar cell may further comprise additional organic material layers. The organic solar cell may reduce the number of organic material layers used by using organic materials having various functions at the same time.

In one embodiment of the present specification, the organic electronic device may be an organic transistor.

One embodiment of the present specification provides an organic transistor comprising a source, a drain, a gate and one or more organic material layers. In one embodiment of the present specification, the organic transistor comprises a charge generation layer, and the charge generation layer may comprise the compound represented by Chemical Formula 1.

In another embodiment, the organic transistor may comprise an insulation layer, and the insulation layer may be located on a substrate and the gate.

When the organic electronic device includes a plurality of organic material layers, the organic material layers may be formed with materials the same as or different from each other.

The organic electronic device of one embodiment of the present specification may have structures as shown in FIG. 1 and FIG. 2, however, the structure is not limited thereto.

FIG. 1 illustrates a structure of an organic electronic device in which a substrate (1), an anode (2), a light emitting layer (3) and a cathode (4) are consecutively laminated.

In such a structure, the compound may be comprised in the light emitting layer (3).

FIG. 2 illustrates a structure of an organic electronic device in which a substrate (1), an anode (2), a hole injection layer (5), a hole transfer layer (6), a light emitting layer (7), an electron transfer layer (8) and a cathode (4) are consecutively laminated. In such a structure, the compound may be included in one or more layers of the hole injection layer (5), the hole transfer layer (6), the light emitting layer (7) and the electron transfer layer (8).

In addition, in the structure, an electron blocking layer may be additionally comprised, and according to one embodiment, the electron blocking layer may be laminated on the hole transfer layer, and the light emitting layer may be laminated thereon in the structure.

The organic electronic device of the present specification may be manufactured using materials and methods known in the art, except that one or more layers of the organic material layers comprise the compound of the present disclosure, that is, the compound of Chemical Formula 1.

For example, the organic electronic device of the present specification may be manufactured by consecutively laminating a first electrode, an organic material layer and a second electrode on a substrate. Herein, the organic electronic device of the present specification may be manufactured by forming an anode on a substrate by depositing a metal, a metal oxide having conductivity, or an alloy thereof using a physical vapor deposition (PVD) method such as sputtering or e-beam evaporation, forming an organic material layer including a hole injection layer, a hole transfer layer, an electron blocking layer, a light emitting layer and an electron transfer layer thereon, and then depositing a material capable of being used as a cathode thereon. In addition to such a method, the organic electronic device may also be manufactured by consecutively depositing a cathode material, an organic material layer and an anode material on a substrate.

In addition, the compound of Chemical Formula 1 may be formed into an organic material layer through a solution coating method as well as a vacuum deposition method when manufacturing the organic electronic device. Herein, the solution coating method means spin coating, dip coating, doctor blading, inkjet printing, screen printing, a spray method, roll coating and the like, but is not limited thereto.

In addition to such a method, the organic electronic device may be also manufactured by consecutively depositing a cathode material, an organic material layer and an anode material on a substrate (International Patent Application Laid-Open Publication No. 2003/012890). However, the manufacturing method is not limited thereto.

As the anode material, materials having large work function are normally preferred so that hole injection to an organic material layer is smooth. Specific examples of the anode material capable of being used in the present disclosure include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as $ZnO:Al$ or $SnO_2:Sb$; conductive polymers such as poly(3- methylthiophene), poly[3,4-(ethylene-1,2-dioxy)thiophene] (PEDOT), polypyrrole and polyaniline, but are not limited thereto.

As the cathode material, materials having small work function are normally preferred so that electron injection to an organic material layer is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

As the hole injection material, materials having a highest occupied molecular orbital (HOMO) between the work function of an anode material and the HOMO of surrounding organic material layers are preferred as materials favorably receiving holes from an anode at a low voltage. Specific examples of the hole injection material include metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto.

As the hole transfer material, materials having high mobility for holes are suited as materials receiving holes from an anode or a hole injection layer and transfers the holes to a light emitting layer. Specific examples thereof include arylamine-based organic materials, conductive polymers, block copolymers having conjugated parts and non-conjugated parts together, and the like, but are not limited thereto.

As the light emitting material, materials having favorable quantum efficiency for fluorescence or phosphorescence are preferred as materials capable of emitting light in a visible light region by receiving holes and electrons from a hole transfer layer and an electron transfer layer, respectively, and binding the holes and the electrons. Specific examples thereof include 8-hydroxy-quinoline aluminum complexes ($Alq_3$); carbazole-based compounds; dimerized styryl compounds; BAlq; 10-hydroxybenzo quinoline-metal compounds; benzoxazole-, benzothiazole- and benzimidazole-based compounds; poly(p-phenylenevinylene) (PPV)-based polymers; spiro compounds; polyfluorene, rubrene, and the like, but are not limited thereto.

The organic material layer comprising the compound represented by Chemical Formula 1 comprises the compound represented by Chemical Formula 1 as a host, and the compound may be used together with an iridium (Ir)-based dopant.

The iridium-based complex used as the dopant is as follows.

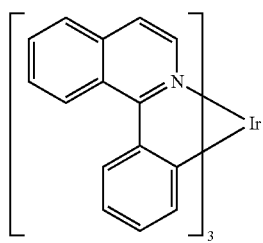

[Ir(piq)₃]

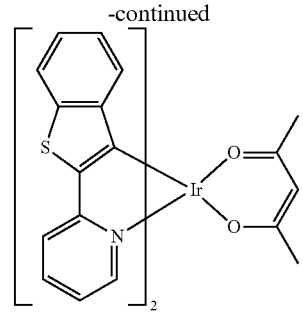

[Btp₂Ir(acac)]

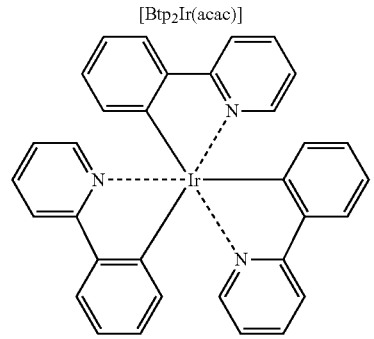

[Ir(ppy)₃]

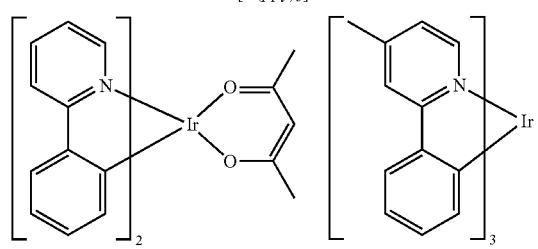

[[Ir(ppy)₂(acac)]     [Ir(mpyp)₃]

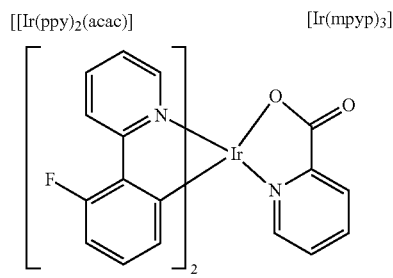

[F₂Irpic]

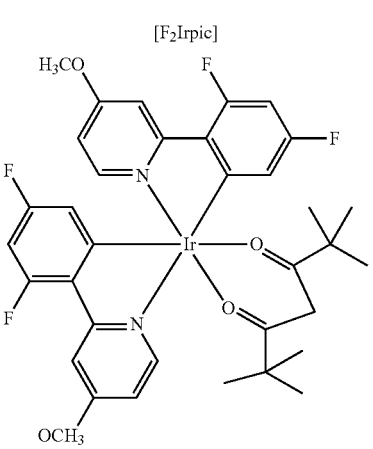

[(F₂ppy)₂Ir(tmd)]

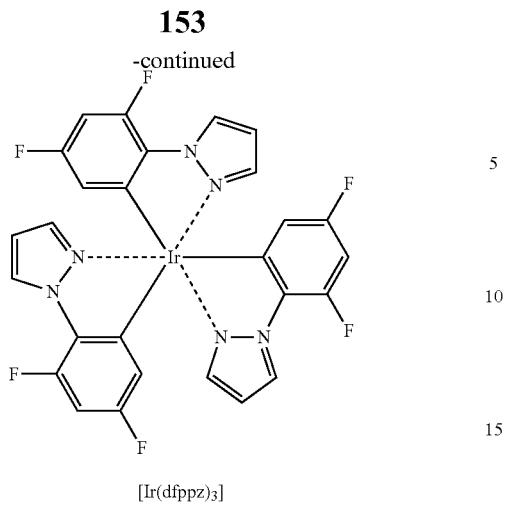

[Ir(dfppz)₃]

As the electron transfer material, materials having high mobility for electrons are suited as materials favorably receiving electrons from a cathode and transferring the electrons to a light emitting layer. Specific examples thereof include Al complexes of 8-hydroxyquinoline; complexes including Alq₃; organic radical compounds; hydroxyflavon-metal complexes and the like, but are not limited thereto.

The organic electronic device according to the present specification may be a top-emission type, a bottom-emission type or a dual-emission type depending on the materials used.

In one embodiment of the present specification, the compound of Chemical Formula 1 may also be comprised in an organic solar cell or an organic transistor in addition to the organic light emitting device.

MODE FOR DISCLOSURE

A method for preparing the compound represented by Chemical Formula 1 and manufacturing an organic light emitting device comprising the same will be described in detail in the following examples. However, the following examples are for illustrative purposes only, and the scope of the present specification is not limited thereto.

PREPARATION EXAMPLE

Preparation Example 1

Preparation of Compound of Chemical Formula 2-1

A compound of Chemical Formula 2-1 was prepared as in the following reaction formula.

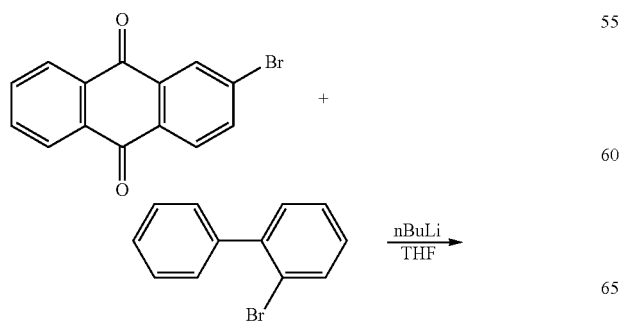

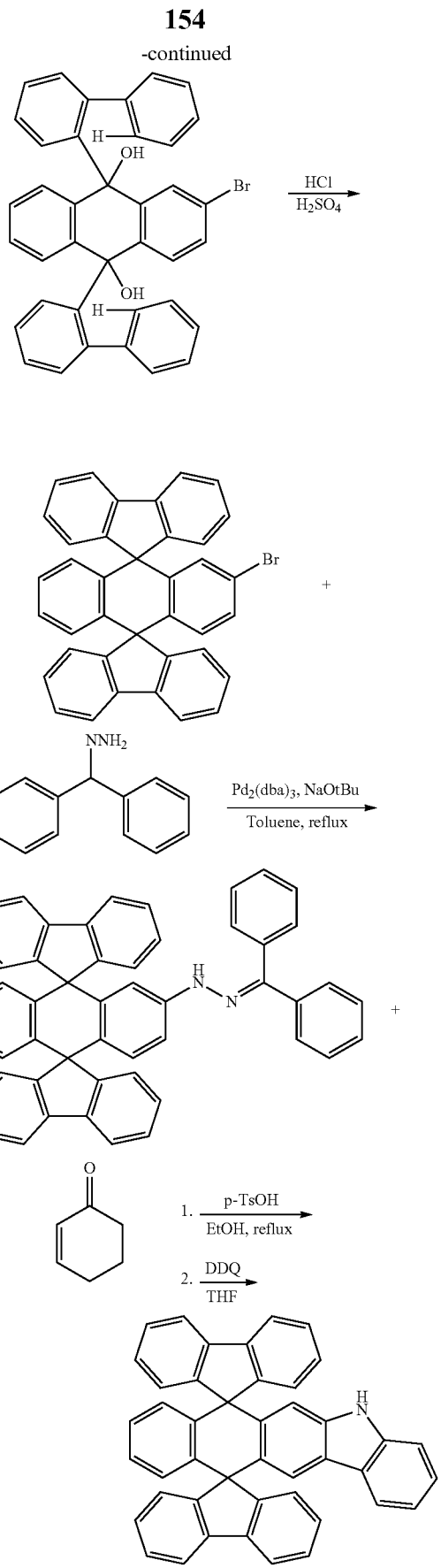

Preparation Example 1-1

Preparation of Compound of Chemical Formula 2-2

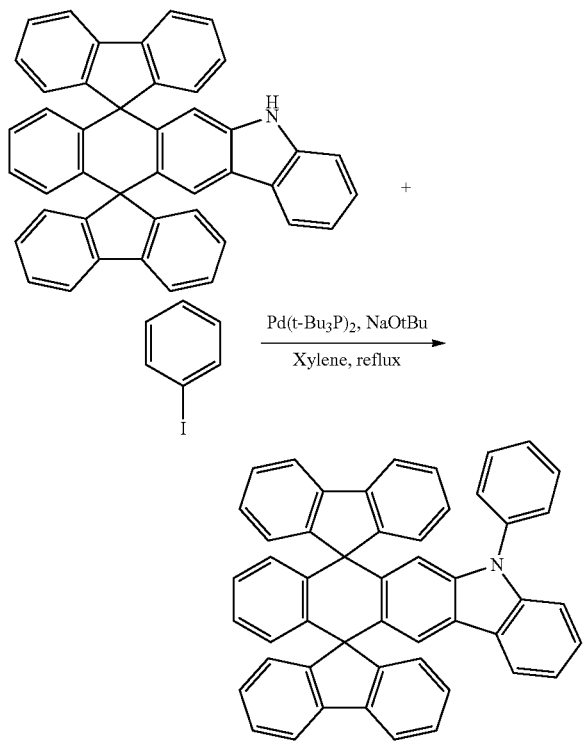

After completely dissolving Chemical Formula 2-1 (10 g, 17.57 mmol) and iodobenzene (3.94 g, 19.33 mmol) in 120 ml of xylene in a 500 ml round bottom flask under nitrogen atmosphere, sodium tert-butoxide (2.19 g, 22.84 mmol) and then bis(tri-tert-butylphosphine) palladium(0) (0.09 g, 0.18 mmol) were added thereto, and the result was heated and stirred for 3 hours. The result was cooled to room temperature and filtered to remove salts, then xylene was vacuum concentrated, and the result was columned using tetrahydrofuran:hexane=1:10 to prepare Compound 1 (9.41 g, yield: 83%).

MS[M+H]$^+$=646

Preparation Example 1-2

Preparation of Compound of Chemical Formula 2-13

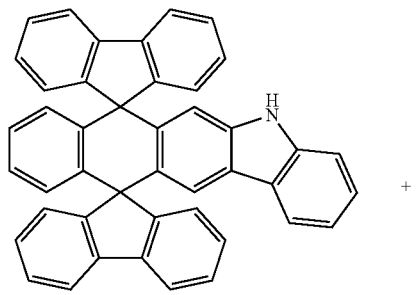

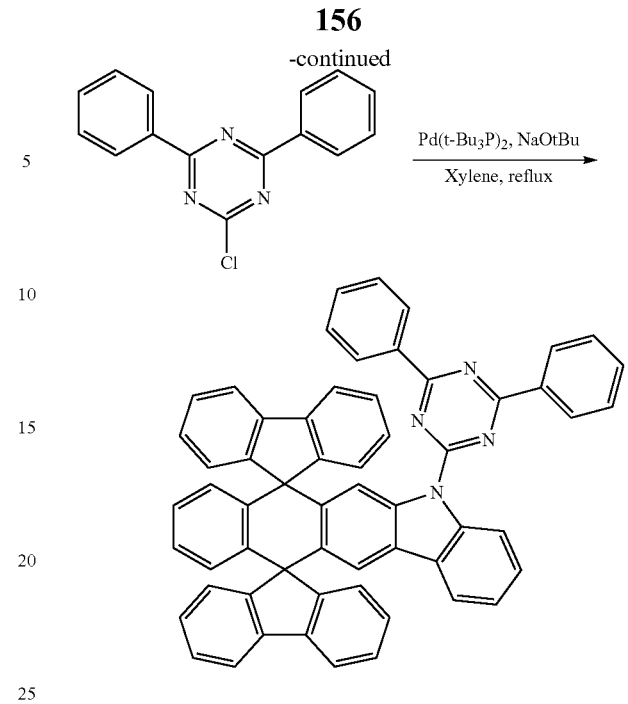

After completely dissolving Chemical Formula 2-1 (10 g, 17.57 mmol) and 2-chloro-4,6-diphenyl-1,3,5-triazine (5.16 g, 19.33 mmol) in 250 ml of xylene in a 500 ml round bottom flask under nitrogen atmosphere, sodium tert-butoxide (2.19 g, 22.84 mmol) and then bis(tri-tert-butylphosphine) palladium(0) (0.09 g, 0.18 mmol) were added thereto, and the result was heated and stirred for 5 hours. The result was cooled to room temperature and filtered to remove salts, then xylene was vacuum concentrated, and the result was recrystallized with 350 ml of ethyl acetate to prepare Compound 2 (12.86 g, yield: 91%).

MS[M+H]$^+$=801

Preparation Example 1-3

Preparation of Compound of Chemical Formula 2-14

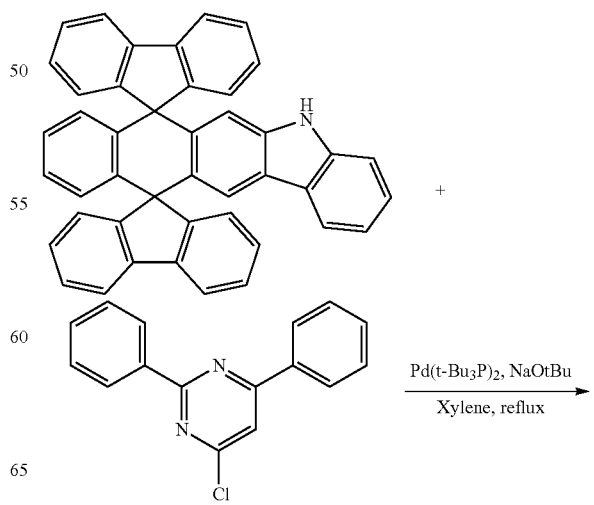

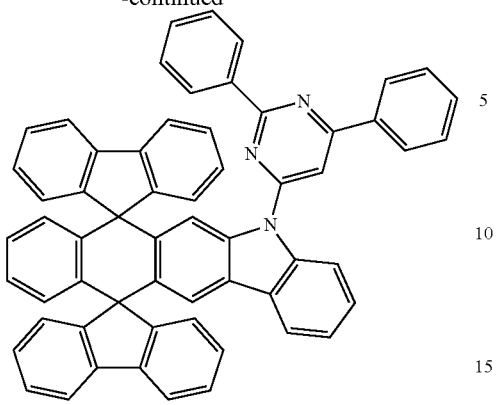

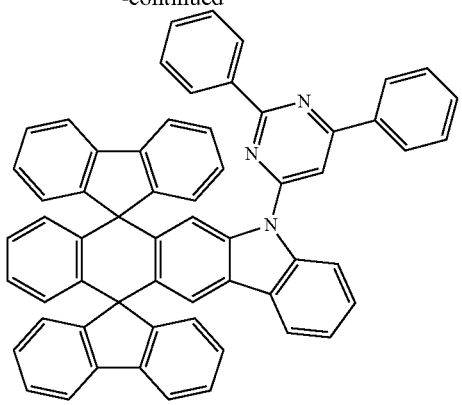

After completely dissolving Chemical Formula 2-1 (10 g, 17.57 mmol) and 2-chloro-4,6-diphenylpyrimidine (5.16 g, 19.33 mmol) in 180 ml of xylene in a 500 ml round bottom flask under nitrogen atmosphere, sodium tert-butoxide (2.19 g, 22.84 mmol) and then bis(tri-tert-butylphosphine) palladium(0) (0.09 g, 0.18 mmol) were added thereto, and the result was heated and stirred for 6 hours. The result was cooled to room temperature and filtered to remove salts, then xylene was vacuum concentrated, and the result was columned using tetrahydrofuran:hexane=1:7 to prepare Compound 3 (11.58 g, yield: 83%).

MS[M+H]$^+$=800

After completely dissolving Chemical Formula 2-1 (10 g, 17.57 mmol) and 4-chloro-2,6-diphenylpyrimidine (5.16 g, 19.33 mmol) in 180 ml of xylene in a 500 ml round bottom flask under nitrogen atmosphere, sodium tert-butoxide (2.19 g, 22.84 mmol) and then bis(tri-tert-butylphosphine) palladium(0) (0.09 g, 0.18 mmol) were added thereto, and the result was heated and stirred for 7 hours. The result was cooled to room temperature and filtered to remove salts, then xylene was vacuum concentrated, and the result was columned using tetrahydrofuran:hexane=1:8 to prepare Compound 4 (10.46 g, yield: 74%).

MS[M+H]$^+$=800

Preparation Example 1-4

Preparation of Compound of Chemical Formula 2-12

Preparation Example 1-5

Preparation of Compound of Chemical Formula 2-15

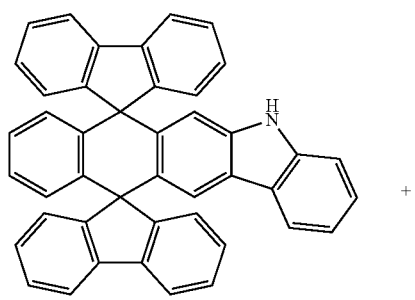

+

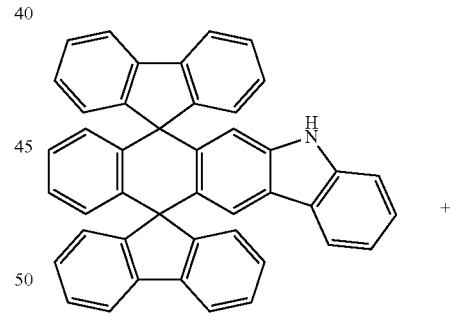

+

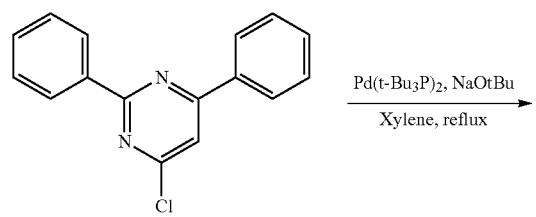

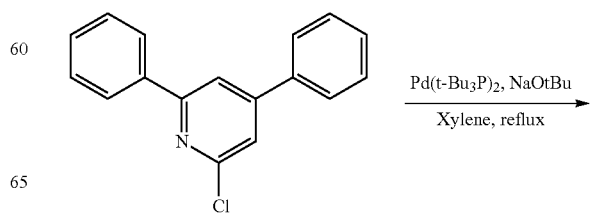

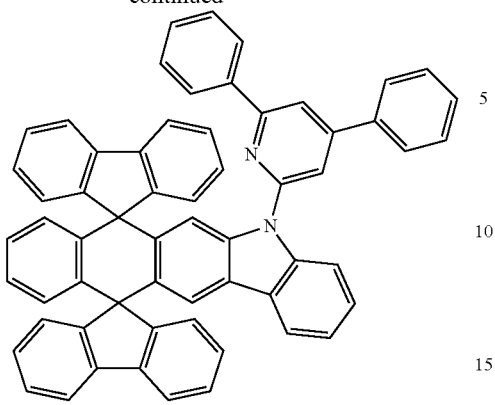

After completely dissolving Chemical Formula 2-1 (10 g, 17.57 mmol) and 2-chloro-4,6-diphenylpyridine (5.15 g, 19.33 mmol) in 180 ml of xylene in a 500 ml round bottom flask under nitrogen atmosphere, sodium tert-butoxide (2.19 g, 22.84 mmol) and then bis(tri-tert-butylphosphine) palladium(0) (0.09 g, 0.18 mmol) were added thereto, and the result was heated and stirred for 3 hours. The result was cooled to room temperature and filtered to remove salts, then xylene was vacuum concentrated, and the result was columned using tetrahydrofuran:hexane=1:12 to prepare Compound 5 (8.96 g, yield: 64%).

MS[M+H]$^+$=799

Preparation Example 1-6

Preparation of Compound of Chemical Formula 2-17

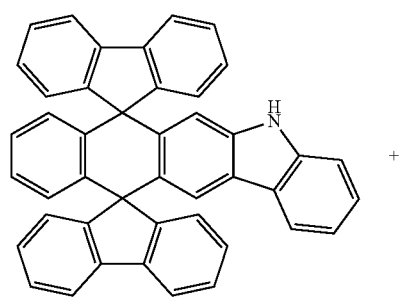

+

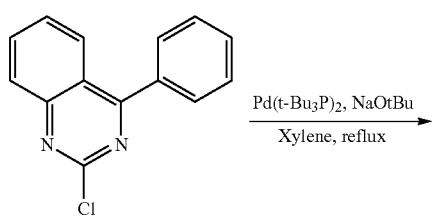

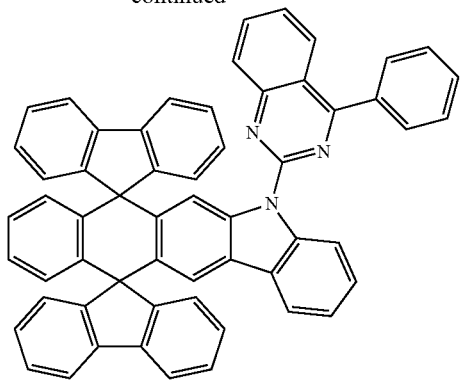

After completely dissolving Chemical Formula 2-1 (10 g, 17.57 mmol) and 2-chloro-4-phenylquinazoline (4.64 g, 19.33 mmol) in 200 ml of xylene in a 500 ml round bottom flask under nitrogen atmosphere, sodium tert-butoxide (2.19 g, 22.84 mmol) and then bis(tri-tert-butylphosphine) palladium(0) (0.09 g, 0.18 mmol) were added thereto, and the result was heated and stirred for 1 hour. The result was cooled to room temperature and filtered to remove salts, then xylene was vacuum concentrated, and the result was recrystallized with 300 ml of ethyl acetate to prepare Compound 6 (11.87 g, yield: 87%).

MS [M+H]$^+$=774

Preparation Example 1-7

Preparation of Compound of Chemical Formula 2-16

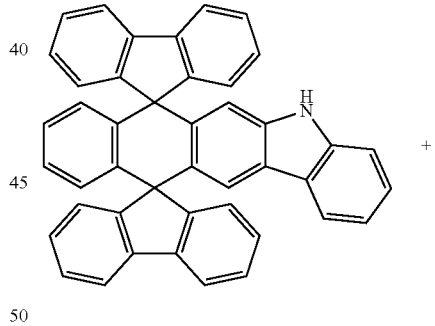

+

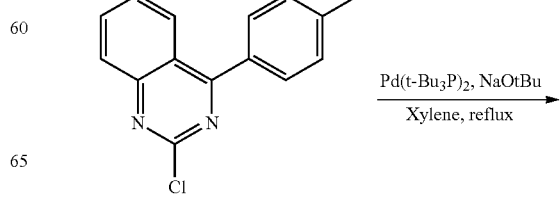

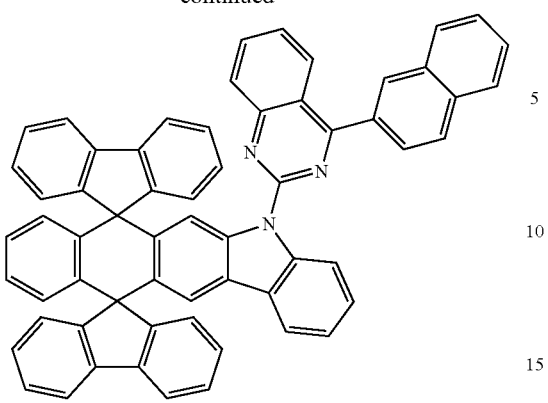

After completely dissolving Chemical Formula 2-1 (10 g, 17.57 mmol) and 2-chloro-4-(naphthalen-2-yl)quinazoline (5.61 g, 19.33 mmol) in 200 ml of xylene in a 500 ml round bottom flask under nitrogen atmosphere, sodium tert-butoxide (2.19 g, 22.84 mmol) and then bis(tri-tert-butylphosphine) palladium(0) (0.09 g, 0.18 mmol) were added thereto, and the result was heated and stirred for 2 hours. The result was cooled to room temperature and filtered to remove salts, then xylene was vacuum concentrated, and the result was recrystallized with 200 ml of ethyl acetate to prepare Compound 7 (12.11 g, yield: 83%).

MS[M+H]$^+$=824

Preparation Example 1-8

Preparation of Compound of Chemical Formula 2-19

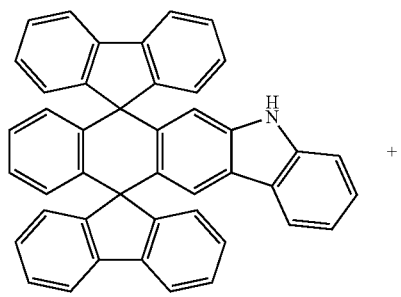 +

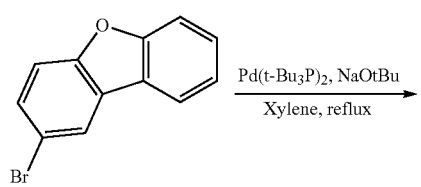

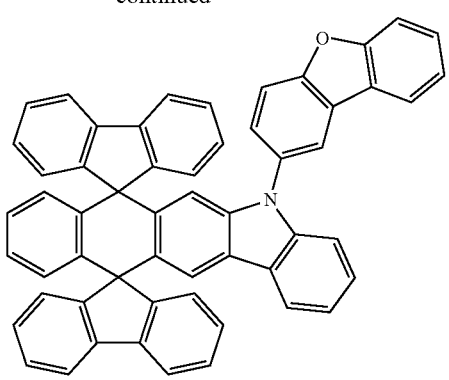

After completely dissolving Chemical Formula 2-1 (10 g, 17.57 mmol) and 2-bromodibenzo[b,d]furan (4.76 g, 19.33 mmol) in 200 ml of xylene in a 500 ml round bottom flask under nitrogen atmosphere, sodium tert-butoxide (2.19 g, 22.84 mmol) and then bis(tri-tert-butylphosphine) palladium (0) (0.09 g, 0.18 mmol) were added thereto, and the result was heated and stirred for 10 hours. The result was cooled to room temperature and filtered to remove salts, then xylene was vacuum concentrated, and the result was recrystallized with 280 ml of ethyl acetate to prepare Compound 8 (10.36 g, yield: 80%).

MS[M+H]$^+$=736

Preparation Example 1-9

Preparation of Compound of Chemical Formula 2-21

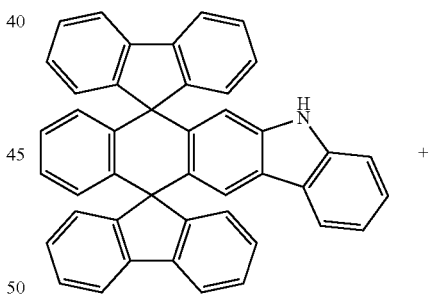 +

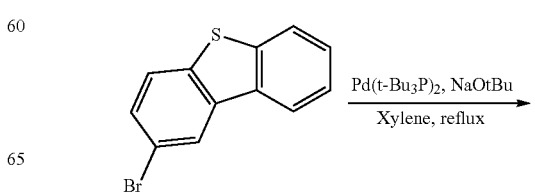

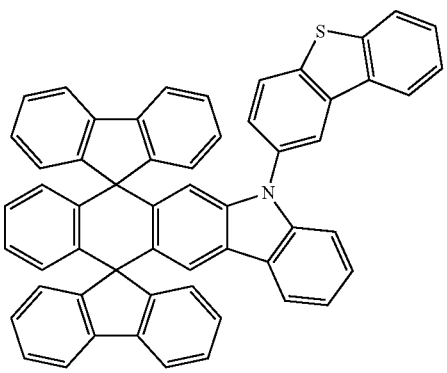

After completely dissolving Chemical Formula 2-1 (10 g, 17.57 mmol) and 2-bromodibenzo[b,d]thiophene (5.06 g, 19.33 mmol) in 200 ml of xylene in a 500 ml round bottom flask under nitrogen atmosphere, sodium tert-butoxide (2.19 g, 22.84 mmol) and then bis(tri-tert-butylphosphine) palladium(0) (0.09 g, 0.18 mmol) were added thereto, and the result was heated and stirred for 8 hours. The result was cooled to room temperature and filtered to remove salts, then xylene was vacuum concentrated, and the result was recrystallized with 220 ml of ethyl acetate to prepare Compound 9 (11.77 g, yield: 89%).

MS[M+H]$^+$=752

Preparation Example 1-10

Preparation of Compound of Chemical Formula 2-20

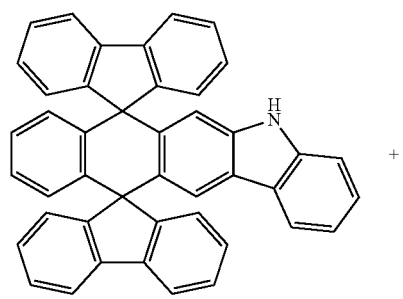

After completely dissolving Chemical Formula 2-1 (10 g, 17.57 mmol) and 3-bromo-9-phenyl-9H-carbazole (6.21 g, 19.33 mmol) in 250 ml of xylene in a 500 ml round bottom flask under nitrogen atmosphere, sodium tert-butoxide (2.19 g, 22.84 mmol) and then bis(tri-tert-butylphosphine) palladium(0) (0.09 g, 0.18 mmol) were added thereto, and the result was heated and stirred for 2 hours. The result was cooled to room temperature and filtered to remove salts, then xylene was vacuum concentrated, and the result was recrystallized with 200 ml of ethyl acetate to prepare Compound 10 (12.66 g, yield: 90%).

MS[M+H]$^+$=811

Preparation Example 1-11

Preparation of Compound of Chemical Formula 2-23

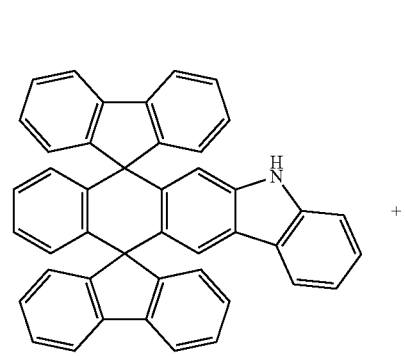

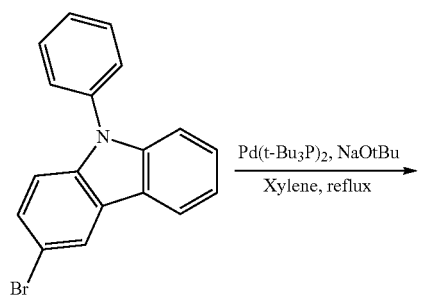

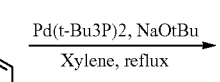

-continued

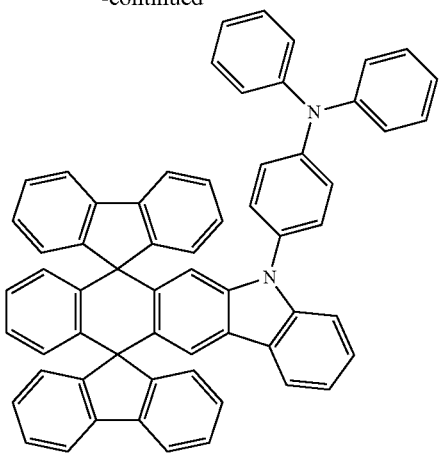

After completely dissolving Chemical Formula 2-1 (10 g, 17.57 mmol) and 4-bromo-N,N-diphenylaniline (6.19 g, 19.33 mmol) in 250 ml of xylene in a 500 ml round bottom flask under nitrogen atmosphere, sodium tert-butoxide (2.19 g, 22.84 mmol) and then bis(tri-tert-butylphosphine) palladium(0) (0.09 g, 0.18 mmol) were added thereto, and the result was heated and stirred for 3 hours. The result was cooled to room temperature and filtered to remove salts, then xylene was vacuum concentrated, and the result was recrystallized with 150 ml of ethyl acetate to prepare Compound 11 (11.41 g, yield: 81%).

MS[M+H]$^+$=813

Preparation Example 2

Preparation of Compound of Chemical Formula 2-25

A compound of Chemical Formula 2-25 was prepared as in the following reaction formula.

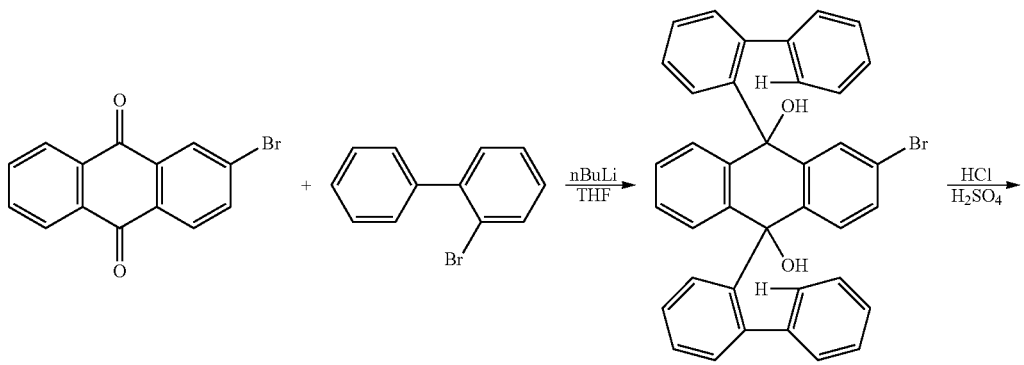

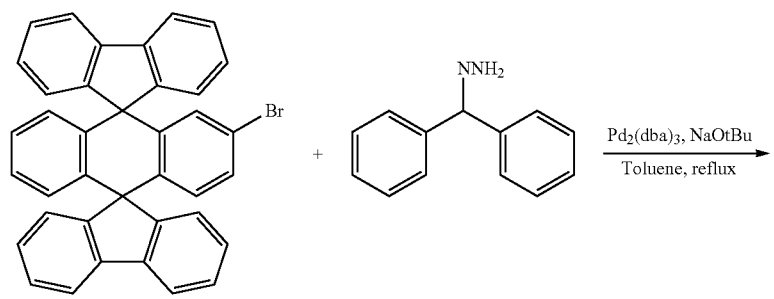

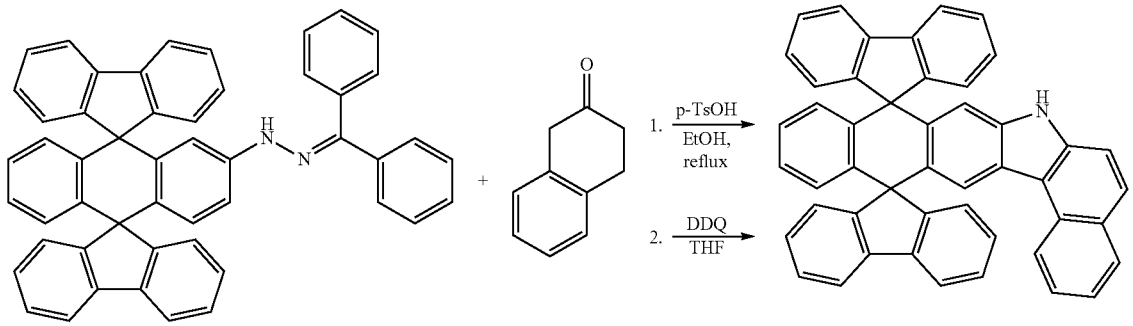

Preparation Example 2-1
Syntheses of Compounds 12 to 22 (Compounds of Chemical Formulae 8-1 to 8-11)
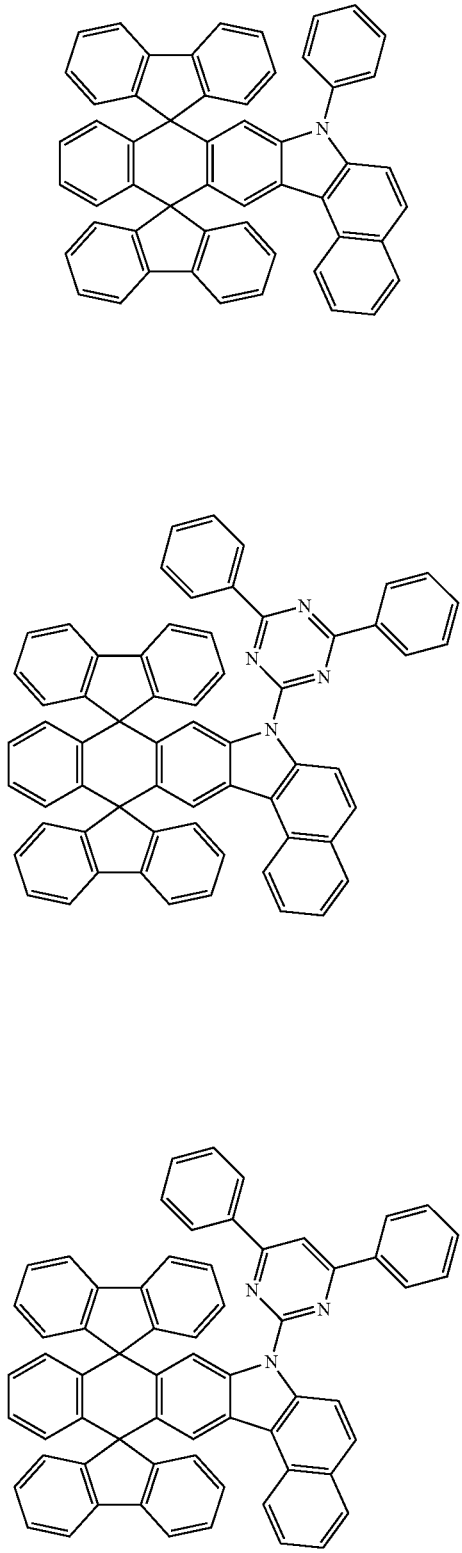
12
13
14
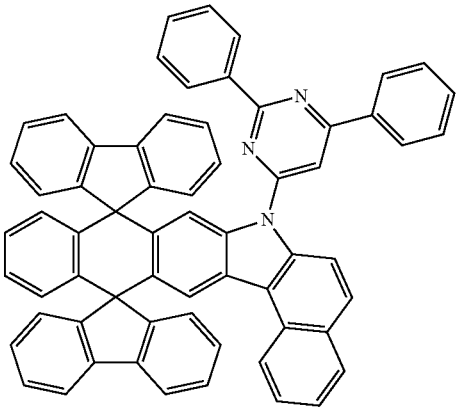
15
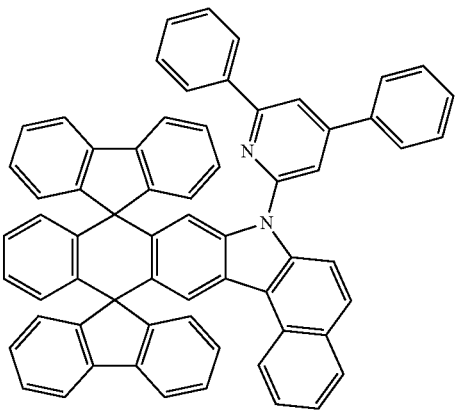
16
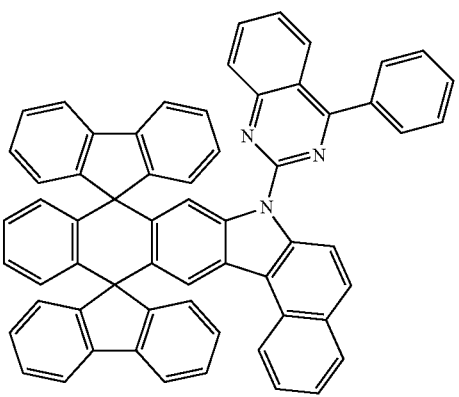
17
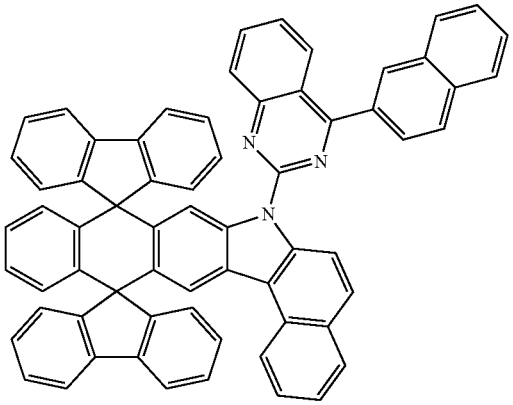
18

19
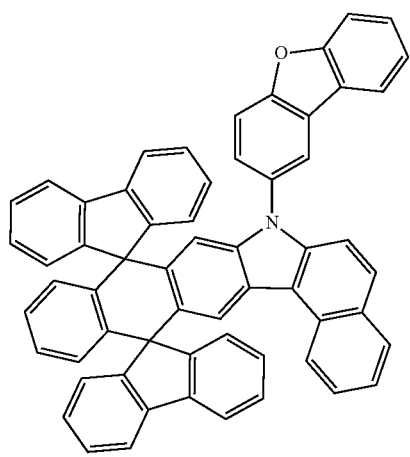
20
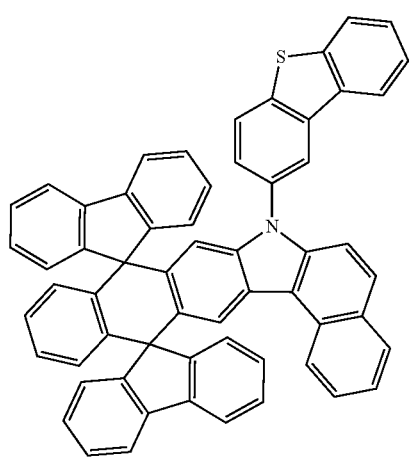
21
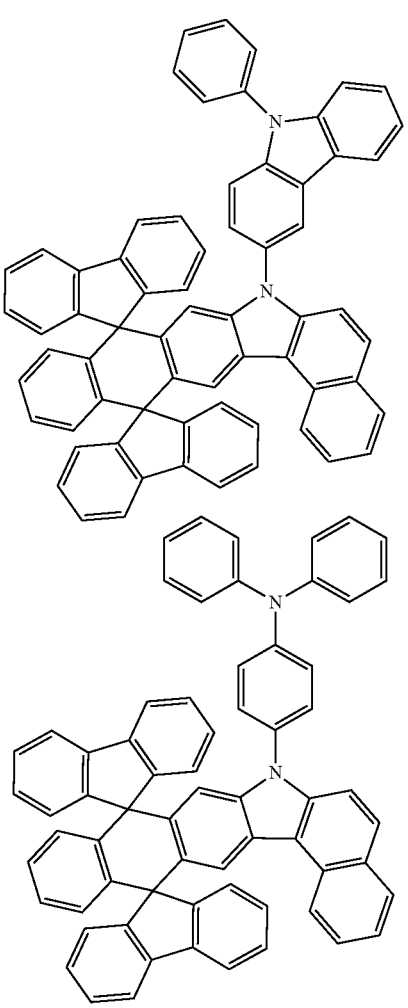
22
Compounds 12 to 22 were prepared in the same manner as in Preparation Examples 1-1 to 1-11, the methods preparing Compounds 1 to 11, except that Chemical Formula 2-25 was used instead of Chemical Formula 2-1 as the starting material.
Preparation Example 3
Preparation of Compound of Chemical Formula 2-26
A compound of Chemical Formula 2-26 was prepared as in the following reaction formula.
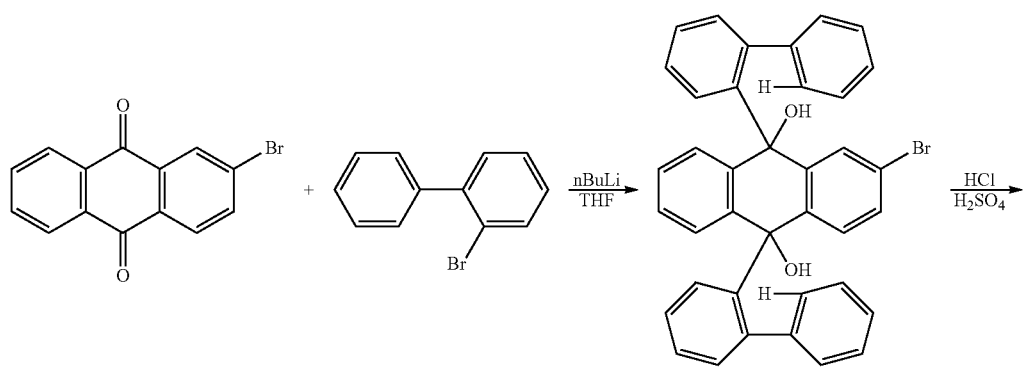

-continued
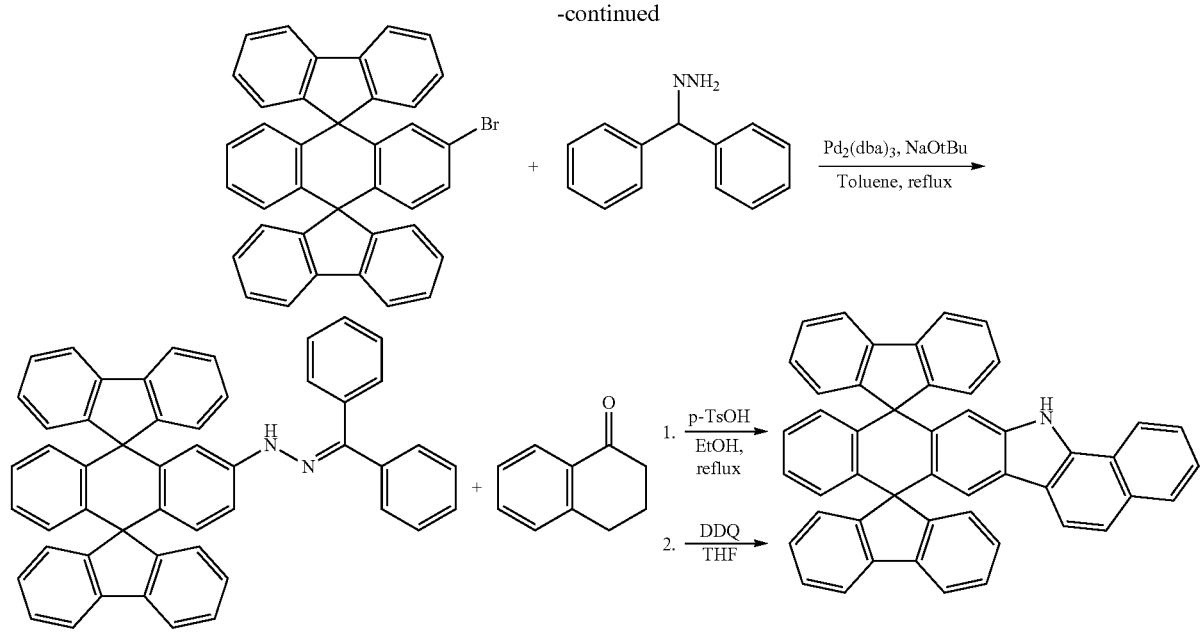
Preparation Example 3-1
Syntheses of Compounds 23 to 33 (Compounds of Chemical Formulae 9-1 to 9-11)
23
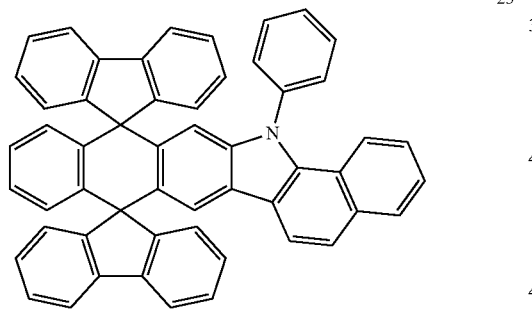
24
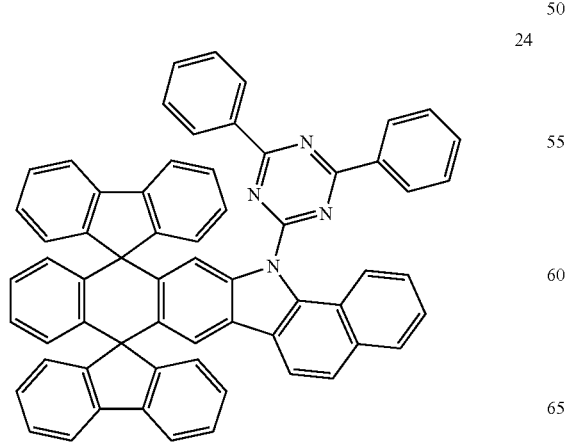
-continued
25
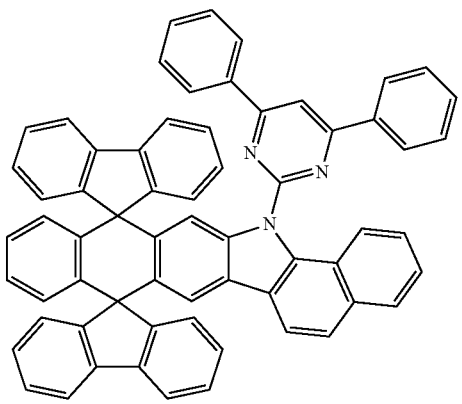
26
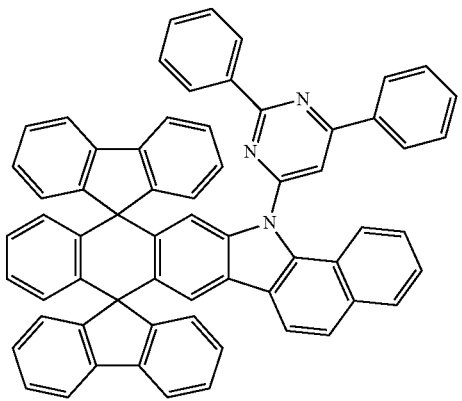

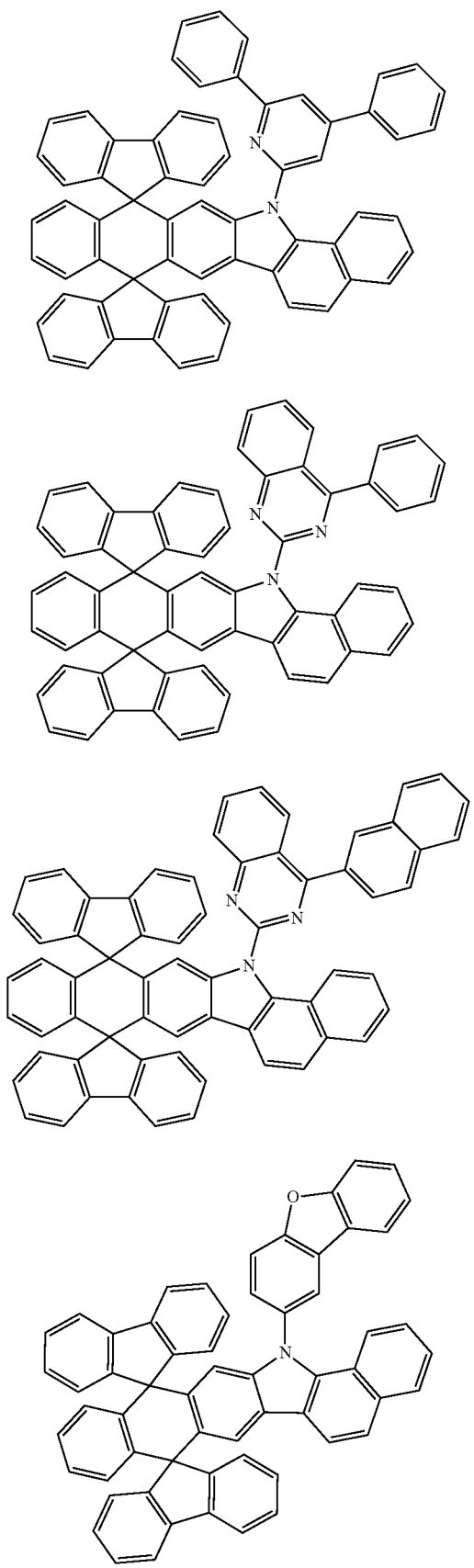
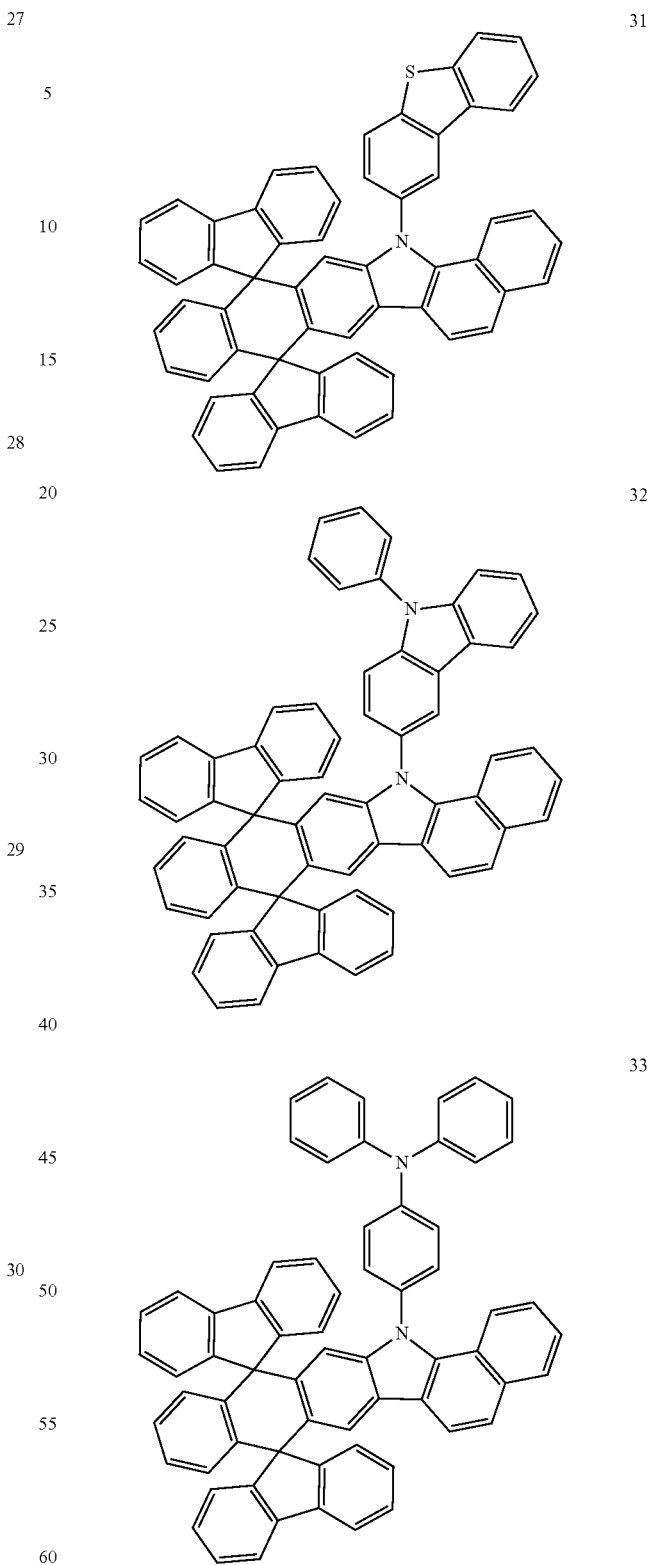
Compounds 23 to 33 were prepared in the same manner as in Preparation Examples 1-1 to 1-11, the methods preparing Compounds 1 to 11, except that Chemical Formula 2-26 was used instead of Chemical Formula 2-1 as the starting material.

Preparation Example 4
Preparation of Compound of Chemical Formula 3-1
A compound of Chemical Formula 3-1 was prepared as in the following reaction formula.
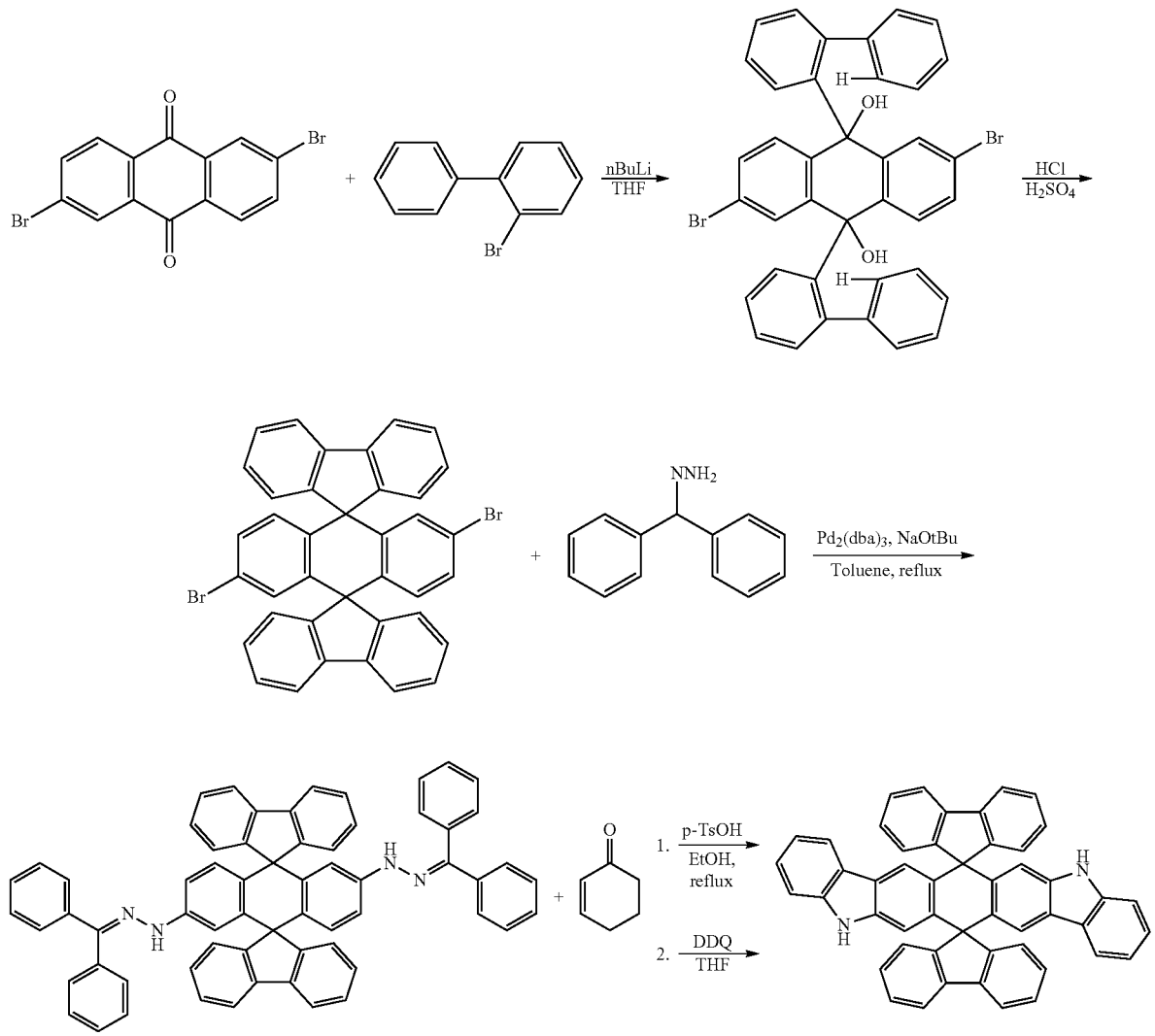
Preparation Example 5
Preparation of Compound of Chemical Formula 4
A compound of Chemical Formula 4 was prepared as in the following reaction formula.
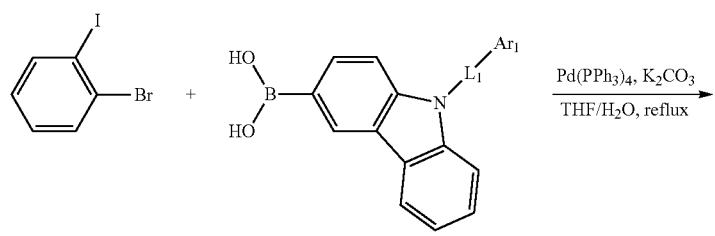

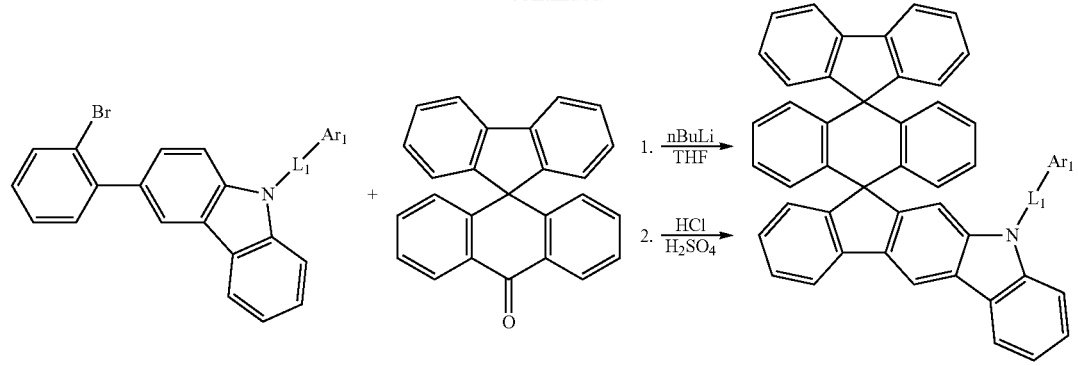
Preparation Example 5-1
Syntheses of Compounds 34 to 44 (Compounds of Chemical Formulae 4-2, 4-13, 4-14, 4-12, 4-15, 4-17, 4-16, 4-19, 4-24, 4-20 and 4-23)
34
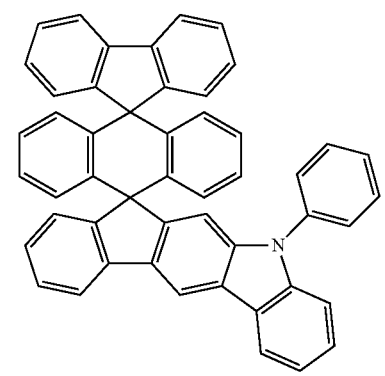
36
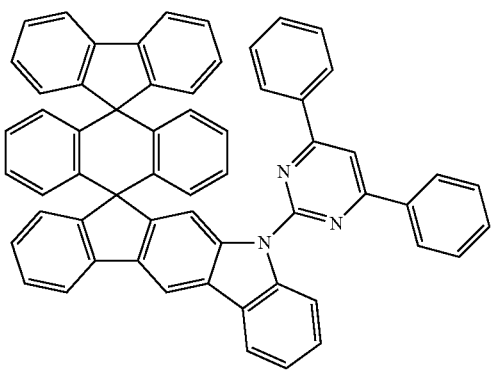
37
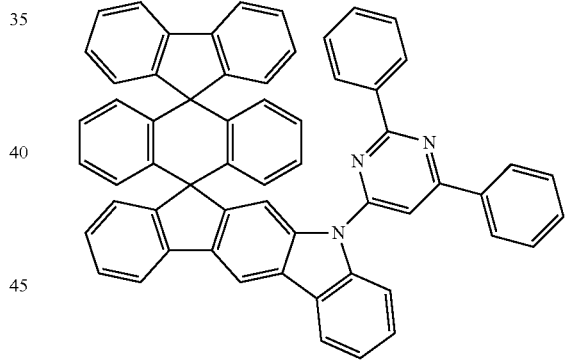
35
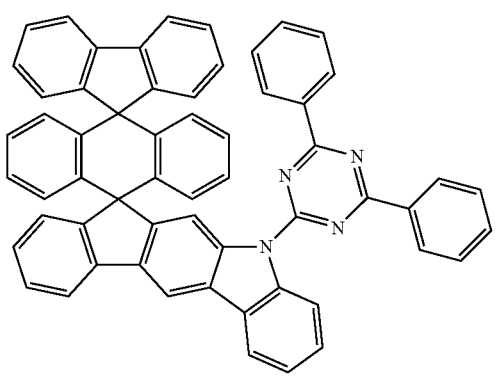
38
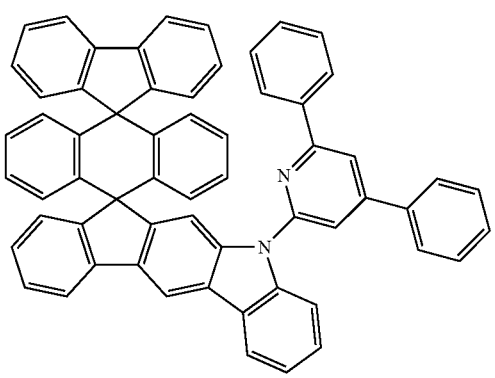

39

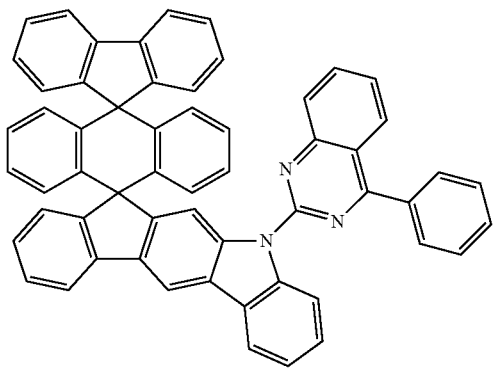

40

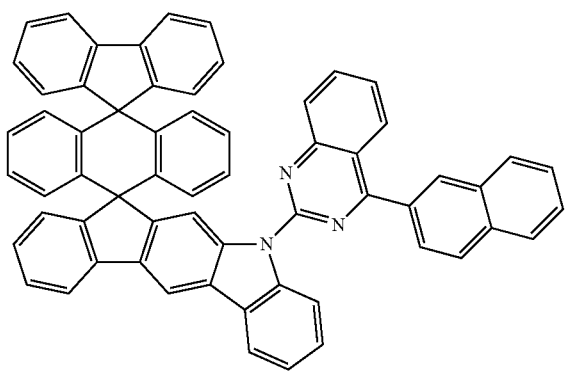

41

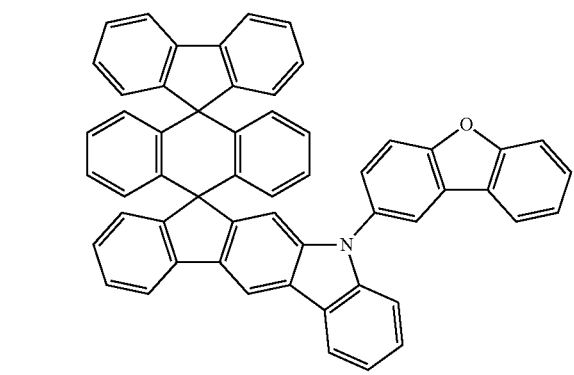

42

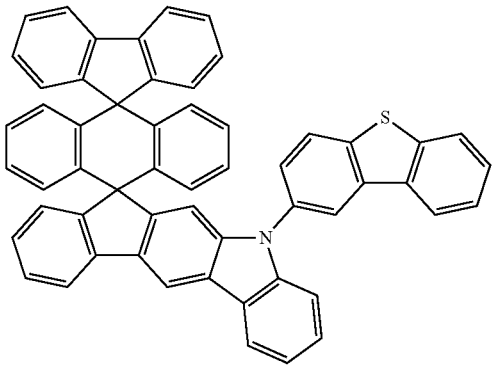

43

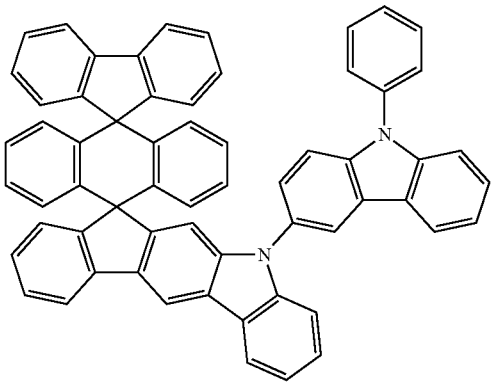

44

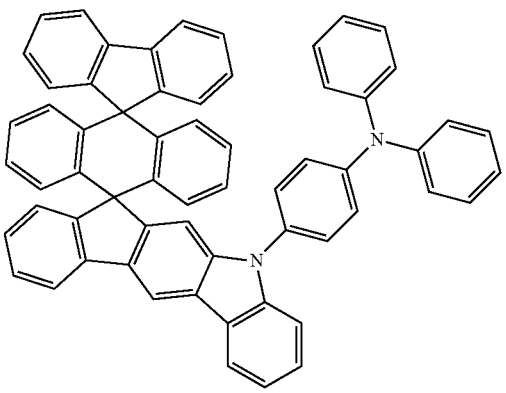

Compounds 34 to 44 were prepared using phenyl, 2-chloro-4,6-diphenyl-1,3,5-triazine, 2-chloro-4,6-diphenylpyrimidine, 4-chloro-2,6-diphenylpyrimidine, 2-chloro-4,6-diphenylpyridine, 2-chloro-4-phenylquinazoline, 2-chloro-4-(naphthalen-2-yl)quinazoline, 2-bromodibenzo[b,d]furan, 2-bromodibenzo[b,d]thiophene, 3-bromo-9-phenyl-9H-carbazole and 4-bromo-N,N-diphenylaniline as Ar1 in Preparation Example 5.

Preparation Example 6

Preparation of Compound of Chemical Formula 5-1

A compound of Chemical Formula 3-1 was prepared as in the following reaction formula.

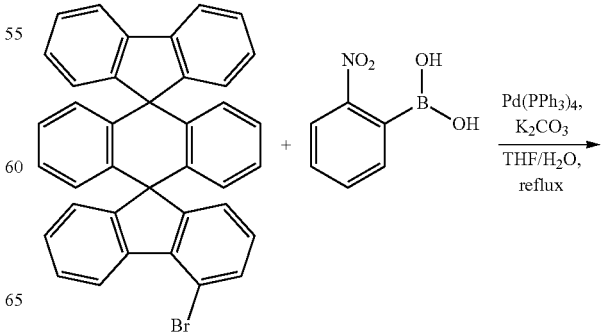

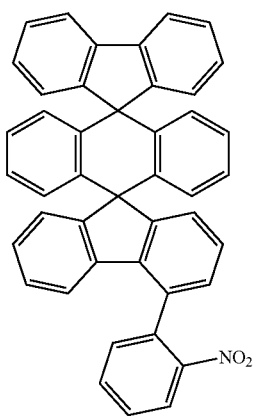
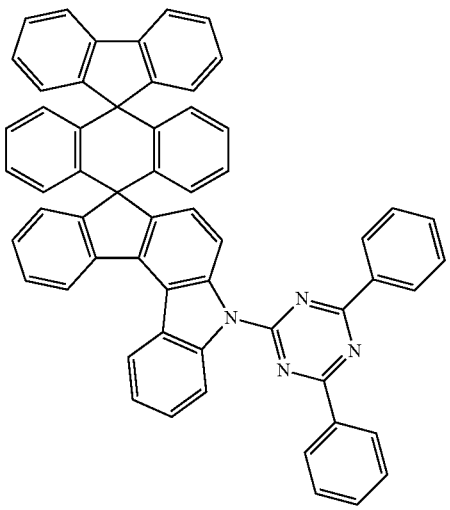
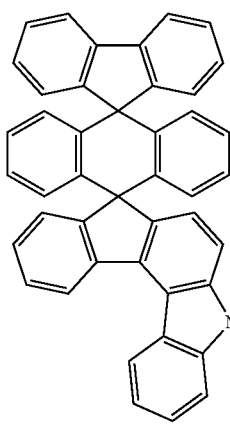
Preparation Example 6-1
Syntheses of Compounds 45 to 55 (Compounds of Chemical Formulae 5-2, 5-13, 5-14, 5-12, 5-15, 5-17, 5-16, 5-19, 5-21, 5-20 and 5-23)
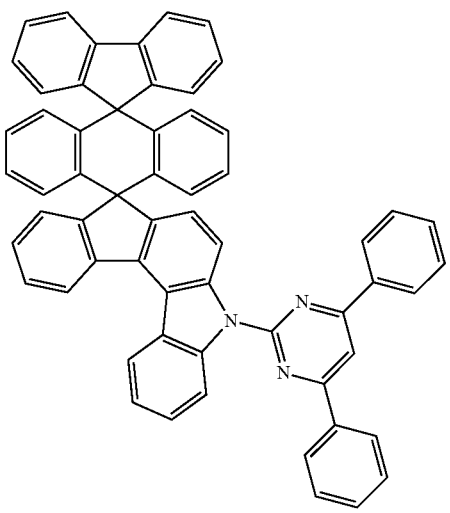
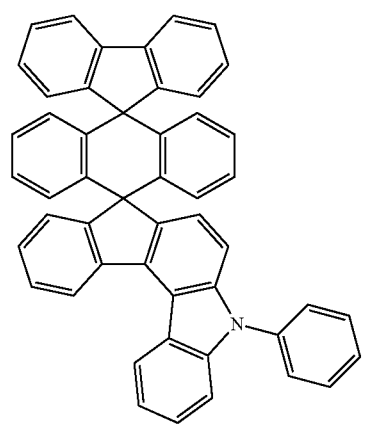
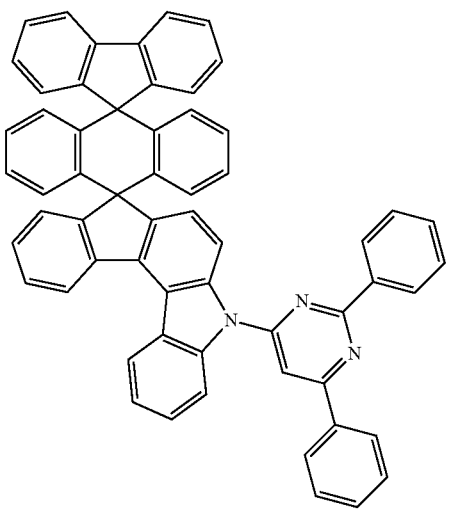

49
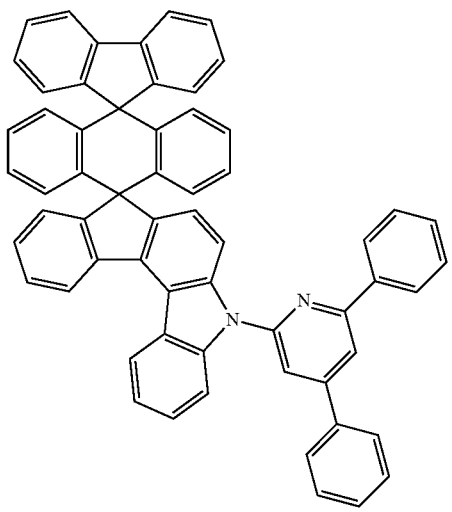
50
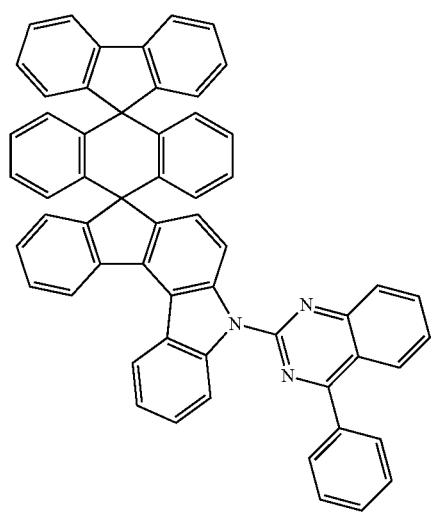
51
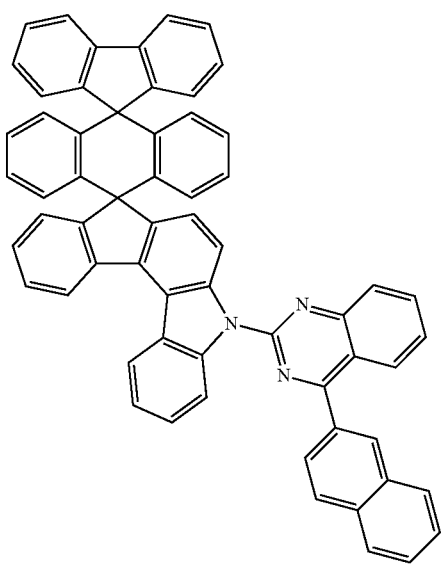
52
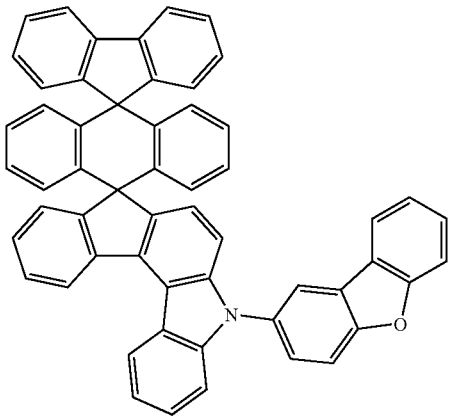
53
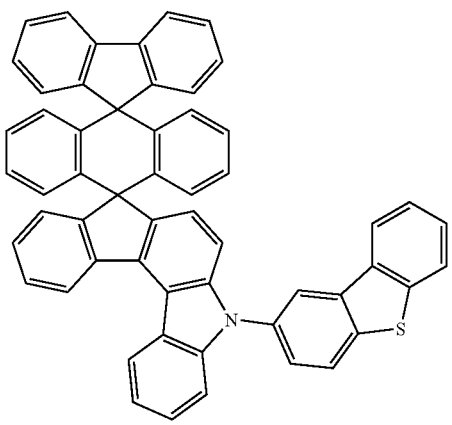
54
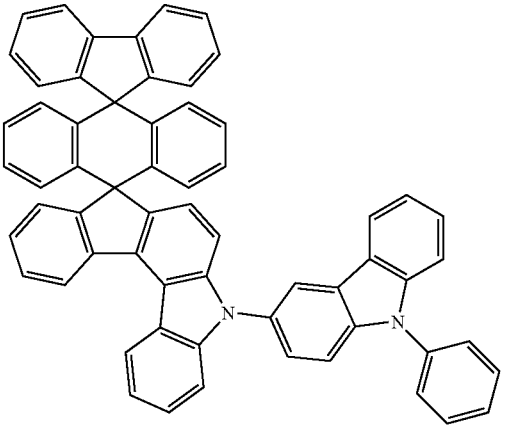

185

-continued

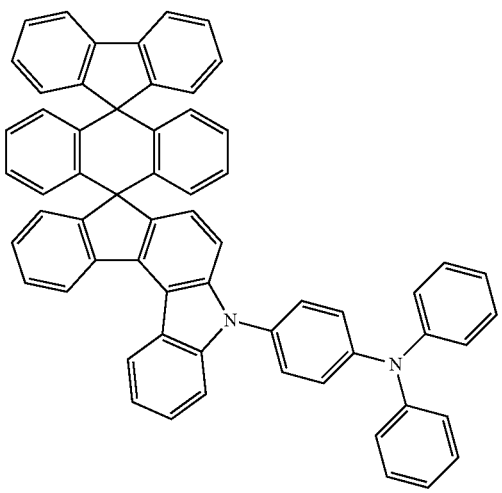

Compounds 45 to 55 were prepared in the same manner as in Preparation Examples 1-1 to 1-11, the methods preparing Compounds 1 to 11, except that Chemical Formula 5-1 was used instead of Chemical Formula 2-1 as the starting material.

Preparation Example 7

Preparation of Compound of Chemical Formula 5-25

A compound of Chemical Formula 5-25 was prepared as in the following reaction formula.

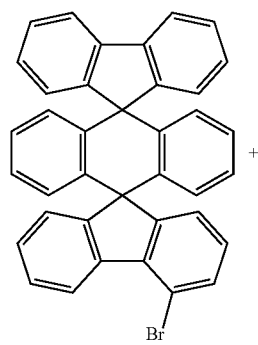

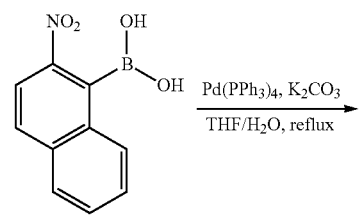

186

-continued

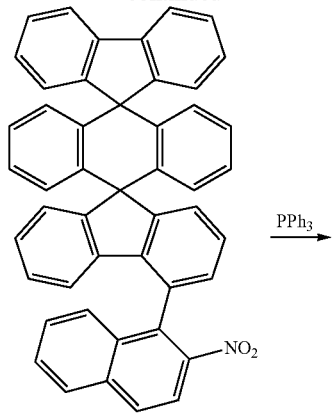

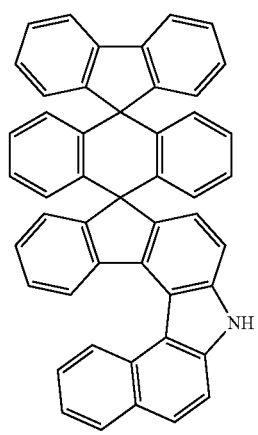

Preparation Example 7-1

Syntheses of Compounds 56 to 66 (Compounds of Chemical Formulae 12-1 to 12-11)

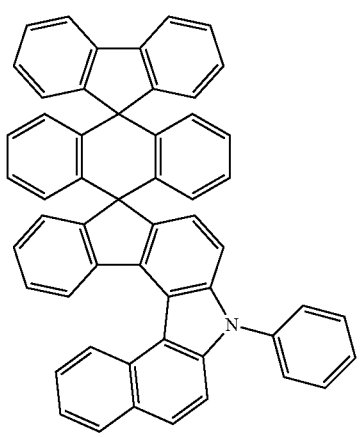

57
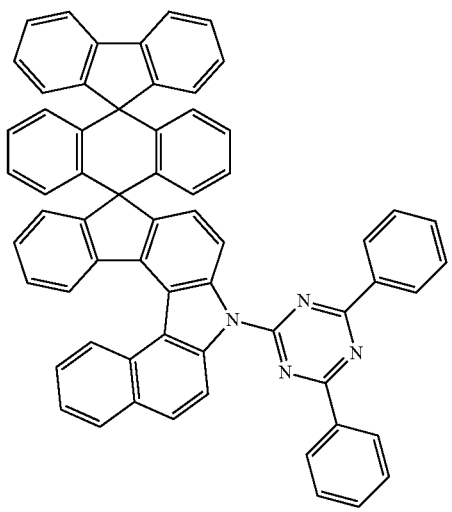
58
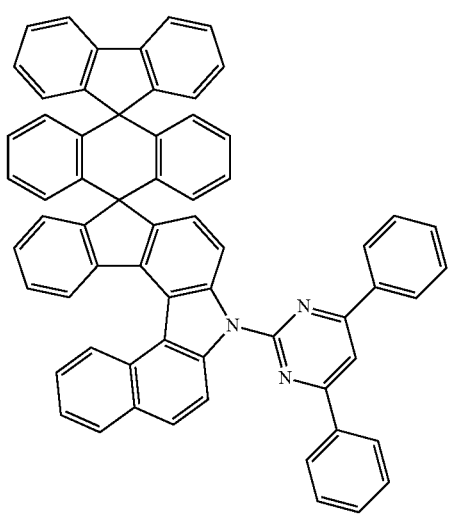
59
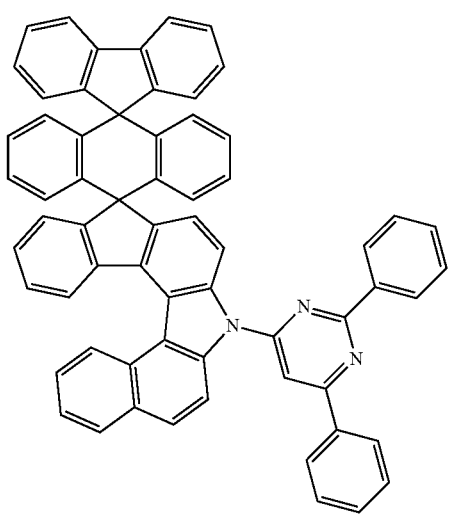
60
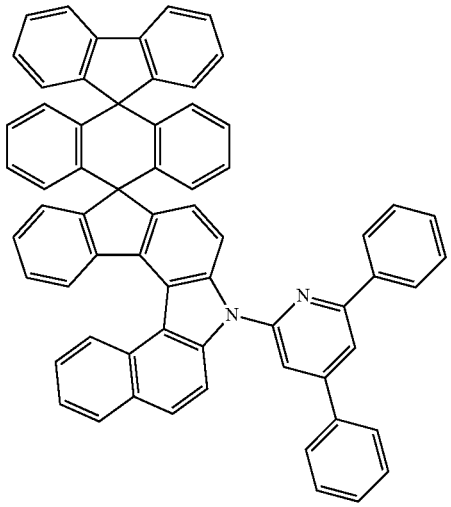
61
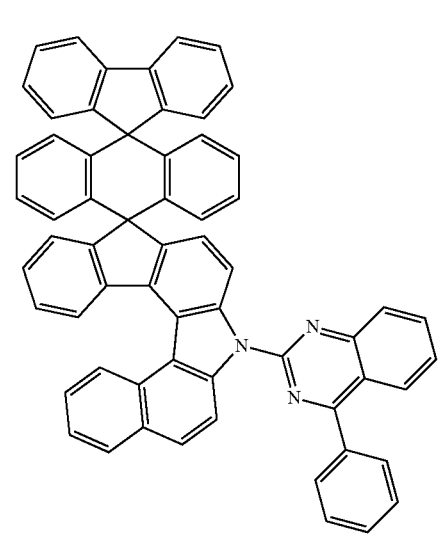
62
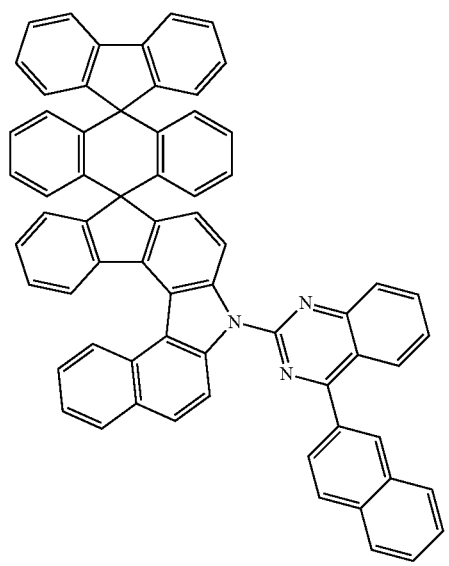

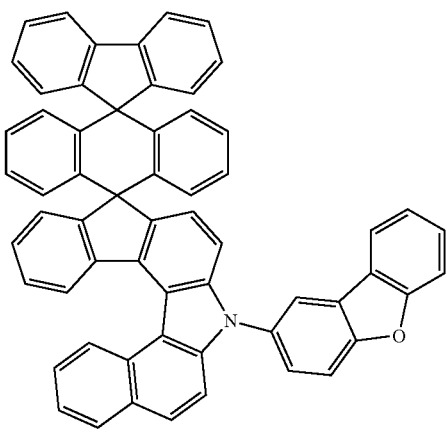
63
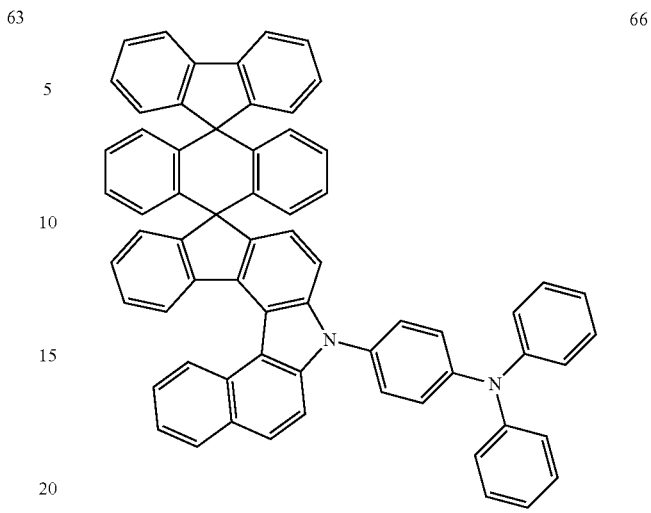
66
Compounds 56 to 66 were prepared in the same manner as in Preparation Examples 1-1 to 1-11, the methods preparing Compounds 1 to 11, except that Chemical Formula 5-25 was used instead of Chemical Formula 2-1 as the starting material.
Preparation Example 8
Preparation of Compound of Chemical Formula 5-26
A compound of Chemical Formula 5-26 was prepared as in the following reaction formula.
64
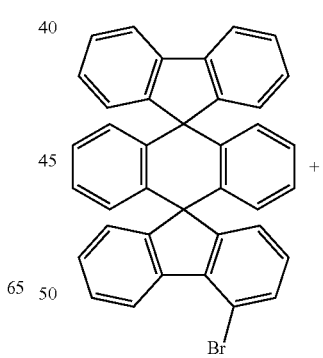
65
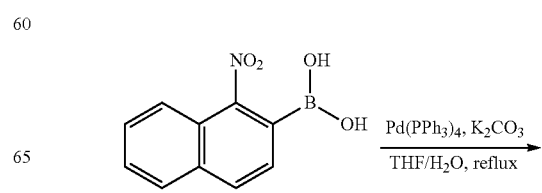

191
-continued
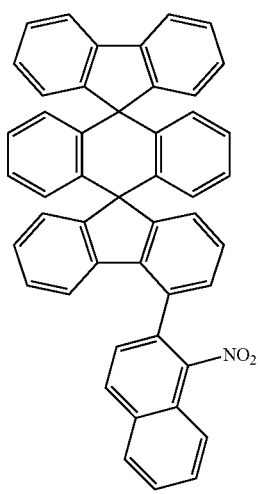
PPh₃ →
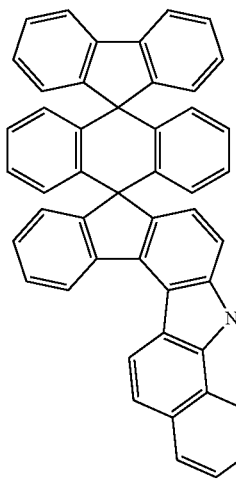
Preparation Example 8-1
Syntheses of Compounds 67 to 77 (Compounds of Chemical Formulae 13-1 to 13-11)
67
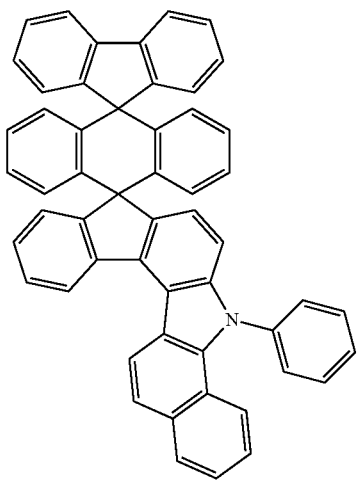
192
-continued
68
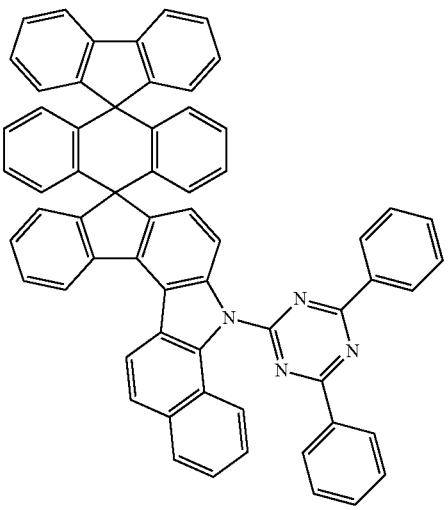
69
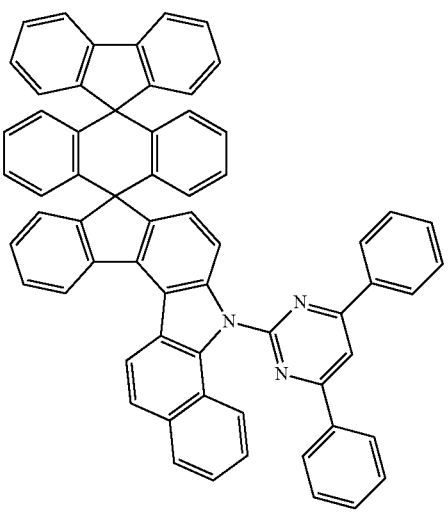
70
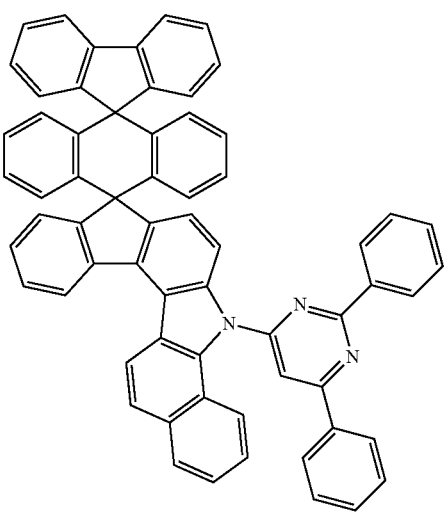

193 -continued
71
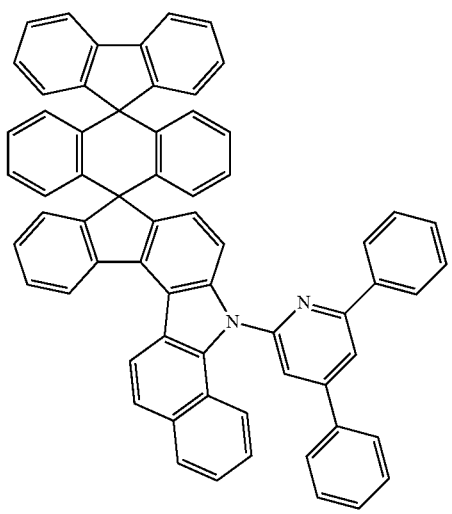
72
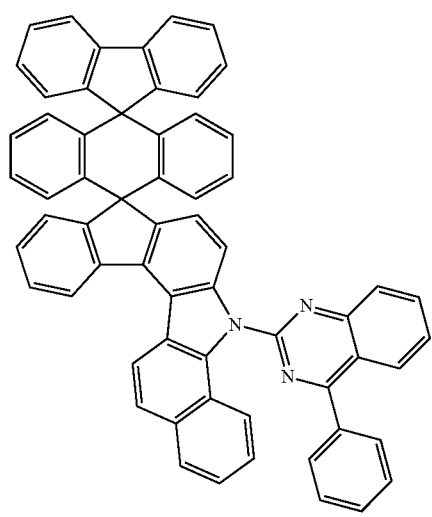
73
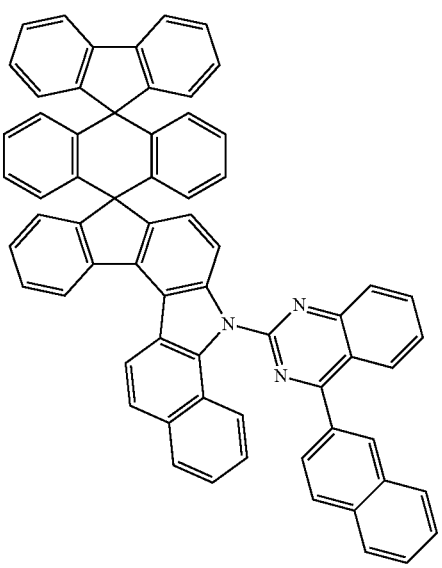
194 -continued
74
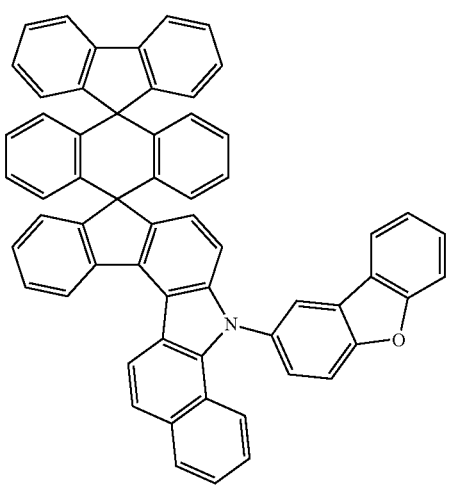
75
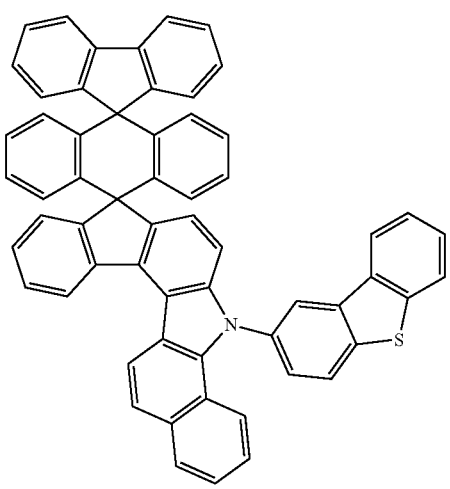
76
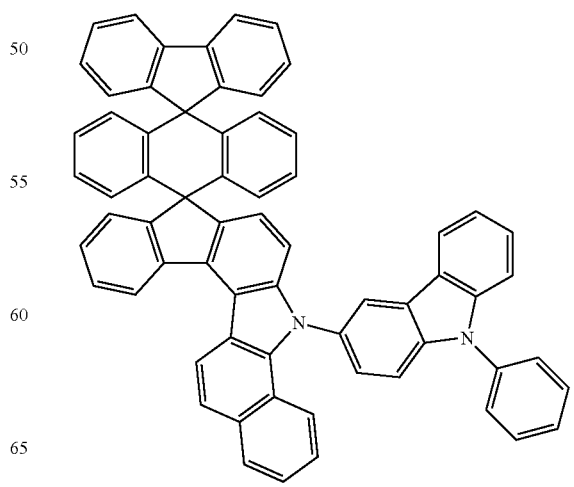

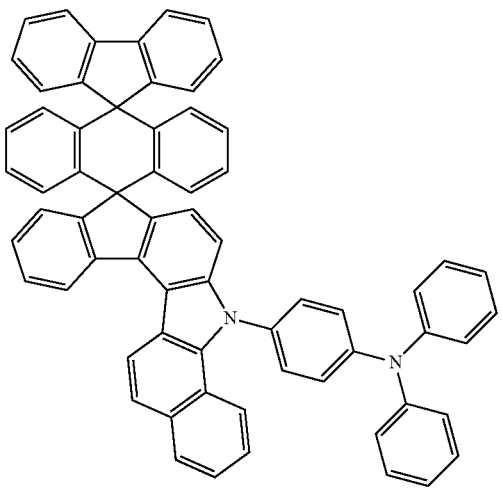
Compounds 67 to 77 were prepared in the same manner as in Preparation Examples 1-1 to 1-11, the methods preparing Compounds 1 to 11, except that Chemical Formula 5-26 was used instead of Chemical Formula 2-1 as the starting material.
Preparation Example 9
Preparation of Compound of Chemical Formula 6-1
A compound of Chemical Formula 6-1 was prepared as in the following reaction formula.
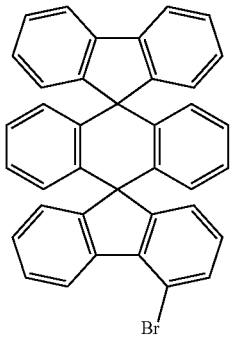
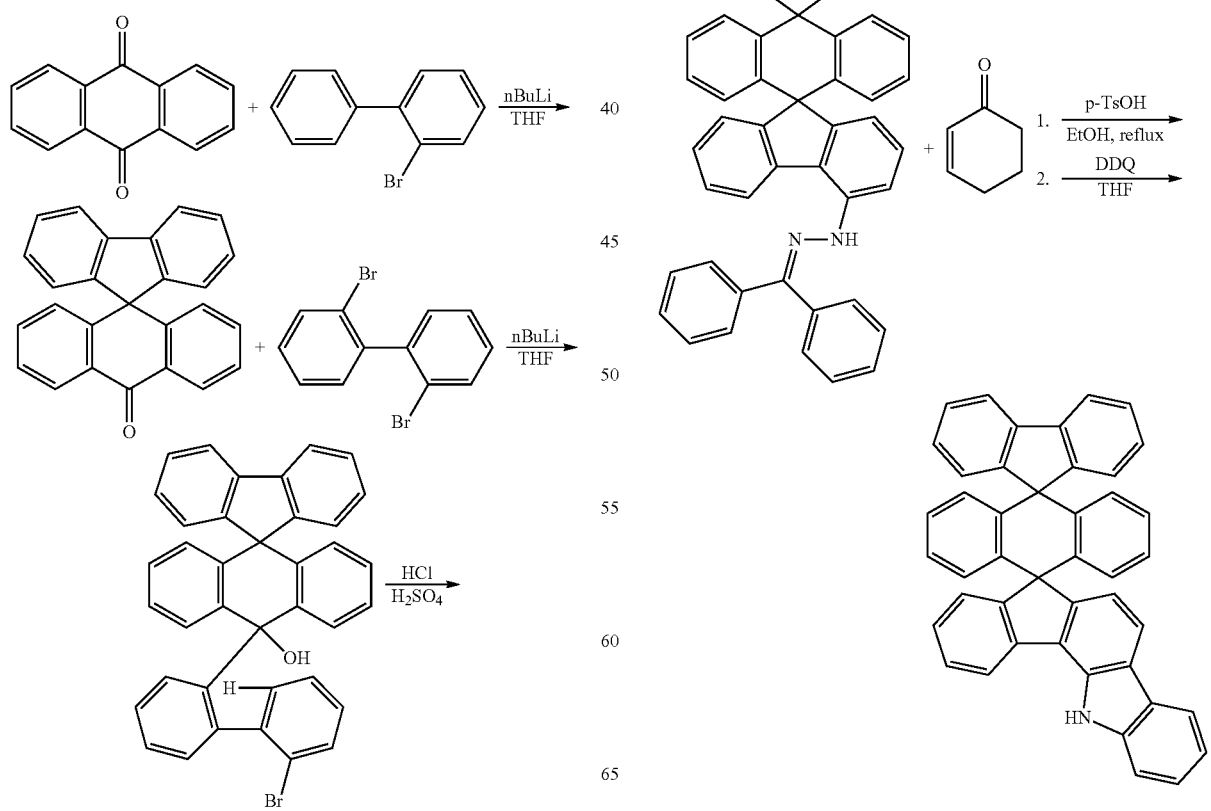

Preparation Example 9-1
Syntheses of Compounds 78 to 88 (Compounds of Chemical Formulae 6-2, 6-13, 6-14, 6-12, 6-15, 6-17, 6-16, 6-19, 6-21, 6-20 and 6-23)
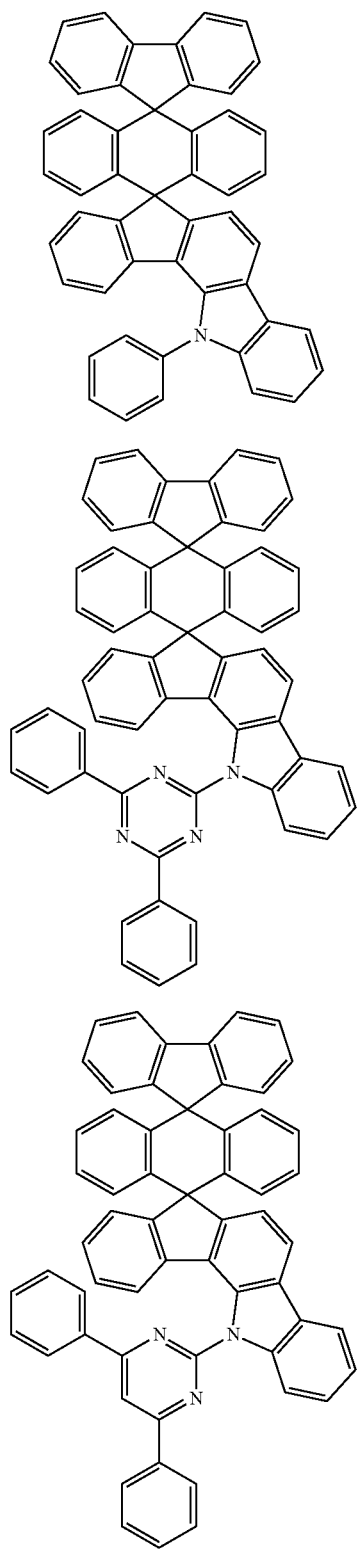
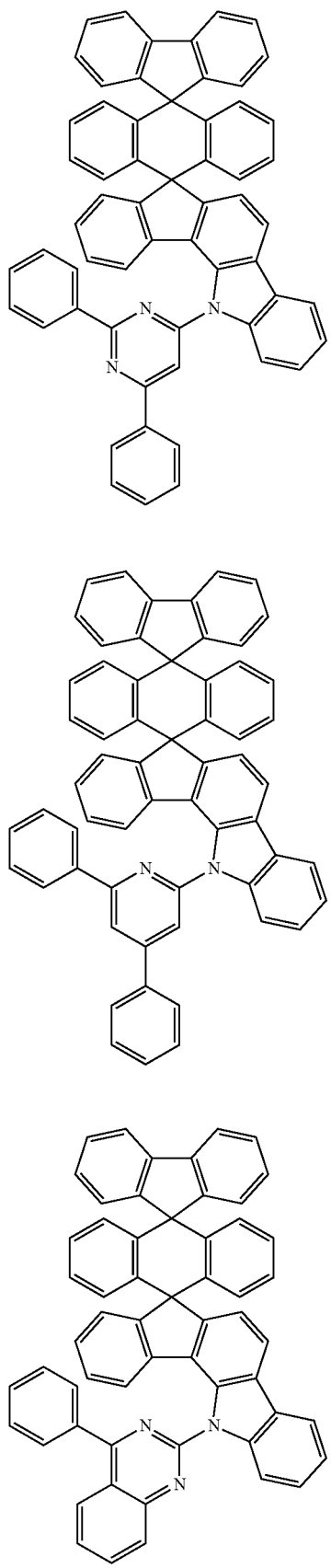

84
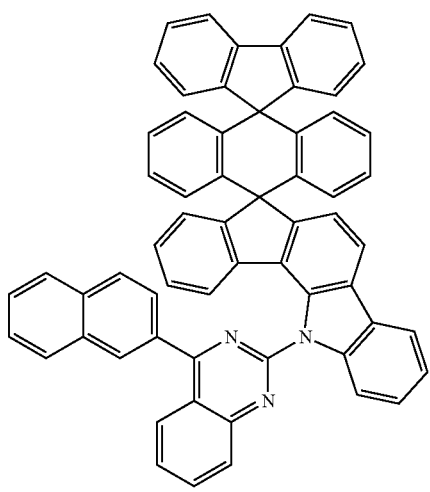
85
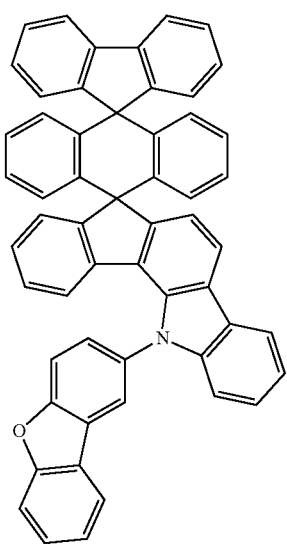
86
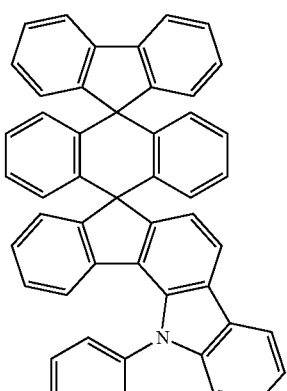
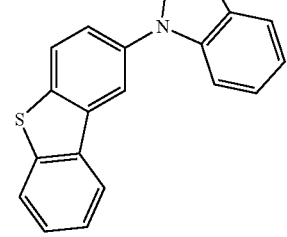
87
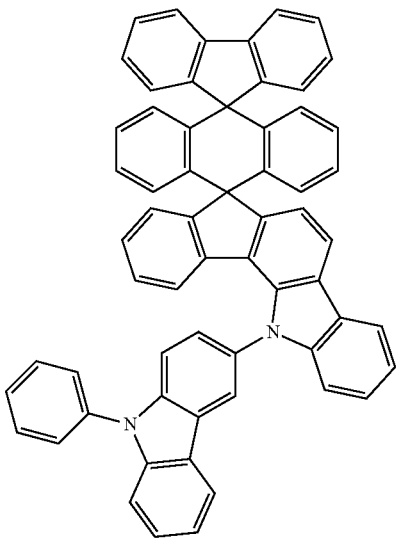
88
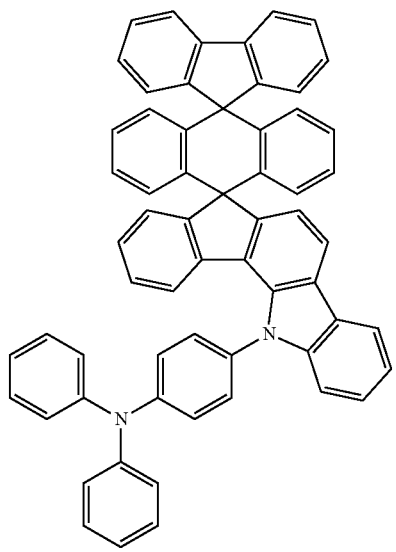
Compounds 78 to 88 were prepared in the same manner as in Preparation Examples 1-1 to 1-11, the methods preparing Compounds 1 to 11, except that Chemical Formula 6-1 was used instead of Chemical Formula 2-1 as the starting material.
Preparation Example 10
Preparation of Compound of Chemical Formula 6-25
A compound of Chemical Formula 6-25 was prepared as in the following reaction formula.
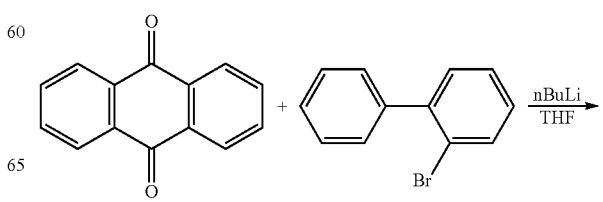

US 11,001,752 B2
201
-continued
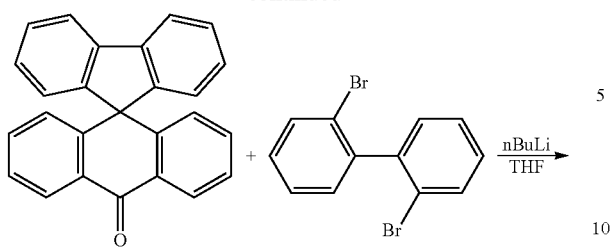
202
-continued
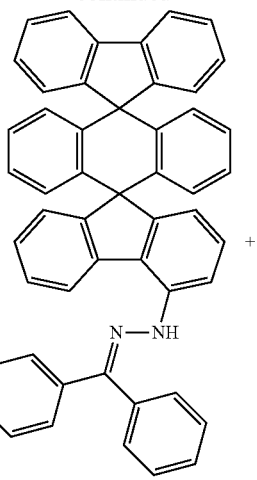
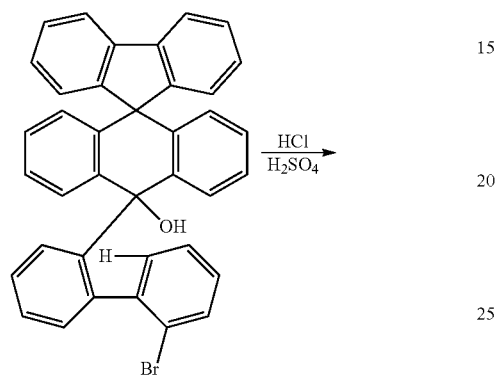
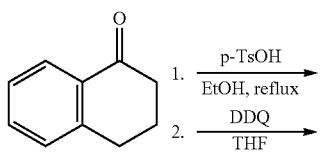
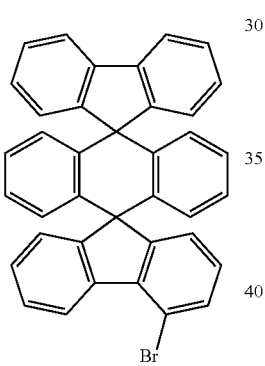
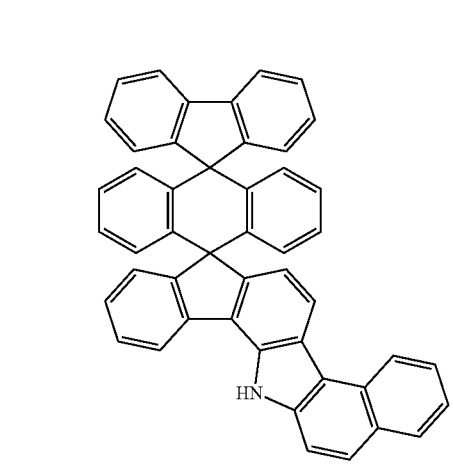
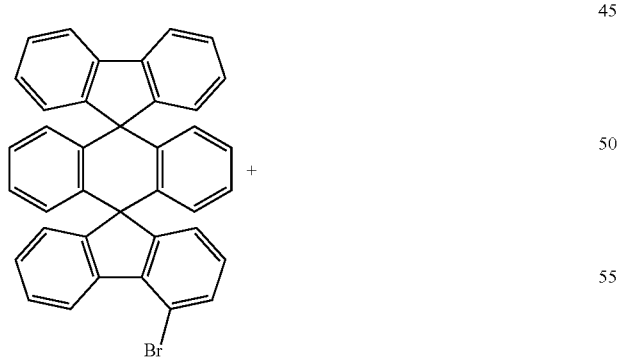
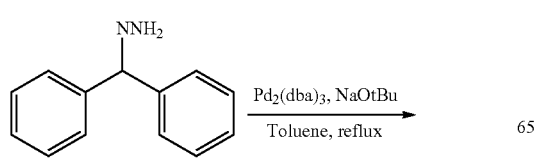
89
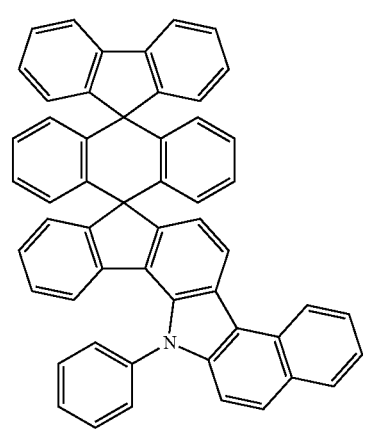

90
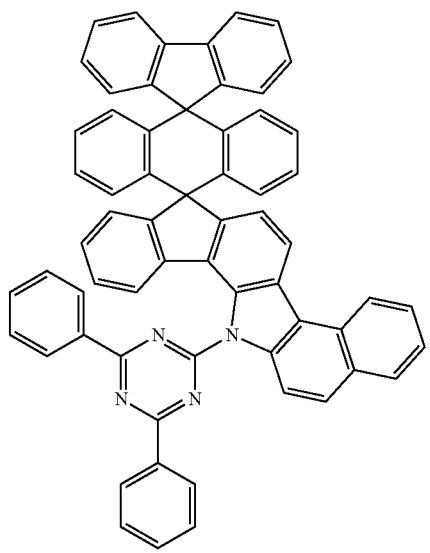
91
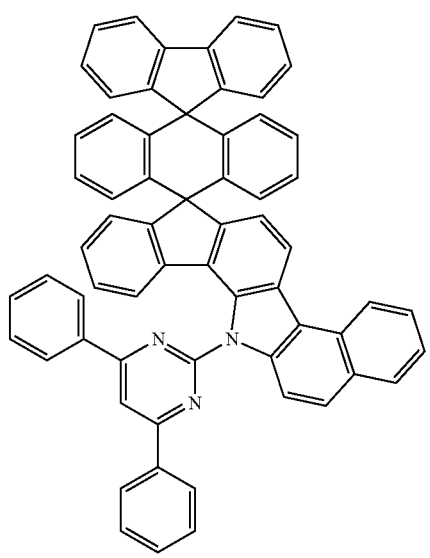
92
93
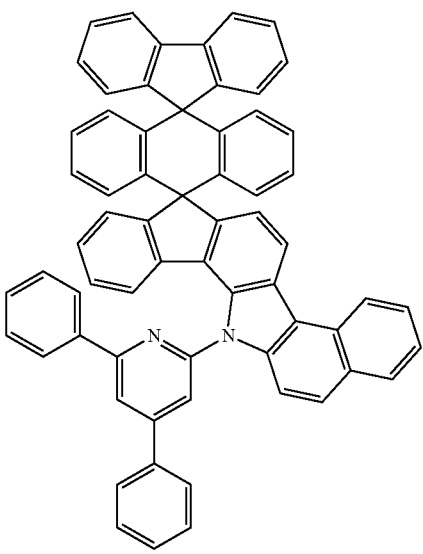
94
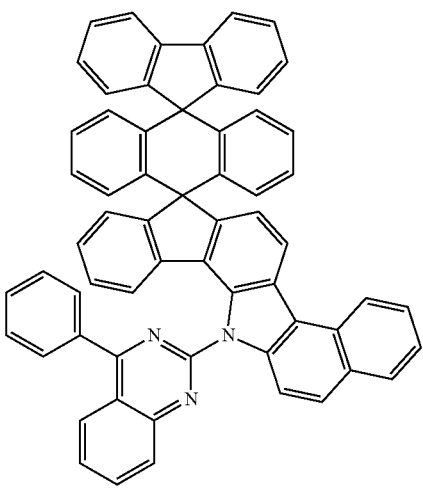
95
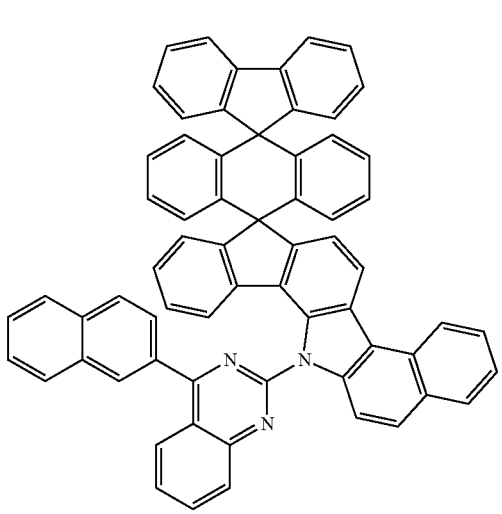

96
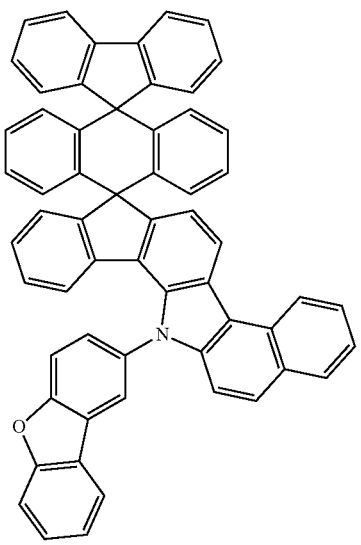
97
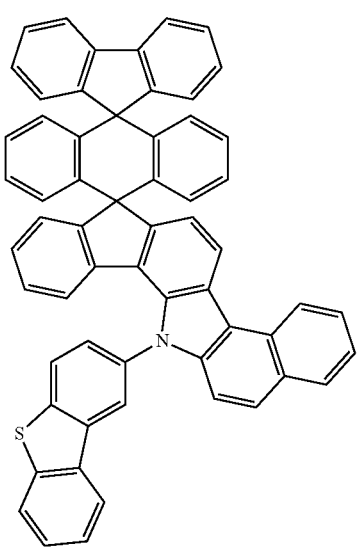
98
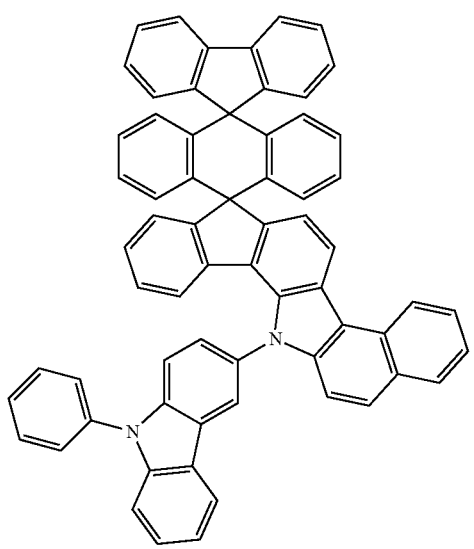
99
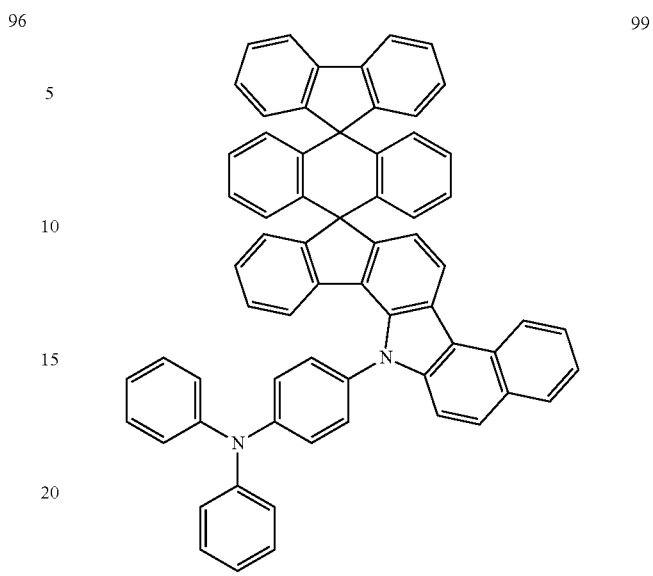
Compounds 89 to 99 were prepared in the same manner as in Preparation Examples 1-1 to 1-11, the methods preparing Compounds 1 to 11, except that Chemical Formula 6-25 was used instead of Chemical Formula 2-1 as the starting material.
Preparation Example 11
Preparation of Compound of Chemical Formula 6-26
A compound of Chemical Formula 6-26 was prepared as in the following reaction formula.
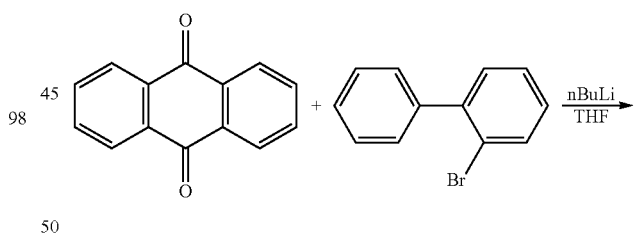
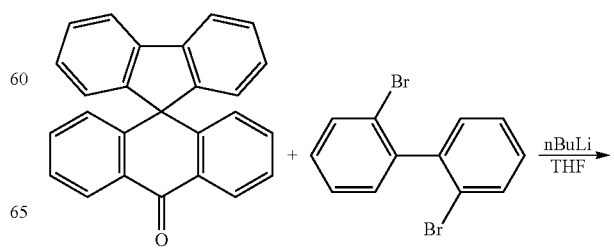

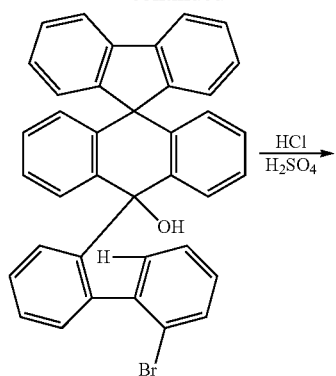
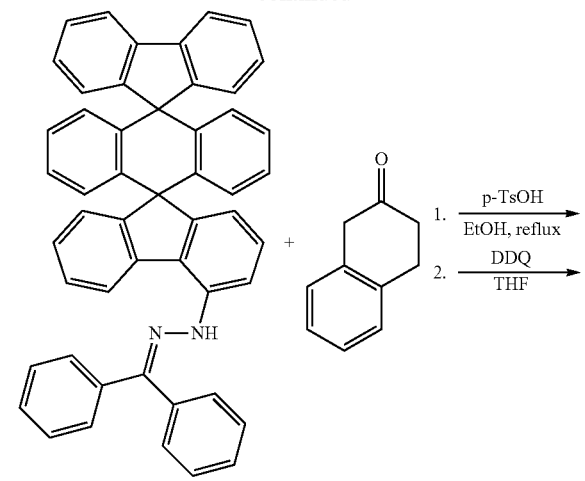
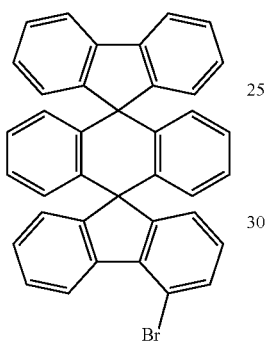
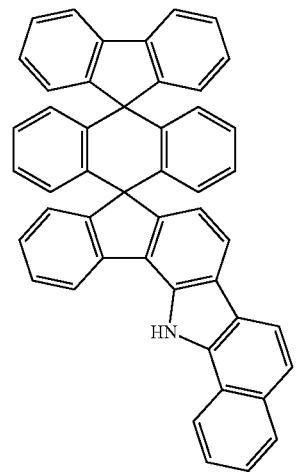
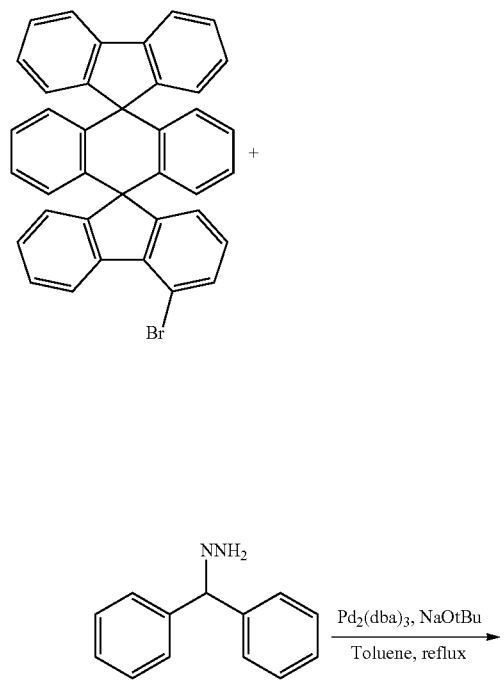
Preparation Example 11-1
Syntheses of Compounds 100 to 110 (Compounds of Chemical Formulae 15-1 to 15-11)
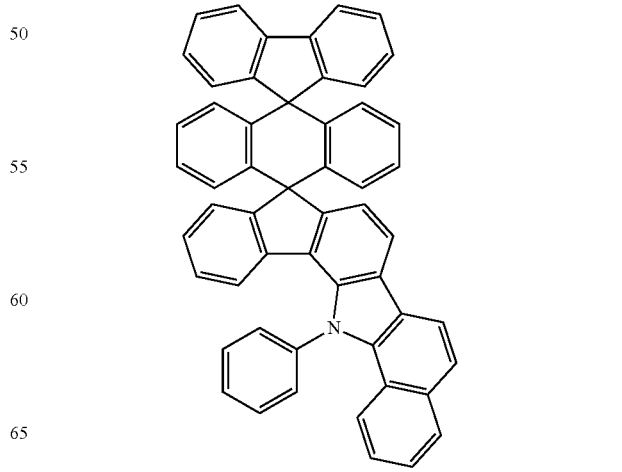

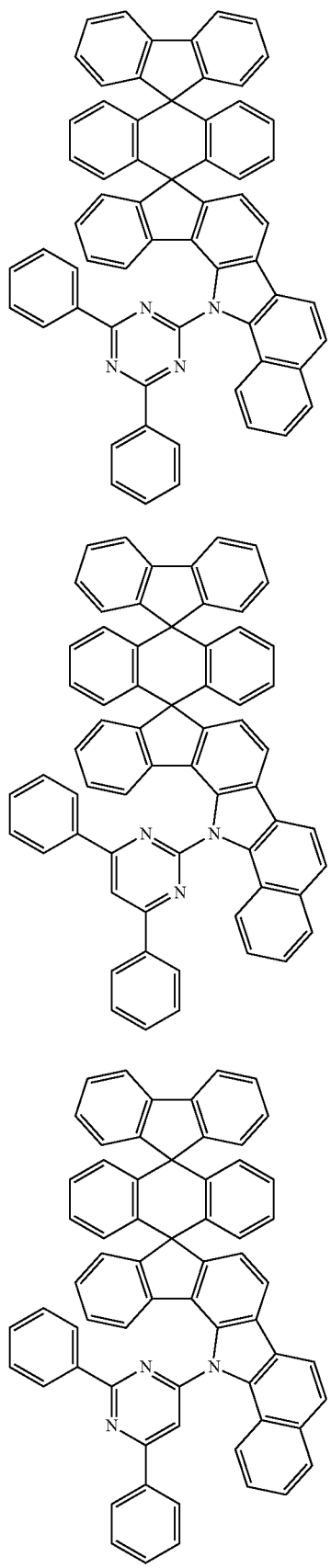
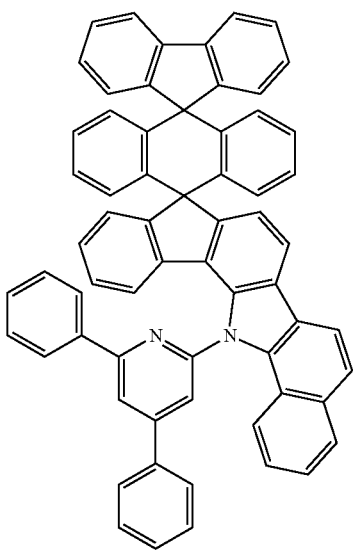
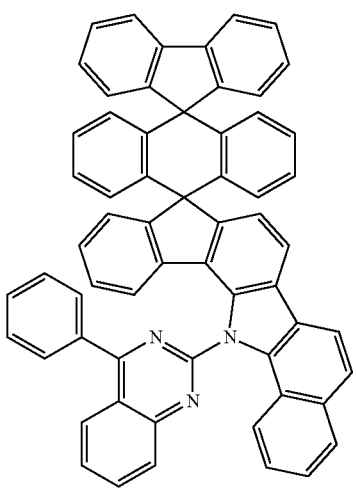
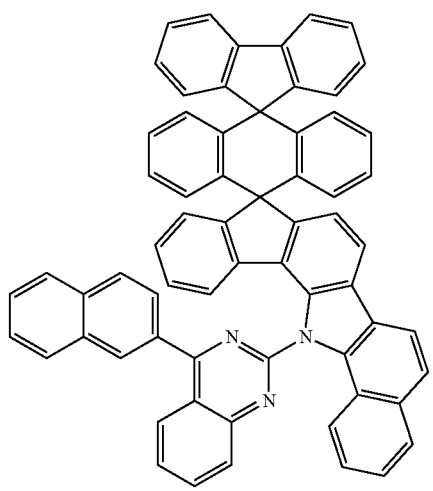

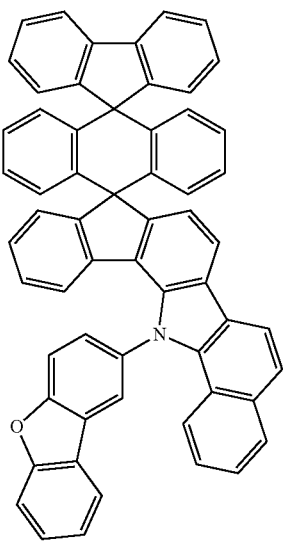
107
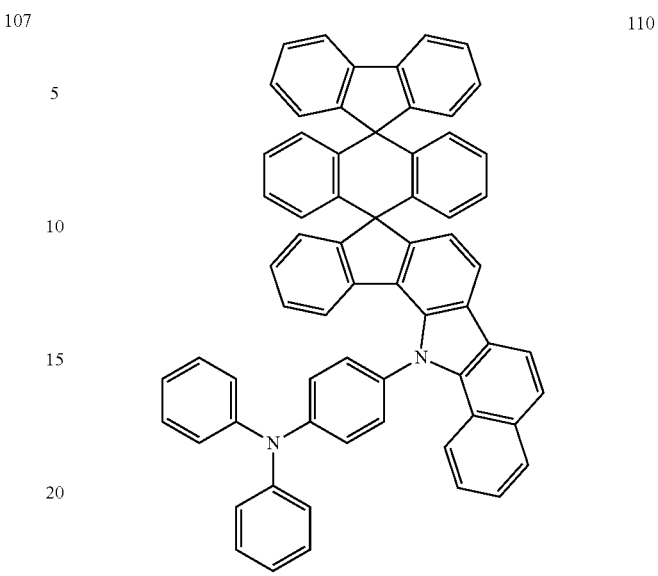
110
Compounds 100 to 110 were prepared in the same manner as in Preparation Examples 1-1 to 1-11, the methods preparing Compounds 1 to 11, except that Chemical Formula 6-25 was used instead of Chemical Formula 2-1 as the starting material.
Preparation Example 12
Preparation of Compound of Chemical Formula 7
A compound of Chemical Formula 7 was prepared as in the following reaction formula.
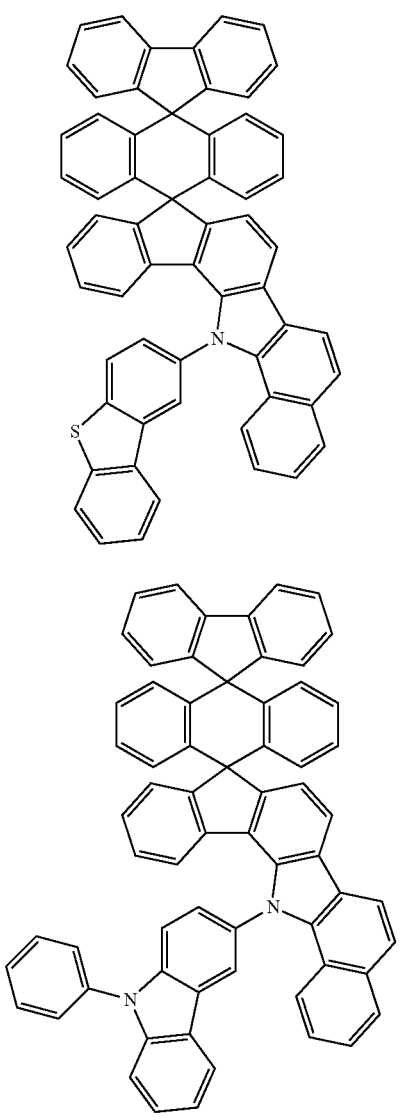

213
-continued
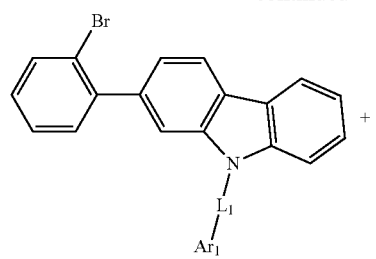
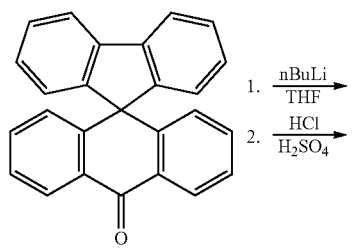
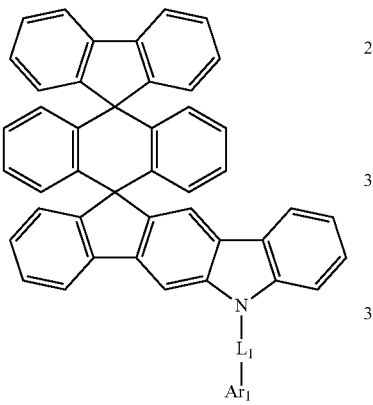
Preparation Example 12-1
Syntheses of Compounds 111 to 121 (Compounds of Chemical Formulae 7-2, 7-13, 7-14, 7-12, 7-15, 7-17, 7-16, 7-19, 7-21, 7-20 and 7-23)
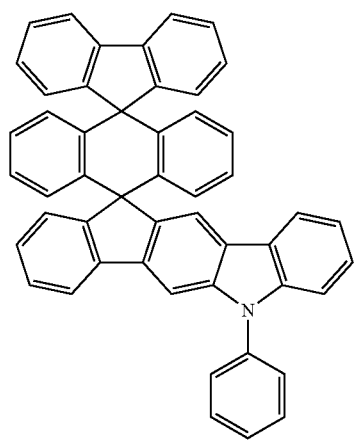
111
214
-continued
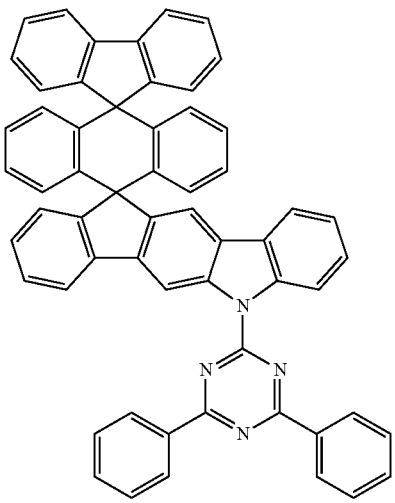
112
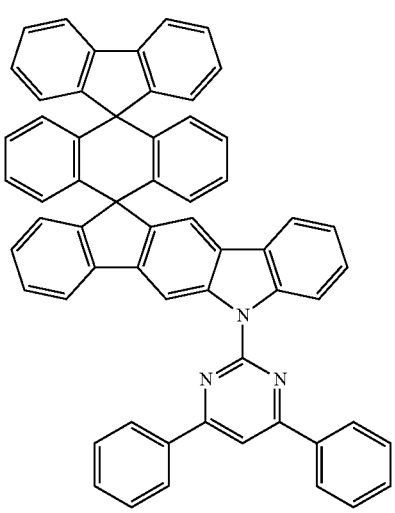
113
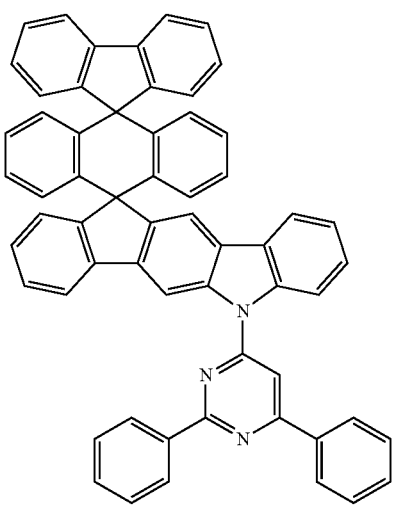
114

-continued

115

116

117

-continued

118

119

120

217

-continued

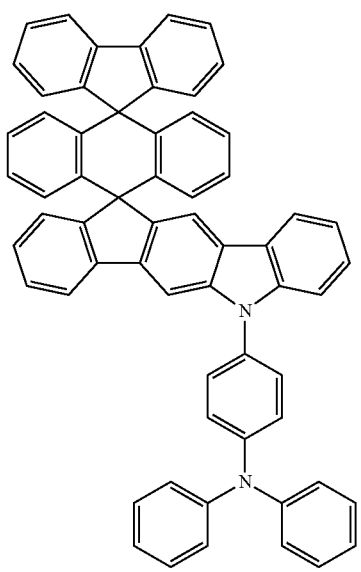

121

Compounds 111 to 121 were prepared using phenyl, 2-chloro-4,6-diphenyl-1,3,5-triazine, 2-chloro-4,6-diphenylpyrimidine, 4-chloro-2,6-diphenylpyrimidine, 2-chloro-4,6-diphenylpyridine, 2-chloro-4-phenylquinazoline, 2-chloro-4-(naphthalen-2-yl)quinazoline, 2-bromodibenzo[b,d]furan, 2-bromodibenzo[b,d]thiophene, 3-bromo-9-phenyl-9H-carbazole, 4-bromo-N,N-diphenylaniline as Ar1 in Preparation Example 12.

Preparation Example 13

Preparation of Compound of Chemical Formula 10

A compound of Chemical Formula 10 was prepared as in the following reaction formula.

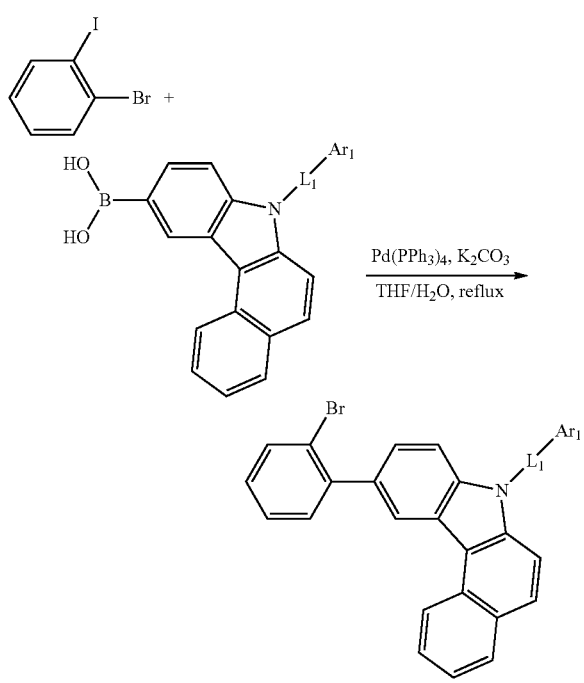

218

-continued

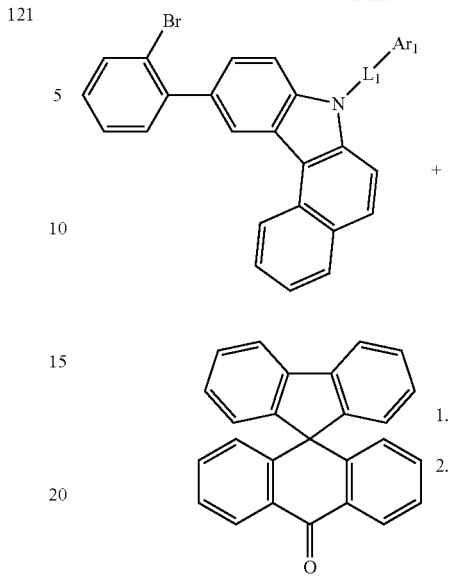

Preparation Example 14

Preparation of Compound of Chemical Formula 11

A compound of Chemical Formula 11 was prepared as in the following reaction formula.

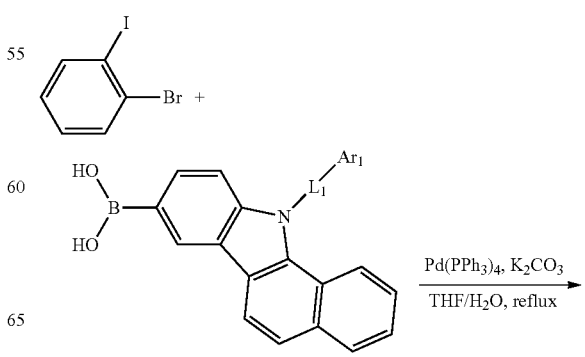

219
-continued
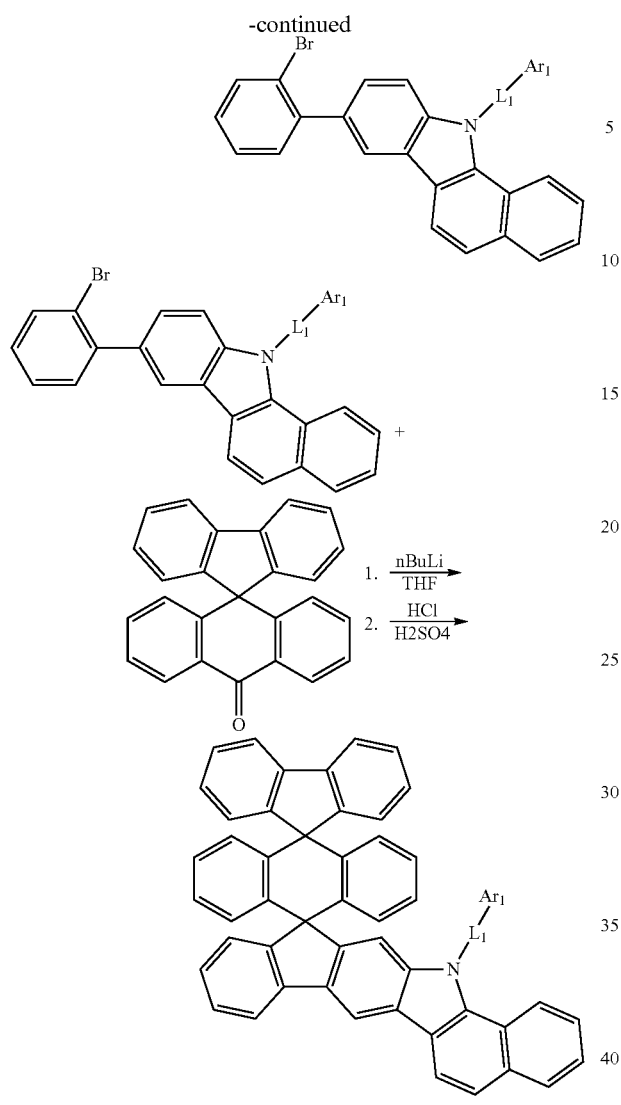
Preparation Example 15
Preparation of Compound of Chemical Formula 16
A compound of Chemical Formula 16 was prepared as in the following reaction formula.
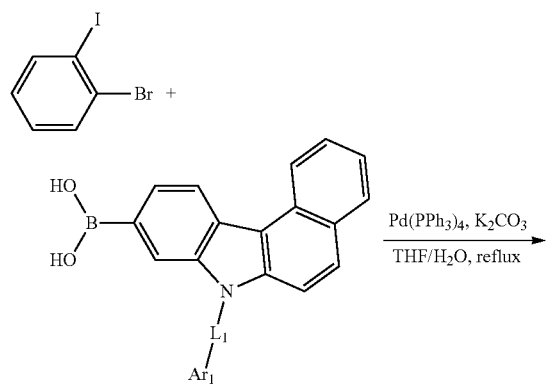
220
-continued
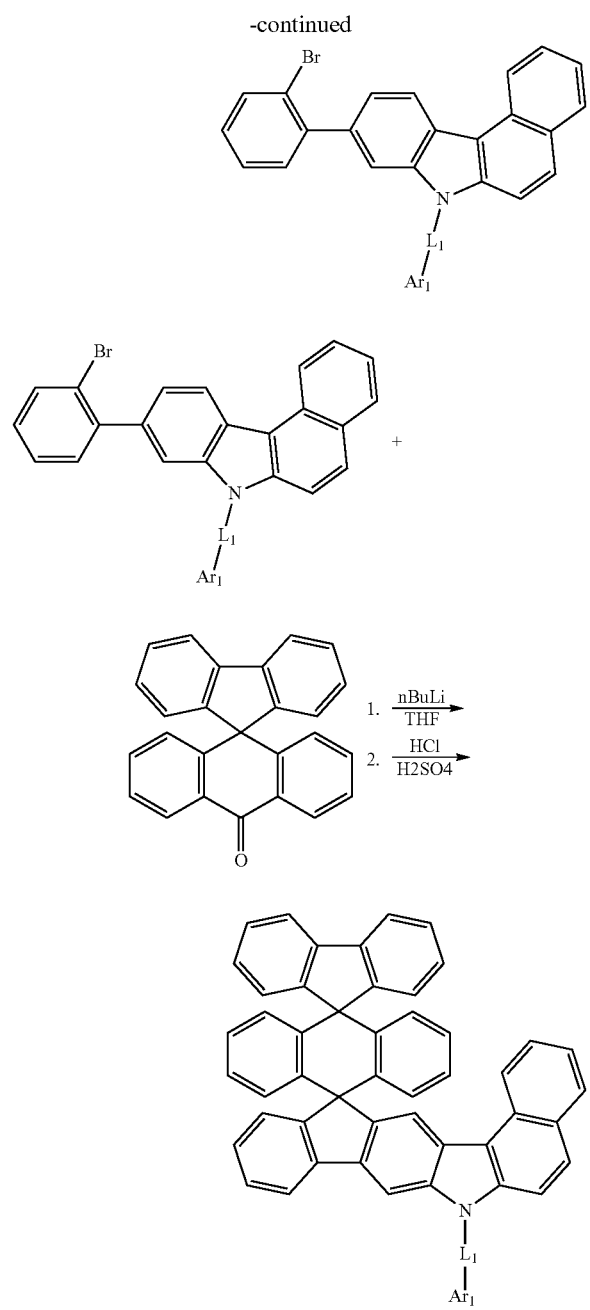
Preparation Example 16
Preparation of Compound of Chemical Formula 17
A compound of Chemical Formula 17 was prepared as in the following reaction formula.
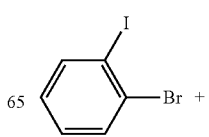

-continued

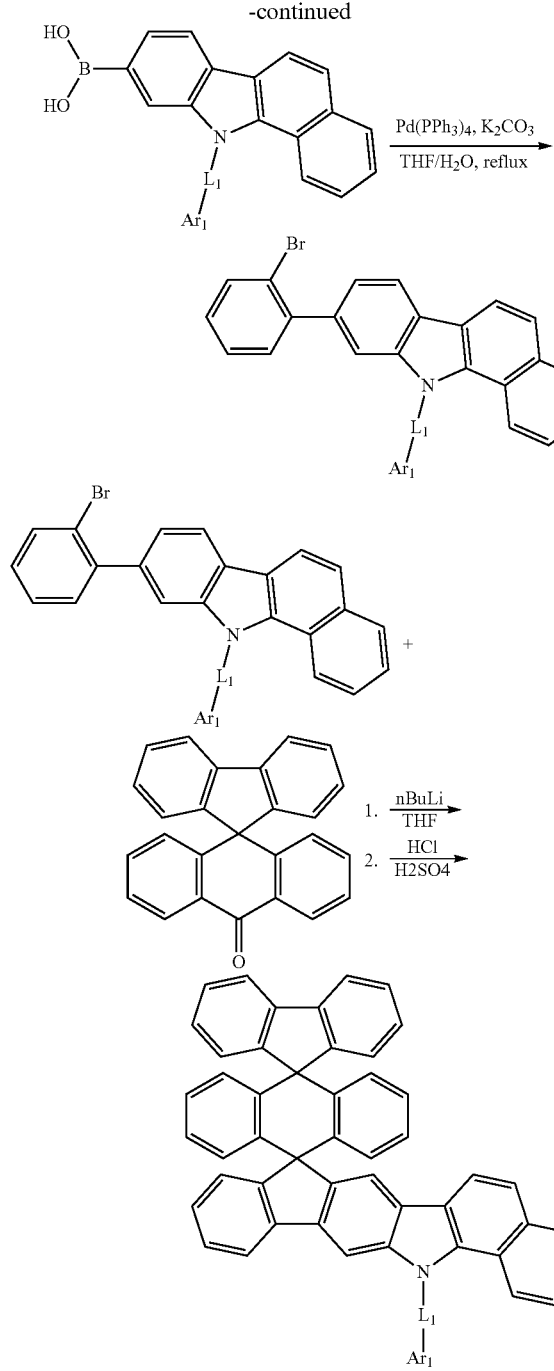

Example 1-1

A glass substrate on which indium tin oxide (ITO) was coated as a thin film to a thickness of 1,000 Å was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. In addition, the substrate was cleaned for 5 minutes using oxygen plasma, and then transferred to a vacuum depositor.

On the transparent ITO electrode prepared as above, a hole injection layer was formed by thermal vacuum depositing hexanitrile hexaazatriphenylene (HAT) of the following chemical formula to a thickness of 500 Å.

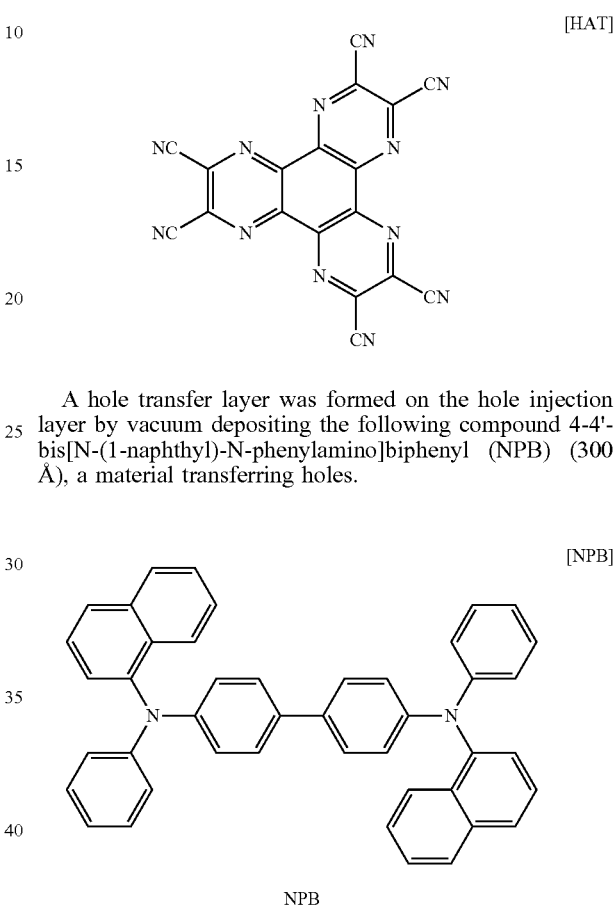

A hole transfer layer was formed on the hole injection layer by vacuum depositing the following compound 4-4'-bis[N-(1-naphthyl)-N-phenylamino]biphenyl (NPB) (300 Å), a material transferring holes.

Subsequently, an electron blocking layer was formed on the hole transfer layer by vacuum depositing the following Compound 1 to a film thickness of 100 Å.

Subsequently, a light emitting layer was formed on the electron blocking layer to a film thickness of 300 Å by vacuum depositing BH and BD as follows in a weight ratio of 25:1.

[BH]

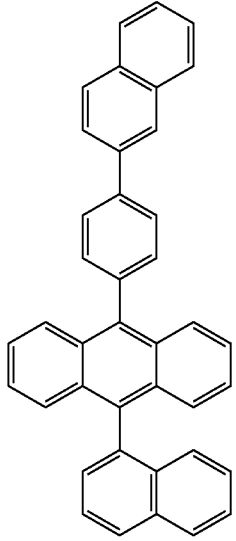

[BD]

[ET1]

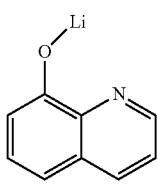

[LiQ]

On the light emitting layer, an electron injection and transfer layer was formed to a thickness of 300 Å by vacuum depositing Compound ET1 and the lithium quinolate (LiQ) compound in a weight ratio of 1:1. A cathode was formed on the electron injection and transfer layer by depositing lithium fluoride (LiF) to a thickness of 12 Å and aluminum to a thickness of 2,000 Å in consecutive order.

An organic light emitting device was manufactured by maintaining, in the above-mentioned processes, the deposition rates of the organic materials at 0.4 Å/sec to 0.7 Å/sec, the deposition rates of the lithium fluoride and the aluminum of the cathode at 0.3 Å/sec and 2 Å/sec, respectively, and the degree of vacuum during the deposition at $2 \times 10^7$ torr to $5 \times 10^{-6}$ torr.

Example 1-2

An organic light emitting device was manufactured in the same manner as in Example 1-1 except that Compound 8 was used instead of Compound 1.

Example 1-3

An organic light emitting device was manufactured in the same manner as in Example 1-1 except that Compound 9 was used instead of Compound 1.

Example 1-4

An organic light emitting device was manufactured in the same manner as in Example 1-1 except that Compound 10 was used instead of Compound 1.

Example 1-5

An organic light emitting device was manufactured in the same manner as in Example 1-1 except that Compound 11 was used instead of Compound 1.

Example 1-6

An organic light emitting device was manufactured in the same manner as in Example 1-1 except that Compound 12 was used instead of Compound 1.

Example 1-7

An organic light emitting device was manufactured in the same manner as in Example 1-1 except that Compound 19 was used instead of Compound 1.

Example 1-8

An organic light emitting device was manufactured in the same manner as in Example 1-1 except that Compound 20 was used instead of Compound 1.

Example 1-9

An organic light emitting device was manufactured in the same manner as in Example 1-1 except that Compound 21 was used instead of Compound 1.

Example 1-10

An organic light emitting device was manufactured in the same manner as in Example 1-1 except that Compound 22 was used instead of Compound 1.

Example 1-11

An organic light emitting device was manufactured in the same manner as in Example 1-1 except that Compound 23 was used instead of Compound 1.

Example 1-12

An organic light emitting device was manufactured in the same manner as in Example 1-1 except that Compound 30 was used instead of Compound 1.

Example 1-13

An organic light emitting device was manufactured in the same manner as in Example 1-1 except that Compound 31 was used instead of Compound 1.

Example 1-14

An organic light emitting device was manufactured in the same manner as in Example 1-1 except that Compound 32 was used instead of Compound 1.

Example 1-15

An organic light emitting device was manufactured in the same manner as in Example 1-1 except that Compound 33 was used instead of Compound 1.

Example 1-16

An organic light emitting device was manufactured in the same manner as in Example 1-1 except that Compound 34 was used instead of Compound 1.

Example 1-17

An organic light emitting device was manufactured in the same manner as in Example 1-1 except that Compound 41 was used instead of Compound 1.

Example 1-18

An organic light emitting device was manufactured in the same manner as in Example 1-1 except that Compound 42 was used instead of Compound 1.

Example 1-19

An organic light emitting device was manufactured in the same manner as in Example 1-1 except that Compound 43 was used instead of Compound 1.

Example 1-20

An organic light emitting device was manufactured in the same manner as in Example 1-1 except that Compound 44 was used instead of Compound 1.

Example 1-21

An organic light emitting device was manufactured in the same manner as in Example 1-1 except that Compound 45 was used instead of Compound 1.

Example 1-22

An organic light emitting device was manufactured in the same manner as in Example 1-1 except that Compound 52 was used instead of Compound 1.

Example 1-23

An organic light emitting device was manufactured in the same manner as in Example 1-1 except that Compound 53 was used instead of Compound 1.

Example 1-24

An organic light emitting device was manufactured in the same manner as in Example 1-1 except that Compound 54 was used instead of Compound 1.

Example 1-25

An organic light emitting device was manufactured in the same manner as in Example 1-1 except that Compound 55 was used instead of Compound 1.

Example 1-26

An organic light emitting device was manufactured in the same manner as in Example 1-1 except that Compound 56 was used instead of Compound 1.

Example 1-27

An organic light emitting device was manufactured in the same manner as in Example 1-1 except that Compound 63 was used instead of Compound 1.

Example 1-28

An organic light emitting device was manufactured in the same manner as in Example 1-1 except that Compound 64 was used instead of Compound 1.

Example 1-29

An organic light emitting device was manufactured in the same manner as in Example 1-1 except that Compound 65 was used instead of Compound 1.

Example 1-30

An organic light emitting device was manufactured in the same manner as in Example 1-1 except that Compound 66 was used instead of Compound 1.

Example 1-31

An organic light emitting device was manufactured in the same manner as in Example 1-1 except that Compound 67 was used instead of Compound 1.

Example 1-32

An organic light emitting device was manufactured in the same manner as in Example 1-1 except that Compound 74 was used instead of Compound 1.

Example 1-33

An organic light emitting device was manufactured in the same manner as in Example 1-1 except that Compound 75 was used instead of Compound 1.

Example 1-34

An organic light emitting device was manufactured in the same manner as in Example 1-1 except that Compound 76 was used instead of Compound 1.

Example 1-35

An organic light emitting device was manufactured in the same manner as in Example 1-1 except that Compound 77 was used instead of Compound 1.

Example 1-36

An organic light emitting device was manufactured in the same manner as in Example 1-1 except that Compound 78 was used instead of Compound 1.

Example 1-37

An organic light emitting device was manufactured in the same manner as in Example 1-1 except that Compound 85 was used instead of Compound 1.

Example 1-38

An organic light emitting device was manufactured in the same manner as in Example 1-1 except that Compound 86 was used instead of Compound 1.

Example 1-39

An organic light emitting device was manufactured in the same manner as in Example 1-1 except that Compound 87 was used instead of Compound 1.

Example 1-40

An organic light emitting device was manufactured in the same manner as in Example 1-1 except that Compound 88 was used instead of Compound 1.

Example 1-41

An organic light emitting device was manufactured in the same manner as in Example 1-1 except that Compound 89 was used instead of Compound 1.

Example 1-42

An organic light emitting device was manufactured in the same manner as in Example 1-1 except that Compound 96 was used instead of Compound 1.

Example 1-43

An organic light emitting device was manufactured in the same manner as in Example 1-1 except that Compound 97 was used instead of Compound 1.

Example 1-44

An organic light emitting device was manufactured in the same manner as in Example 1-1 except that Compound 98 was used instead of Compound 1.

Example 1-45

An organic light emitting device was manufactured in the same manner as in Example 1-1 except that Compound 99 was used instead of Compound 1.

Example 1-46

An organic light emitting device was manufactured in the same manner as in Example 1-1 except that Compound 100 was used instead of Compound 1.

Example 1-47

An organic light emitting device was manufactured in the same manner as in Example 1-1 except that Compound 107 was used instead of Compound 1.

Example 1-48

An organic light emitting device was manufactured in the same manner as in Example 1-1 except that Compound 108 was used instead of Compound 1.

Example 1-49

An organic light emitting device was manufactured in the same manner as in Example 1-1 except that Compound 109 was used instead of Compound 1.

Example 1-50

An organic light emitting device was manufactured in the same manner as in Example 1-1 except that Compound 110 was used instead of Compound 1.

Example 1-51

An organic light emitting device was manufactured in the same manner as in Example 1-1 except that Compound 111 was used instead of Compound 1.

Example 1-52

An organic light emitting device was manufactured in the same manner as in Example 1-1 except that Compound 118 was used instead of Compound 1.

Example 1-53

An organic light emitting device was manufactured in the same manner as in Example 1-1 except that Compound 119 was used instead of Compound 1.

Example 1-54

An organic light emitting device was manufactured in the same manner as in Example 1-1 except that Compound 120 was used instead of Compound 1.

Example 1-55

An organic light emitting device was manufactured in the same manner as in Example 1-1 except that Compound 121 was used instead of Compound 1.

Comparative Example 1-1

An organic light emitting device was manufactured in the same manner as in Example 1-1 except that the following Compound EB1 was used instead of Compound 1.

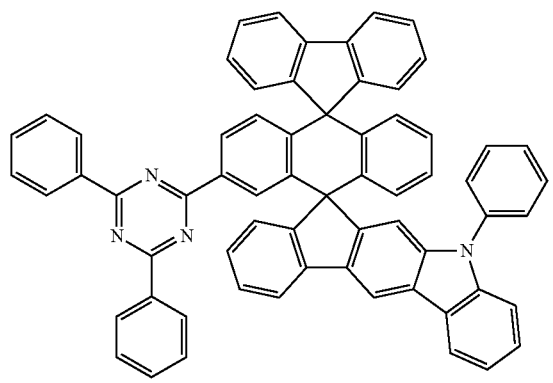

[EB1]

Comparative Example 1-2

An organic light emitting device was manufactured in the same manner as in Example 1-1 except that the following Compound EB2 was used instead of Compound 1.

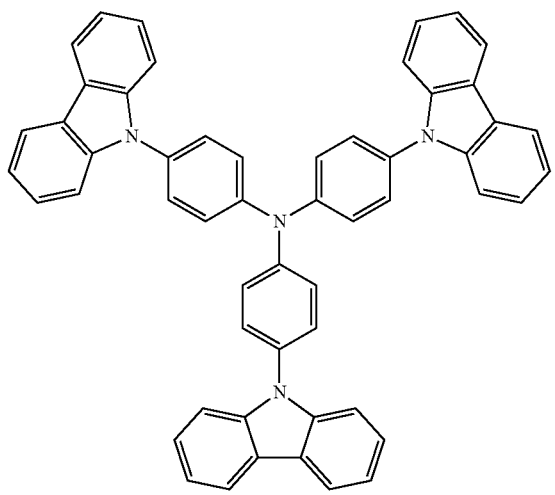

[EB2]

TCTA

When a current was applied to the organic light emitting devices manufactured in Examples 1-1 to 1-55 and Comparative Examples 1-1 and 1-2, results of Table 1 were obtained.

TABLE 1

| | Compound (Electron Blocking Layer) | Voltage (V@10 mA/cm$^2$) | Efficiency (cd/A@10 mA/cm$^2$) | Color Coordinate (x, y) |
|---|---|---|---|---|
| Example 1-1 | Compound 1 | 3.65 | 6.63 | (0.138, 0.127) |
| Example 1-2 | Compound 8 | 3.61 | 6.62 | (0.139, 0.122) |
| Example 1-3 | Compound 9 | 3.69 | 6.69 | (0.138, 0.126) |
| Example 1-4 | Compound 10 | 3.69 | 6.68 | (0.138, 0.127) |
| Example 1-5 | Compound 11 | 3.64 | 6.68 | (0.137, 0.125) |
| Example 1-6 | Compound 12 | 3.85 | 6.33 | (0.136, 0.125) |
| Example 1-7 | Compound 19 | 3.81 | 6.32 | (0.136, 0.127) |
| Example 1-8 | Compound 20 | 3.89 | 6.30 | (0.136, 0.125) |
| Example 1-9 | Compound 21 | 3.89 | 6.50 | (0.137, 0.125) |
| Example 1-10 | Compound 22 | 3.84 | 6.52 | (0.138, 0.125) |
| Example 1-11 | Compound 23 | 3.85 | 6.33 | (0.136, 0.125) |
| Example 1-12 | Compound 30 | 3.81 | 6.32 | (0.137, 0.125) |
| Example 1-13 | Compound 31 | 3.89 | 6.30 | (0.136, 0.125) |
| Example 1-14 | Compound 32 | 3.89 | 6.50 | (0.138, 0.126) |
| Example 1-15 | Compound 33 | 3.84 | 6.52 | (0.137, 0.125) |
| Example 1-16 | Compound 34 | 3.62 | 6.53 | (0.136, 0.127) |
| Example 1-17 | Compound 41 | 3.61 | 6.67 | (0.135, 0.127) |
| Example 1-18 | Compound 42 | 3.68 | 6.68 | (0.138, 0.127) |
| Example 1-19 | Compound 43 | 3.66 | 6.65 | (0.137, 0.125) |
| Example 1-20 | Compound 44 | 3.64 | 6.66 | (0.137, 0.125) |
| Example 1-21 | Compound 45 | 3.85 | 6.33 | (0.136, 0.125) |
| Example 1-22 | Compound 52 | 3.81 | 6.32 | (0.137, 0.125) |
| Example 1-23 | Compound 53 | 3.89 | 6.30 | (0.136, 0.125) |
| Example 1-24 | Compound 54 | 3.89 | 6.50 | (0.138, 0.126) |
| Example 1-25 | Compound 55 | 3.84 | 6.52 | (0.137, 0.125) |
| Example 1-26 | Compound 56 | 3.85 | 6.33 | (0.136, 0.127) |
| Example 1-27 | Compound 63 | 3.81 | 6.32 | (0.135, 0.127) |
| Example 1-28 | Compound 64 | 3.89 | 6.30 | (0.138, 0.127) |
| Example 1-29 | Compound 65 | 3.89 | 6.50 | (0.137, 0.125) |
| Example 1-30 | Compound 66 | 3.84 | 6.52 | (0.137, 0.125) |
| Example 1-31 | Compound 67 | 3.65 | 6.69 | (0.136, 0.125) |
| Example 1-32 | Compound 74 | 3.61 | 6.62 | (0.137, 0.125) |
| Example 1-33 | Compound 75 | 3.65 | 6.65 | (0.136, 0.125) |
| Example 1-34 | Compound 76 | 3.64 | 6.64 | (0.138, 0.126) |
| Example 1-35 | Compound 77 | 3.69 | 6.61 | (0.137, 0.125) |
| Example 1-36 | Compound 78 | 3.85 | 6.33 | (0.136, 0.127) |
| Example 1-37 | Compound 85 | 3.81 | 6.32 | (0.135, 0.127) |
| Example 1-38 | Compound 86 | 3.89 | 6.30 | (0.138, 0.127) |
| Example 1-39 | Compound 87 | 3.89 | 6.50 | (0.137, 0.125) |
| Example 1-40 | Compound 88 | 3.84 | 6.52 | (0.137, 0.125) |
| Example 1-41 | Compound 89 | 3.85 | 6.33 | (0.136, 0.125) |
| Example 1-42 | Compound 96 | 3.81 | 6.32 | (0.137, 0.125) |
| Example 1-43 | Compound 97 | 3.84 | 6.36 | (0.136, 0.125) |
| Example 1-44 | Compound 98 | 3.89 | 6.50 | (0.138, 0.126) |
| Example 1-45 | Compound 99 | 3.83 | 6.32 | (0.137, 0.125) |
| Example 1-46 | Compound 100 | 3.82 | 6.31 | (0.136, 0.127) |
| Example 1-47 | Compound 107 | 3.80 | 6.49 | (0.135, 0.127) |
| Example 1-48 | Compound 108 | 3.81 | 6.52 | (0.138, 0.127) |
| Example 1-49 | Compound 109 | 3.85 | 6.33 | (0.137, 0.125) |
| Example 1-50 | Compound 110 | 3.81 | 6.32 | (0.137, 0.125) |
| Example 1-51 | Compound 111 | 3.67 | 6.64 | (0.136, 0.125) |
| Example 1-52 | Compound 118 | 3.63 | 6.65 | (0.137, 0.125) |
| Example 1-53 | Compound 119 | 3.62 | 6.66 | (0.136, 0.125) |
| Example 1-54 | Compound 120 | 3.63 | 6.67 | (0.138, 0.126) |
| Example 1-55 | Compound 121 | 3.65 | 6.65 | (0.137, 0.125) |
| Comparative Example 1-1 | EB1 | 4.53 | 5.41 | (0.136, 0.127) |
| Comparative Example 1-2 | EB2 (TCTA) | 4.83 | 5.11 | (0.136, 0.127) |

As shown in Table 1, the organic light emitting device manufactured using the compound of the present disclosure as an electron blocking layer exhibited excellent properties in terms of efficiency, driving voltage and/or stability of the organic light emitting device when compared to the existing organic light emitting device using TCTA since the compound of the present disclosure performed a role of blocking electrons.

When comparing Examples 1-1 to 1-5, 1-16 to 1-20, 1-31 to 1-35, and 1-51 to 1-55 with other examples, properties of low voltage and high efficiency were obtained compared to the compounds forming a ring once more in the fused form.

Based on the results of Table 1, it was identified that the compound according to the present disclosure had an excellent electron blocking ability and was capable of being used in an organic light emitting device.

Example 2-1 to Example 2-55

Experiments were carried out in the same manner as in Example 1-1 except that Compounds 1, 8, 9, 10, 11, 12, 19, 20, 21, 22, 23, 30, 31, 32, 33, 34, 41, 42, 43, 44, 45, 52, 53, 54, 55, 56, 63, 64, 65, 66, 67, 74, 75, 76, 77, 78, 85, 86, 87, 88, 89, 96, 97, 98, 99, 100, 107, 108, 109, 110, 111, 118, 119, 120 and 121 were used as the hole transfer layer instead of NPB.

Comparative Example 2-1

An organic light emitting device was manufactured in the same manner as in Example 2-1 except that the following Compound HT1 (NPB) was used instead of Compound 1-1.

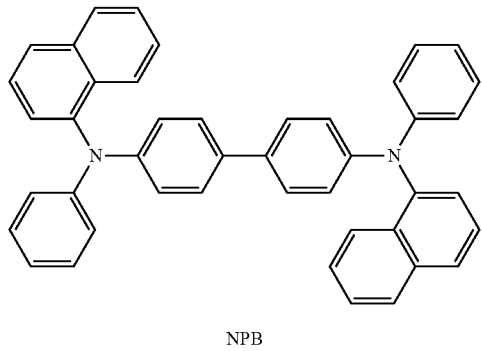

[HT1]

NPB

Comparative Example 2-2

An organic light emitting device was manufactured in the same manner as in Example 2-1 except that the following Compound HT2 (TCTA) was used instead of Compound 1-1.

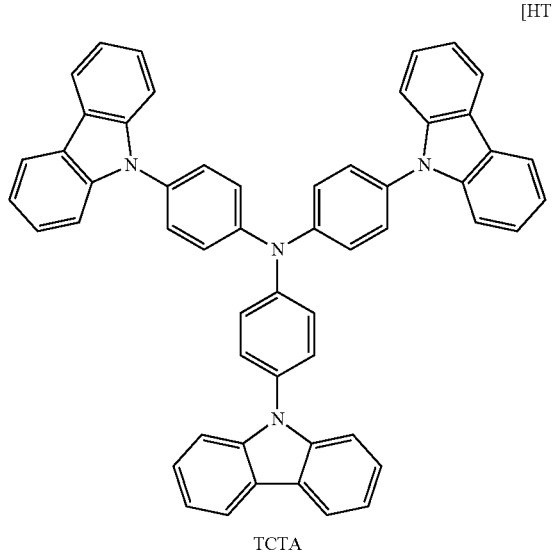

[HT2]

TCTA

When a current was applied to the organic light emitting devices manufactured in Example 2-1 to Example 2-20 and Comparative Examples 2-1 and 2-2, results of Table 2 were obtained.

TABLE 2

| | Compound (Hole Transfer Layer) | Voltage (V@10 mA/cm$^2$) | Efficiency (cd/A@10 mA/cm$^2$) | Color Coordinate (x, y) |
| --- | --- | --- | --- | --- |
| Example 2-1 | Compound 1 | 3.65 | 5.15 | (0.138, 0.127) |
| Example 2-2 | Compound 8 | 3.74 | 5.21 | (0.139, 0.122) |
| Example 2-3 | Compound 9 | 3.71 | 5.18 | (0.138, 0.126) |
| Example 2-4 | Compound 10 | 3.61 | 5.20 | (0.138, 0.127) |
| Example 2-5 | Compound 11 | 3.62 | 5.11 | (0.137, 0.125) |
| Example 2-6 | Compound 12 | 3.74 | 4.92 | (0.136, 0.125) |
| Example 2-7 | Compound 19 | 3.84 | 4.91 | (0.136, 0.127) |
| Example 2-8 | Compound 20 | 3.81 | 5.05 | (0.136, 0.125) |
| Example 2-9 | Compound 21 | 3.83 | 4.90 | (0.137, 0.125) |
| Example 2-10 | Compound 22 | 3.75 | 4.88 | (0.138, 0.125) |
| Example 2-11 | Compound 23 | 3.72 | 4.76 | (0.136, 0.125) |
| Example 2-12 | Compound 30 | 3.78 | 4.95 | (0.137, 0.125) |
| Example 2-13 | Compound 31 | 3.73 | 5.05 | (0.136, 0.125) |
| Example 2-14 | Compound 32 | 3.70 | 4.93 | (0.138, 0.126) |
| Example 2-15 | Compound 33 | 3.74 | 4.89 | (0.137, 0.125) |
| Example 2-16 | Compound 34 | 3.65 | 5.15 | (0.136, 0.127) |
| Example 2-17 | Compound 41 | 3.74 | 5.21 | (0.135, 0.127) |
| Example 2-18 | Compound 42 | 3.71 | 5.18 | (0.138, 0.127) |
| Example 2-19 | Compound 43 | 3.61 | 5.20 | (0.137, 0.125) |
| Example 2-20 | Compound 44 | 3.62 | 5.16 | (0.137, 0.125) |
| Example 2-21 | Compound 45 | 3.78 | 5.01 | (0.136, 0.125) |
| Example 2-22 | Compound 52 | 3.74 | 4.98 | (0.137, 0.125) |
| Example 2-23 | Compound 53 | 3.84 | 4.95 | (0.136, 0.125) |
| Example 2-24 | Compound 54 | 3.80 | 5.05 | (0.138, 0.126) |
| Example 2-25 | Compound 55 | 3.83 | 4.93 | (0.137, 0.125) |
| Example 2-26 | Compound 56 | 3.76 | 4.88 | (0.136, 0.127) |
| Example 2-27 | Compound 63 | 3.74 | 4.76 | (0.135, 0.127) |
| Example 2-28 | Compound 64 | 3.79 | 4.95 | (0.138, 0.127) |
| Example 2-29 | Compound 65 | 3.73 | 5.05 | (0.137, 0.125) |
| Example 2-30 | Compound 66 | 3.70 | 4.93 | (0.137, 0.125) |
| Example 2-31 | Compound 67 | 3.65 | 5.15 | (0.136, 0.125) |
| Example 2-32 | Compound 74 | 3.74 | 5.21 | (0.137, 0.125) |
| Example 2-33 | Compound 75 | 3.71 | 5.18 | (0.136, 0.125) |
| Example 2-34 | Compound 76 | 3.61 | 5.20 | (0.138, 0.126) |
| Example 2-35 | Compound 77 | 3.62 | 5.16 | (0.137, 0.125) |
| Example 2-36 | Compound 78 | 3.78 | 5.01 | (0.136, 0.127) |
| Example 2-37 | Compound 85 | 3.74 | 4.95 | (0.135, 0.127) |
| Example 2-38 | Compound 86 | 3.84 | 4.95 | (0.138, 0.127) |
| Example 2-39 | Compound 87 | 3.80 | 5.05 | (0.137, 0.125) |
| Example 2-40 | Compound 88 | 3.81 | 4.93 | (0.137, 0.125) |
| Example 2-41 | Compound 89 | 3.76 | 4.85 | (0.136, 0.125) |
| Example 2-42 | Compound 96 | 3.74 | 4.76 | (0.137, 0.125) |
| Example 2-43 | Compound 97 | 3.79 | 4.95 | (0.136, 0.125) |
| Example 2-44 | Compound 98 | 3.73 | 5.01 | (0.138, 0.126) |
| Example 2-45 | Compound 99 | 3.71 | 4.93 | (0.137, 0.125) |
| Example 2-46 | Compound 100 | 3.74 | 4.76 | (0.136, 0.125) |
| Example 2-47 | Compound 107 | 3.79 | 4.95 | (0.135, 0.127) |
| Example 2-48 | Compound 108 | 3.73 | 5.05 | (0.138, 0.127) |
| Example 2-49 | Compound 109 | 3.79 | 4.95 | (0.137, 0.125) |
| Example 2-50 | Compound 110 | 3.73 | 5.05 | (0.137, 0.125) |
| Example 2-51 | Compound 111 | 3.65 | 5.15 | (0.138, 0.126) |
| Example 2-52 | Compound 118 | 3.74 | 5.21 | (0.137, 0.125) |
| Example 2-53 | Compound 119 | 3.71 | 5.18 | (0.136, 0.127) |
| Example 2-54 | Compound 120 | 3.61 | 5.20 | (0.135, 0.127) |
| Example 2-55 | Compound 121 | 3.62 | 5.16 | (0.138, 0.127) |
| Comparative Example 2-1 | HT1 (NPB) | 4.21 | 4.53 | (0.136, 0.127) |
| Comparative Example 2-2 | HT2 (TCTA) | 4.45 | 4.32 | (0.136, 0.127) |

The compound of the present disclosure exhibited excellent properties in terms of efficiency, driving voltage and/or stability of the organic light emitting device compared to Comparative Examples 1 and 2.

Based on the results of Table 1, it was identified that the compound according to the present disclosure had an excellent hole transfer ability and was capable of being used in an organic light emitting device.

Based on the results of Tables 1 and 2, it was identified that the compound according to the present disclosure had an excellent hole transfer ability as well as an excellent electron blocking ability, and was capable of being used in an organic light emitting device.

Comparative Example 3

A glass substrate on which indium tin oxide (ITO) was coated as a thin film to a thickness of 1,000 Å was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. In addition, the substrate was cleaned for 5 minutes using oxygen plasma, and then transferred to a vacuum depositor.

A green organic light emitting device was manufactured by forming a light emitting element in the order of m-MTDATA (60 nm)/TCTA (80 nm)/CBP+10% Ir(ppy)$_3$ (300 nm)/BCP (10 nm)/Alq$_3$ (30 nm)/LiF (1 nm)/Al (200 nm) on the transparent ITO electrode prepared as above using CBP as a host.

Structures of the m-MTDATA, the TCTA, the Ir(ppy)$_3$, the BCP and the CBP are each as follows.

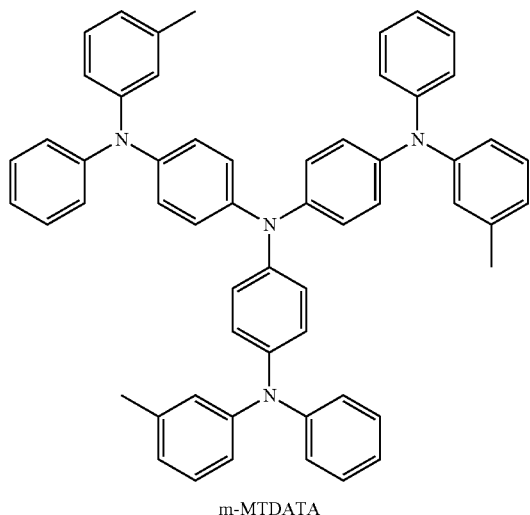

m-MTDATA

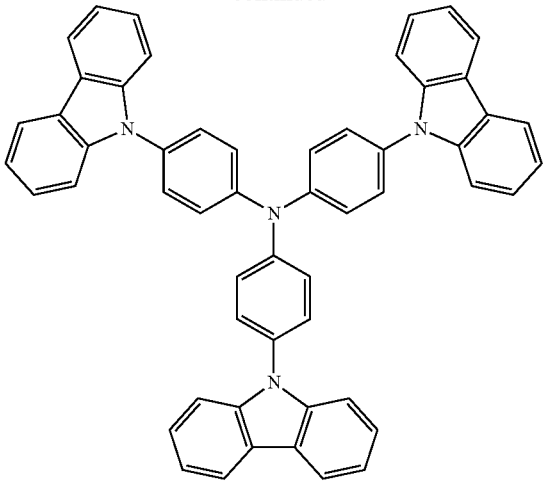

TCTA

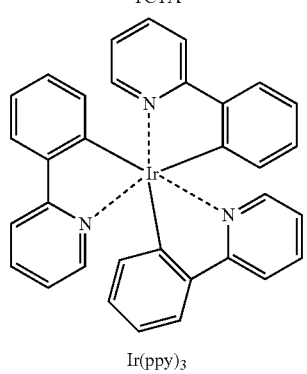

Ir(ppy)$_3$

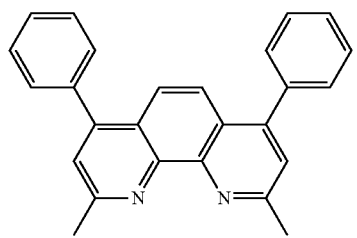

BCP

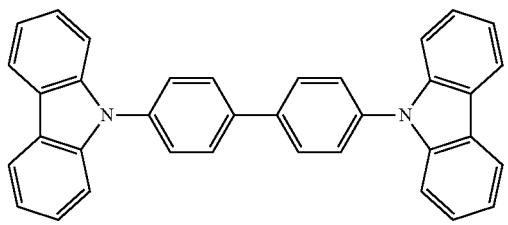

CBP

The compounds synthesized in the synthesis examples were high-purity sublimation purified using commonly known methods, and then a green organic light emitting device was manufactured using a method as below.

Example 3-1

An organic light emitting device was manufactured in the same manner as in Comparative Example 3 except that Compound 2 was used instead of CBP.

Example 3-2

An organic light emitting device was manufactured in the same manner as in Comparative Example 3 except that Compound 3 was used instead of Compound CBP.

Example 3-3

An organic light emitting device was manufactured in the same manner as in Comparative Example 3 except that Compound 4 was used instead of Compound CBP.

Example 3-4

An organic light emitting device was manufactured in the same manner as in Comparative Example 3 except that Compound 5 was used instead of Compound CBP.

Example 3-5

An organic light emitting device was manufactured in the same manner as in Comparative Example 3 except that Compound 8 was used instead of Compound CBP.

Example 3-6

An organic light emitting device was manufactured in the same manner as in Comparative Example 3 except that Compound 10 was used instead of Compound CBP.

Example 3-7

An organic light emitting device was manufactured in the same manner as in Comparative Example 3 except that Compound 13 was used instead of Compound CBP.

Example 3-8

An organic light emitting device was manufactured in the same manner as in Comparative Example 3 except that Compound 24 was used instead of Compound CBP.

Example 3-9

An organic light emitting device was manufactured in the same manner as in Comparative Example 3 except that Compound 35 was used instead of Compound CBP.

Example 3-10

An organic light emitting device was manufactured in the same manner as in Comparative Example 3 except that Compound 41 was used instead of Compound CBP.

Example 3-11

An organic light emitting device was manufactured in the same manner as in Comparative Example 3 except that Compound 43 was used instead of Compound CBP.

Example 3-12

An organic light emitting device was manufactured in the same manner as in Comparative Example 3 except that Compound 57 was used instead of Compound CBP.

Example 3-13

An organic light emitting device was manufactured in the same manner as in Comparative Example 3 except that Compound 68 was used instead of Compound CBP.

Example 3-14

An organic light emitting device was manufactured in the same manner as in Comparative Example 3 except that Compound 79 was used instead of Compound CBP.

Example 3-15

An organic light emitting device was manufactured in the same manner as in Comparative Example 3 except that Compound 85 was used instead of Compound CBP.

Example 3-16

An organic light emitting device was manufactured in the same manner as in Comparative Example 3 except that Compound 87 was used instead of Compound CBP.

Example 3-17

An organic light emitting device was manufactured in the same manner as in Comparative Example 3 except that Compound 90 was used instead of Compound CBP.

Example 3-18

An organic light emitting device was manufactured in the same manner as in Comparative Example 3 except that Compound 101 was used instead of Compound CBP.

Example 3-19

An organic light emitting device was manufactured in the same manner as in Comparative Example 3 except that Compound 112 was used instead of Compound CBP.

Example 3-20

An organic light emitting device was manufactured in the same manner as in Comparative Example 3 except that Compound 118 was used instead of Compound CBP.

Example 3-21

An organic light emitting device was manufactured in the same manner as in Comparative Example 3 except that Compound 120 was used instead of Compound CBP.

When a current was applied to the organic light emitting devices manufactured in Comparative Example 3, and Examples 3-1 to 3-21, results of Table 3 were obtained.

TABLE 3

| | Compound (Host) | Voltage (V@10 mA/cm$^2$) | Efficiency (cd/A@10 mA/cm$^2$) | EL Peak (nm) |
|---|---|---|---|---|
| Comparative Example 3 | CBP | 7.62 | 36.12 | 516 |
| Example 3-1 | Compound 2 | 6.60 | 42.93 | 517 |
| Example 3-2 | Compound 3 | 6.62 | 42.24 | 516 |
| Example 3-3 | Compound 4 | 6.61 | 42.72 | 517 |
| Example 3-4 | Compound 5 | 6.52 | 42.65 | 518 |

TABLE 3-continued

| | Compound (Host) | Voltage (V@10 mA/cm²) | Efficiency (cd/A@10 mA/cm²) | EL Peak (nm) |
|---|---|---|---|---|
| Example 3-5 | Compound 8 | 6.60 | 42.31 | 517 |
| Example 3-6 | Compound 10 | 6.53 | 42.63 | 517 |
| Example 3-7 | Compound 13 | 6.61 | 42.62 | 516 |
| Example 3-8 | Compound 24 | 6.62 | 42.64 | 517 |
| Example 3-9 | Compound 35 | 6.52 | 42.08 | 516 |
| Example 3-10 | Compound 41 | 6.61 | 42.72 | 518 |
| Example 3-11 | Compound 43 | 6.62 | 42.70 | 517 |
| Example 3-12 | Compound 57 | 6.3 | 42.76 | 516 |
| Example 3-13 | Compound 68 | 6.60 | 44.93 | 517 |
| Example 3-14 | Compound 79 | 6.56 | 45.24 | 516 |
| Example 3-15 | Compound 85 | 6.61 | 44.72 | 518 |
| Example 3-16 | Compound 87 | 6.59 | 44.65 | 517 |
| Example 3-17 | Compound 90 | 6.68 | 44.31 | 515 |
| Example 3-18 | Compound 101 | 6.53 | 44.63 | 516 |
| Example 3-19 | Compound 112 | 6.54 | 44.62 | 516 |
| Example 3-20 | Compound 118 | 6.57 | 44.64 | 517 |
| Example 3-21 | Compound 120 | 6.54 | 45.08 | 518 |

As a result of the tests, it was identified that the green organic light emitting devices of Examples 3-1 to 3-21 using the compound 2, 3, 4, 5, 8, 10, 13, 24, 35, 41, 43, 57, 68, 79, 85, 87, 90, 101, 112, 118 or 120 as a host material of a light emitting layer exhibited excellent performance in terms of current efficiency and driving voltage compared to the green organic light emitting device of Comparative Example 3 using existing CBP.

Example 4-1 to Example 4-38

The compounds synthesized in the synthesis examples were high-purity sublimation purified using commonly known methods, and then a red organic light emitting device was manufactured using a method as below.

An ITO glass was patterned so that a light emitting area became a 2 mm×2 mm size, and then cleaned. After installing the substrate in a vacuum chamber, the base pressure was set at $1 \times 10^6$ torr, and as organic materials on the ITO, DNTPD (700 Å) and α-NPB (300 Å) were formed, 2, 3, 4, 5, 6, 7, 8, 10, 13, 17, 18, 24, 28, 29, 35, 39, 40, 46, 50, 51, 57, 61, 62, 68, 72, 73, 79, 83, 84, 90, 94, 95, 101, 105, 106, 112, 116 and 117 prepared by the present disclosure were used as a host (90 wt %), the following (piq)₂Ir(acac) (10 wt %) was vacuum deposited (300 Å) as a dopant, and Alq₃ (350 Å), LiF (5 Å) and Al (1,000 Å) were formed in a film form in this order, and measurements were carried out at 0.4 mA.

Structures of the DNTPD, the α-NPB, the (piq)₂Ir(acac) and the Alq3 are as follows.

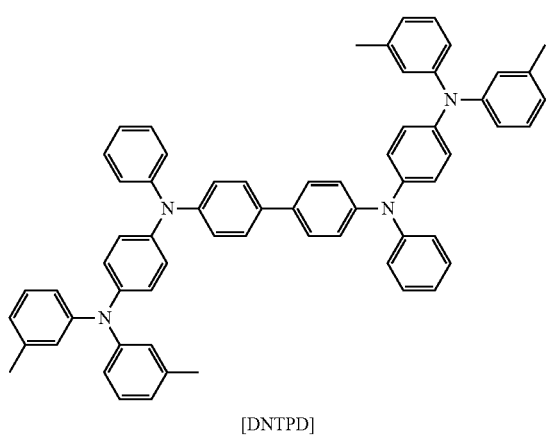

[DNTPD]

[α-NPB]

[(piq)₂Ir(acac)]

[Alq₃]

Comparative Example 4

An organic light emitting device for Comparative Example 4 was manufactured in the same manner as in the examples except that, in the device structure, CBP that is much used as a general phosphorescent host material was used as a host of the light emitting layer instead of the organic light emitting compound prepared by the present disclosure.

For the organic electroluminescent devices manufactured according to Examples 4-1 to 4-38 and Comparative Example 4, a voltage, current density, luminance, a color coordinate and a lifespan were measured, and the results are shown in the following Table 4. T95 means time taken for the luminance decreasing to 95% from its initial luminance (5000 nit).

TABLE 4

| Category | Host | Dopant | Voltage (V@10 mA/cm$^2$) | Luminance (V) | CIEx (cd/m$^2$) | CIEy | T95 (hr) |
|---|---|---|---|---|---|---|---|
| Example 4-1 | Compound 2 | [(piq)$_2$Ir(acac)] | 4.4 | 1860 | 0.670 | 0.329 | 465 |
| Example 4-2 | Compound 3 | [(piq)$_2$Ir(acac)] | 4.2 | 1850 | 0.674 | 0.325 | 445 |
| Example 4-3 | Compound 4 | [(piq)$_2$Ir(acac)] | 4.1 | 1900 | 0.672 | 0.327 | 440 |
| Example 4-4 | Compound 5 | [(piq)$_2$Ir(acac)] | 4.3 | 1840 | 0.673 | 0.335 | 435 |
| Example 4-5 | Compound 6 | [(piq)$_2$Ir(acac)] | 4.4 | 1790 | 0.675 | 0.333 | 445 |
| Example 4-6 | Compound 7 | [(piq)$_2$Ir(acac)] | 4.2 | 1810 | 0.670 | 0.339 | 440 |
| Example 4-7 | Compound 8 | [(piq)$_2$Ir(acac)] | 4.3 | 1970 | 0.671 | 0.338 | 455 |
| Example 4-8 | Compound 10 | [(piq)$_2$Ir(acac)] | 4.3 | 1860 | 0.668 | 0.329 | 445 |
| Example 4-9 | Compound 13 | [(piq)$_2$Ir(acac)] | 4.2 | 1950 | 0.673 | 0.325 | 455 |
| Example 4-10 | Compound 17 | [(piq)$_2$Ir(acac)] | 4.4 | 1900 | 0.670 | 0.327 | 440 |
| Example 4-11 | Compound 18 | [(piq)$_2$Ir(acac)] | 4.3 | 1940 | 0.671 | 0.335 | 455 |
| Example 4-12 | Compound 24 | [(piq)$_2$Ir(acac)] | 4.1 | 1990 | 0.674 | 0.333 | 445 |
| Example 4-13 | Compound 28 | [(piq)$_2$Ir(acac)] | 4.2 | 1910 | 0.675 | 0.339 | 450 |
| Example 4-14 | Compound 29 | [(piq)$_2$Ir(acac)] | 4.3 | 1970 | 0.671 | 0.338 | 425 |
| Example 4-15 | Compound 35 | [(piq)$_2$Ir(acac)] | 4.3 | 1860 | 0.668 | 0.329 | 435 |
| Example 4-16 | Compound 39 | [(piq)$_2$Ir(acac)] | 4.4 | 1950 | 0.674 | 0.325 | 435 |
| Example 4-17 | Compound 40 | [(piq)$_2$Ir(acac)] | 4.3 | 1760 | 0.668 | 0.329 | 435 |
| Example 4-18 | Compound 46 | [(piq)$_2$Ir(acac)] | 4.2 | 1950 | 0.674 | 0.325 | 455 |
| Example 4-19 | Compound 50 | [(piq)$_2$Ir(acac)] | 4.3 | 1860 | 0.668 | 0.329 | 445 |
| Example 4-20 | Compound 51 | [(piq)$_2$Ir(acac)] | 4.4 | 1950 | 0.674 | 0.325 | 435 |
| Example 4-21 | Compound 57 | [(piq)$_2$Ir(acac)] | 4.2 | 1750 | 0.674 | 0.325 | 445 |
| Example 4-22 | Compound 61 | [(piq)$_2$Ir(acac)] | 4.2 | 1950 | 0.674 | 0.325 | 455 |
| Example 4-23 | Compound 62 | [(piq)$_2$Ir(acac)] | 4.4 | 1850 | 0.674 | 0.325 | 425 |
| Example 4-24 | Compound 68 | [(piq)$_2$Ir(acac)] | 4.2 | 1850 | 0.674 | 0.325 | 425 |
| Example 4-25 | Compound 72 | [(piq)$_2$Ir(acac)] | 4.3 | 1950 | 0.674 | 0.325 | 415 |
| Example 4-26 | Compound 73 | [(piq)$_2$Ir(acac)] | 4.2 | 1950 | 0.674 | 0.325 | 435 |
| Example 4-27 | Compound 79 | [(piq)$_2$Ir(acac)] | 4.1 | 1950 | 0.674 | 0.325 | 435 |
| Example 4-28 | Compound 83 | [(piq)$_2$Ir(acac)] | 4.2 | 1950 | 0.674 | 0.325 | 425 |
| Example 4-29 | Compound 84 | [(piq)$_2$Ir(acac)] | 4.2 | 1850 | 0.674 | 0.325 | 445 |
| Example 4-30 | Compound 90 | [(piq)$_2$Ir(acac)] | 4.4 | 1850 | 0.674 | 0.325 | 425 |
| Example 4-31 | Compound 94 | [(piq)$_2$Ir(acac)] | 4.3 | 1950 | 0.674 | 0.325 | 455 |
| Example 4-32 | Compound 95 | [(piq)$_2$Ir(acac)] | 4.2 | 1750 | 0.674 | 0.325 | 435 |
| Example 4-33 | Compound 101 | [(piq)$_2$Ir(acac)] | 4.3 | 1950 | 0.674 | 0.325 | 445 |
| Example 4-34 | Compound 105 | [(piq)$_2$Ir(acac)] | 4.2 | 1750 | 0.674 | 0.325 | 425 |
| Example 4-35 | Compound 106 | [(piq)$_2$Ir(acac)] | 4.2 | 1950 | 0.674 | 0.325 | 455 |
| Example 4-36 | Compound 112 | [(piq)$_2$Ir(acac)] | 4.2 | 1950 | 0.674 | 0.325 | 445 |

TABLE 4-continued

| Category | Host | Dopant | Voltage (V@10 mA/cm$^2$) | Luminance (V) | CIEx (cd/m$^2$) | CIEy | T95 (hr) |
|---|---|---|---|---|---|---|---|
| Example 4-37 | Compound 116 | [(piq)$_2$Ir(acac)] | 4.2 | 1950 | 0.674 | 0.325 | 435 |
| Example 4-38 | Compound117 | [(piq)$_2$Ir(acac)] | 4.2 | 1950 | 0.674 | 0.325 | 425 |
| Comparative Example 4 | CBP | [(piq)$_2$Ir(acac)] | 7.5 | 920 | 0.679 | 0.339 | 160 |

As a result of the tests, it was identified that the red organic light emitting devices of Examples 4-1 to 4-38 using the compounds represented by 2, 3, 4, 5, 6, 7, 8, 10, 13, 17, 18, 24, 28, 29, 35, 39, 40, 46, 50, 51, 57, 61, 62, 68, 72, 73, 79, 83, 84, 90, 94, 95, 101, 105, 106, 112, 116 and 117 prepared according to the present disclosure as a host material of a light emitting layer exhibited excellent performance in terms of current efficiency, driving voltage and lifespan compared to the red organic light emitting device of Comparative Example 4 using existing CBP.

Hereinbefore, preferred embodiments of the present disclosure (electron blocking layer, hole transfer layer, green light emitting layer and red light emitting layer) have been described, however, the present disclosure is not limited thereto, and various modifications may be made within the scope of the claims and the detailed descriptions of the disclosure, and the modifications are also included in the scope of the present disclosure.

The invention claimed is:

1. An organic compound having a double Spiro structure represented by the following Chemical Formula 1:

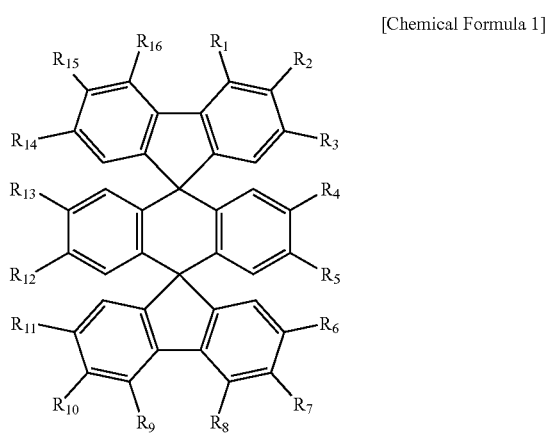

[Chemical Formula 1]

wherein, in Chemical Formula 1,
at least one of $R_1$ to $R_3$, $R_6$ to $R_{11}$, and $R_{14}$ to $R_{16}$ bonds to adjacent groups to form a ring structure of Chemical Formula 1-1, and
$R_4$, $R_5$, $R_{12}$, $R_{13}$, and groups that do not form the ring among $R_1$ to $R_3$, $R_6$ to $R_{11}$, and $R_{14}$ to $R_{16}$ are hydrogen,

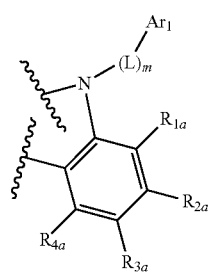

[Chemical Formula 1-1]

in Chemical Formula 1-1,
m is an integer of 0 to 5,
when m is 2 or greater, Ls are the same as or different from each other,
L is a direct bond; a substituted or unsubstituted arylene group; or a substituted or unsubstituted heteroarylene group,
$Ar_1$ is hydrogen; deuterium; a halogen group; a nitrile group; a nitro group; a hydroxyl group; a carbonyl group; an ester group; an imide group; an amino group; a substituted or unsubstituted silyl group; a substituted or unsubstituted boron group; a substituted or unsubstituted alkyl group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylphosphine group; a substituted or unsubstituted phosphine oxide group; a substituted or unsubstituted aryl group; or a substituted or unsubstituted heterocyclic group, and
$R_{1a}$ to $R_{4a}$ are the same as or different from each other, and each independently hydrogen; deuterium; a halogen group; a nitrile group; a nitro group; a hydroxyl group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphine oxide group; a substituted or unsubstituted aryl group; or a substituted or unsubstituted heterocyclic group, or bond to adjacent groups to form a substituted or unsubstituted ring.

2. The organic compound having a double spiro structure of claim 1, wherein Chemical Formula 1 is represented by any one of the following Chemical Formula 4 to Chemical Formula 7:

[Chemical Formula 4]

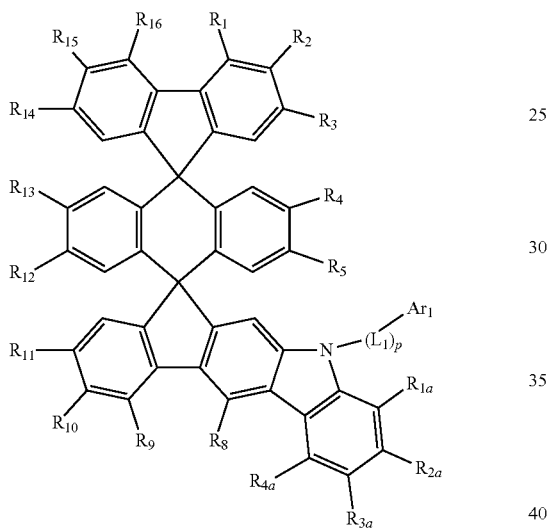

[Chemical Formula 5]

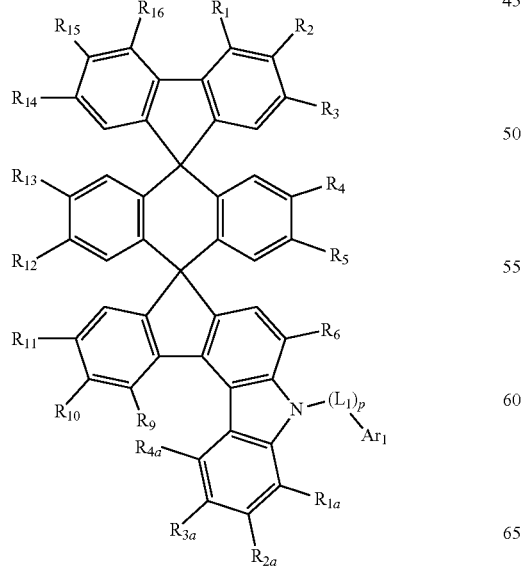

[Chemical Formula 6]

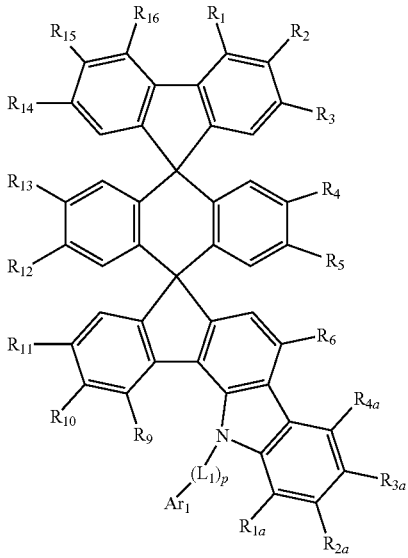

[Chemical Formula 7]

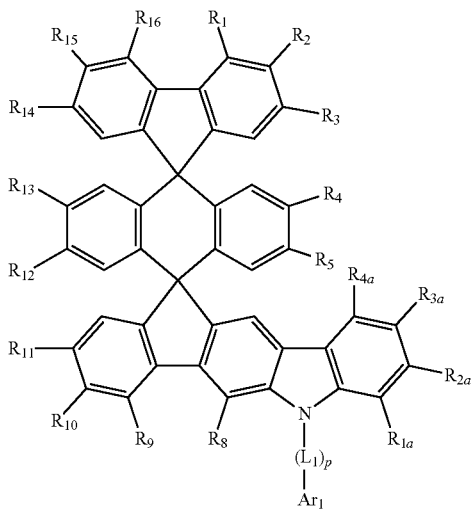

wherein, in Chemical Formula 4 to Chemical Formula 7, $R_1$ to $R_6$ and $R_8$ to $R_{16}$ each independently have the same definition as in Chemical Formula 1, p is an integer of 0 to 5, when p is 2 or greater, $L_1$s are the same as or different from each other, $L_1$ has the same definition as L in Chemical Formula 1-1, $Ar_1$ has the same definition as $Ar_1$ in Chemical Formula 1-1, and $R_{1a}$ to $R_{4a}$ each independently have the same definition as in Chemical Formula 1-1.

3. The organic compound having a double spiro structure of claim 1, wherein Chemical Formula 1 is represented by any one of the following Chemical Formula 10 to Chemical Formula 17:

[Chemical Formula 10]
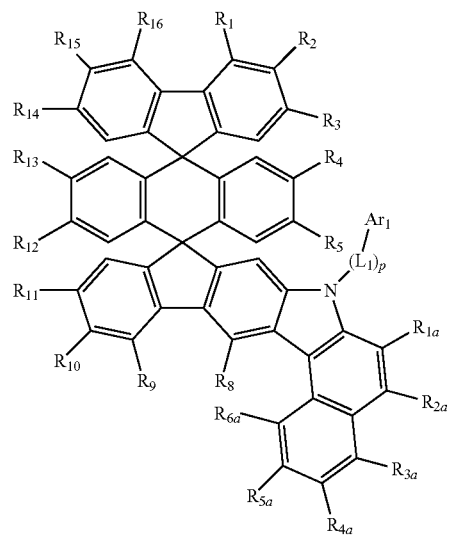
[Chemical Formula 11]
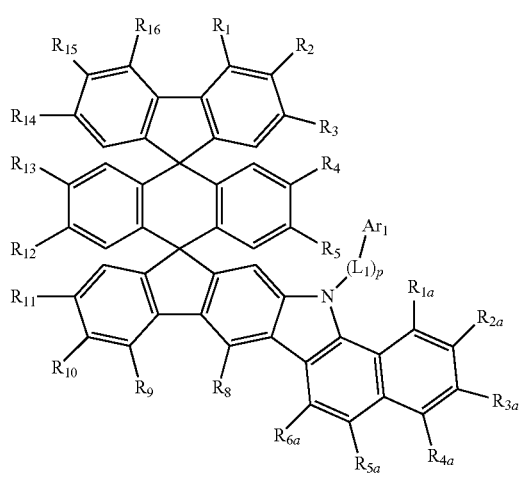
[Chemical Formula 12]
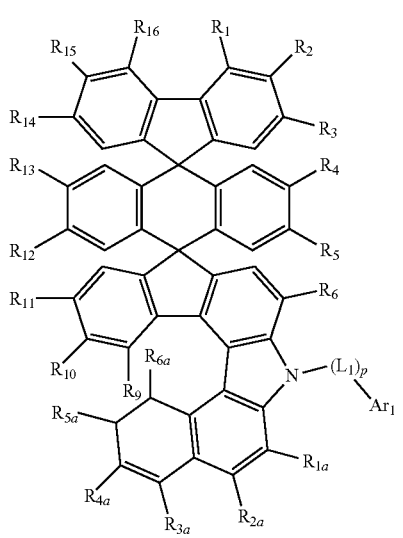
-continued
[Chemical Formula 13]
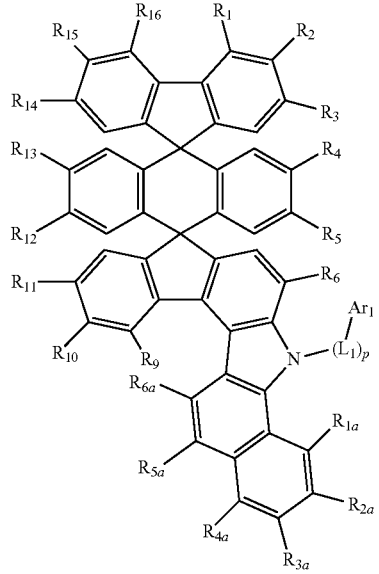
[Chemical Formula 14]
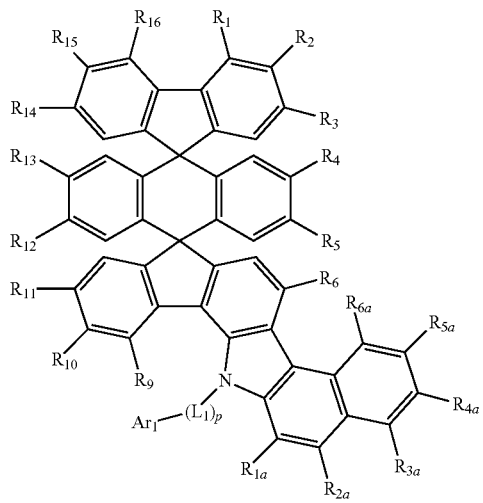

247
-continued

[Chemical Formula 15]

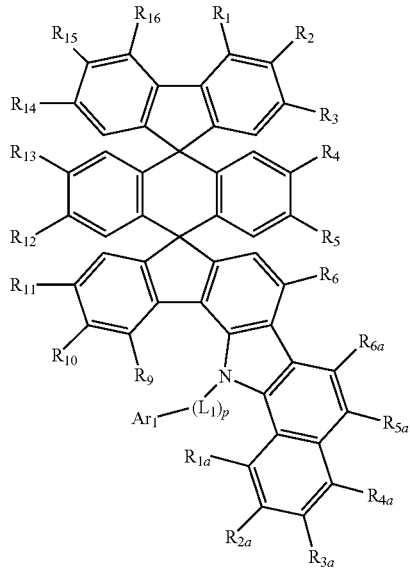

[Chemical Formula 16]

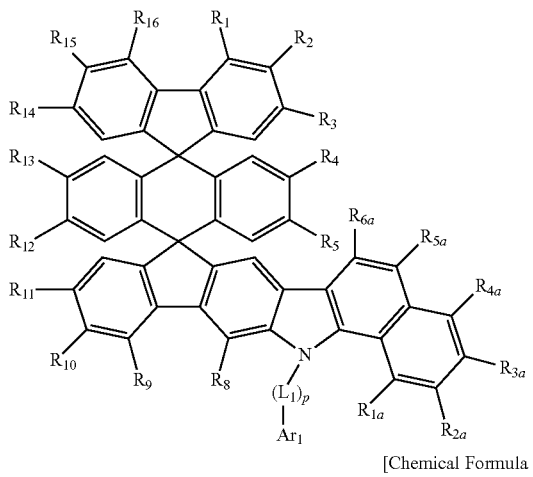

[Chemical Formula 17]

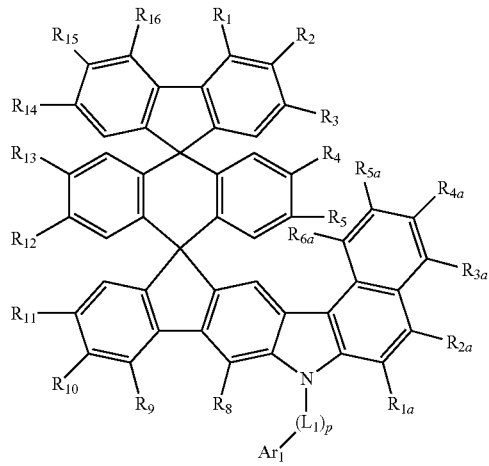

wherein, in Chemical Formula 10 to Chemical Formula 17, $R_1$ to $R_6$ and $R_8$ to $R_{16}$ each independently have the same definition as in Chemical Formula 1,

248 p is an integer of 0 to 5, when p is 2 or greater, $L_1$s are the same as or different from each other, $L_1$ has the same definition as L in Chemical Formula 1-1, $Ar_1$ has the same definition as in Chemical Formula 1-1, and $R_{1a}$ to $R_{6a}$ are the same as or different from each other, and each independently have the same definition as $R_{1a}$ to $R_{4a}$ in Chemical Formula 1-1.

4. The organic compound having a double Spiro structure of claim 1, wherein Chemical Formula 1 is any one selected from among the following structures:

4-1

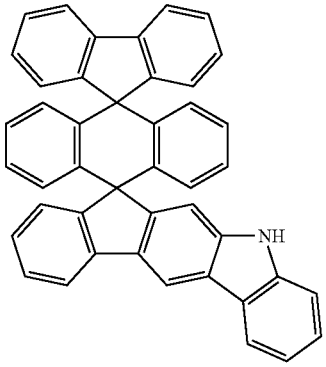

4-2

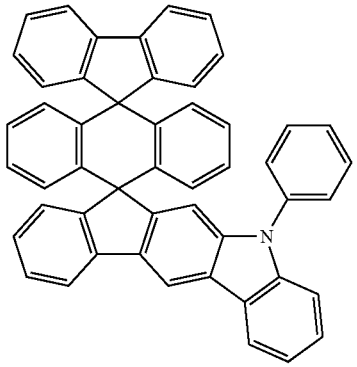

4-3

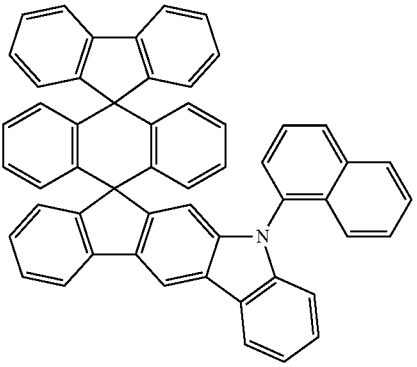

4-4
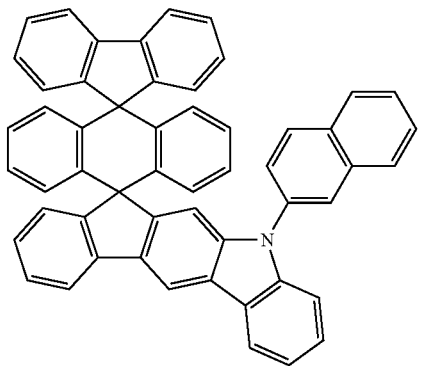
4-5
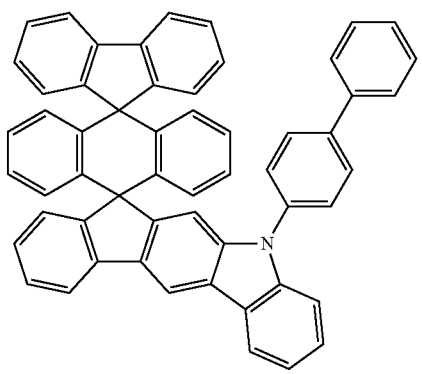
4-6
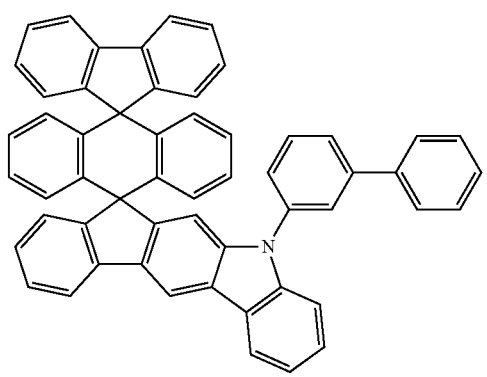
4-7
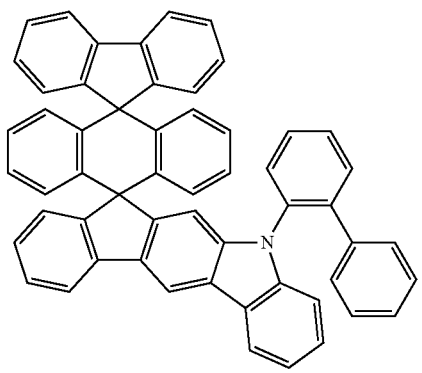
4-8
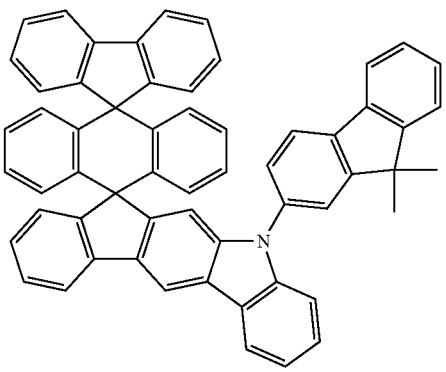
4-9
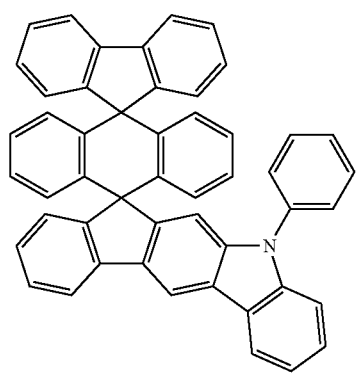
4-10
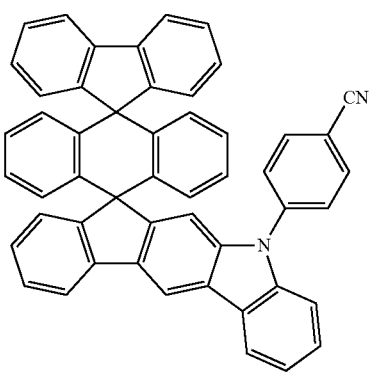
4-11
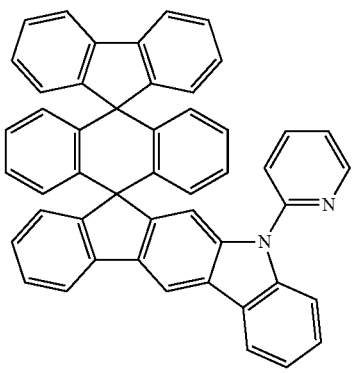

4-12
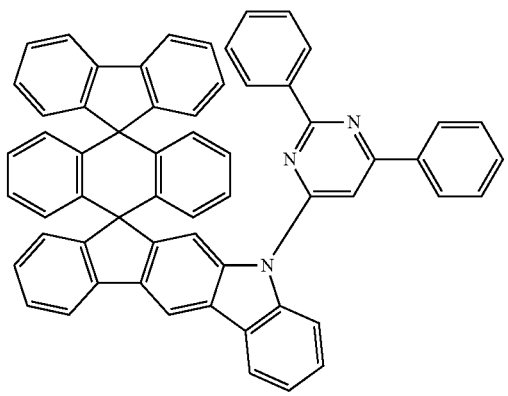
4-13
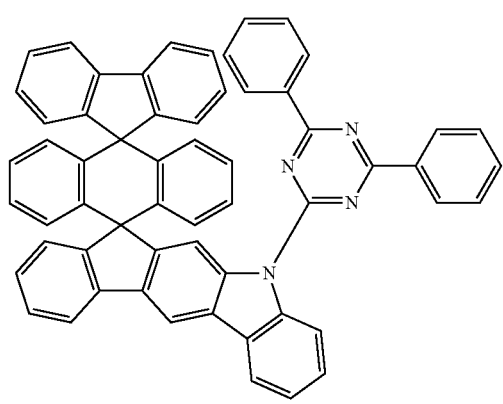
4-14
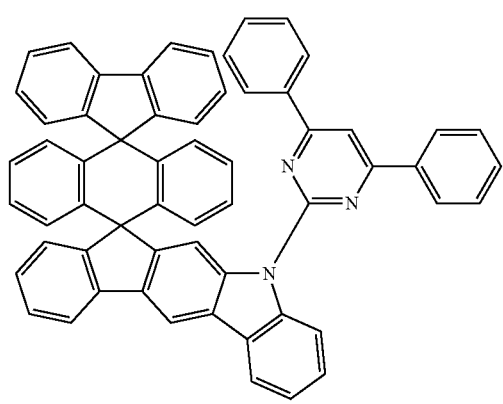
4-15
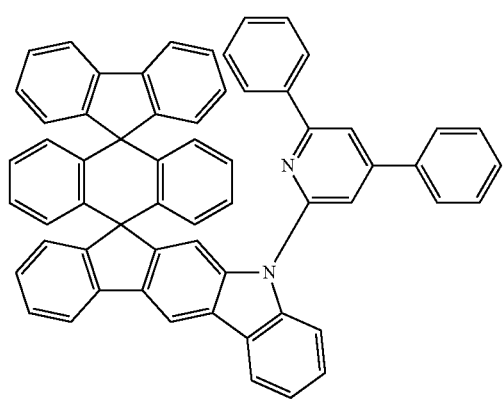
4-16
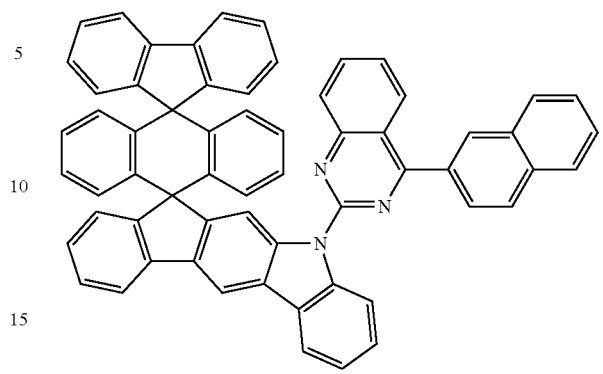
4-17
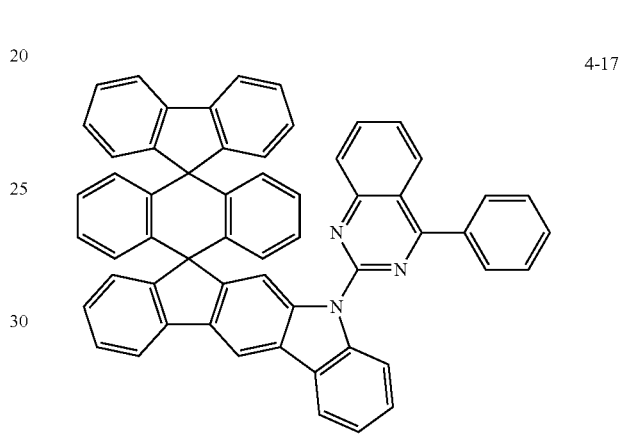
4-18
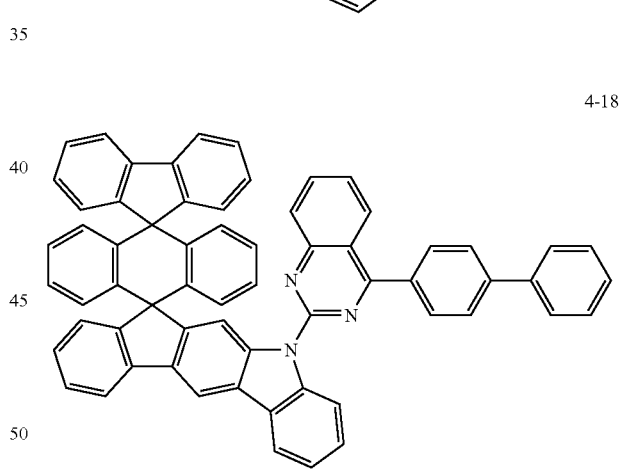
4-19
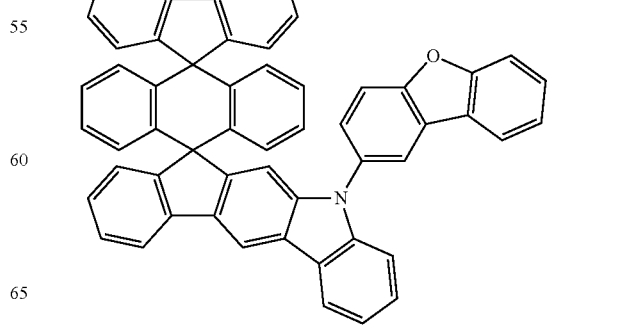

4-20
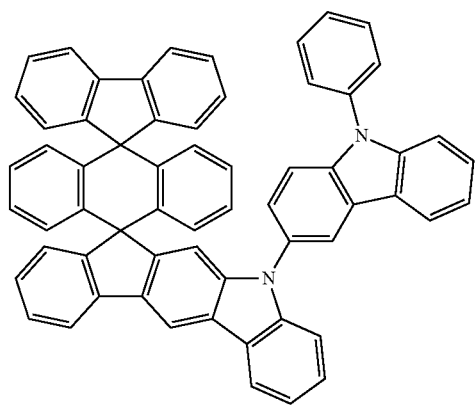
4-21
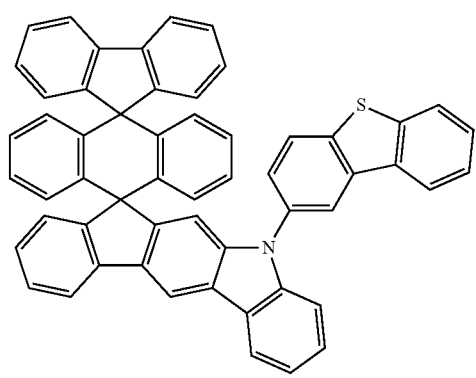
4-22
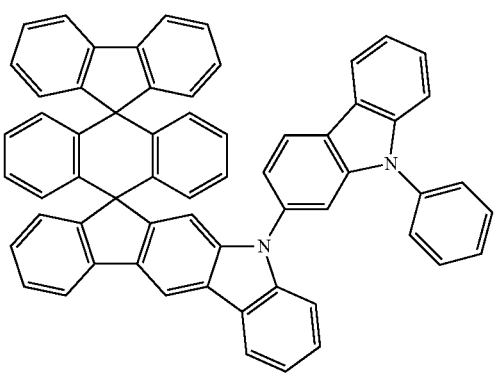
4-23
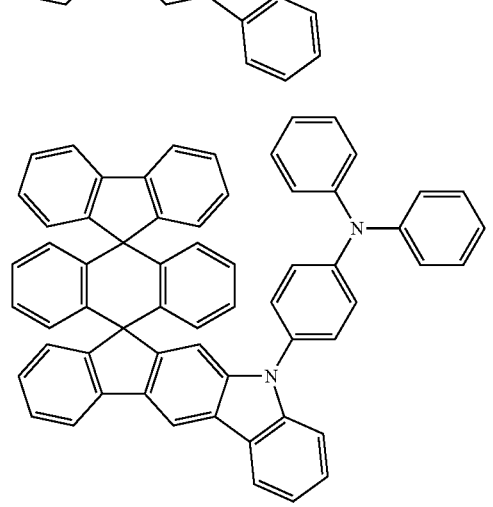
4-24
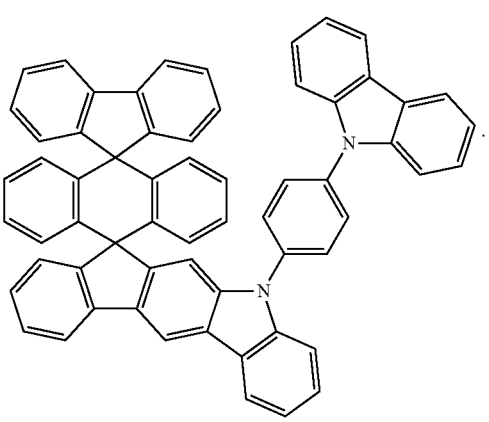
5. The organic compound having a double Spiro structure of claim 1, wherein Chemical Formula 1 is any one selected from among the following structures:
5-1
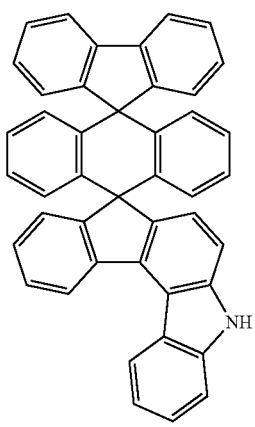
5-2
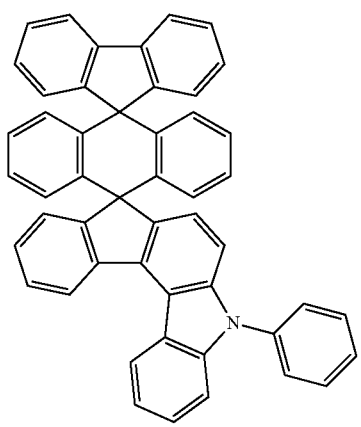

5-3
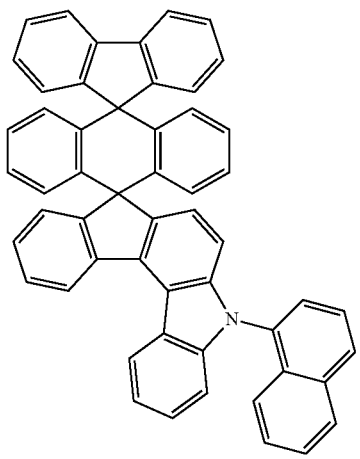
5-4
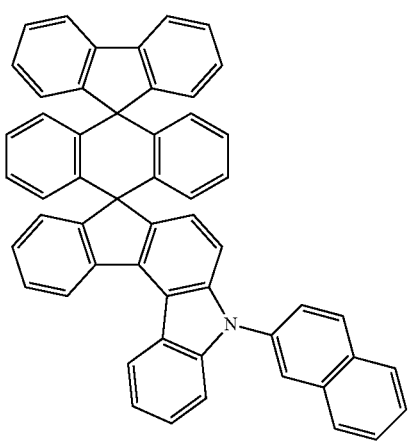
5-5
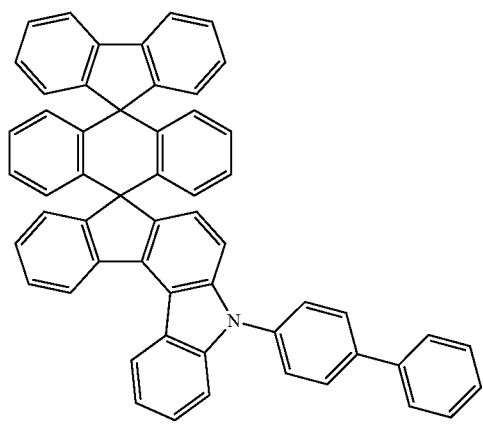
5-6
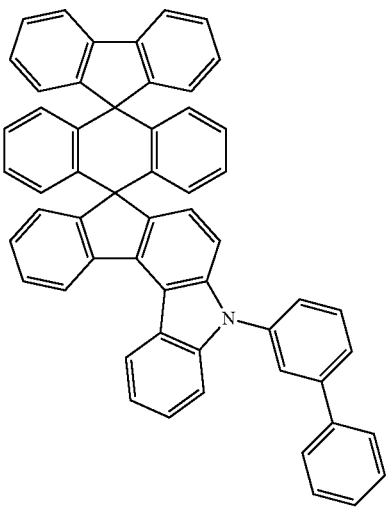
5-7
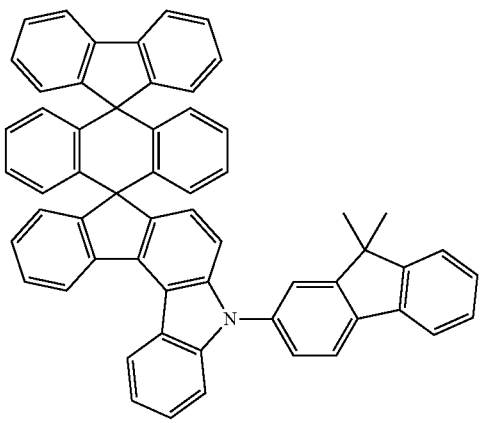
5-8

-continued
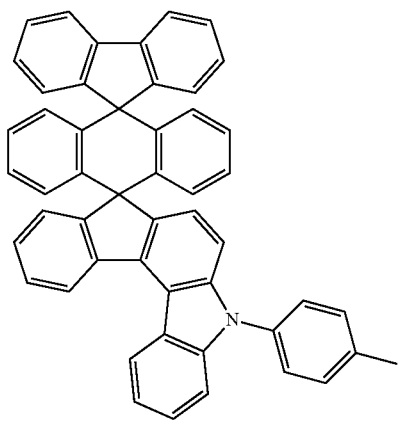
5-9
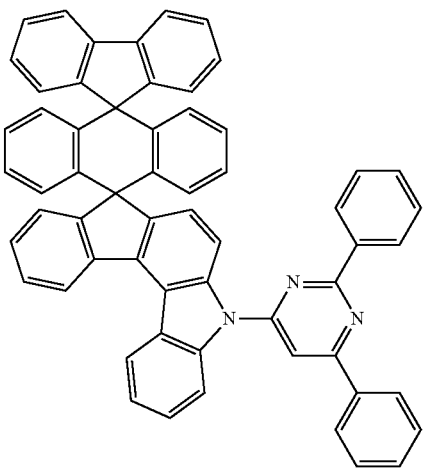
5-12
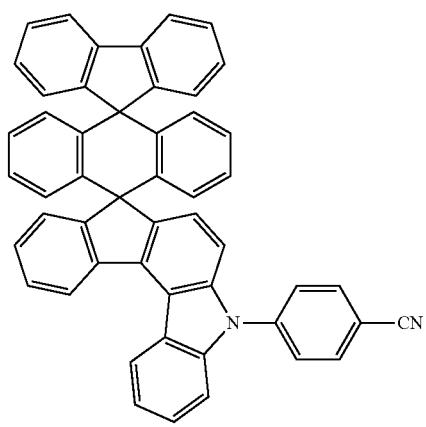
5-10
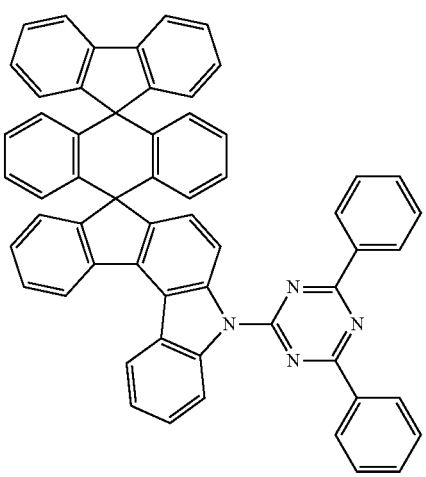
5-13
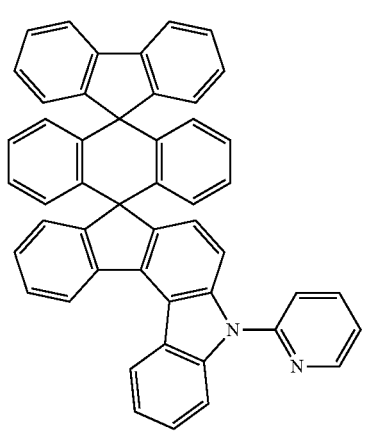
5-11
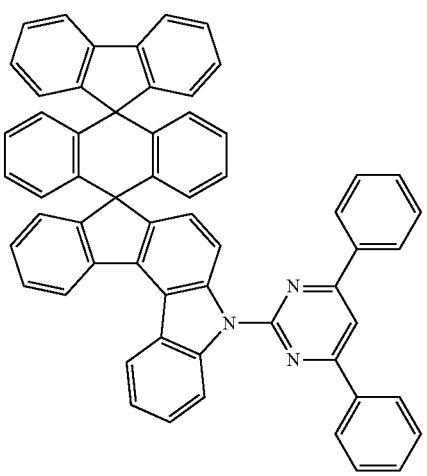
5-14

5-15
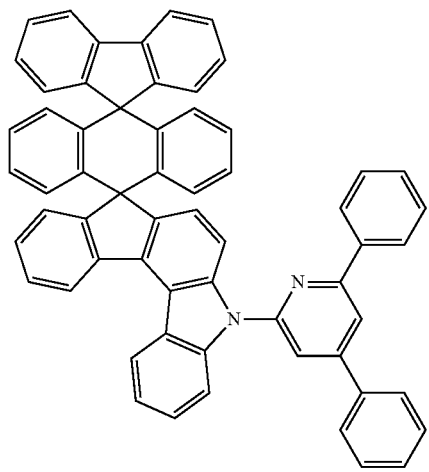
5-16
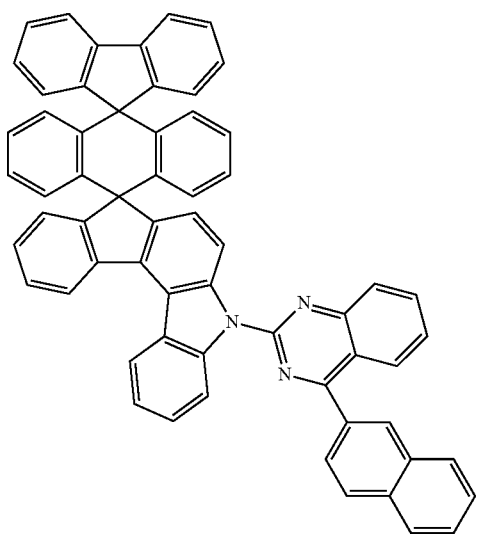
5-17
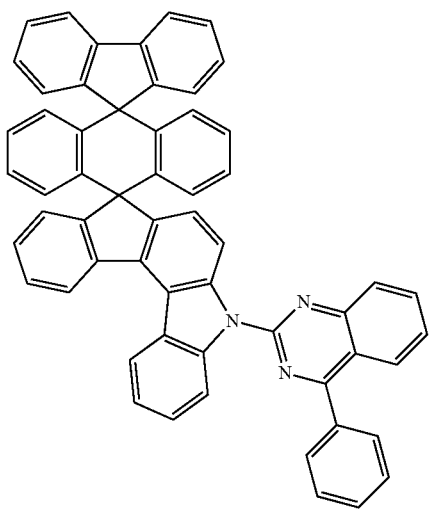
5-18
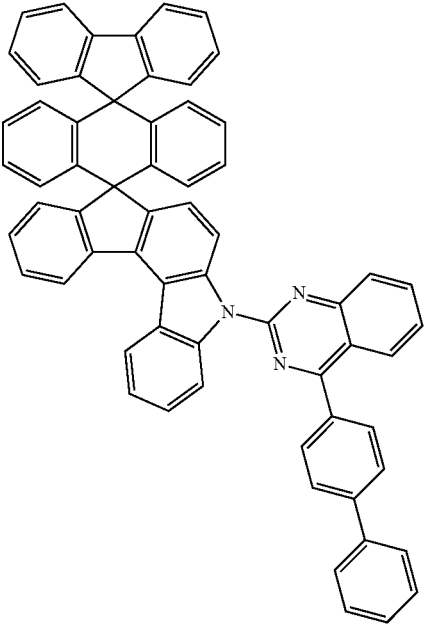
5-19
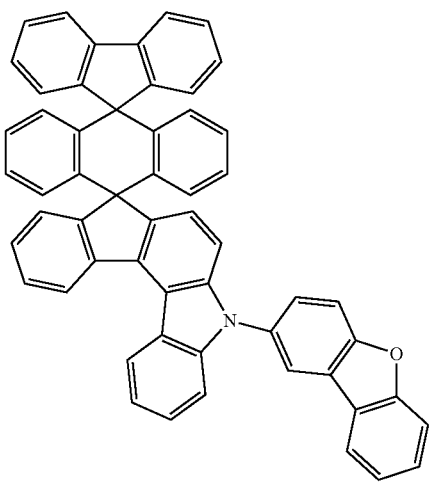
5-20
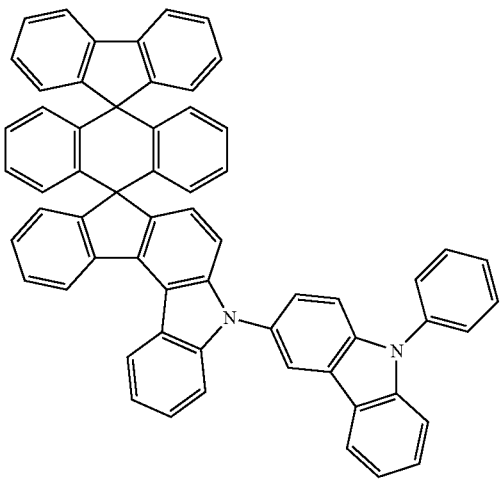

5-21
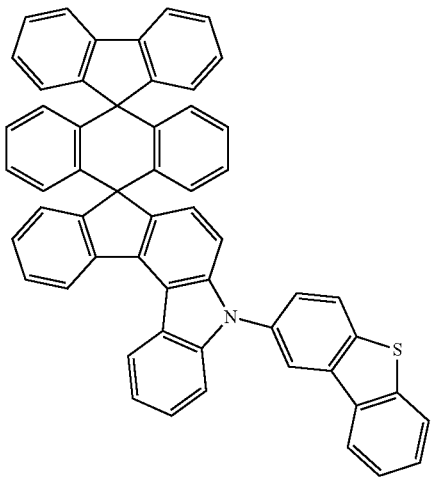
5-22
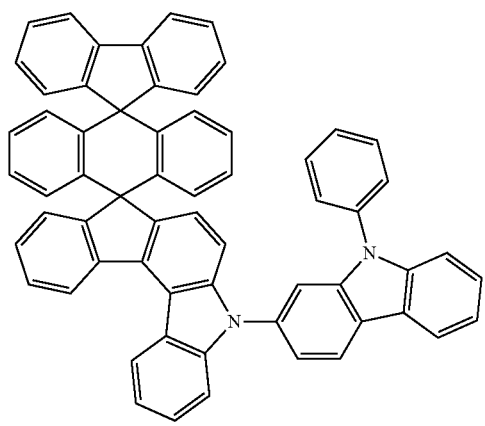
5-23
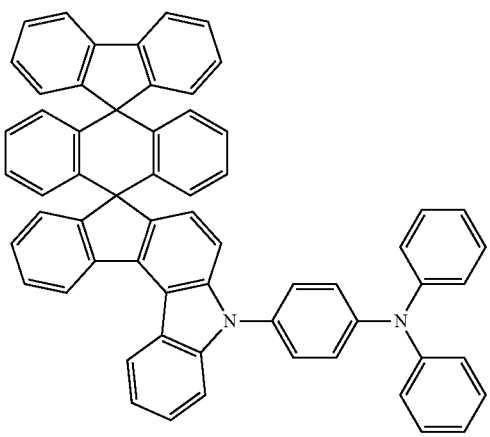
5-24
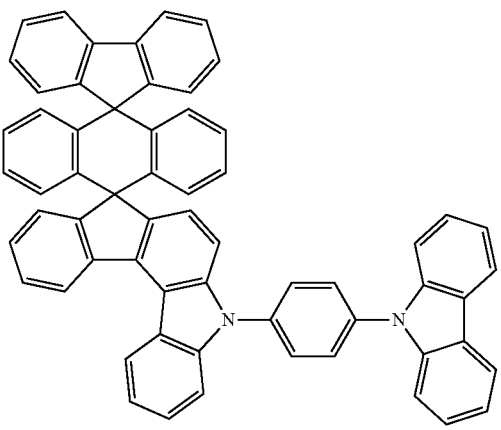
5-25
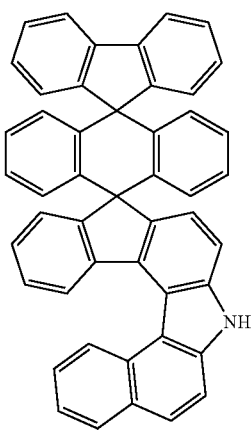
5-26
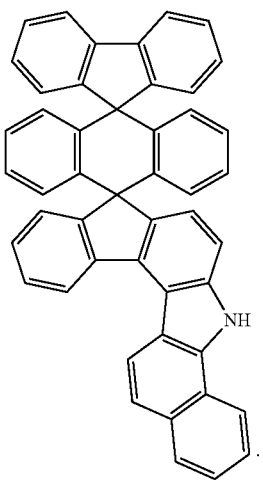
6. The organic compound having a double Spiro structure of claim 1, wherein Chemical Formula 1 is any one selected from among the following structures:

6-1
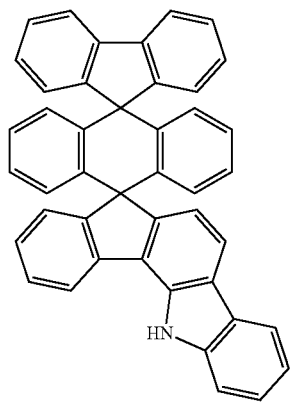
6-2
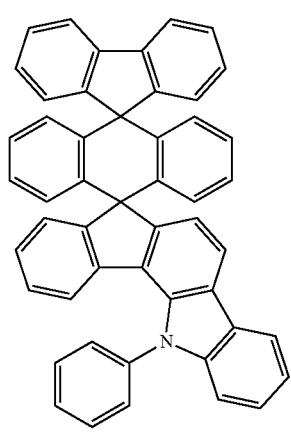
6-3
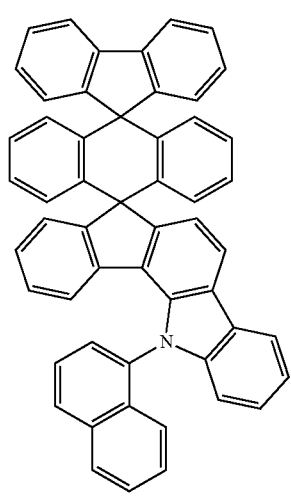
6-4
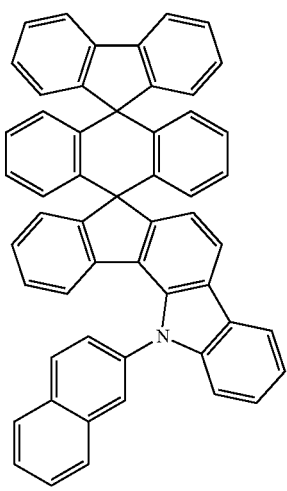
6-5
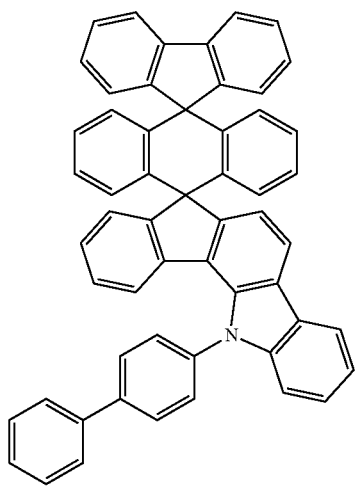
6-6
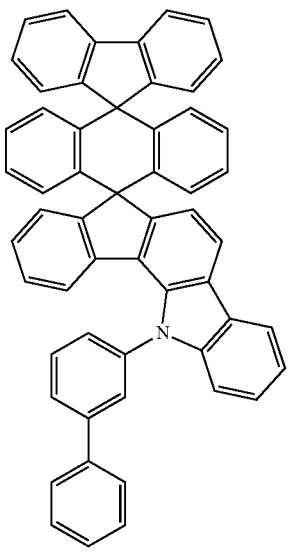

265
-continued
6-7
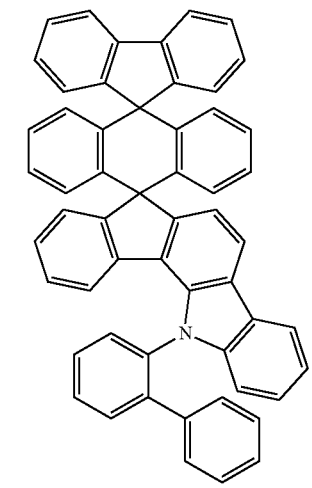
6-8
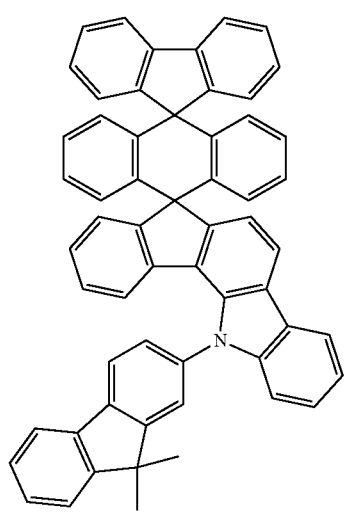
6-9
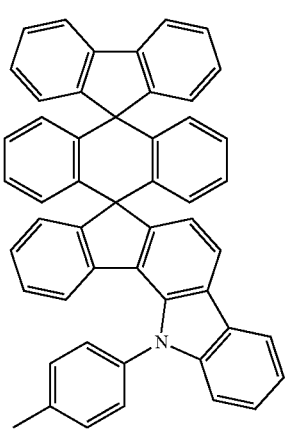
266
-continued
6-10
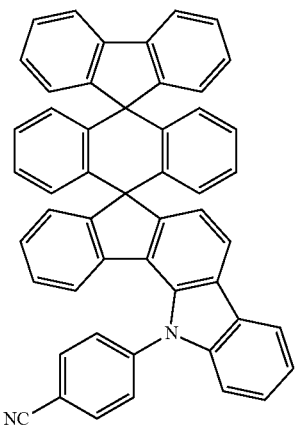
6-11
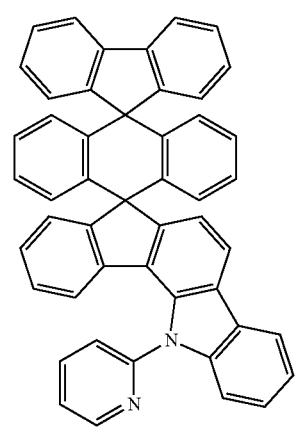
6-12
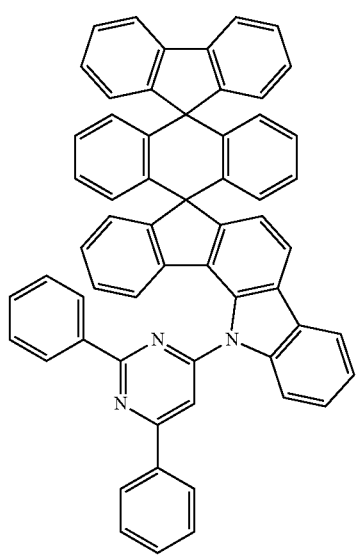

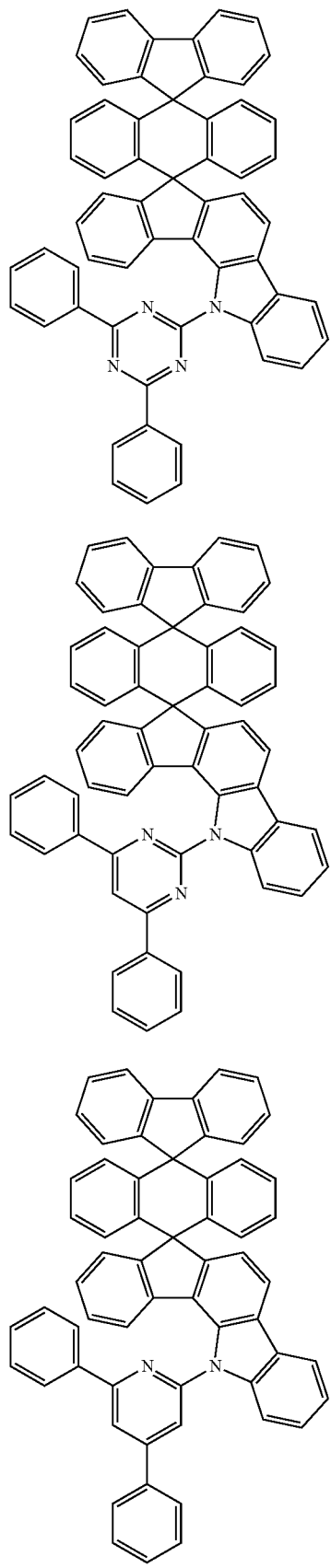
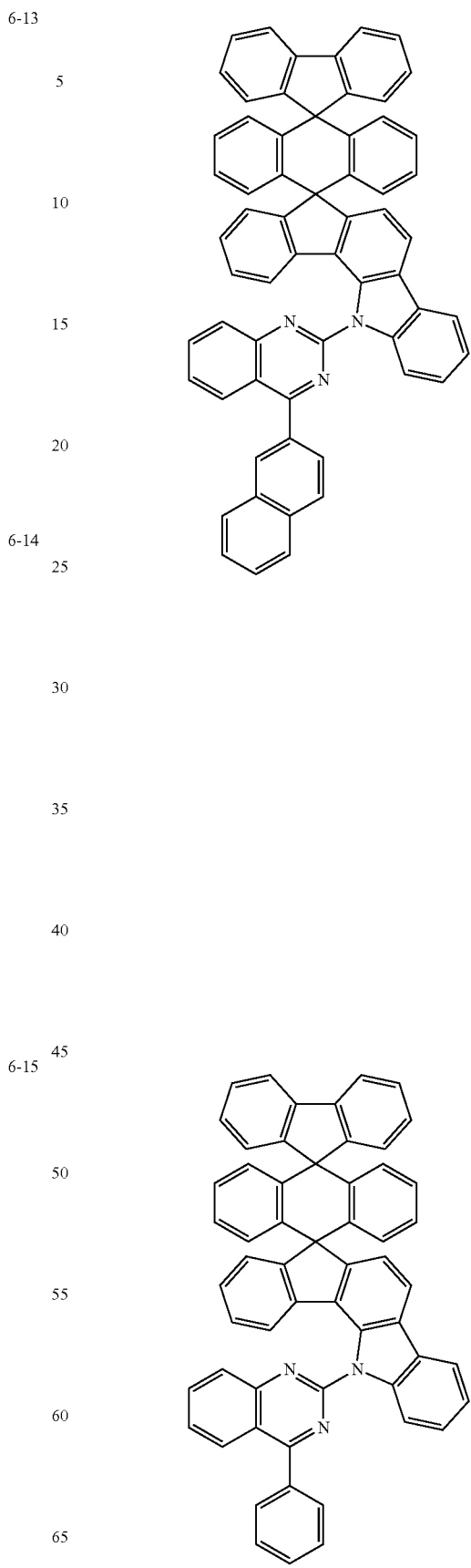

6-18
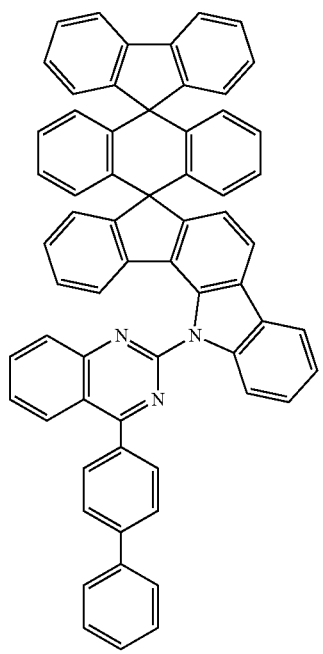
6-19
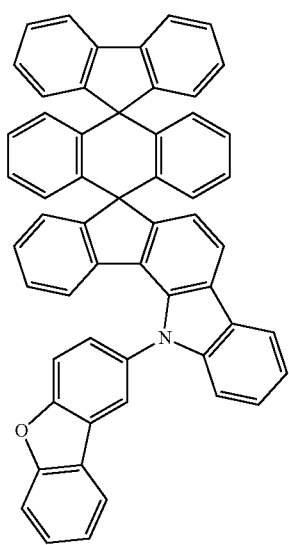
6-20
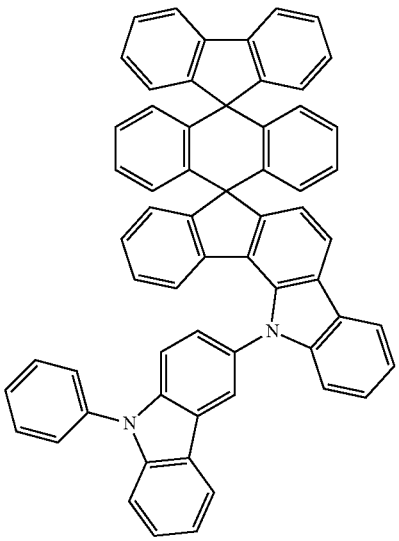
6-21
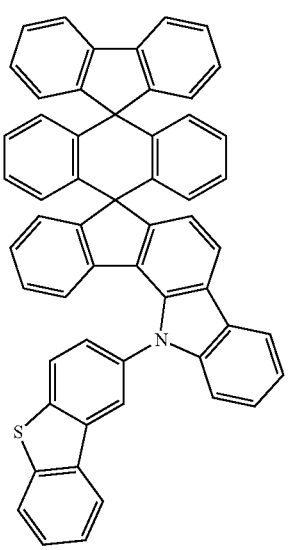
6-22
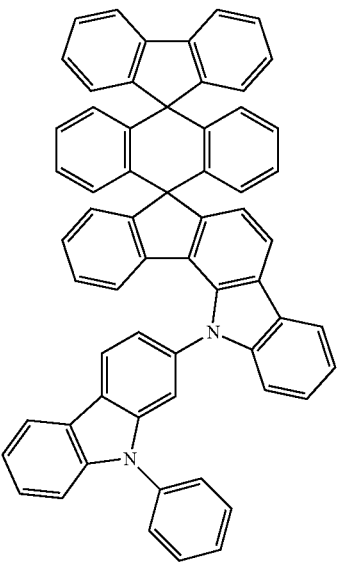

6-23
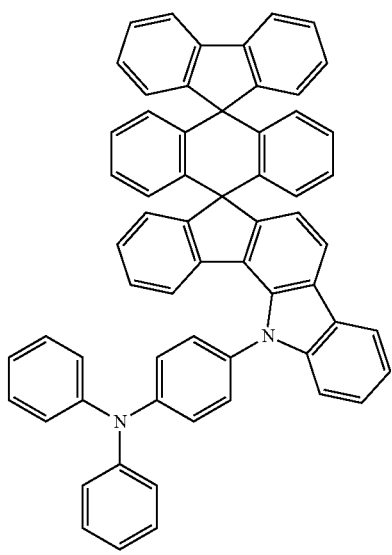
6-24
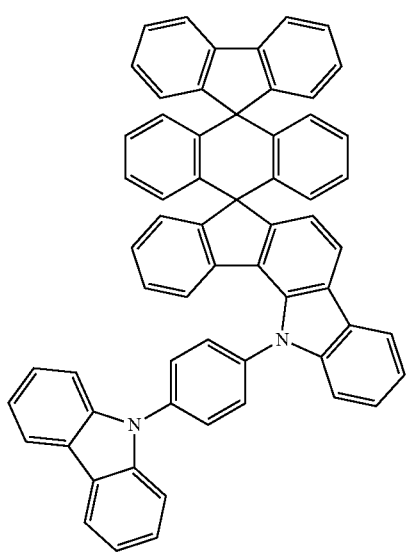
6-25
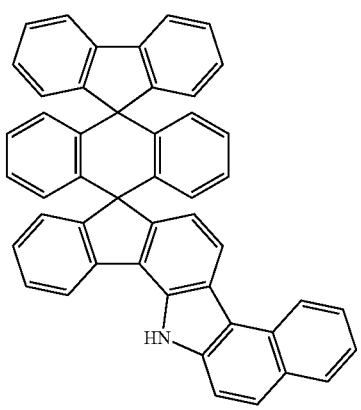
6-26
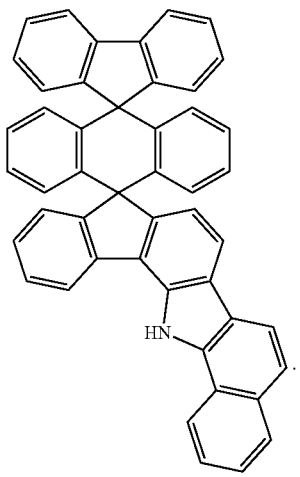
7. The organic compound having a double Spiro structure of claim 1, wherein Chemical Formula 1 is any one selected from among the following structures:
7-1
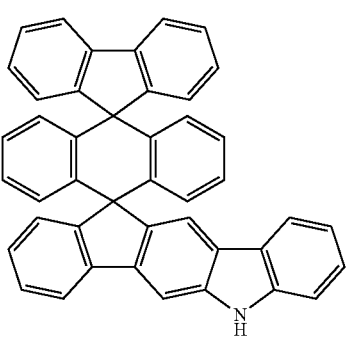
7-2
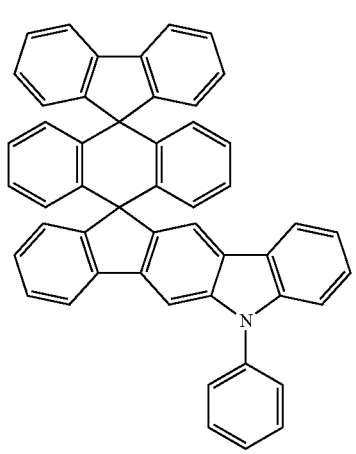

7-3
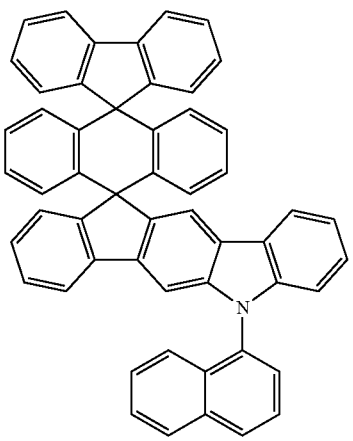
7-4
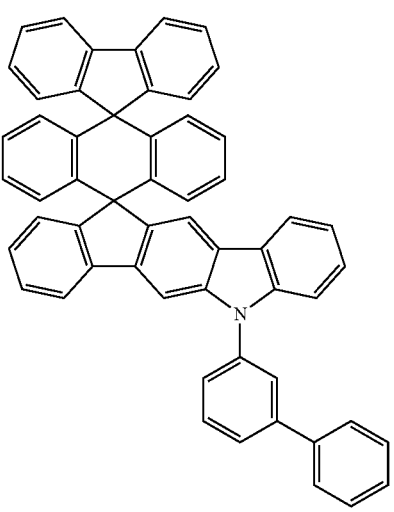
7-5
7-6
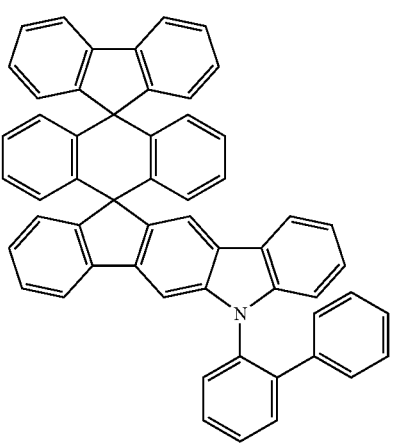
7-7
7-8
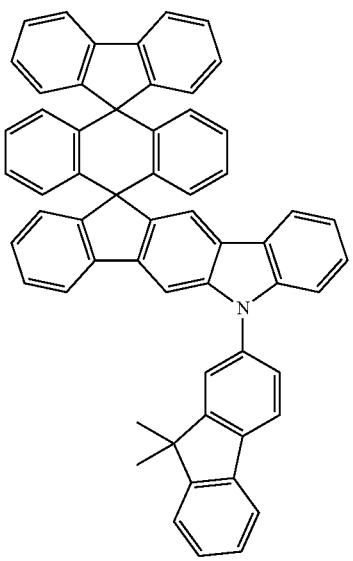

7-9
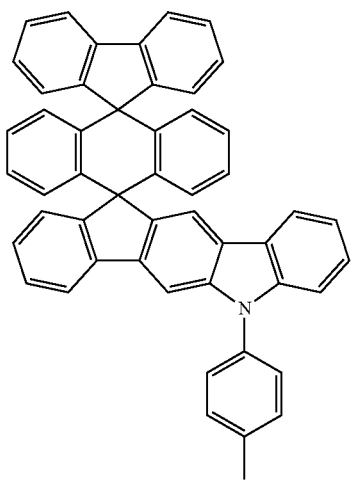
7-10
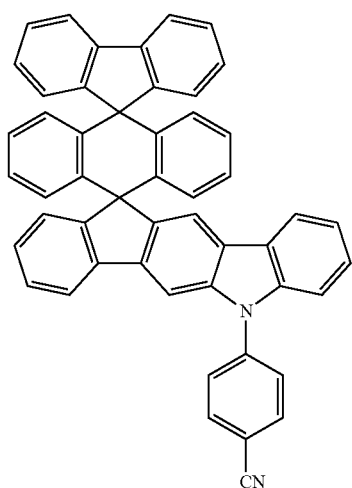
7-11
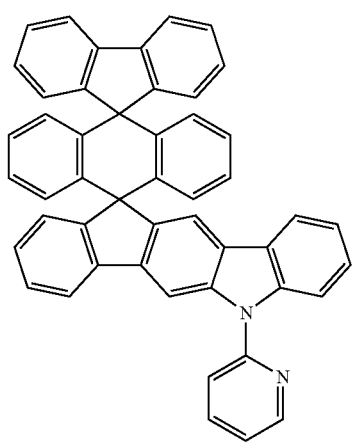
7-12
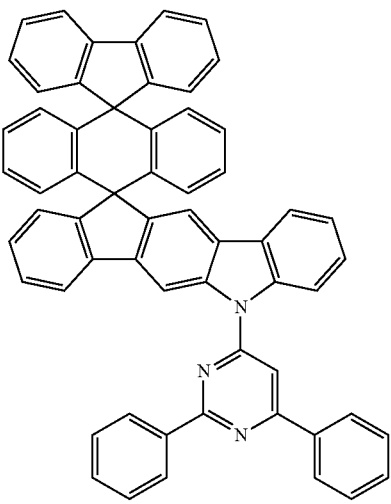
7-13
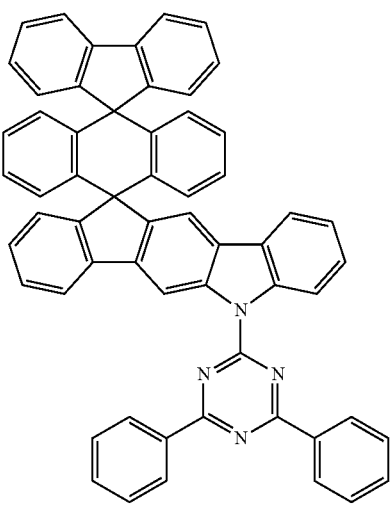
7-14
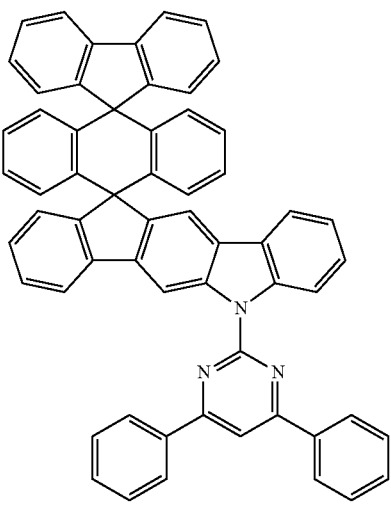

7-15
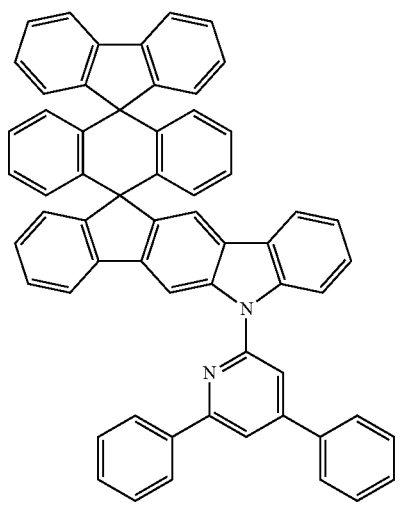
7-16
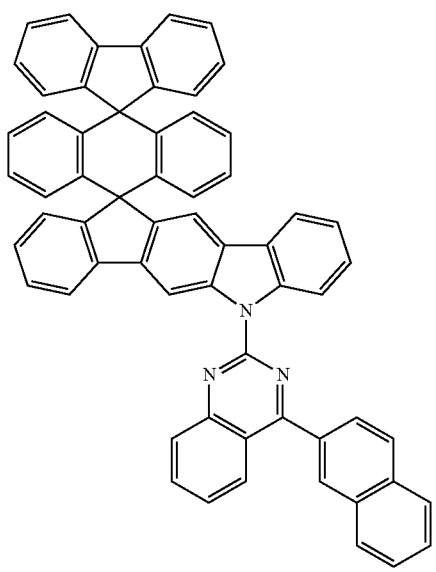
7-17
7-18
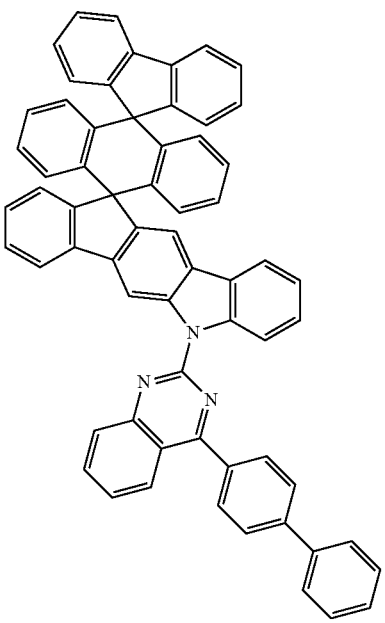
7-19

279
-continued
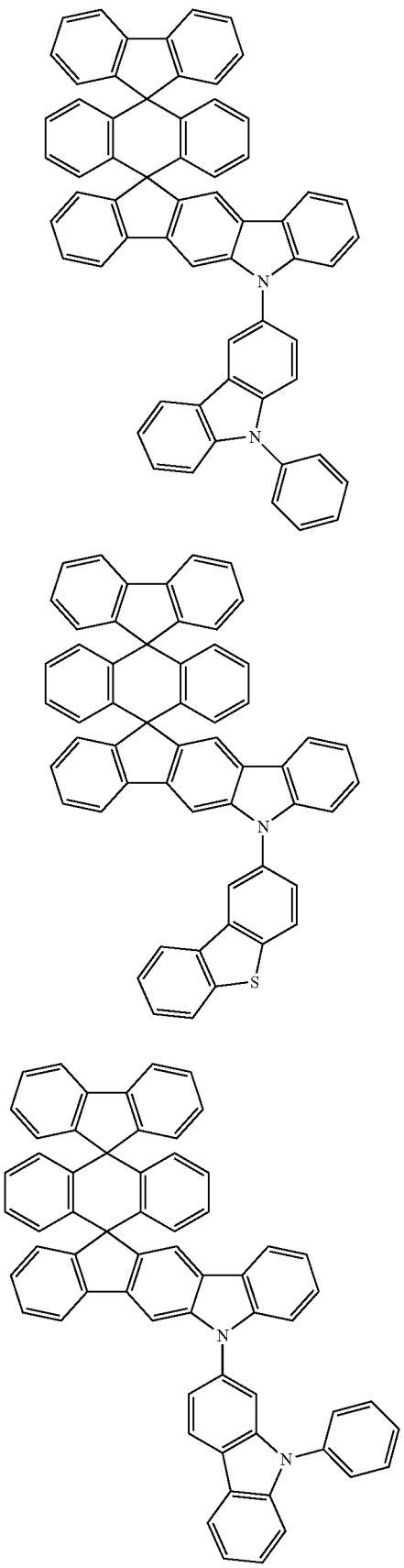
7-20
7-21
7-22
280
-continued
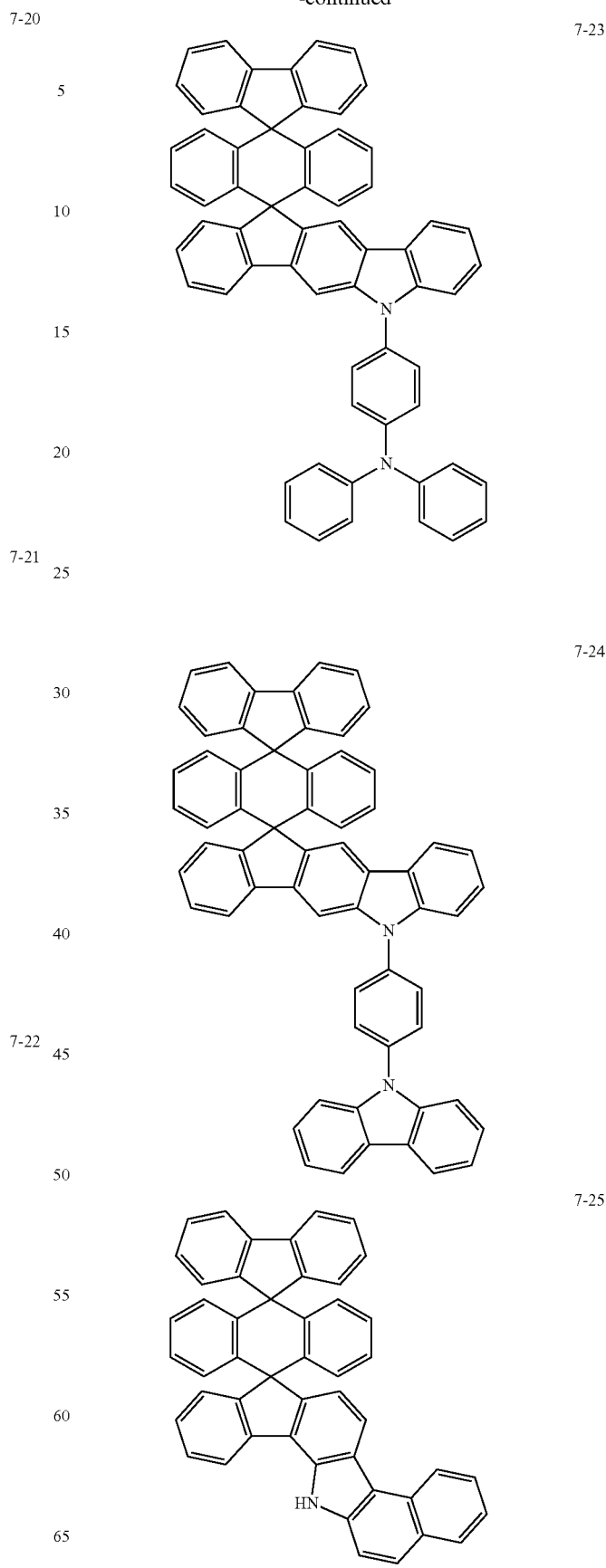
7-23
7-24
7-25

7-26
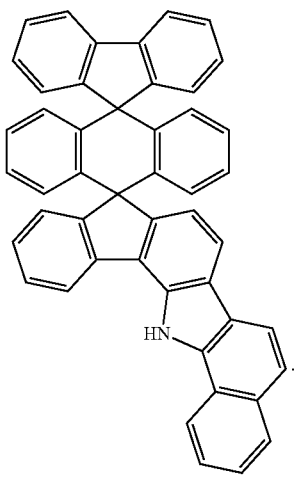
8. The organic compound having a double Spiro structure of claim 1, wherein Chemical Formula 1 is any one selected from among the following structures:
10-1
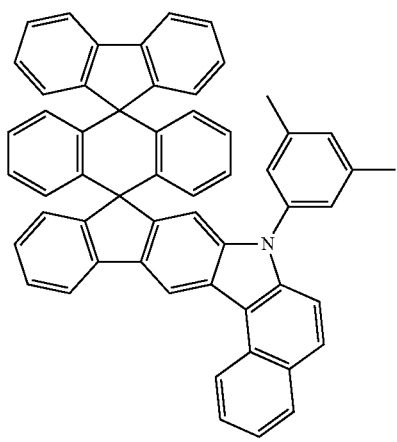
10-2
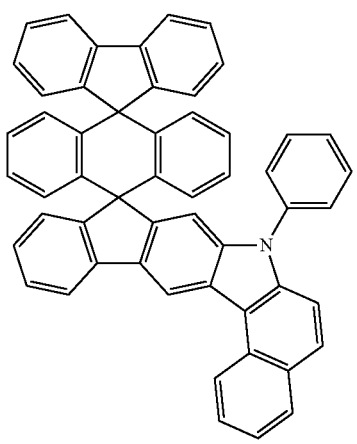
10-3
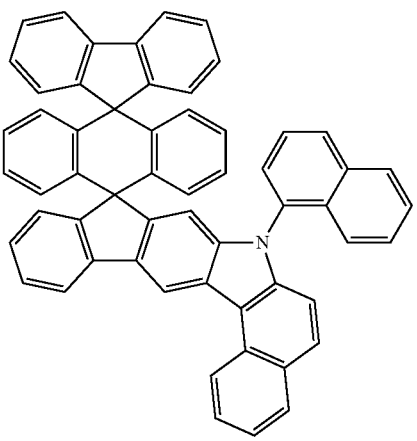
10-4
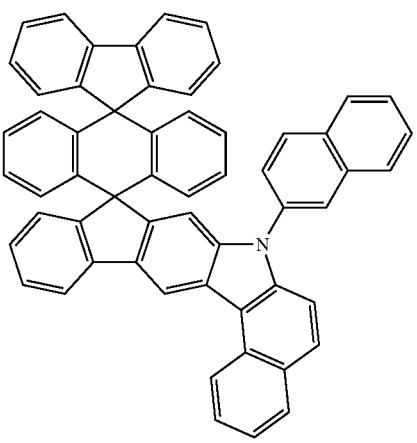
10-5
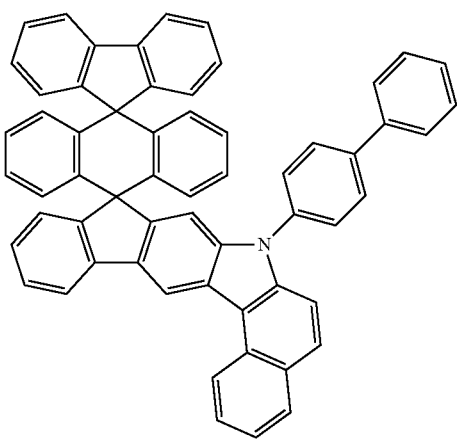

10-6
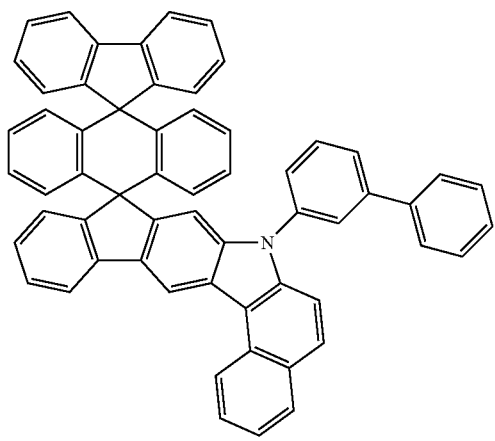
10-7
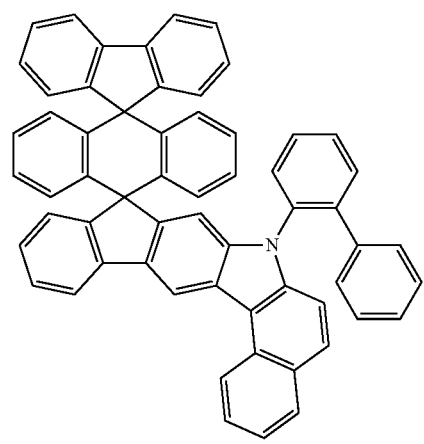
10-8
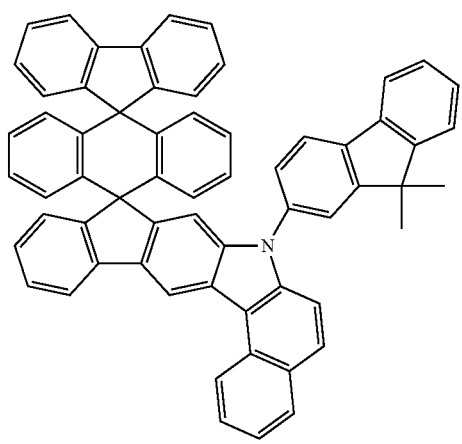
10-9
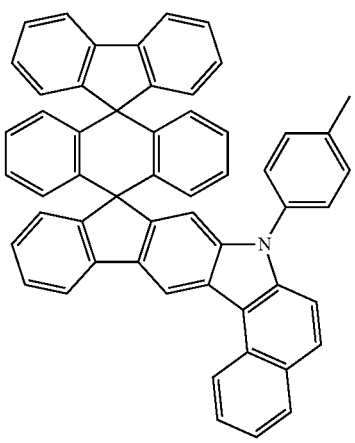
10-10
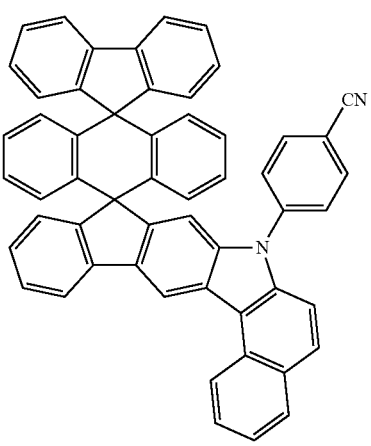
10-11
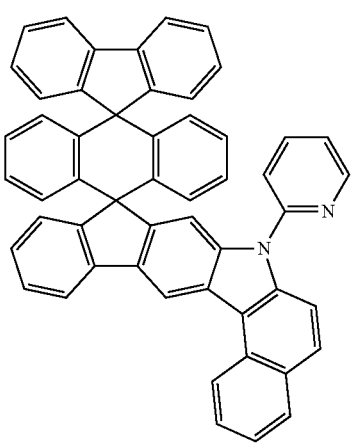

10-12
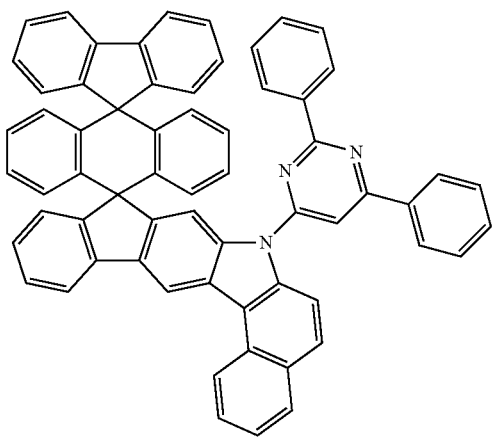
10-13
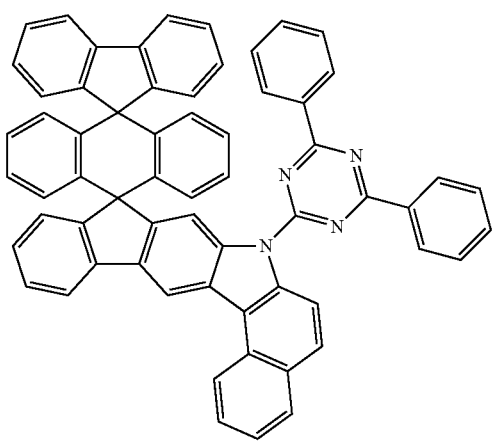
10-14
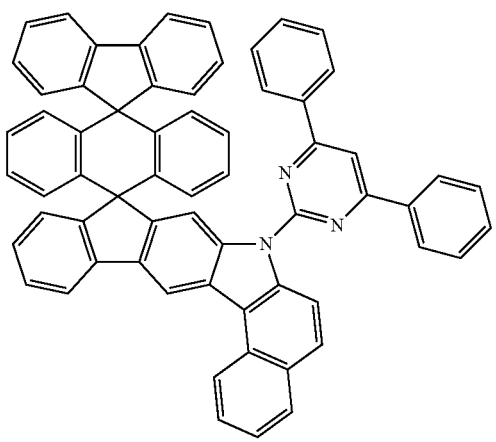
10-15
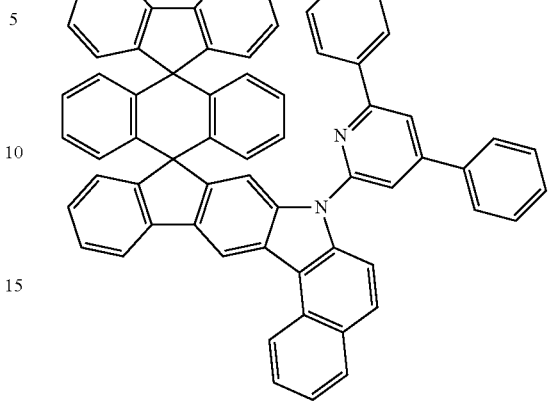
10-16
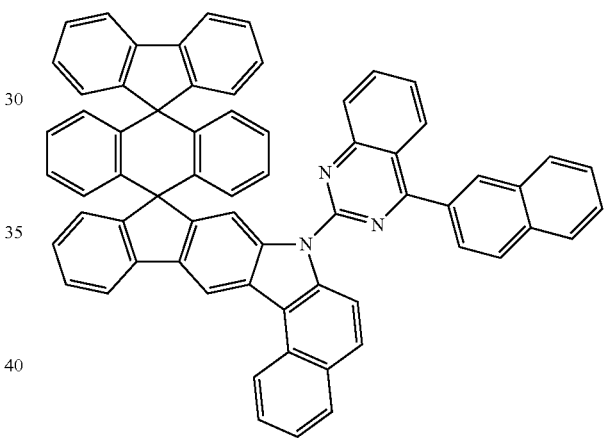
10-17
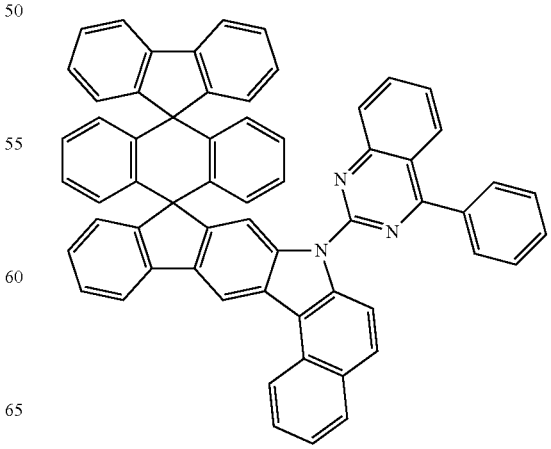

-continued
10-18
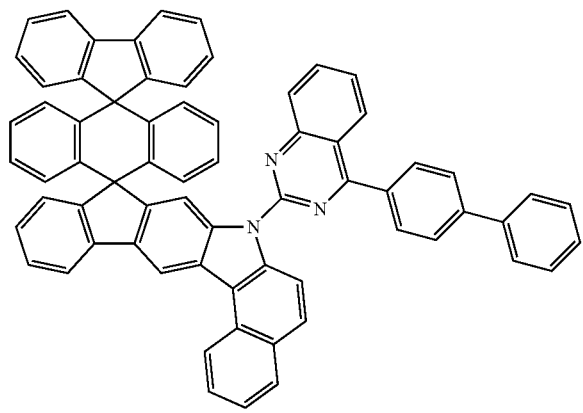
10-19
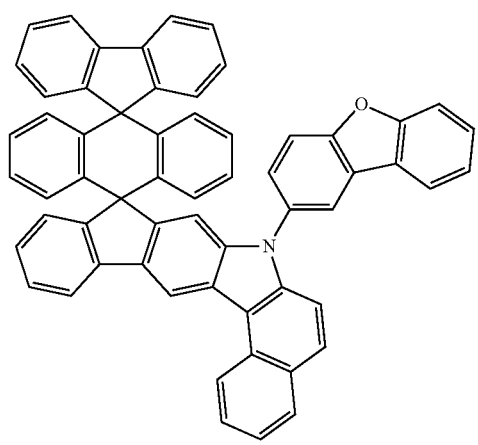
10-20
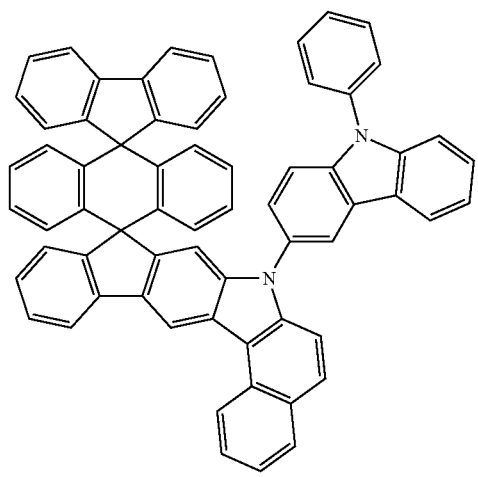
-continued
10-21
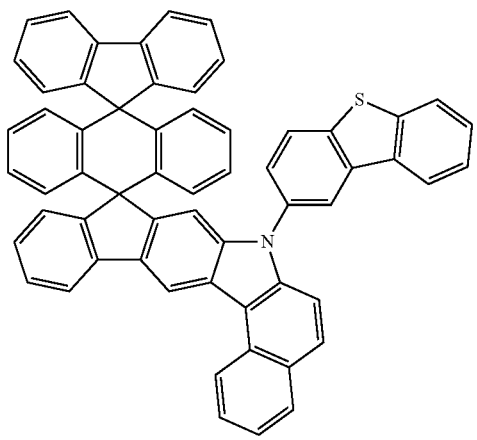
10-22
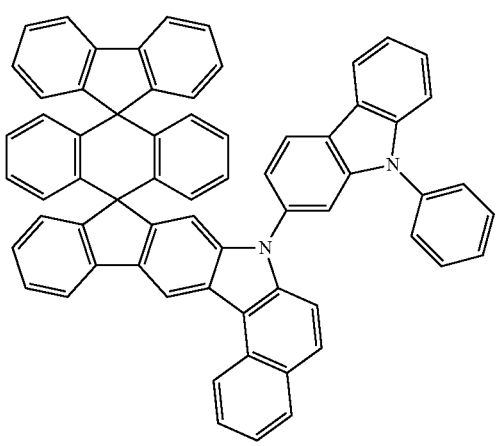
10-23
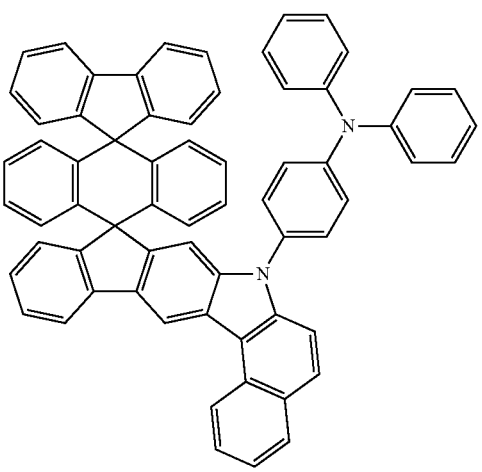

10-24
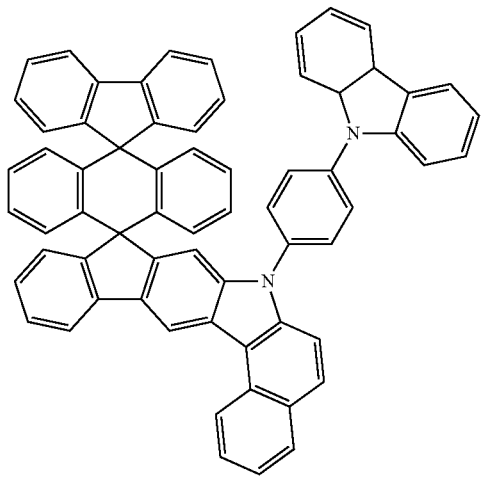
11-1
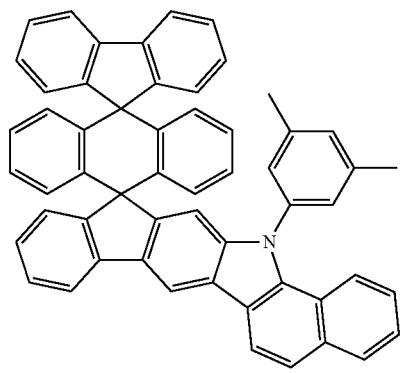
11-2
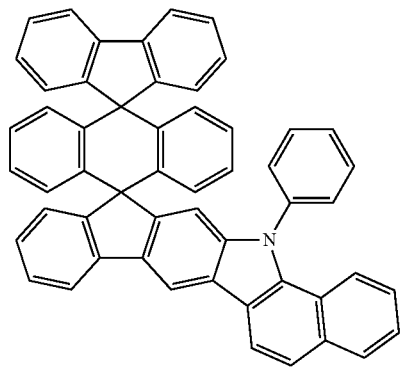
11-3
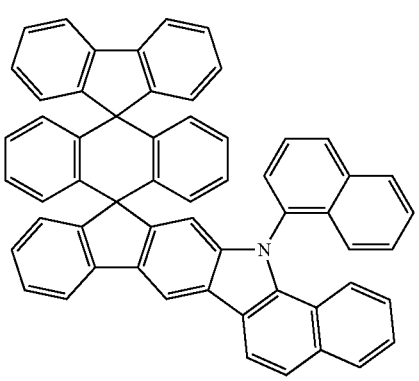
11-4
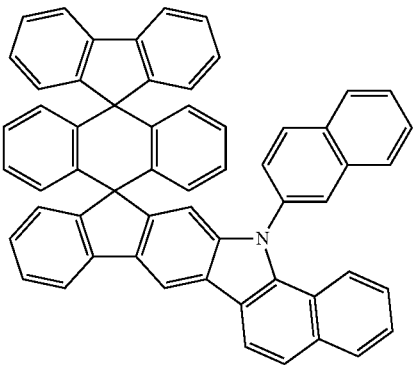
11-5
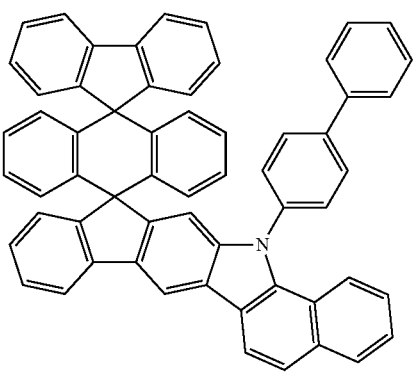
11-6
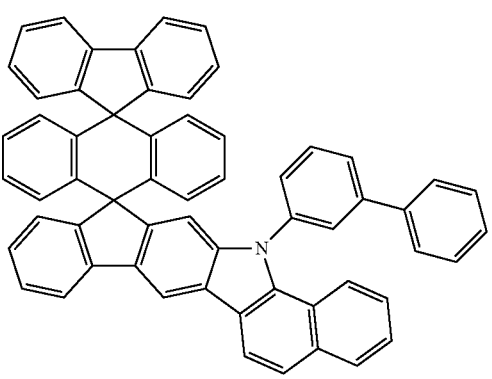
11-7
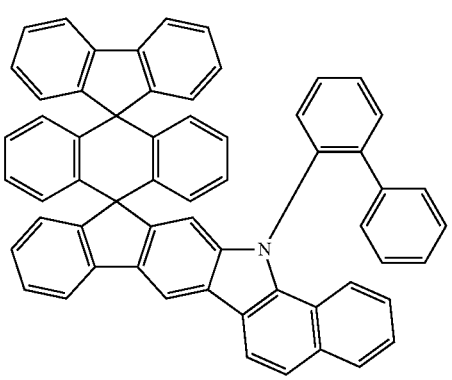

11-8
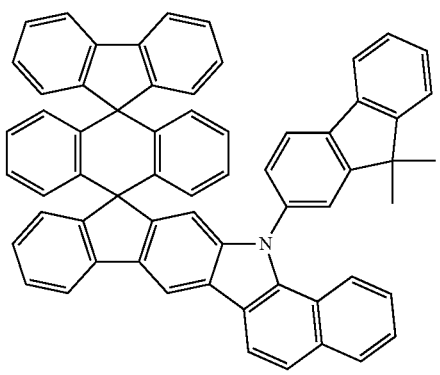
11-12
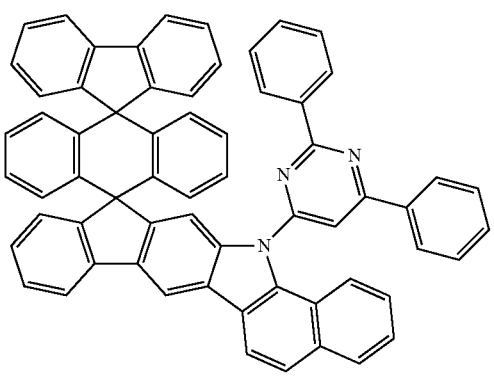
11-9
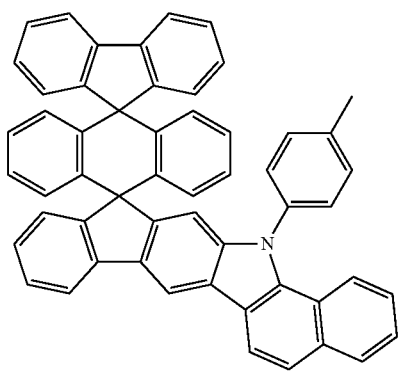
11-13
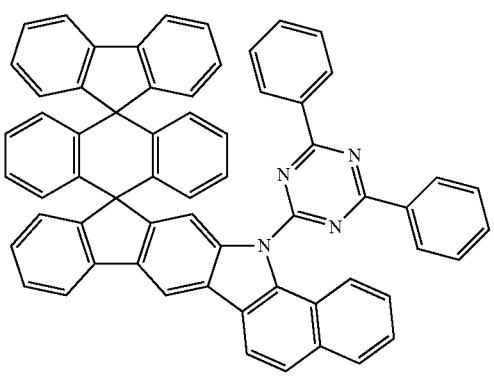
11-10
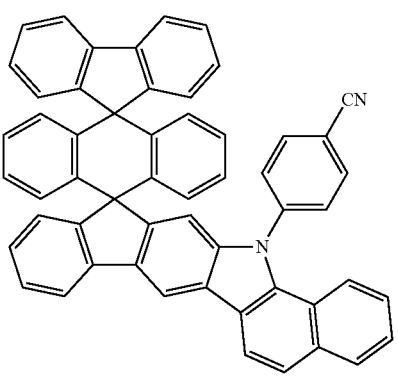
11-14
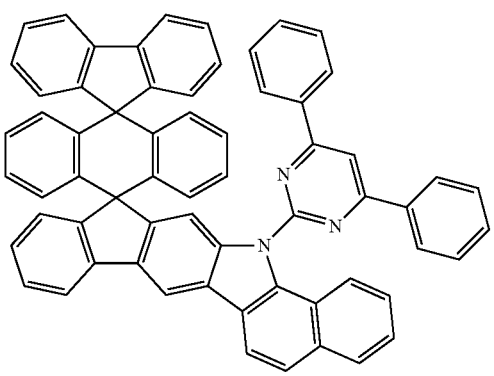
11-11
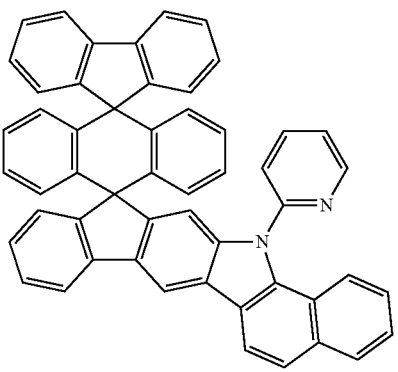
11-15
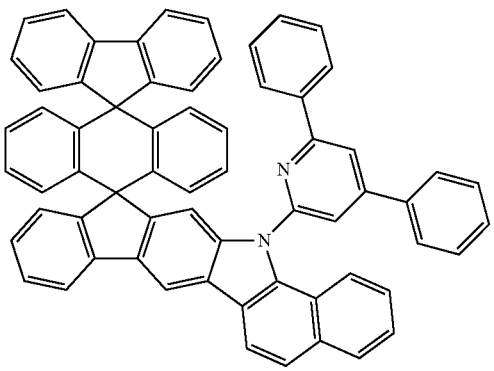

11-16
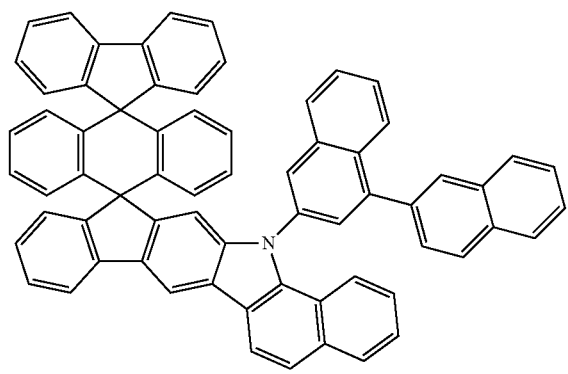
11-17
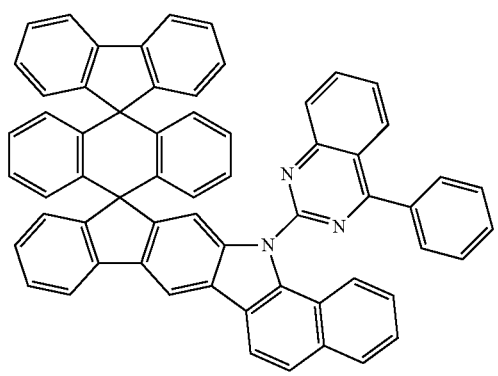
11-18
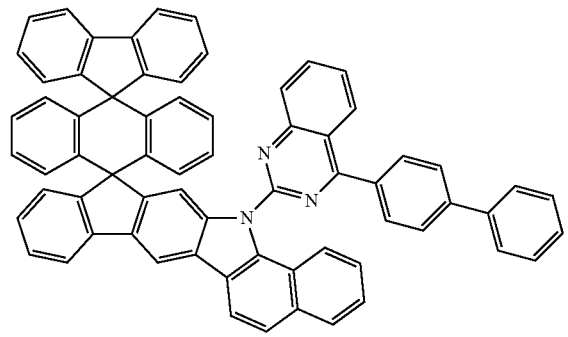
11-19
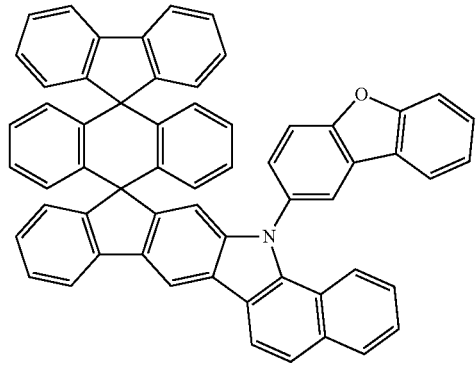
11-20
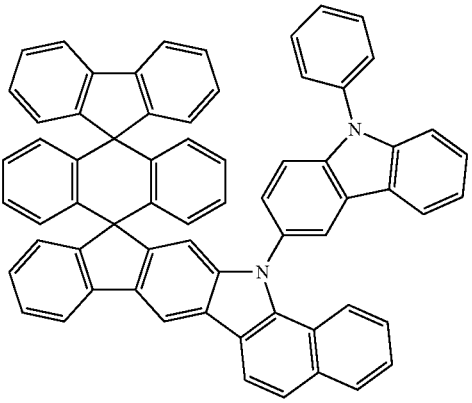
11-21
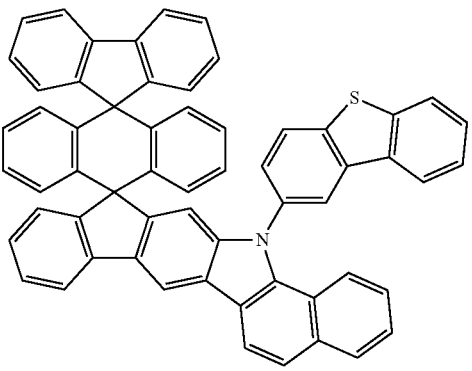
11-22
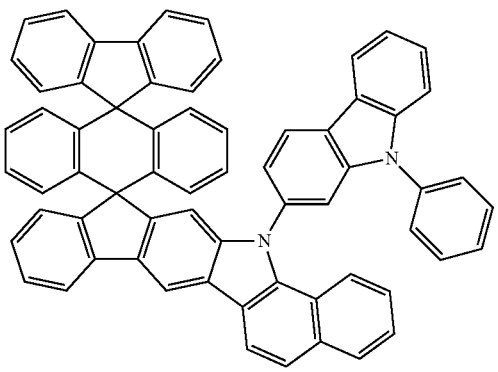
11-23
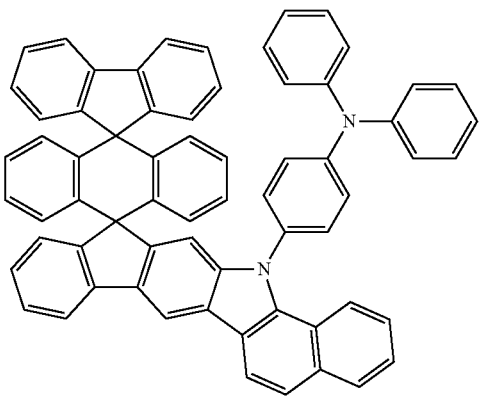

11-24
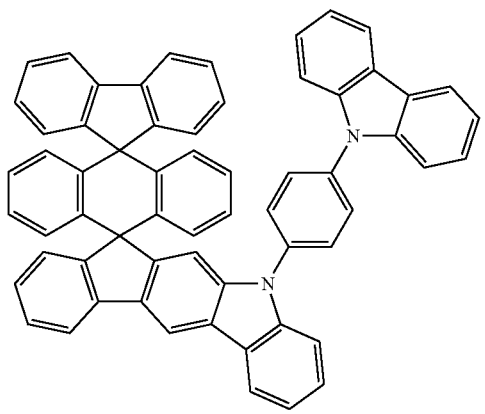
12-1
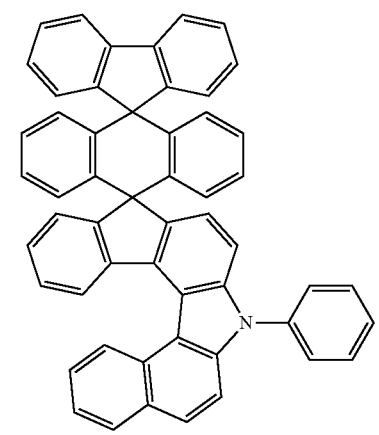
12-2
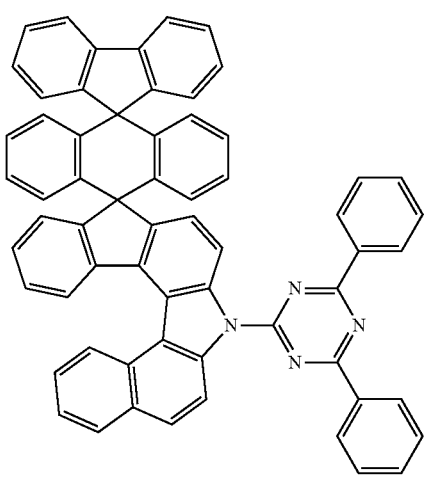
12-3
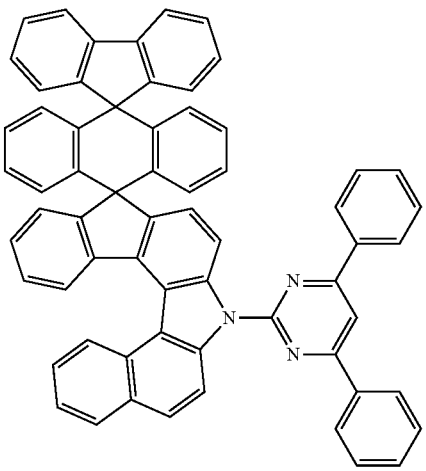
12-4
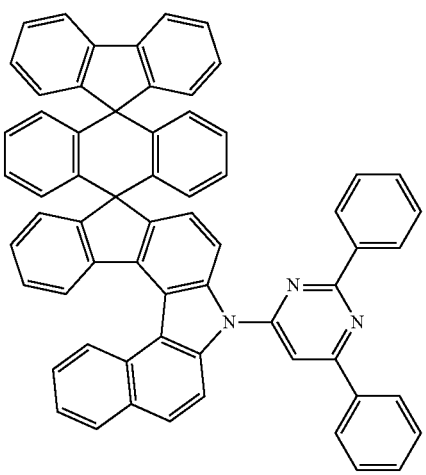
12-5
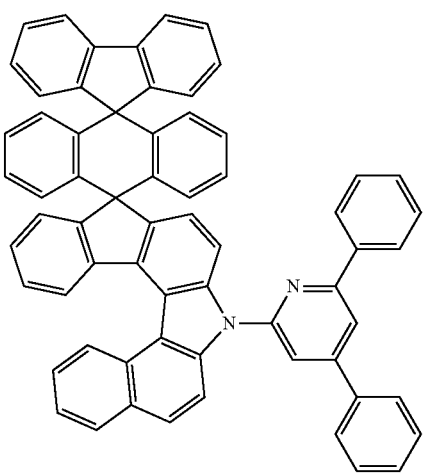

12-6
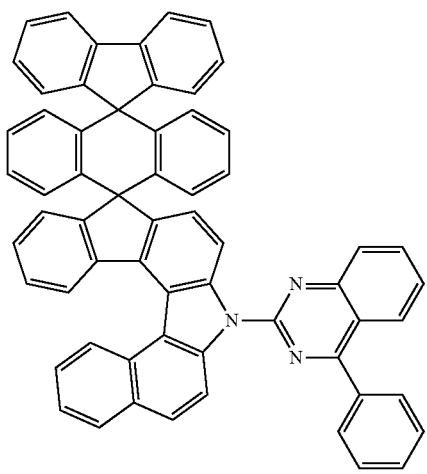
12-7
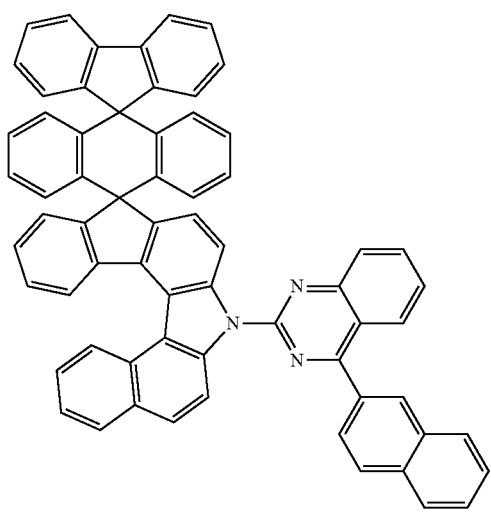
12-8
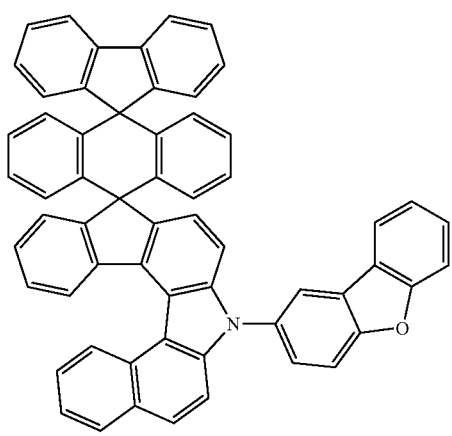
12-9
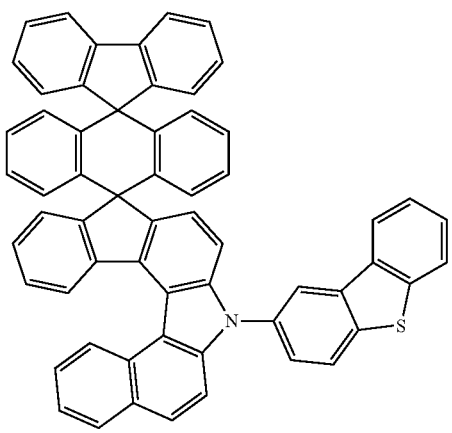
12-10
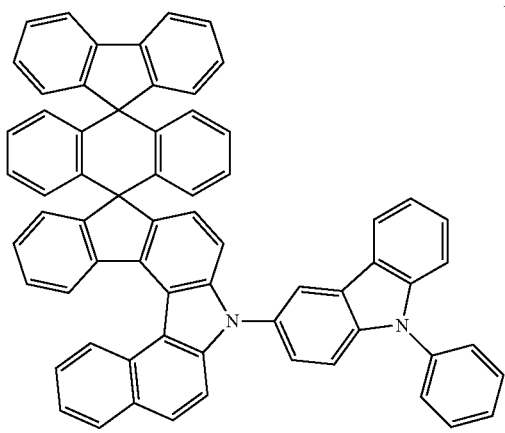
12-11
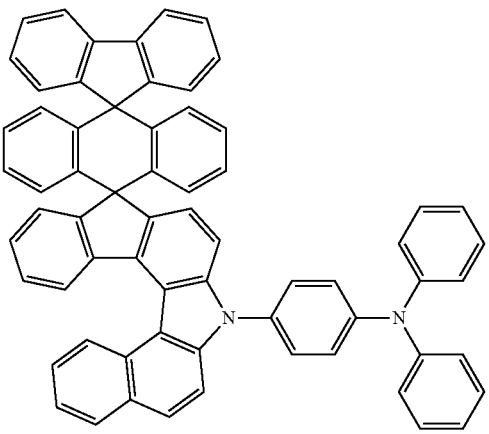

| | |
|---|---|
| 13-1 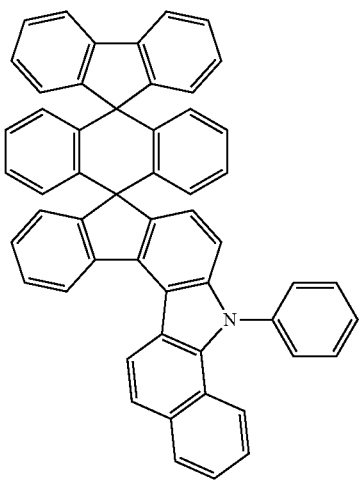 | 13-4 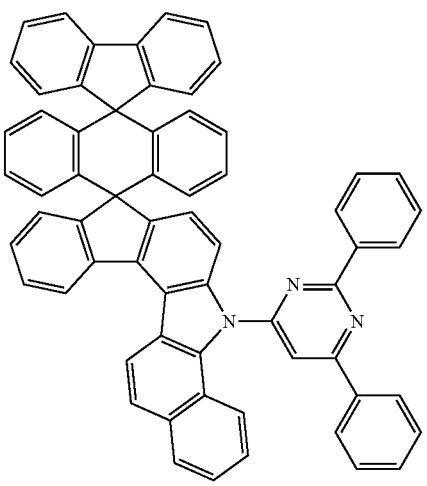 |
| 13-2 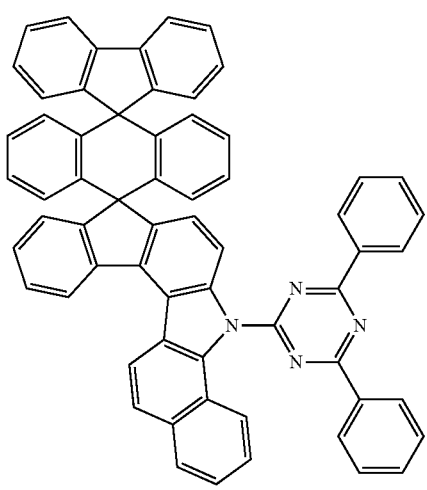 | 13-5 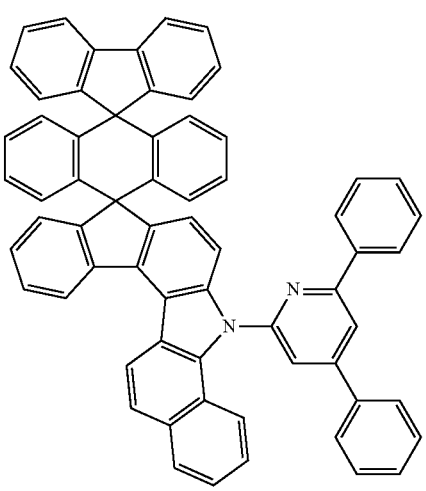 |
| 13-3 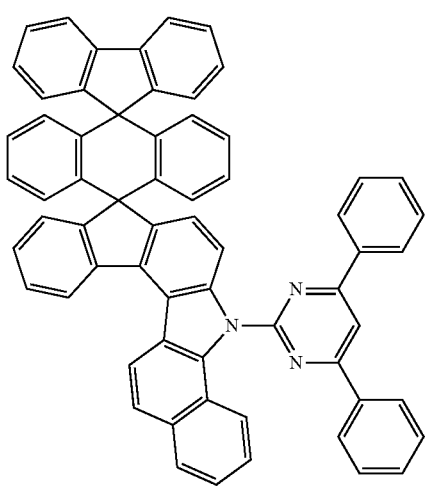 | 13-6 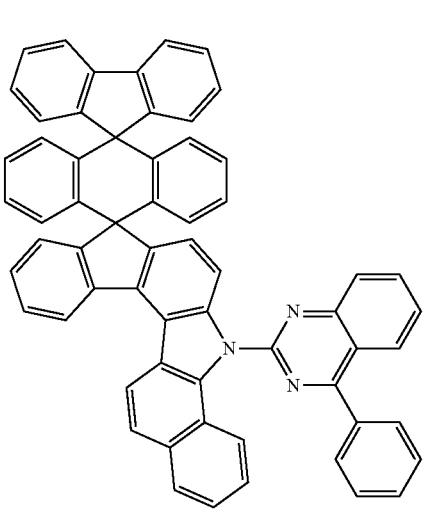 |

13-7
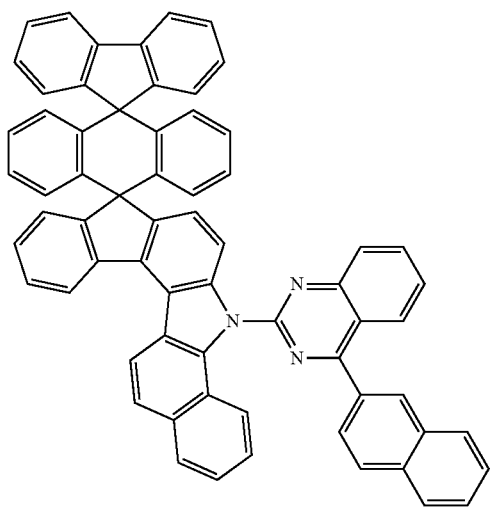
13-8
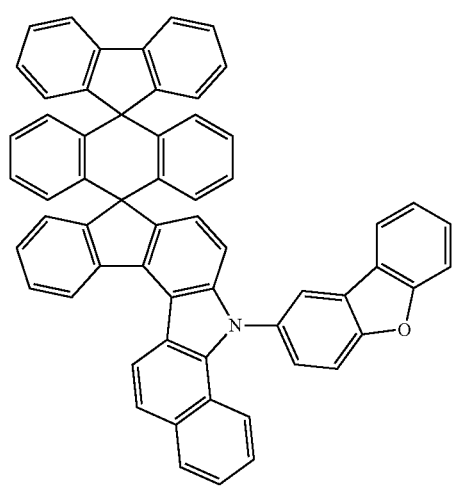
13-9
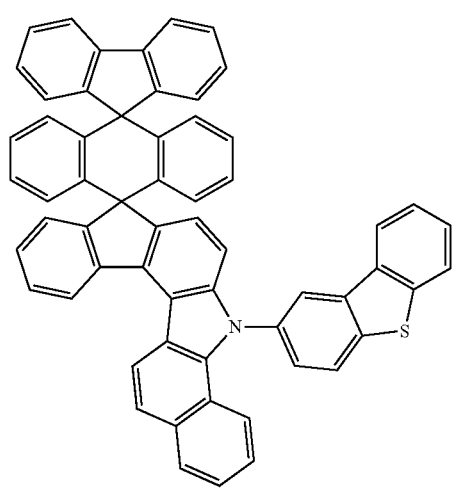
13-10
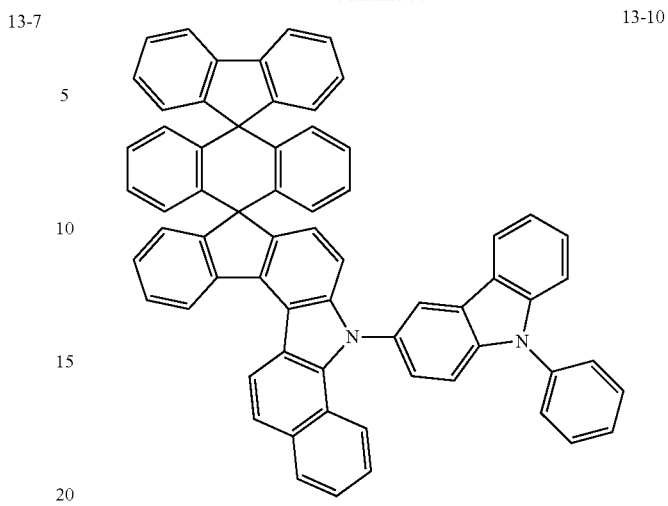
13-11
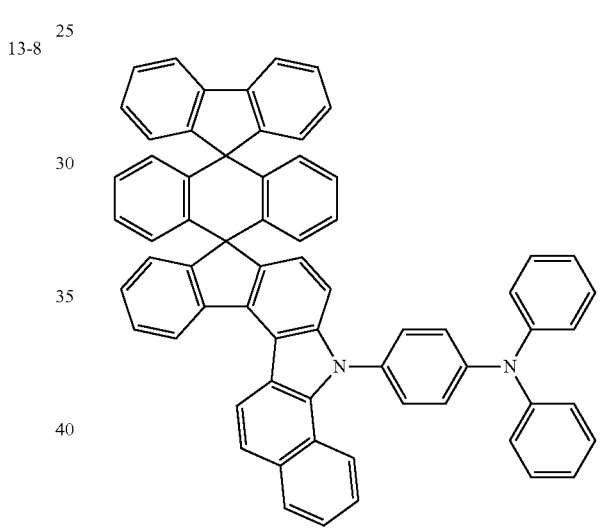
14-1
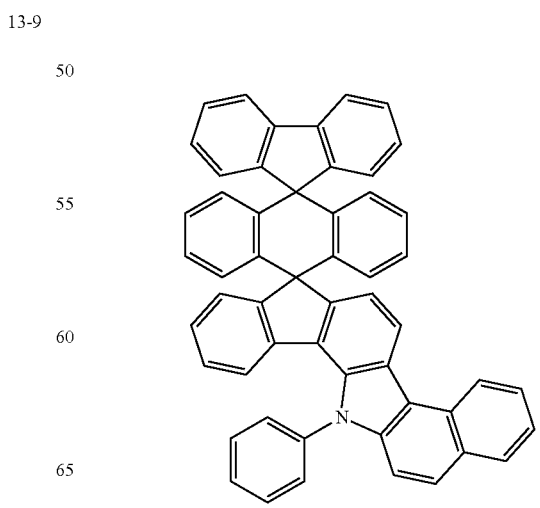

14-2
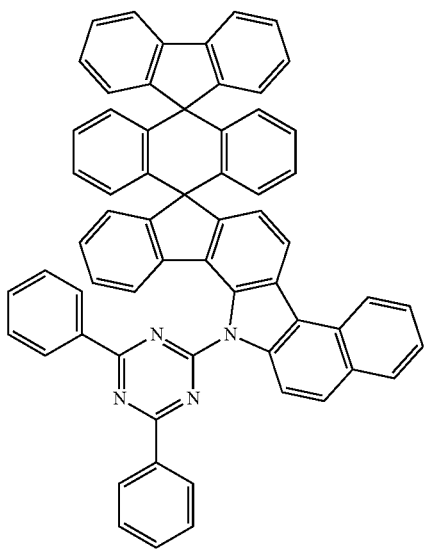
14-3
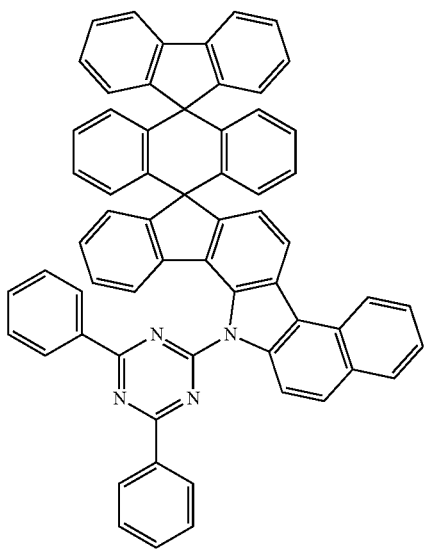
14-4
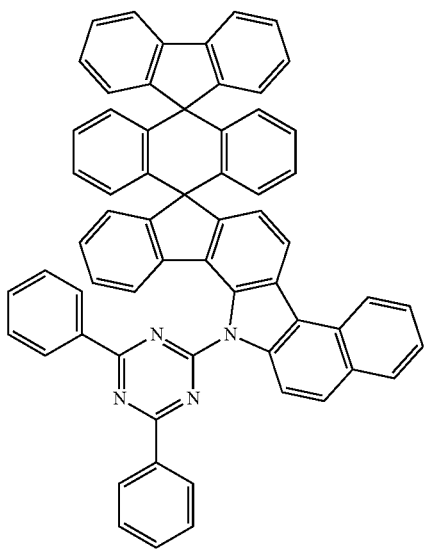
14-5
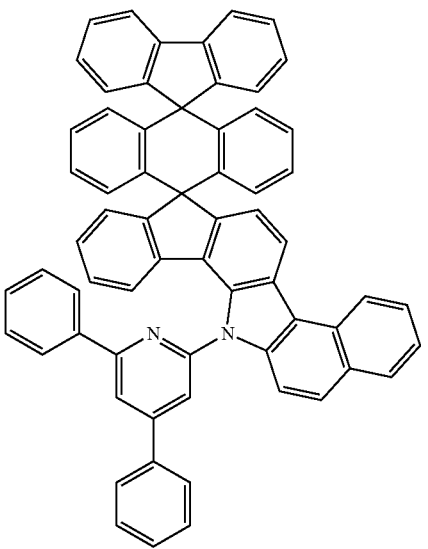
14-6
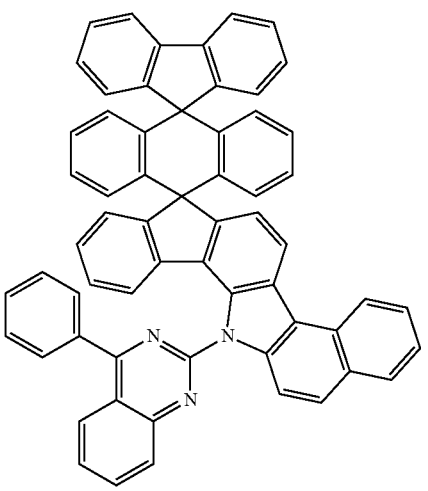
14-7
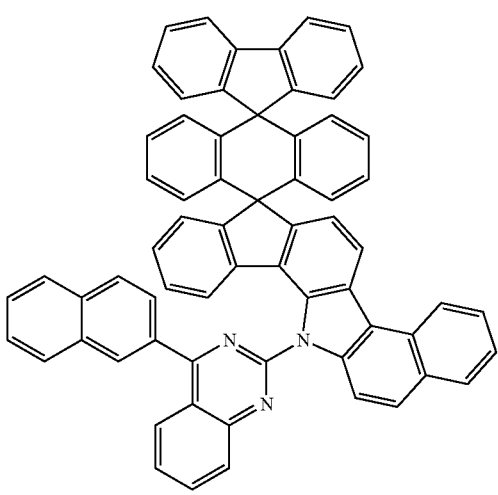

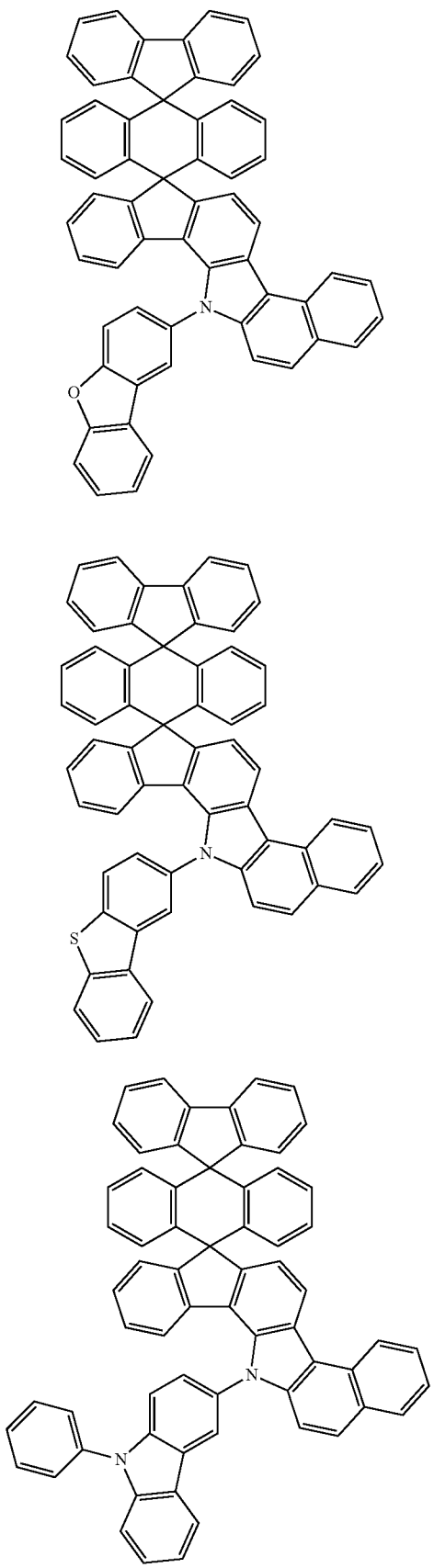
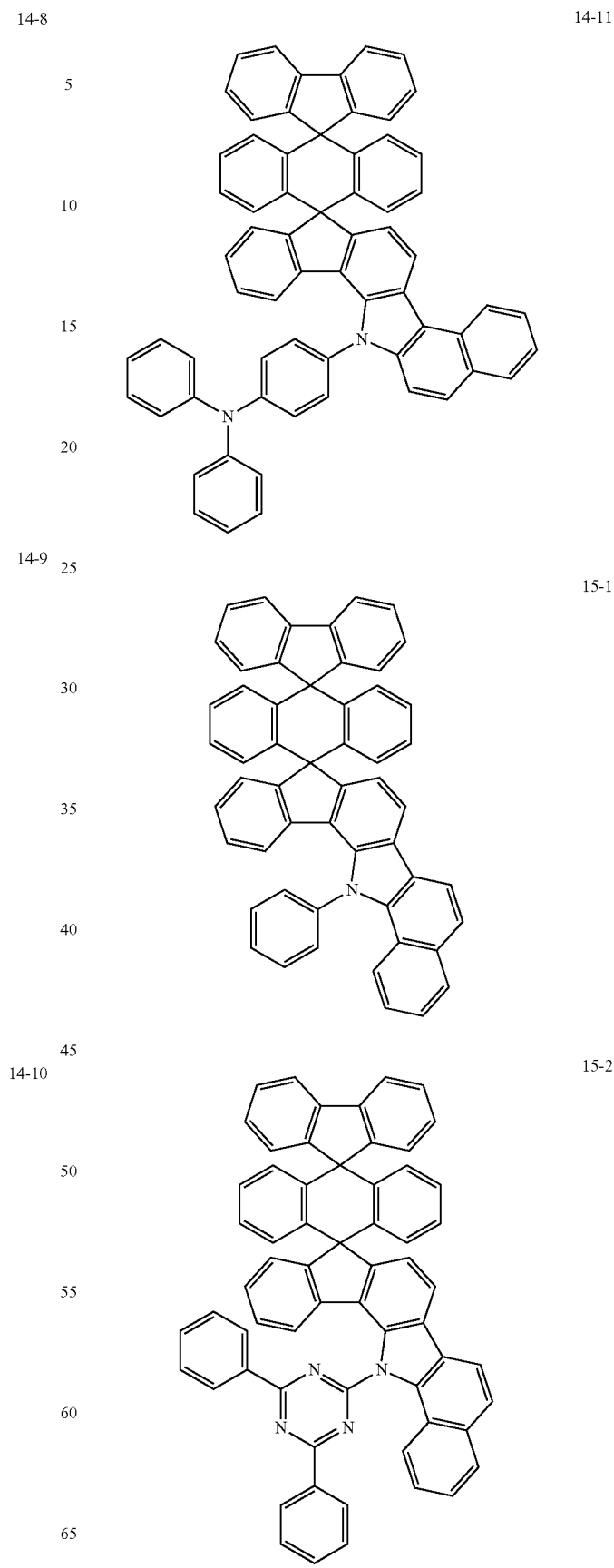

15-3
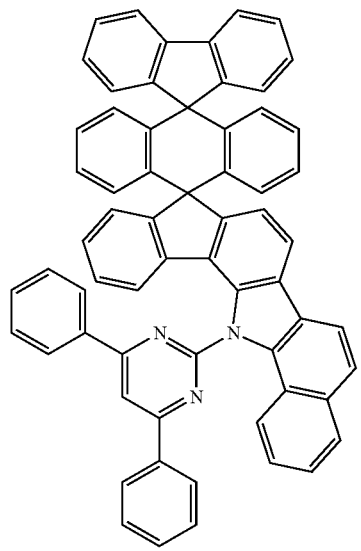
15-4
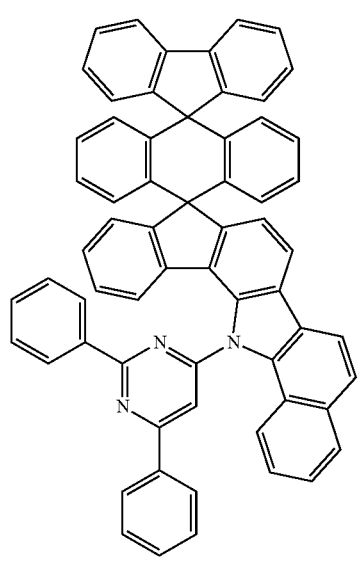
15-5
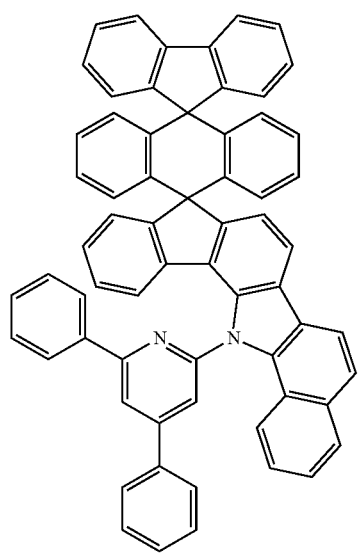
15-6
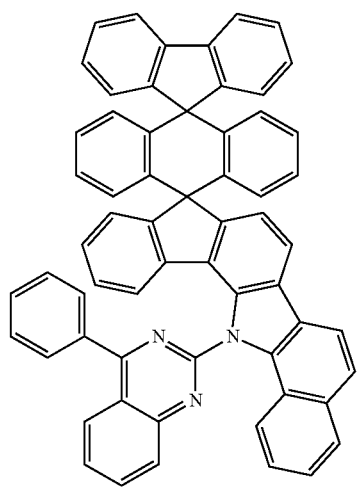
15-7
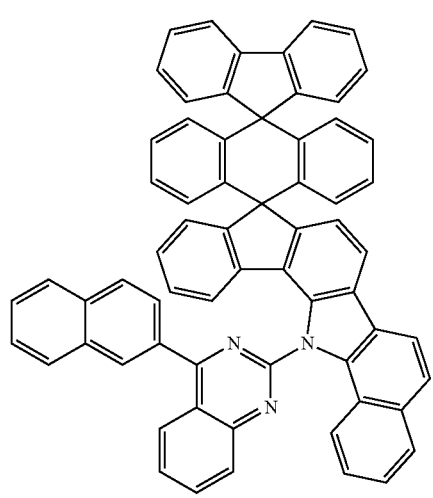
15-8
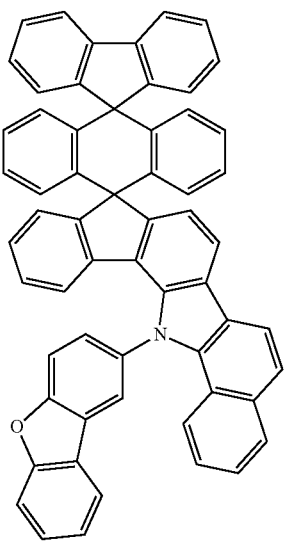

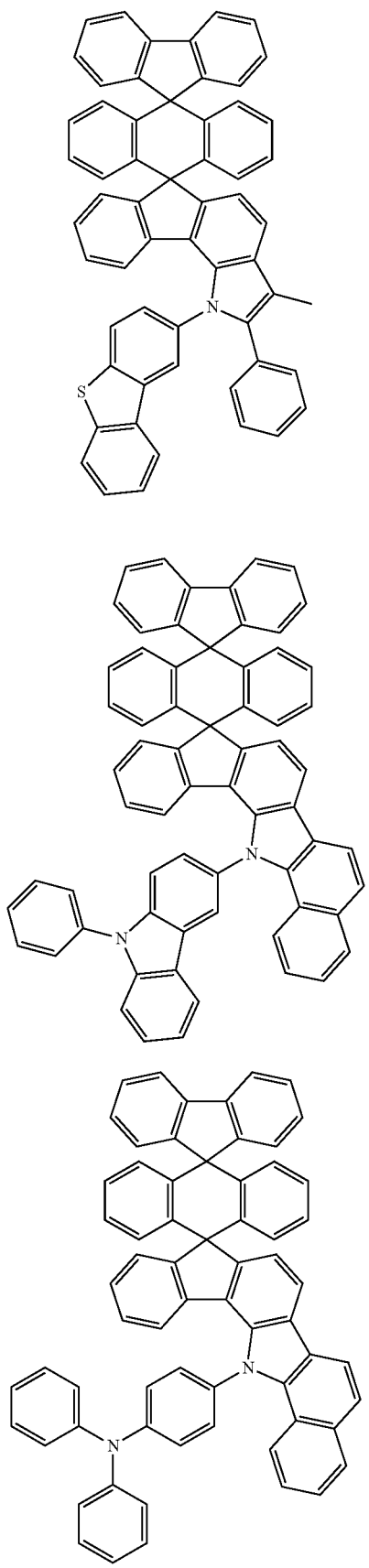
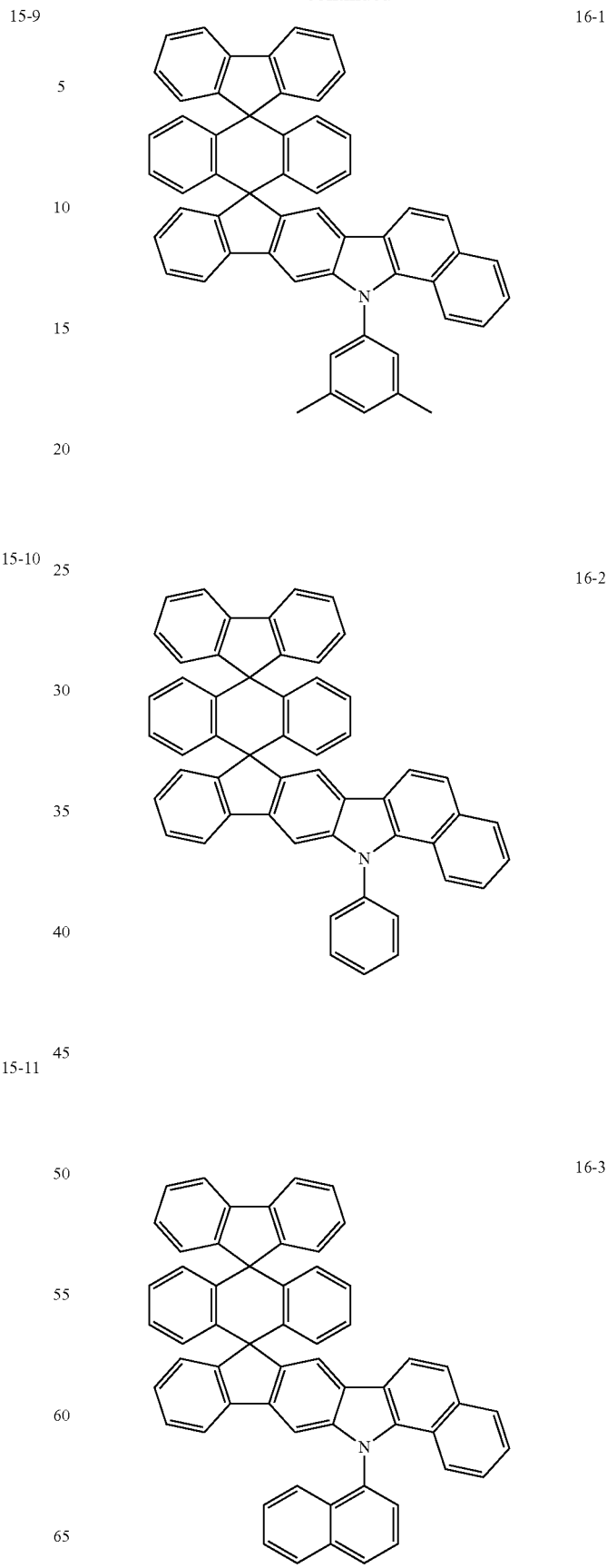

16-4
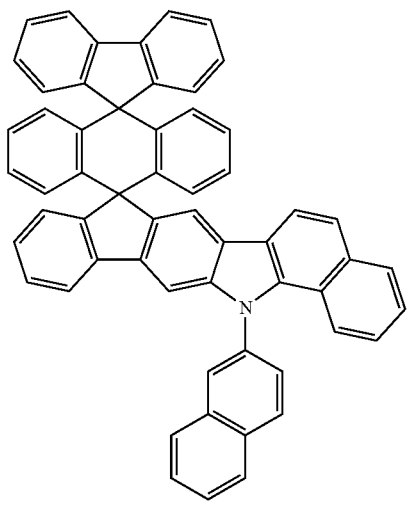
16-5
16-6
16-7
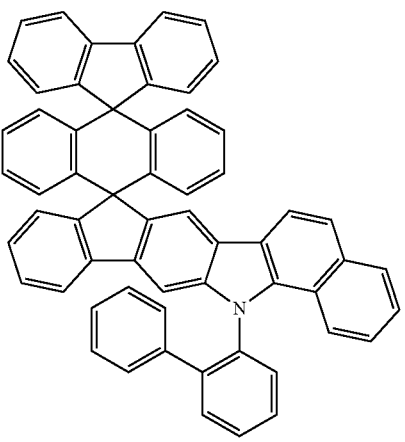
16-8
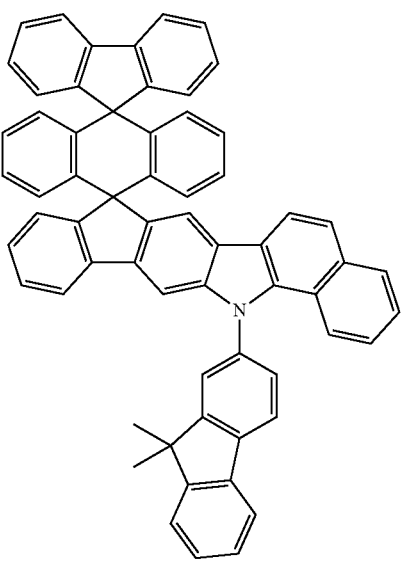
16-9
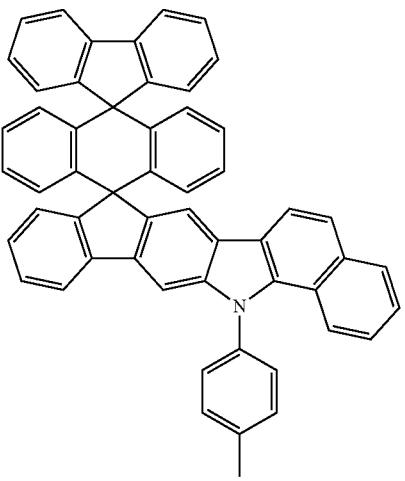

313
-continued
16-10
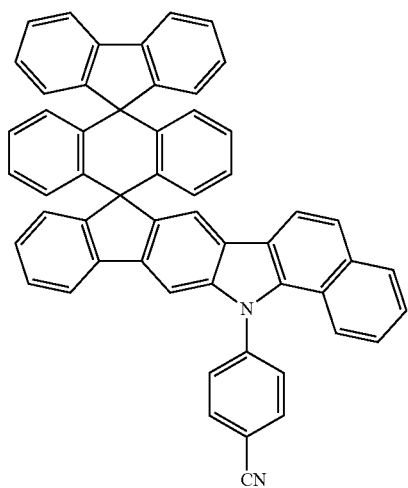
16-11
16-12
314
-continued
16-13
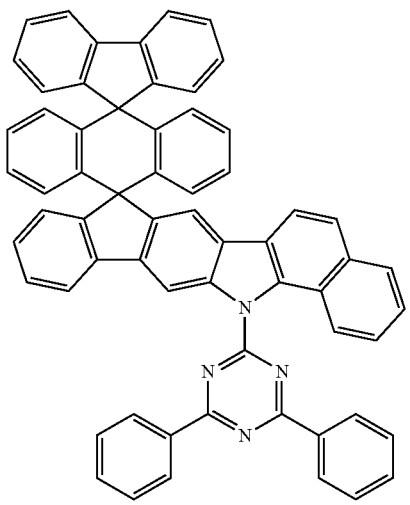
16-14
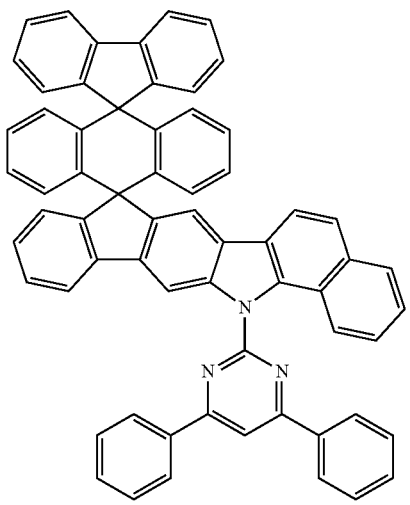
16-15
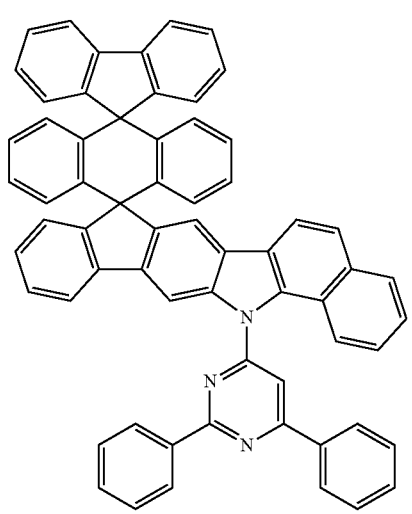
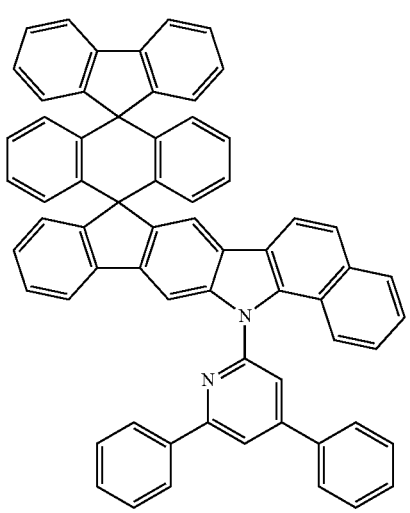

16-16
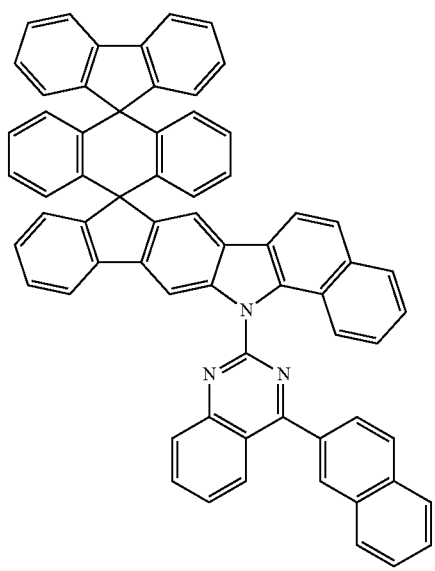
16-17
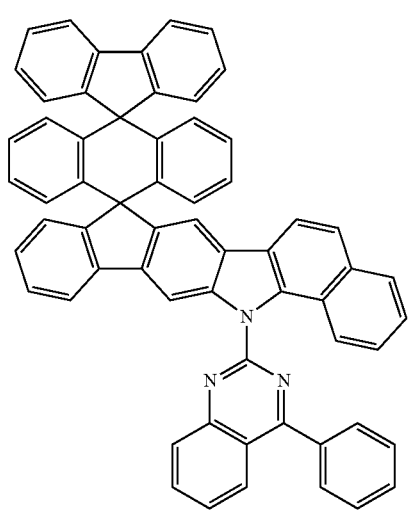
16-18
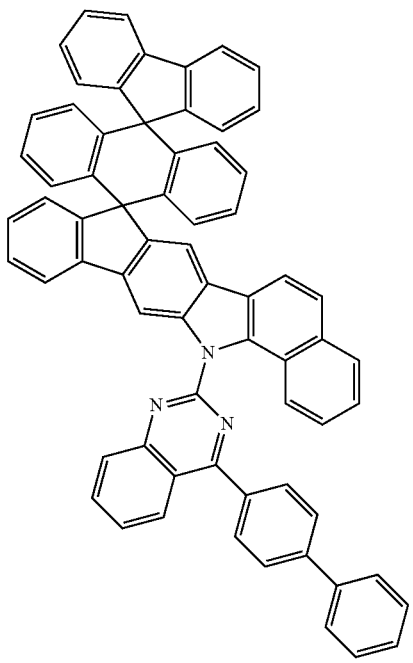
16-19
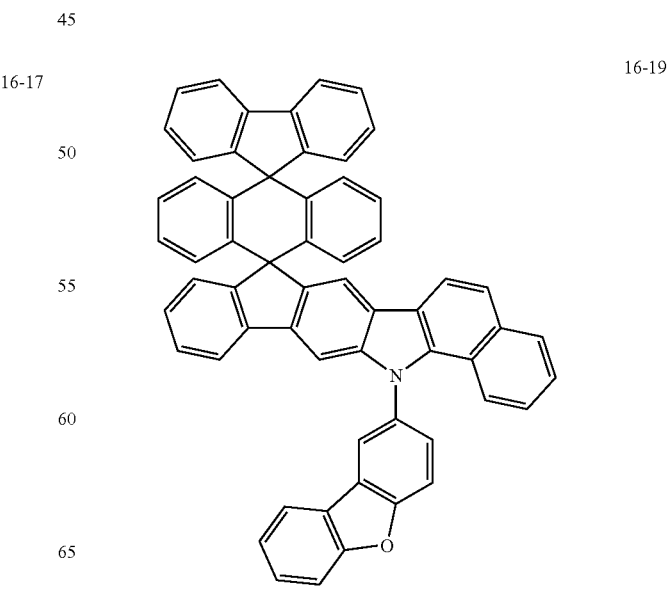

16-20
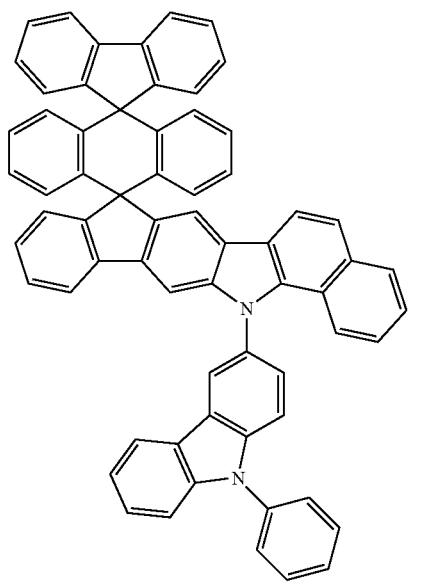
16-21
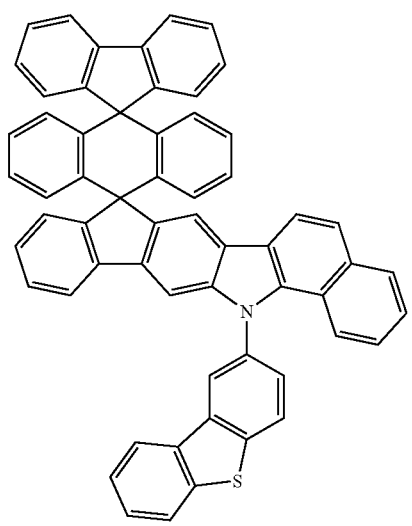
16-22
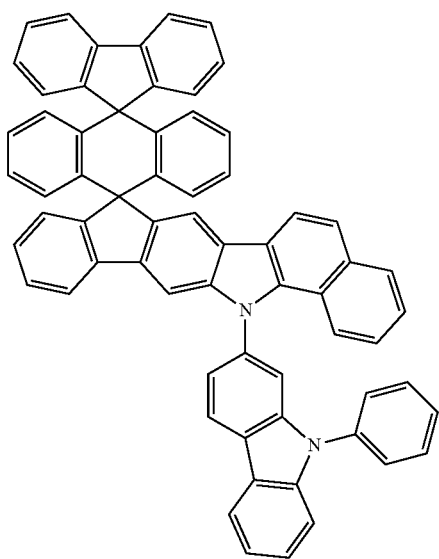
16-23
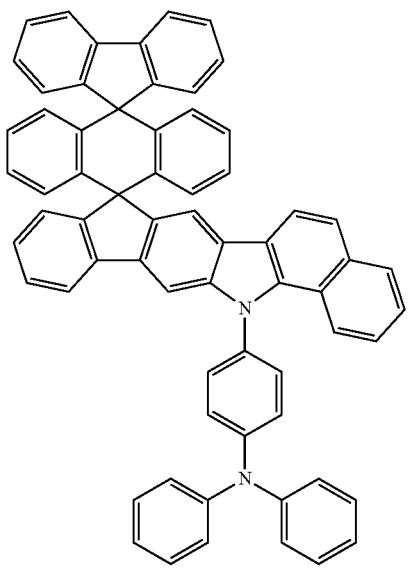
16-24
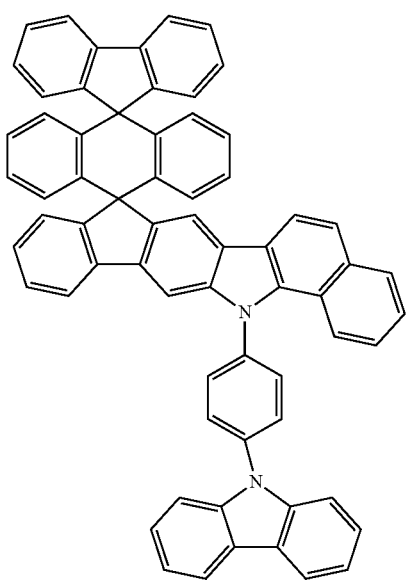
17-1
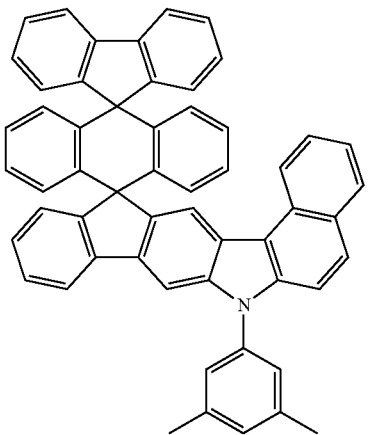

-continued
17-2
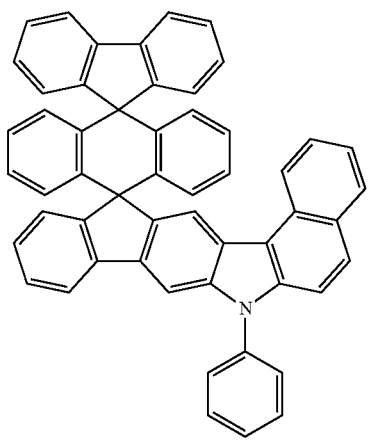
17-3
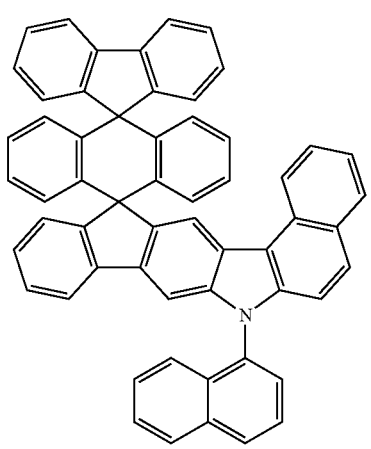
17-4
-continued
17-5
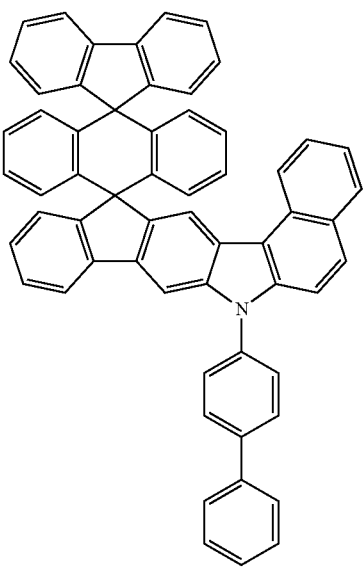
17-6
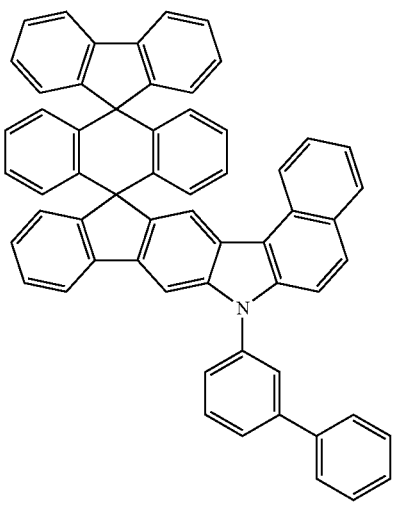
17-7
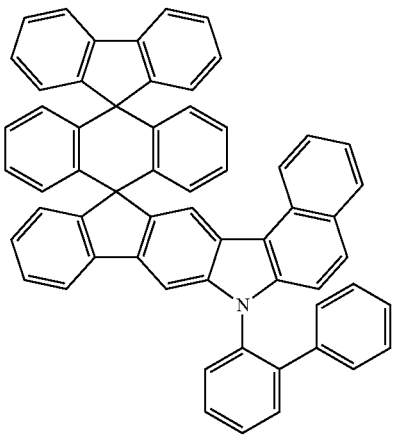

-continued
17-8
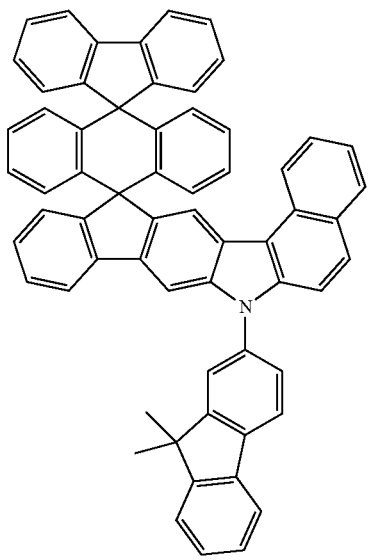
17-9
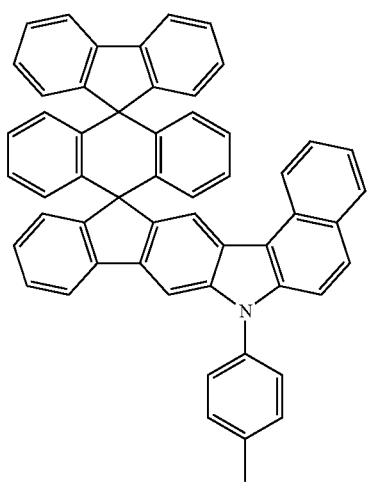
17-10
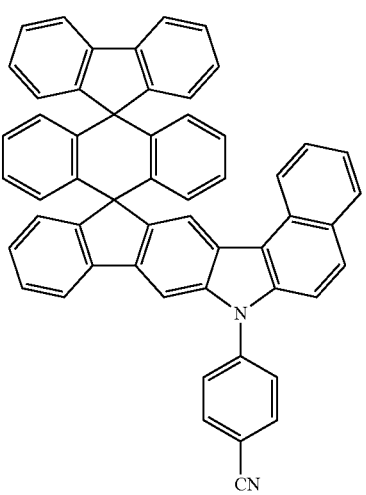
-continued
17-11
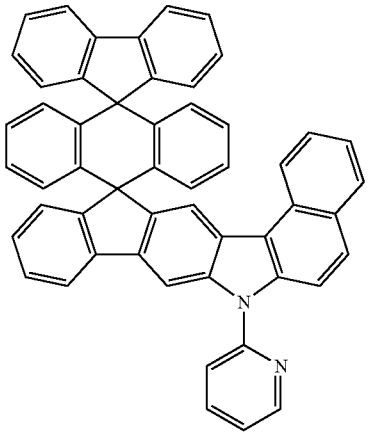
17-12
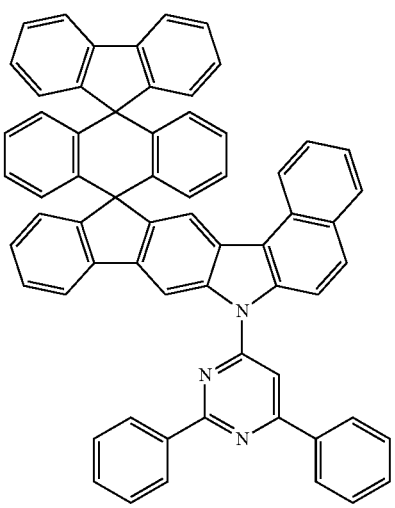
17-13
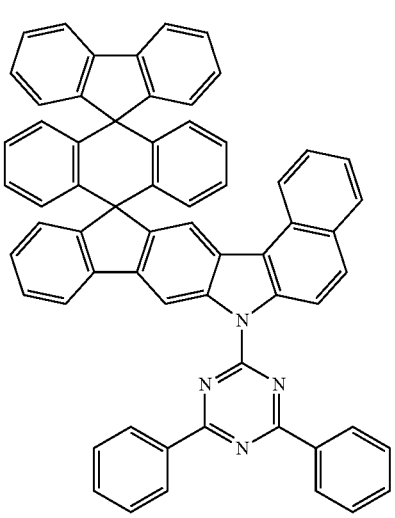

17-14
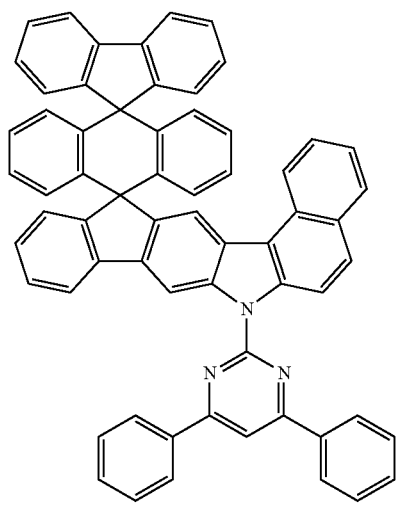
17-15
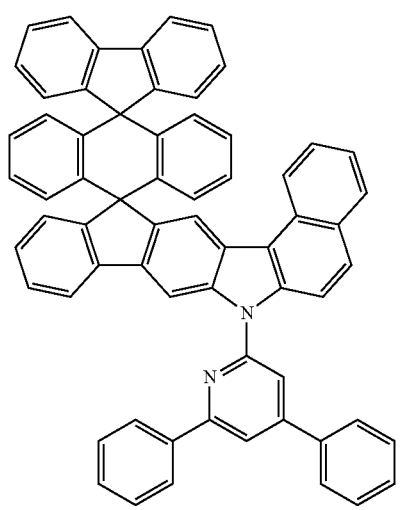
17-16
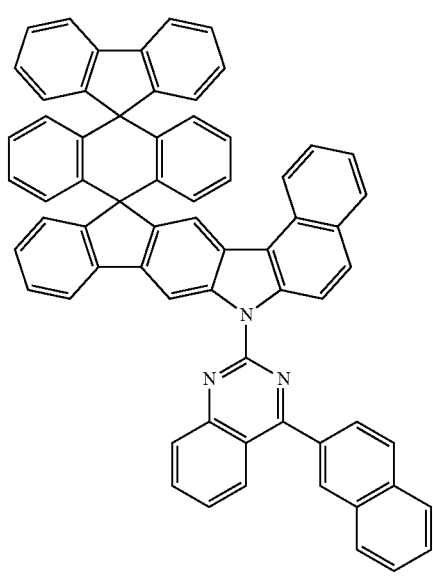
17-17
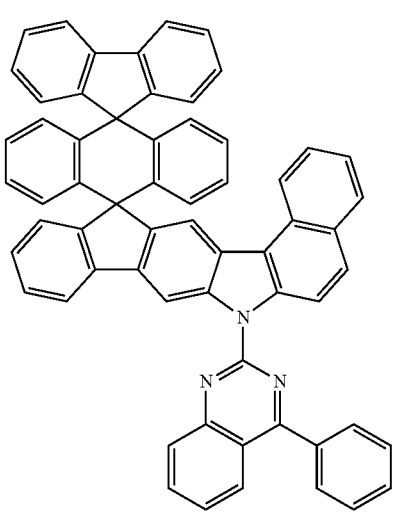
17-18
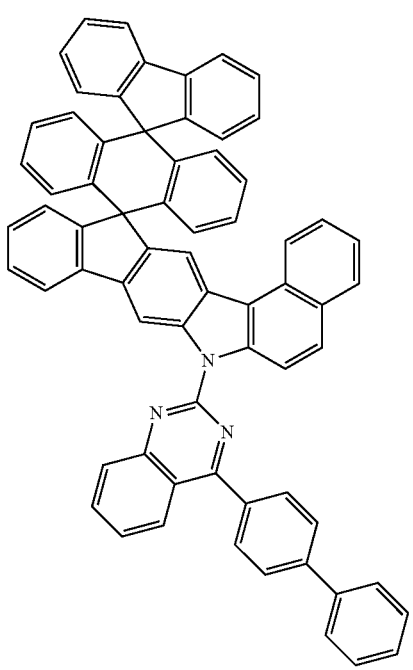

-continued
17-19
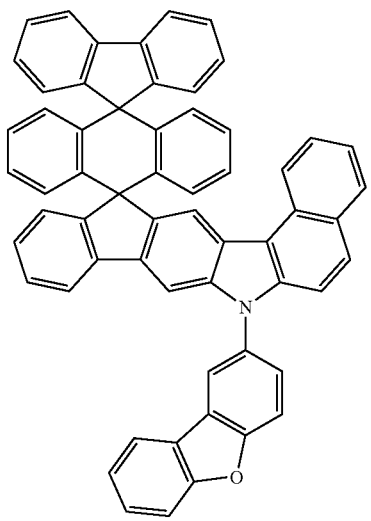
17-20
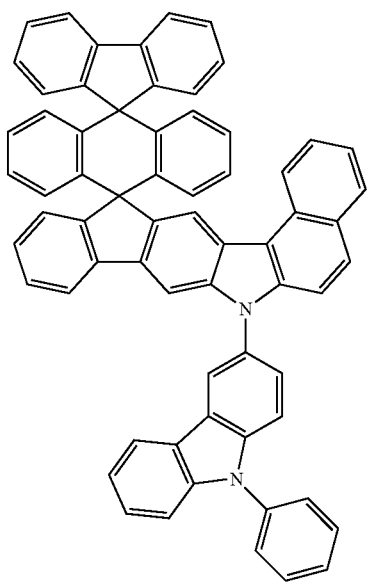
17-21
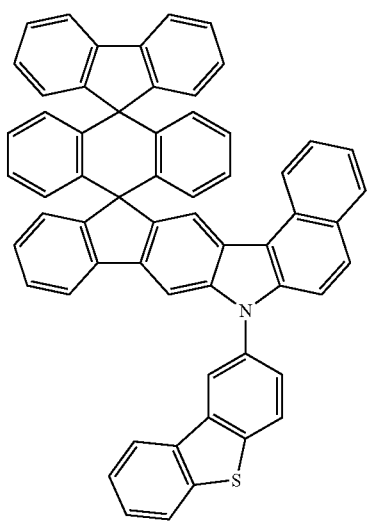
-continued
17-22
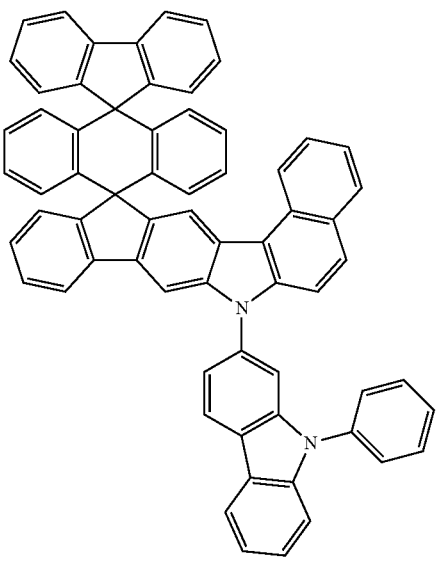
17-23
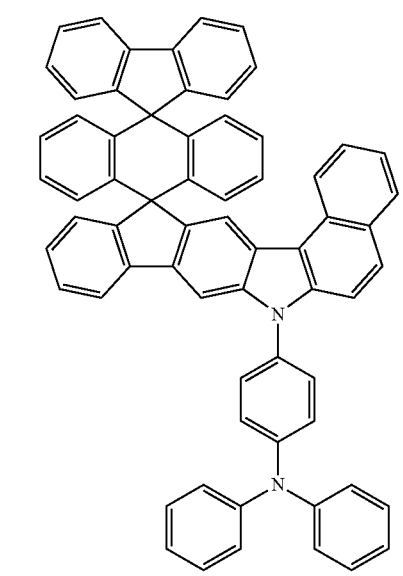

-continued 17-24

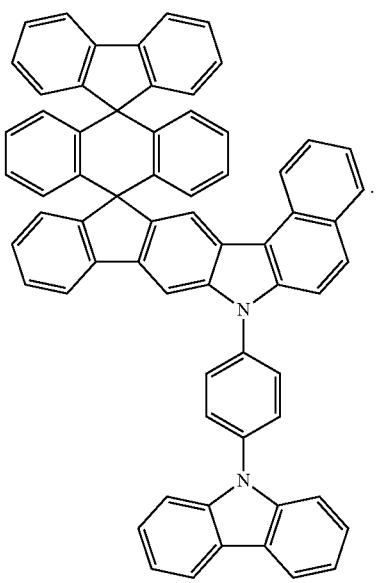

9. An organic electronic device comprising:
a first electrode;
a second electrode; and
one or more organic material layers disposed between the first electrode and the second electrode,
wherein one or more layers of the organic material layers comprise the organic compound having a double spiro structure of claim 1.

10. The organic electronic device of claim 9, which is selected from the group consisting of an organic light emitting device, an organic solar cell and an organic transistor.

11. The organic electronic device of claim 9 as an organic light emitting device comprising:
a first electrode;
a second electrode; and
one or more organic material layers disposed between the first electrode and the second electrode,
wherein one or more layers of the organic material layers comprise the organic compound having a double spiro structure.

12. The organic electronic device of claim 11, wherein the organic material layer comprises a hole injection layer or a hole transfer layer, and the hole injection layer or the hole transfer layer comprises the organic compound having a double spiro structure.

13. The organic electronic device of claim 11, wherein the organic material layer includes a light emitting layer, and the light emitting layer comprises the organic compound having a double spiro structure as a host of the light emitting layer.

14. The organic electronic device of claim 11, wherein the organic material layer comprises an electron blocking layer, and the electron blocking layer comprises the compound of Chemical Formula 1.

15. The organic electronic device of claim 11, wherein the organic material layer comprises an electron transfer layer, and the electron transfer layer comprises the organic compound having a double spiro structure.

16. The organic electronic device of claim 11, wherein the organic material layer comprising the organic compound having a double spiro structure comprises the organic compound having a double spiro structure as a host, and other organic compounds, metals or metal compounds as a dopant.

17. The organic electronic device of claim 9 as an organic solar cell comprising:
a first electrode;
a second electrode; and
one or more organic material layers comprising a photo-active layer disposed between the first electrode and the second electrode,
wherein one or more layers of the organic material layers comprise the organic compound having a double spiro structure.

18. The organic electronic device of claim 9 as an organic transistor comprising:
a source;
a drain;
a gate; and
one or more organic material layers,
wherein one or more layers of the organic material layers comprise the organic compound having a double spiro structure.

19. The organic electronic device of claim 9, wherein the organic material layer comprises a light emitting layer comprising a compound of the following Chemical Formula 18:

[Chemical Formula 18]

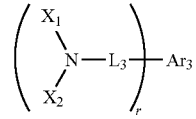

wherein, in Chemical Formula 18,
Ar$_3$ is a benzofluorene skeleton, a fluoranthene skeleton, a pyrene skeleton or a chrysene skeleton;
L$_3$ is a single bond, a C$_6$ to C$_{30}$ arylene group or a C$_5$ to C$_{30}$ divalent heterocyclic group;
X$_1$ and X$_2$ are the same as or different from each other, and each independently selected from the group consisting of a substituted or unsubstituted C$_6$ to C$_{30}$ aryl group, a substituted or unsubstituted C$_5$ to C$_{30}$ heterocyclic group, a substituted or unsubstituted C$_1$ to C$_{30}$ alkyl group and a substituted or unsubstituted C$_7$ to C$_{30}$ aralkyl group, and X$_1$ and X$_2$ bond to each other to form a saturated or unsaturated ring;
r is an integer of 1 or greater; and
when r is 2 or greater, X$_1$s are the same as or different from each other, and X$_2$s are the same as or different from each other.

20. The organic electronic device of claim 19, wherein Ar$_3$ is a pyrene skeleton, L$_3$ is a single bond, X$_1$ and X$_2$ are the same as or different from each other and each independently an aryl group unsubstituted or substituted with a germanium group, and r is 2.

21. The organic electronic device of claim 9, wherein the organic material layer comprises a light emitting layer comprising a compound of the following Chemical Formula 19,

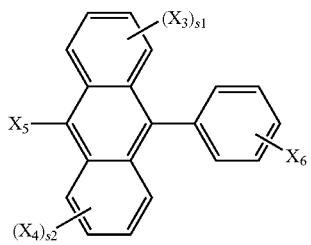

[Chemical Formula 19]

wherein, in Chemical Formula 19,

X₅ is a substituted or unsubstituted 1-naphthyl group, a substituted or unsubstituted 2-naphthyl group, a substituted or unsubstituted 1-anthryl group, a substituted or unsubstituted 2-anthryl group, a substituted or unsubstituted 1-phenanthryl group, a substituted or unsubstituted 2-phenanthryl group, a substituted or unsubstituted 3-phenanthryl group, a substituted or unsubstituted 4-phenanthryl group, a substituted or unsubstituted 9-phenanthryl group, a substituted or unsubstituted 1-naphthacenyl group, a substituted or unsubstituted 2-naphthacenyl group, a substituted or unsubstituted 9-naphthacenyl group, a substituted or unsubstituted 1-pyrenyl group, a substituted or unsubstituted 2-pyrenyl group, a substituted or unsubstituted 4-pyrenyl group, a substituted or unsubstituted 3-methyl-2-naphthyl group, a substituted or unsubstituted 4-methyl-1-naphthyl group or the following structural formula

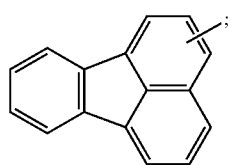

X₆ is a group selected from the group consisting of a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl) phenyl group, a 3-methyl-2-naphthyl group, a 4-methyl-1-naphthyl group, a 4-methyl-1-anthryl group, a 4'-methylbiphenylyl group, a 4''-t-butyl-p-terphenyl-4-yl group and a 3-fluoranthenyl group;

X₃ and X₄ are the same as or different from each other, and each independently a substituted or unsubstituted aryl group having 6 to 50 carbon atoms, a substituted or unsubstituted heteroaryl group having 5 to 50 nuclear atoms, a substituted or unsubstituted alkyl group having 1 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 nuclear atoms, a substituted or unsubstituted arylthio group having 5 to 50 nuclear atoms, a substituted or unsubstituted alkoxycarbonyl group having 1 to 50 carbon atoms, a carboxyl group, a halogen atom, a cyano group, a nitro group or a hydroxyl group; and s1 and s2 are each an integer of 0 to 4.

22. The organic electronic device of claim 21, wherein X₅ and X₆ are the same as or different from each other and each independently a 1-naphthyl group or a 2-naphthyl group, and s1 and s2 are 0.

23. The organic electronic device of claim 19, wherein the light emitting layer further comprises a compound of the following Chemical Formula 19:

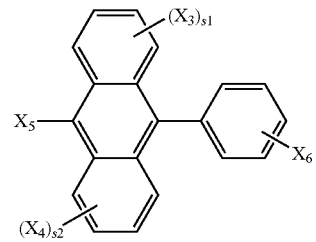

[Chemical Formula 19]

wherein, in Chemical Formula 19,

X₅ is a substituted or unsubstituted 1-naphthyl group, a substituted or unsubstituted 2-naphthyl group, a substituted or unsubstituted 1-anthryl group, a substituted or unsubstituted 2-anthryl group, a substituted or unsubstituted 1-phenanthryl group, a substituted or unsubstituted 2-phenanthryl group, a substituted or unsubstituted 3-phenanthryl group, a substituted or unsubstituted 4-phenanthryl group, a substituted or unsubstituted 9-phenanthryl group, a substituted or unsubstituted 1-naphthacenyl group, a substituted or unsubstituted 2-naphthacenyl group, a substituted or unsubstituted 9-naphthacenyl group, a substituted or unsubstituted 1-pyrenyl group, a substituted or unsubstituted 2-pyrenyl group, a substituted or unsubstituted 4-pyrenyl group, a substituted or unsubstituted 3-methyl-2-naphthyl group, a substituted or unsubstituted 4-methyl-1-naphthyl group or the following structural formula

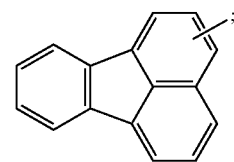

X₆ is a group selected from the group consisting of a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl- 3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl) phenyl group, a 3-methyl-2-naphthyl group, a 4-methyl-1-naphthyl group, a 4-methyl-1-anthryl group, a 4'-methylbiphenylyl group, a 4''-t-butyl-p-terphenyl-4-yl group and a 3-fluoranthenyl group;

$X_3$ and $X_4$ are the same as or different from each other, and each independently a substituted or unsubstituted aryl group having 6 to 50 carbon atoms, a substituted or unsubstituted heteroaryl group having 5 to 50 nuclear atoms, a substituted or unsubstituted alkyl group having 1 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 nuclear atoms, a substituted or unsubstituted arylthio group having 5 to 50 nuclear atoms, a substituted or unsubstituted alkoxycarbonyl group having 1 to 50 carbon atoms, a carboxyl group, a halogen atom, a cyano group, a nitro group or a hydroxyl group; and s1 and s2 are each an integer of 0 to 4.

24. The organic electronic device of claim 23, wherein, in Chemical Formula 18, $Ar_3$ is a pyrene skeleton, $L_3$ is a single bond, $X_1$ and $X_2$ are the same as or different from each other and each independently an aryl group unsubstituted or substituted with a germanium group, and r is 2; and, in Chemical Formula 19, $X_5$ and $X_6$ are the same as or different from each other and each independently a 1-naphthyl group or a 2-naphthyl group, and s1 and s2 are 0.

25. An organic compound having a double spiro structure represented by the following Chemical Formula A:

[Chemical Formula A]

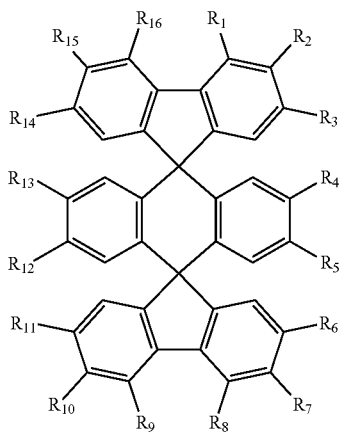

wherein in Chemical Formula A, $R_4$ and $R_5$ bonds to adjacent groups to form a ring structure of Chemical Formula A-1, and $R_1$ to $R_3$ and $R_6$ to $R_{16}$ are each hydrogen,

[Chemical Formula A-1]

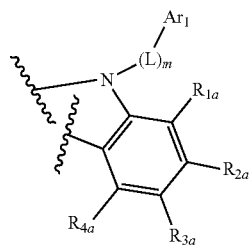

wherein in Chemical Formula A-1, m is an integer of 0 to 5, when m is 2 or greater, Ls are the same as or different from each other, L is a direct bond; phenylene; biphenylene; naphthylene; dimethylfluorenylene; pyridinylene unsubstituted or substituted with a phenyl group; pyrimidinylene unsubstituted or substituted with a phenyl group; triazinylene unsubstituted or substituted with a phenyl group; quinolylene unsubstituted or substituted with a phenyl group; quinazolylene unsubstituted or substituted with a phenyl group; dibenzothiophenylene; dibenzofuranylene; or carbazolylene unsubstituted or substituted with a phenyl group, $Ar_1$ is hydrogen; deuterium; a phenyl group unsubstituted or substituted with a nitrile group, a methyl group or phenyl group; a biphenyl group; a naphthyl group; a dimethylfluorenyl group; a diphenylamine group; a triphenylamine group; a pyridinyl group unsubstituted or substituted with a phenyl group; a pyrimidinyl group unsubstituted or substituted with a phenyl group; a triazinyl group unsubstituted or substituted with a phenyl group; a quinazoline group unsubstituted or substituted with a phenyl group; a dibenzothiophene group; a dibenzofuranyl group; or a carbazole group unsubstituted or substituted with a phenyl group, and $R_{1a}$ to $R_{4a}$ are each hydrogen, or bond to adjacent groups to form a benzene ring.

26. The organic compound having a double spiro structure of claim 25, wherein Chemical Formula A is represented by any one of the following Chemical Formulae 2, 8 and 9:

[Chemical Formula 2]

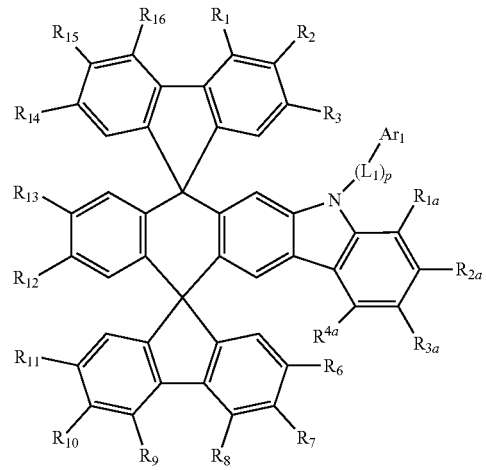

[Chemical Formula 8]

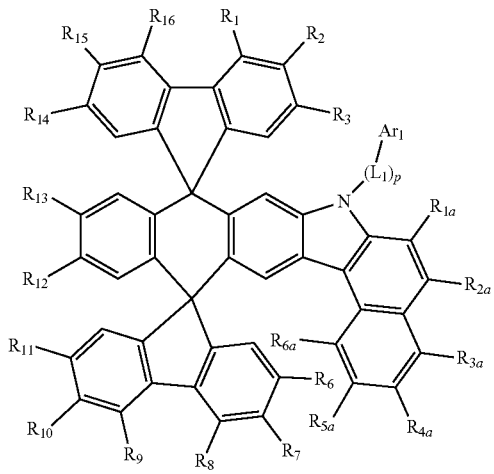

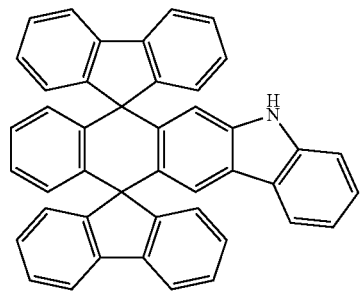

2-1

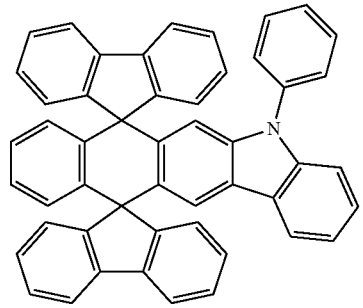

2-2

[Chemical Formula 9]

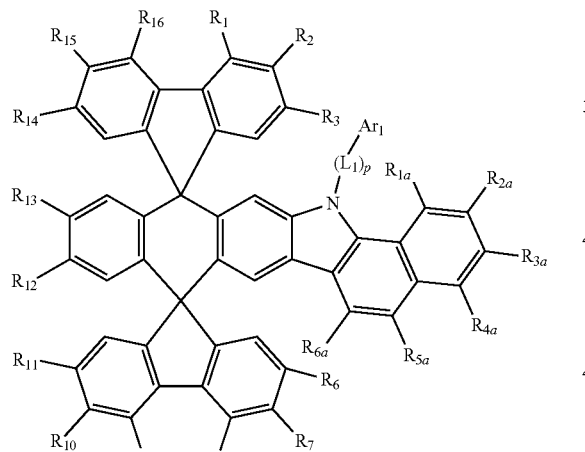

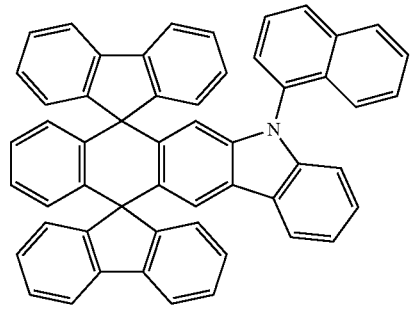

2-3 wherein in Chemical Formulae 2, 8 and 9, $R_1$ to $R_3$ and $R_6$ to $R_{16}$ each independently have the same definition as in Chemical Formula A, p is an integer of 0 to 5, when p is 2 or greater, $L_1$s are the same as or different from each other, $L_1$ has the same definition as L in Chemical Formula A-1, $Ar_1$ has the same definition as $Ar_1$ in Chemical Formula A-1, and $R_{1a}$ to $R_{6a}$ each independently have the same definition as $R_{1a}$ to $R_{4a}$ in Chemical Formula A-1.

27. The organic compound having a double spiro structure of claim 25, wherein Chemical Formula A is any one selected from among the following structures:

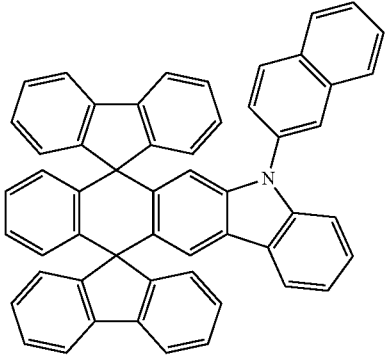

2-4

335
-continued
336
-continued
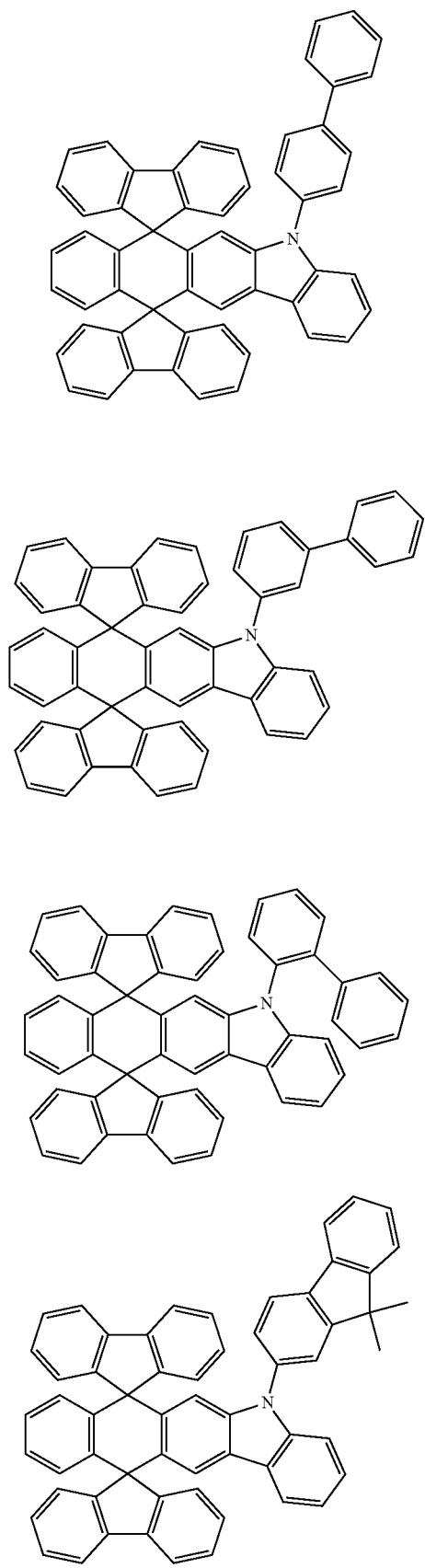
2-5
2-6
2-7
2-8
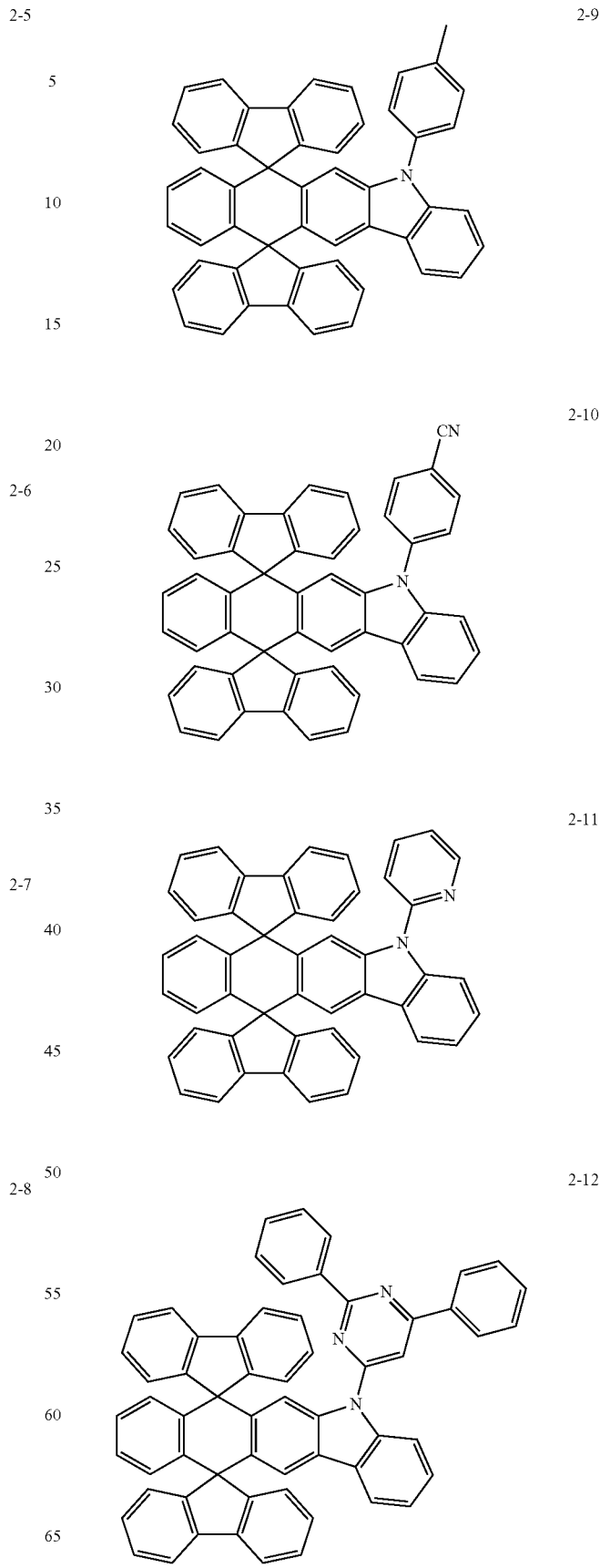
2-9
2-10
2-11
2-12

-continued
2-13
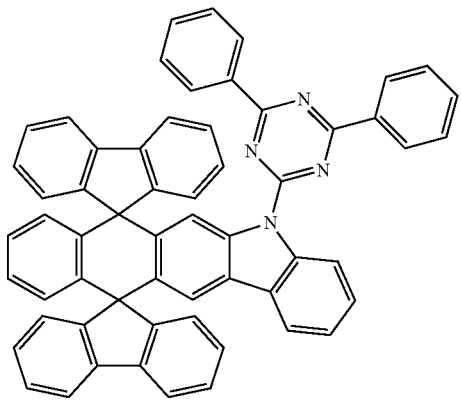
2-14
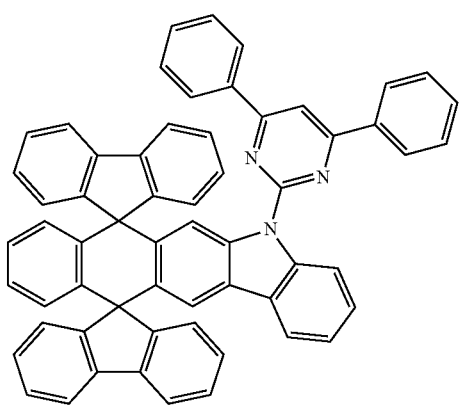
2-15
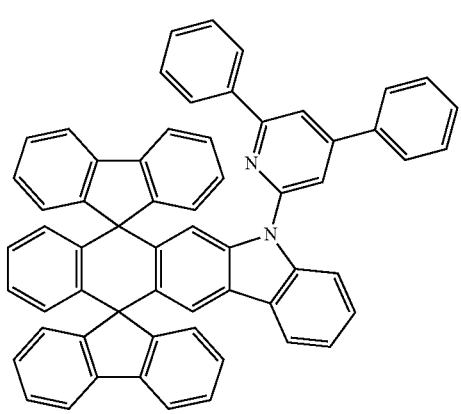
2-16
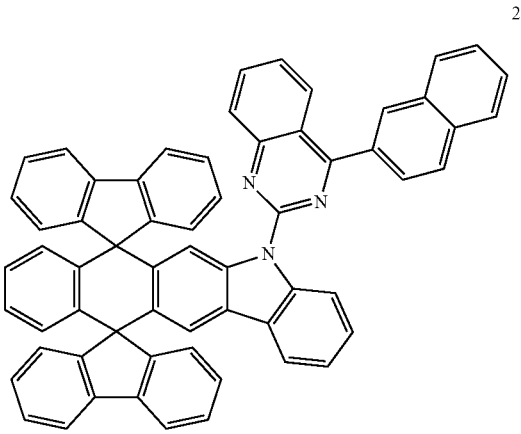
-continued
2-17
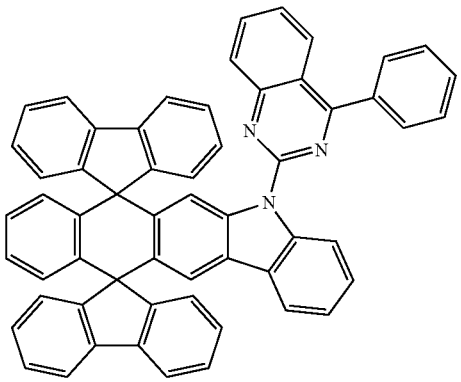
2-18
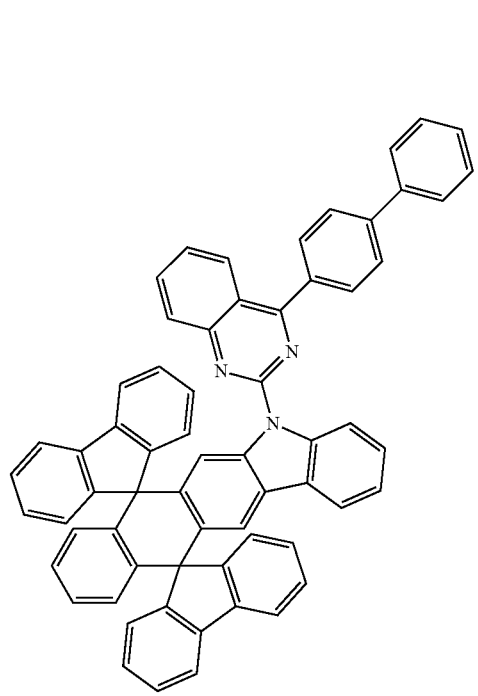
2-19
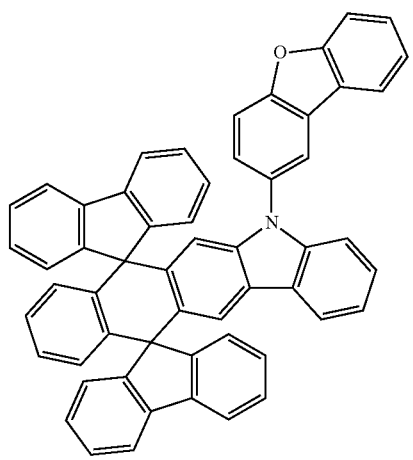

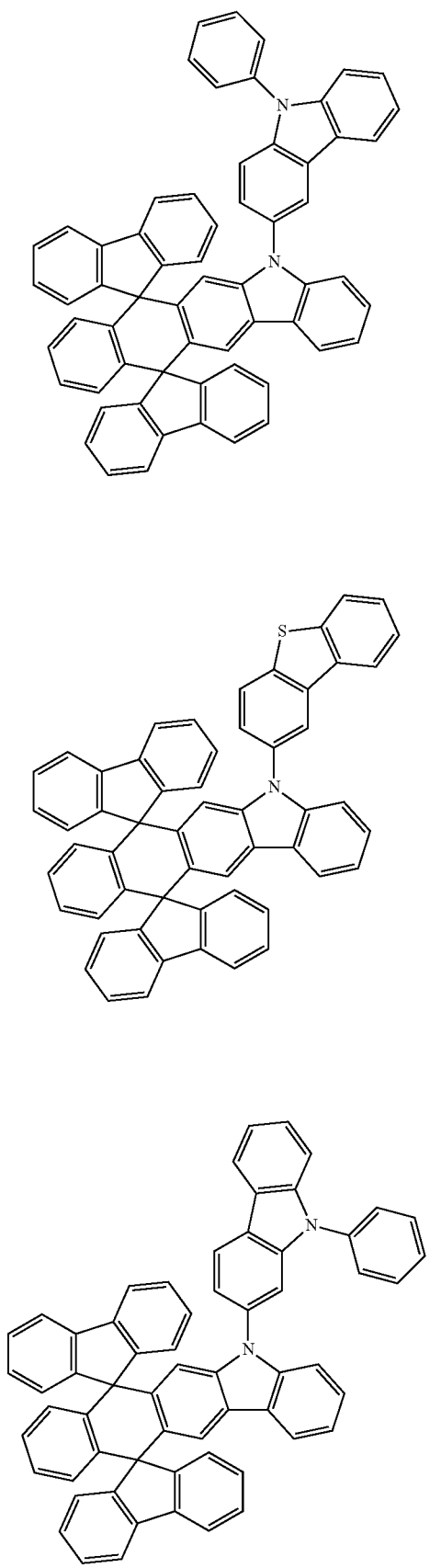
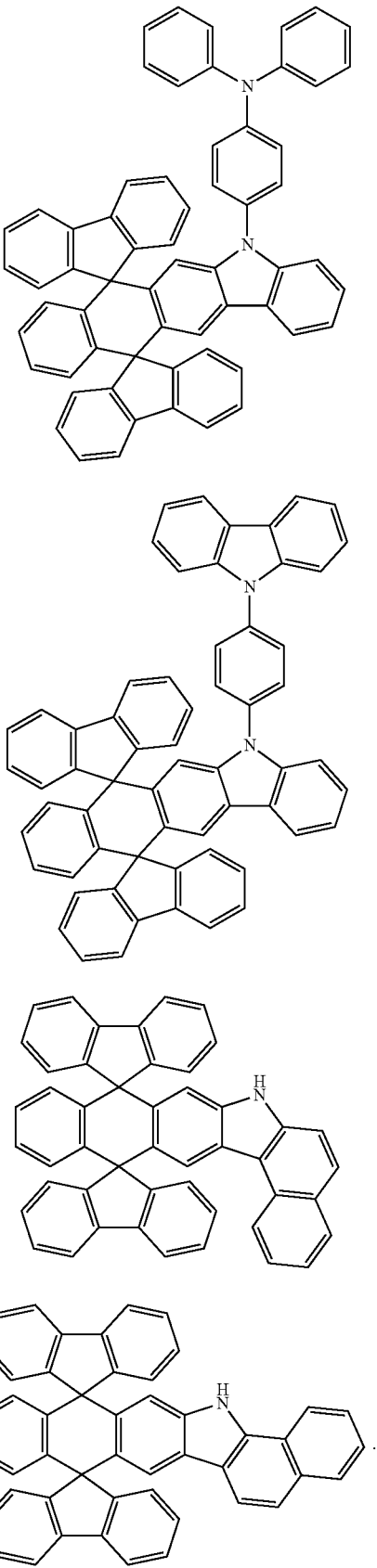

4-25
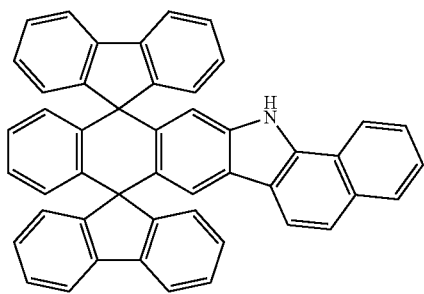
4-26
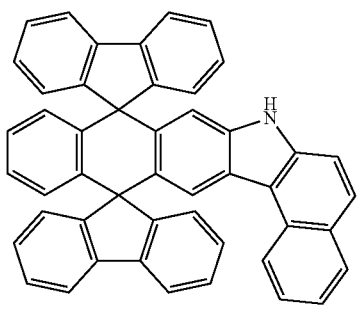
8-1
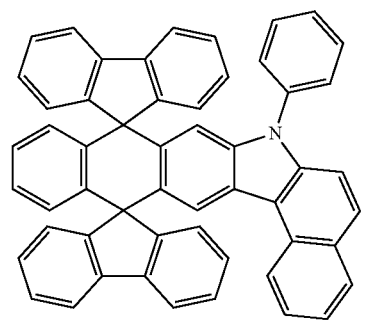
8-2
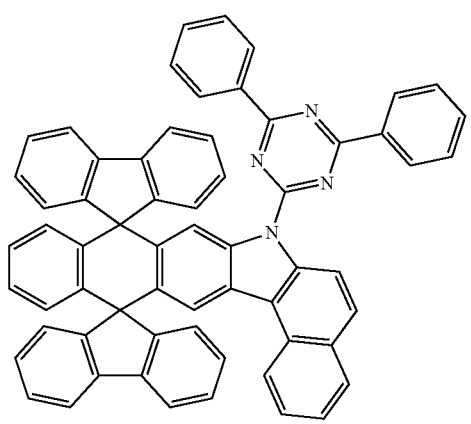
8-3
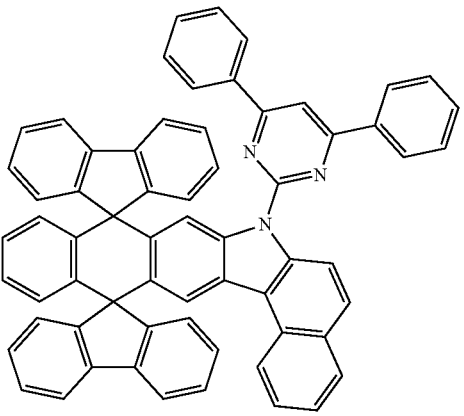
8-4
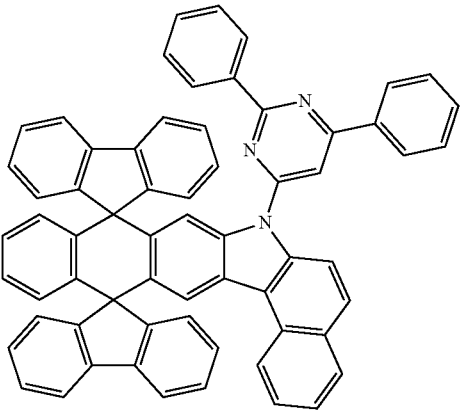
8-5
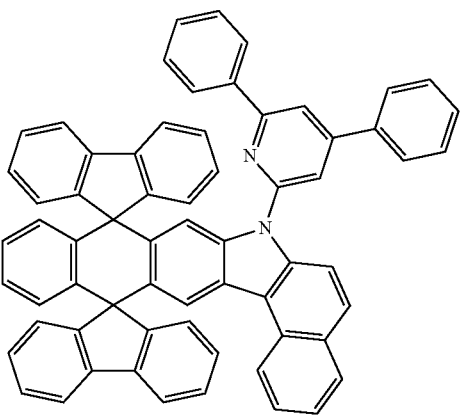

-continued
8-6
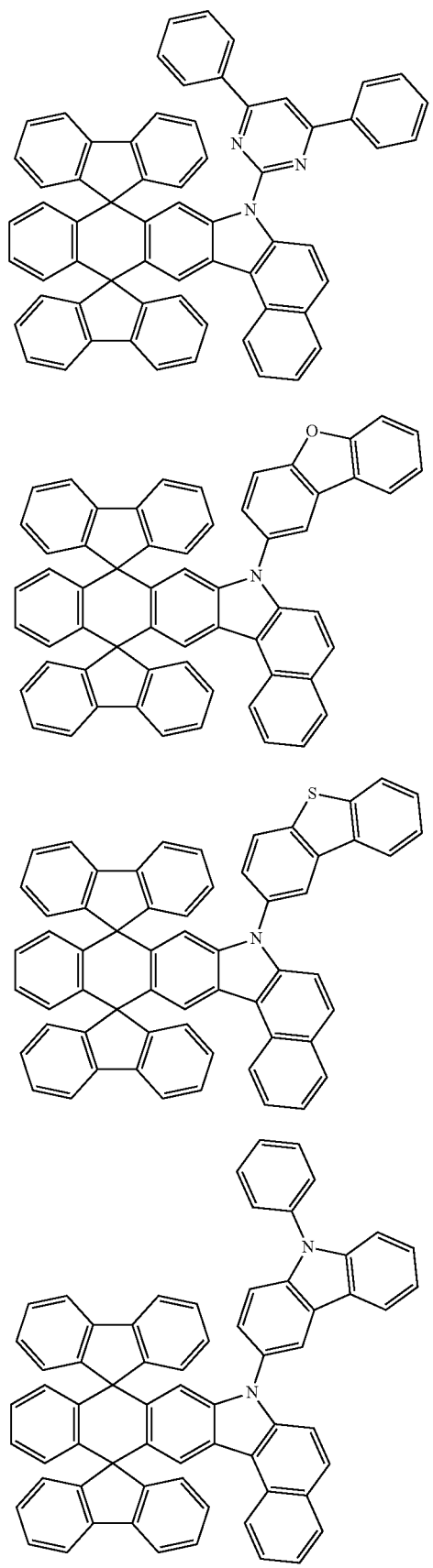
8-8
8-9
8-10
-continued
8-11
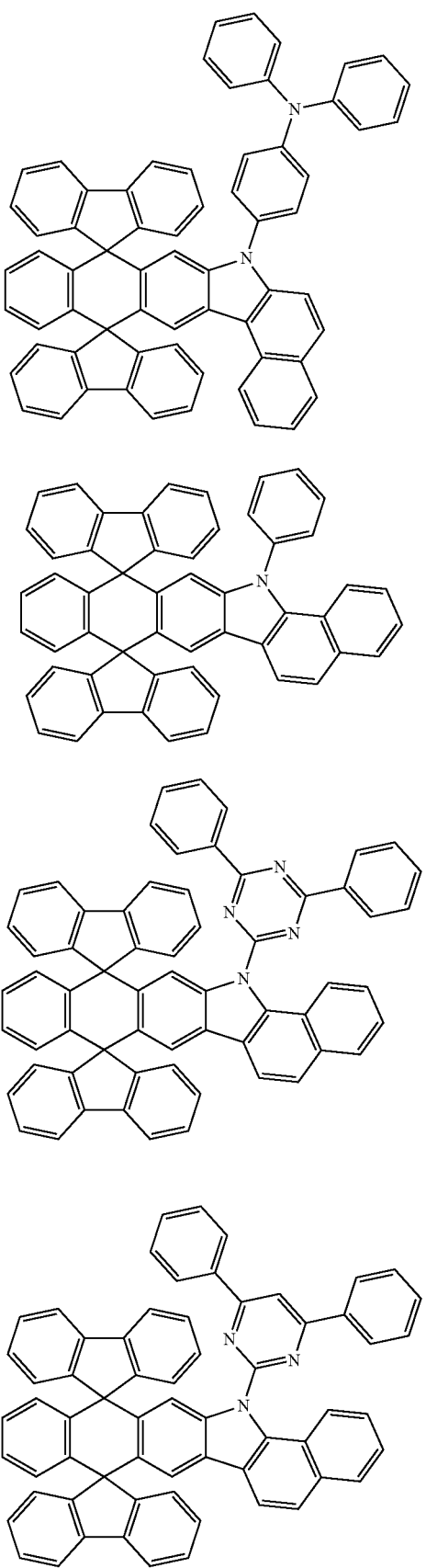
9-1
9-2
9-3

-continued
9-4
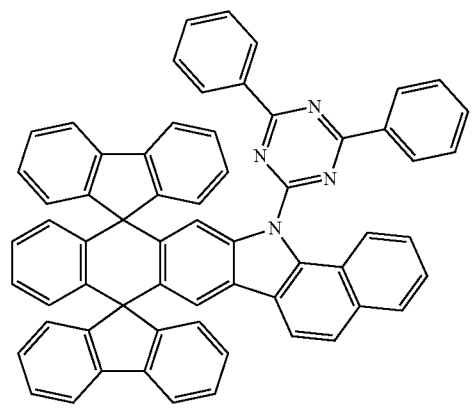
9-5
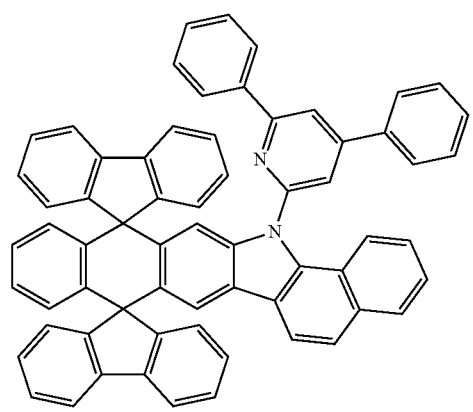
9-6
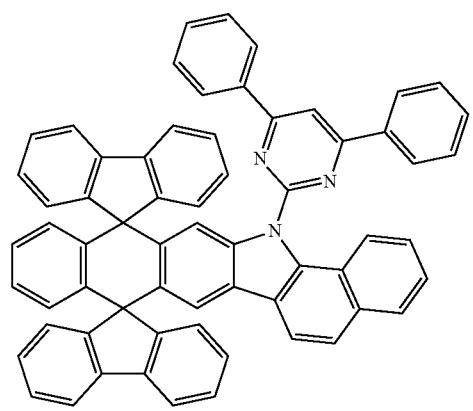
9-7
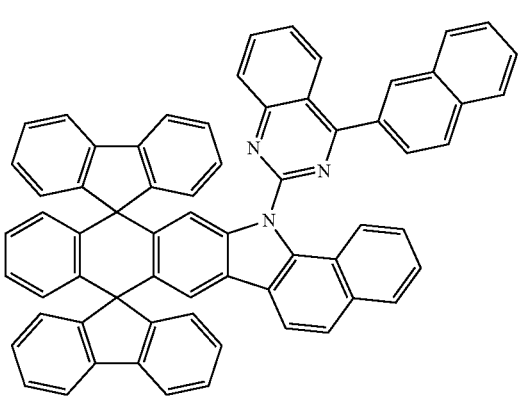
-continued
9-8
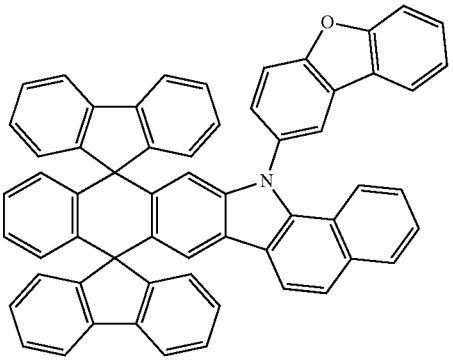
9-9
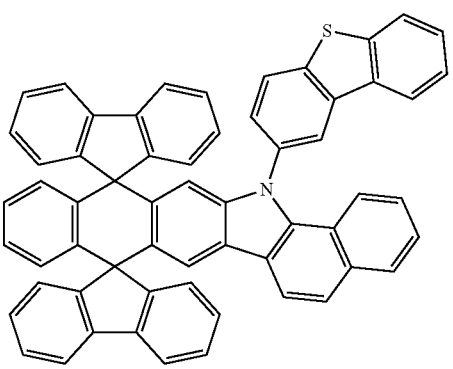
9-10
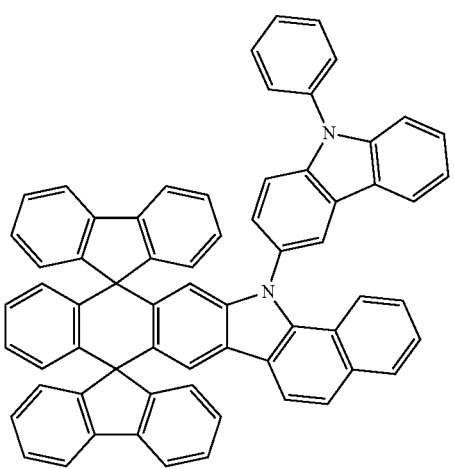

-continued

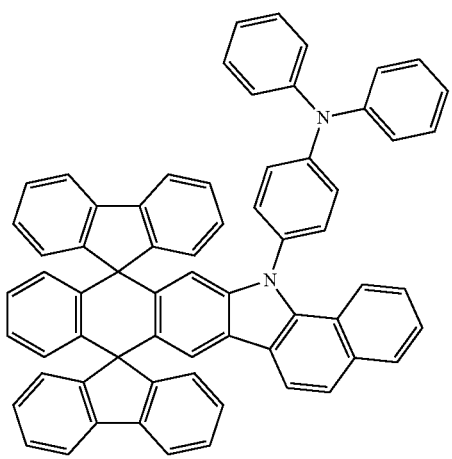

28. An organic electronic device comprising:
   a first electrode,
   a second electrode, and
   one or more organic material layers disposed between the first electrode and the second electrode,
   wherein one or more layers of the organic material layers comprise the organic compound having a double spiro structure of claim 25.

29. The organic electronic device of claim 28 as an organic light emitting device comprising:
   a first electrode,
   a second electrode, and
   one or more organic material layers disposed between the first electrode and the second electrode,
   wherein one or more layers of the organic material layers comprise the organic compound having a double spiro structure.

* * * * *